US009845362B2

(12) United States Patent
Mukherjee

(10) Patent No.: US 9,845,362 B2
(45) Date of Patent: Dec. 19, 2017

(54) COMPOSITIONS COMPRISING CHIMERIC ANTIGEN RECEPTORS, T CELLS COMPRISING THE SAME, AND METHODS OF USING THE SAME

(71) Applicant: The University of North Carolina at Charlotte, Charlotte, NC (US)

(72) Inventor: Pinku Mukherjee, Waxhaw, NC (US)

(73) Assignee: The University of North Carolina at Charlotte, Charlotte, NC (US)

(*) Notice: Subject to any disclaimer, the term of this patent is extended or adjusted under 35 U.S.C. 154(b) by 0 days.

(21) Appl. No.: 14/991,145

(22) Filed: Jan. 8, 2016

(65) Prior Publication Data
US 2016/0130357 A1 May 12, 2016

(51) Int. Cl.
*A61K 39/395* (2006.01)
*C07K 16/30* (2006.01)
*A61K 49/00* (2006.01)
*A61K 31/7088* (2006.01)
*C07K 16/28* (2006.01)
*G01N 33/574* (2006.01)
*C07K 14/725* (2006.01)
*C07K 14/705* (2006.01)
*A61K 47/68* (2017.01)
*A61K 39/00* (2006.01)

(52) U.S. Cl.
CPC ...... *C07K 16/3092* (2013.01); *A61K 31/7088* (2013.01); *A61K 39/39558* (2013.01); *A61K 47/6849* (2017.08); *A61K 47/6851* (2017.08); *A61K 47/6859* (2017.08); *A61K 49/0002* (2013.01); *C07K 14/7051* (2013.01); *C07K 14/70517* (2013.01); *C07K 14/70521* (2013.01); *C07K 14/70578* (2013.01); *C07K 16/2821* (2013.01); *C07K 16/2866* (2013.01); *C07K 16/30* (2013.01); *G01N 33/57438* (2013.01); *A61K 2039/505* (2013.01); *C07K 2317/33* (2013.01); *C07K 2317/34* (2013.01); *C07K 2317/622* (2013.01); *C07K 2317/73* (2013.01); *C07K 2319/00* (2013.01); *C07K 2319/02* (2013.01); *C07K 2319/03* (2013.01); *C07K 2319/41* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 7,183,388 B2 | 2/2007 | Denardo et al. | |
| 7,919,314 B2 | 4/2011 | Zvirbliene et al. | |
| 8,440,798 B2 | 5/2013 | Clausen et al. | |
| 8,518,405 B2 | 8/2013 | Mukherjee | |
| 8,722,856 B2 | 5/2014 | Nishimura et al. | |
| 8,912,311 B2 | 12/2014 | Clausen et al. | |
| 9,090,698 B2 * | 7/2015 | Mukherjee | A61K 47/48561 |
| 2003/0170761 A1 | 9/2003 | Stephens et al. | |
| 2004/0091480 A1 | 5/2004 | Hanai et al. | |
| 2005/0014207 A1 | 1/2005 | Goldenberg et al. | |
| 2006/0223096 A1 | 10/2006 | Umana et al. | |
| 2006/0292643 A1 | 12/2006 | Goletz et al. | |
| 2008/0057519 A1 | 3/2008 | McWhirter | |
| 2008/0214406 A1 | 9/2008 | Crea | |
| 2009/0053230 A1 | 2/2009 | Martin | |
| 2011/0123442 A1 | 5/2011 | Mukherjee | |
| 2012/0040375 A1 | 2/2012 | Nishimura et al. | |
| 2014/0010759 A1 | 1/2014 | Mukherjee | |
| 2015/0368356 A1 | 12/2015 | Mukherjee | |

FOREIGN PATENT DOCUMENTS

| | | |
|---|---|---|
| AU | 2011312830 | 7/2016 |
| EP | 2 199 390 | 6/2010 |
| WO | WO 2006/108658 | 10/2006 |
| WO | WO 2006/109592 | 10/2006 |
| WO | WO 2008/040362 | 4/2008 |
| WO | WO 2008/070171 | 6/2008 |
| WO | WO 2010/042562 | 4/2010 |
| WO | WO 2010/050528 | 5/2010 |

(Continued)

OTHER PUBLICATIONS

Sadelain et al, Current Opinions in Immunology vol. 21 p. 215 (2009).*
Till et al, Blood vol. 119 p. 3940 (2012).*
Skolnick et al. (Trends in Biotech., 18(1):34-39, 2000).*
Office action corresponding to U.S. Appl. No. 14/845,999 dated Jun. 24, 2016.
Decision to Grant corresponding to Russian Patent Application No. 2013120483/10 (030302) dated Feb. 18, 2016.
Notice of Granting Patent Right for Inventions corresponding to Chinese Patent Application No. 20110059040.8 dated May 16, 2016.
Office action corresponding to Canadian Patent Application No. 2,813,814 dated Mar. 31, 2016.

(Continued)

*Primary Examiner* — Sheela J. Huff
(74) *Attorney, Agent, or Firm* — Jenkins, Wilson, Taylor & Hunt, P.A.

(57) ABSTRACT

Provided are isolated nucleic acid molecules encoding chimeric antigen receptors (CARs) that bind to tumor antigens. Also provided are isolated polypeptides and CARs encoded by the isolated nucleic acid molecules, vectors that include the isolated nucleic acid molecules, cells that include the isolated nucleic acid molecules, methods of making the same, and methods for using the same to generate a persisting population of genetically engineered T cells in a subject, expanding a population of genetically engineered T cells in a subject, modulating the amount of cytokine secreted by a T cell, reducing the amount of activation-induced calcium influx into a T cell, providing an anti-tumor immunity to a subject, treating a mammal having a MUC1-associated disease or disorder, stimulating a T cell-mediated immune response to a target cell population or tissue in a subject, and imaging a MUC1-associated tumor.

16 Claims, 32 Drawing Sheets
(20 of 32 Drawing Sheet(s) Filed in Color)

(56) References Cited

FOREIGN PATENT DOCUMENTS

| WO | WO 2010/077854 | 7/2010 |
|---|---|---|
| WO | WO 2010/113117 | 10/2010 |
| WO | WO 2011/012309 | 2/2011 |
| WO | WO 2012/004317 | 4/2012 |

OTHER PUBLICATIONS

Office action corresponding to Mexican Patent Application No. MX/a/2013/003825 dated Jul. 8, 2016.
Office Action corresponding to U.S. Appl. No. 14/810,209 dated May 20, 2016.
Rudikoff et al., "Single amino acid substitution altering antigen-binding specificity," PNAS, 79, pp. 1979-1983 (Mar. 15, 1982).
Bieche & Lidereau (1997) Cancer Genetics and Cytogenetics 98:75-80.
Brown et al., J. Immunol. May 1996; 156(9):3285-3291.
Casset et al. (2003) BBRC 307, 198-205.
Curry et al., "The Use of a Novel MUC1 Antibody to Identify Cancer Stem Cells and Circulating MUC1 in Mice and Patients With Pancreatic Cancer," Journal of Surgical Oncology, vol. 107, pp. 713-722 (2013).
Danielczyk et al., "PankoMab: a potent new generation anti-tumour MUCI antibody", Cancer Immunology, Immunotherapy, vol. 55, No. 11, pp. 1337-1347 (Feb. 17, 2006).
Decision of Rejection corresponding to Japanese Patent Application No. 2013-532795 dated Aug. 3, 2015.
Deutscher, Methods in Enzymology vol. 182 p. 663-670 (1990).
DeVita et al. (eds) Biologicheskie Metody Lecheniya Onkologicheskih Zabolev Aniy: translated from English (2002), p. 530, lines 20-24, p. 539, last line-540, left column, lines 1-4, p. 546 chapter "Problems and prospects" (Translation).
European Search Report corresponding to European Application No. 11831066.3-1403 / 2624866 dated Feb. 4, 2014.
Henderson et al. (1998) J Immunother 21:247-256.
Hingorani et al., "Preinvasive and invasive ductal pancreatic cancer and its early detection in the mouse," Cancer Cell, vol. 4, pp. 437-450 (2003).
Interview Summary corresponding to U.S. Appl. No. 13/948,580 dated Jun. 30, 2015.
Jackson et al., "Analysis of lung tumor initiation and progression using conditional expression of oncogenic K-ras," Genes Dev., vol. 15, pp. 3243-3248 (2001).
Kahn et al. (1987) Anticancer Res 7(4A):639-652.
Kawaguchi et al. (2002) Nat Genet 32:128-134.
Kirschenbaum et al., "MUCI expression in prostate carcinoma: Correlation with grade and stage", Molecular Urology, vol. 3, No. 3, pp. 163-167 (Jan. 1, 1999).
Leroy et al.,"Anatomic Pathology MUC1 in Renal Cell Carcinoma MUCI—Expression Is Correlated With Nuclear Grade and Tumor Progression in pTI Renal Clear Cell Carcinoma," Jan. 1, 2002. URL:http://ajcp.ascpjournals.org/content/I18/1/47.full.pdf [retrieved on Jan. 29, 2014].
McGuckin et al. (1995) Human Pathology 26: 432-439.
Moiseenko, V.M., "Monoklonalnyie antitela v lechenii zlokachestvennyh opuholey", Practical Oncology, vol. 4, No. 3, 2003, p. 148-156, p. 151, left column. (Translation).
Moreno et al., "High level of MUCI in serum of ovarian and breast cancer patients inhibits huHMFG-1 dependent cell-mediated cytotoxicity (ADCC)", Cancer Letters, vol. 257, No. 1, pp. 47-55 (Sep. 27, 2007).
Mukherjee et al., "Mice with Spontaneous Pancreatic Cancer Naturally Develop MUC-1-Specific CTLs That Eradicate Tumors When Adoptively Transferred," J. Immunol., vol. 165, pp. 3451-3460 (2000).
Mukherjee et al., "MUC1-specific immune therapy generates a strong anti-tumor response in a MUC1-tolerant colon cancer model," Vaccine, vol. 25, pp. 1607-1618 (2007).
Mukherjee et al., "Progression of Pancreatic Adenocarcinoma Is Significantly Impeded with a Combination of Vaccine and COX-2 Inhibition," J. Immunol., vol. 182, pp. 216-224 (2009).
Notice of Acceptance corresponding to Australian Patent Application No. 2011312830 dated Mar. 9, 2016.
Notice of Allowance corresponding to U.S. Appl. No. 12/924,952 dated Jul. 10, 2013.
Notice of Allowance corresponding to U.S. Appl. No. 13/877,582 dated Apr. 24, 2015.
Notification of Transmittal of the International Search Report and the Written Opinion of the International Searching Authority, or the Declaration corresponding to International Application No. PCT/US11/37972 dated Apr. 2, 2012.
Office Action (Examination Report) corresponding to Australian Patent Application No. 2011312830 dated Feb. 8, 2016.
Office Action and Search Report corresponding to Chinese Patent Application No. 201180059040.8 dated Aug. 22, 2014, (Translation).
Office Action corresponding to Australian Patent Application No. 2011312830 dated Dec. 21, 2015.
Office Action corresponding to Australian Patent Application No. 2011312830 dated May 30, 2014.
Office Action corresponding to Canadian Patent Application No. 2,813,814 dated Oct. 21, 2014.
Office Action corresponding to Chinese Patent Application No. 201180059040.8 dated Dec. 3, 2015. (Translation).
Office Action corresponding to Chinese Patent Application No. 201180059040.8 dated Jul. 1, 2015.
Office Action corresponding to European Patent Application No. 11831066.3 dated Jan. 4, 2016. (Translation).
Office Action corresponding to Israeli Patent Application No. 225545 dated Dec. 2, 2015 (Translation).
Office Action corresponding to Japanese Patent Application No. 2013-532795 dated Nov. 18, 2014.
Office Action corresponding to Russian Patent Application No. 2013120483 dated Nov. 14, 2014.
Office Action corresponding to U.S. Appl. No. 12/924,952 dated Sep. 14, 2012.
Office Action corresponding to U.S. Appl. No. 13/877,582 dated Feb. 20, 2015.
Office Action corresponding to U.S. Appl. No. 13/877,582 dated Jul. 21, 2014.
Office Action corresponding to U.S. Appl. No. 13/948,580 dated Apr. 29, 2014.
Office Action corresponding to U.S. Appl. No. 13/948,580 dated Mar. 27, 2015.
Office Action corresponding to U.S. Appl. No. 13/948,580 dated Nov. 7, 2014.
Office Action corresponding to U.S. Appl. No. 13/948,580 dated Feb. 16, 2016.
Office Action corresponding to U.S. Appl. No. 13/948,580 dated Sep. 14, 2015.
Pascalis et al (The Journal of Immunology (2002) 169, 3076-3084).
Quin et al. (2000) Int J Cancer 87:499-506.
Rothenfusser et al. (2002) Human Immunology 63:1111-1119.
Rowse et al., "Tolerance and Immunity to MUC1 in a Human MUC1 Transgenic Murine Model,"Cancer Res., vol. 58, pp. 315-321 (1998).
Rudikoff et al (Proc. Natl. Acad. Sci. USA 1982 vol. 79: p. 1979).
Tinder et al., "MUC1 Enhances Tumor Progression and Contributes Toward Immunosuppression in a Mouse Model of Spontaneous Pancreatic Adenocarcinoma," J. Immunol., vol. 181, pp. 3116-3125 (2008).
Vajdos et al (J. Mol. Biol. Jul. 5, 2002;320(2); 415-428).
Letter regarding Office Action corresponding to Mexican Patent Application No. MX/a/2013/003825 dated Sep. 22, 2016.
Decision to Grant corresponding to Japanese Patent Application No. 2013532795 dated Feb. 1, 2016.
Decision to grant corresponding to Japanese Patent Application No. 2015229461 dated Oct. 31, 2016.
Letter Regarding Examination Report corresponding to Israeli Patent Application No. 225545 dated Dec. 26, 2016.

(56) References Cited

OTHER PUBLICATIONS

Letter regarding Office Action corresponding to Mexican Patent Application No. MX/a/2013/003825 dated Dec. 14, 2016.
Letter regarding official notice of allowance corresponding to Mexican Patent Application No. MX/a/2013/003825 dated Mar. 2, 2017.
Office Action corresponding to European Patent Application No. 11831066.3 dated Jan. 10, 2017.
Office Action corresponding to Israeli Patent Application No. 225545 dated Mar. 31, 2015. (Translation).
Office Action corresponding to U.S. Appl. No. 14/991,145 dated Feb. 1, 2017.
Office Action corresponding to U.S. Appl. No. 14/845,999 dated Apr. 3, 2017.
Office Action corresponding to U.S. Appl. No. 15/154,596 dated May 19, 2017.

* cited by examiner

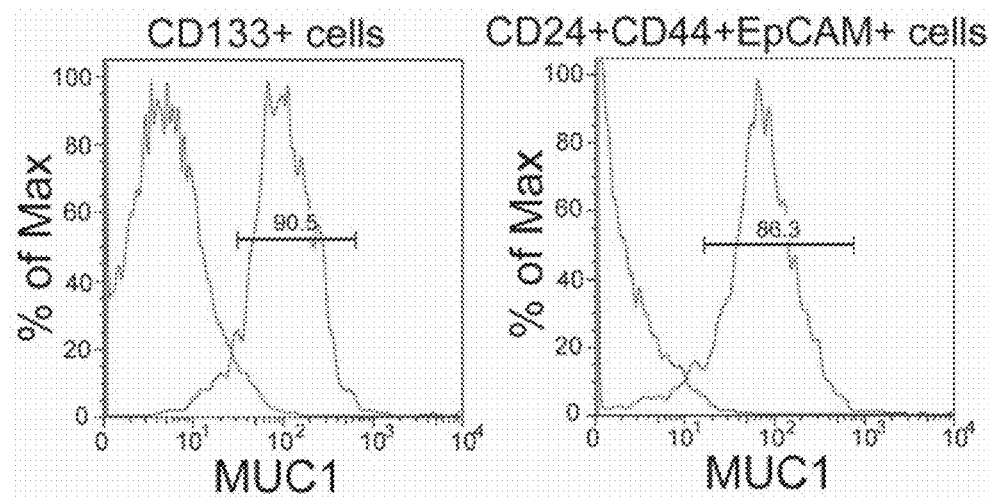
*FIG. 7A*  *FIG. 7B*

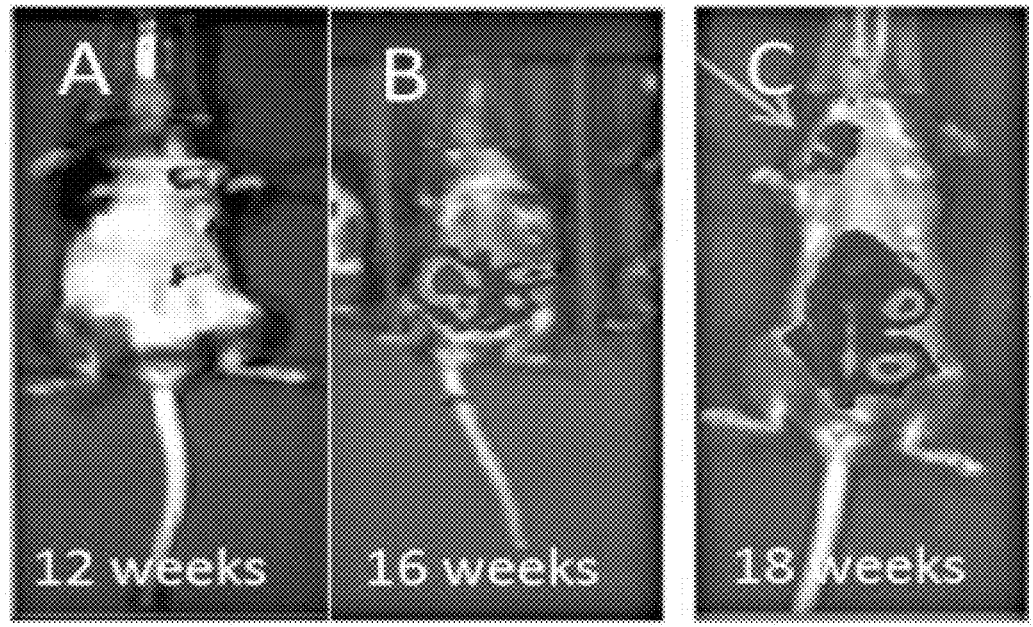
FIG. 17A  FIG. 17B  FIG. 17C
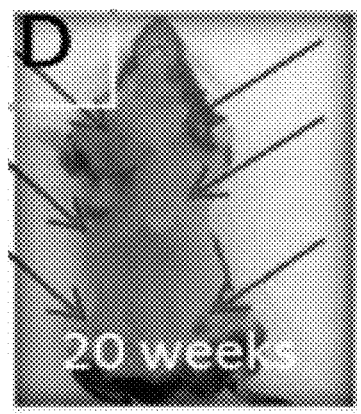
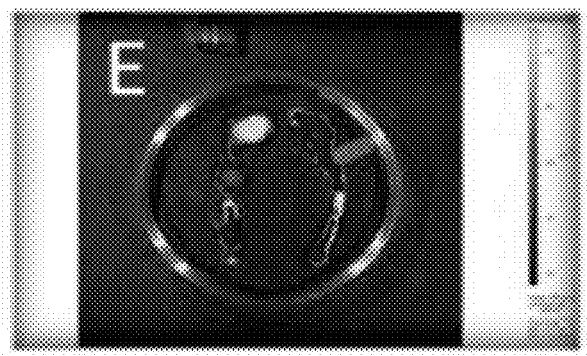
FIG. 17D  FIG. 17E

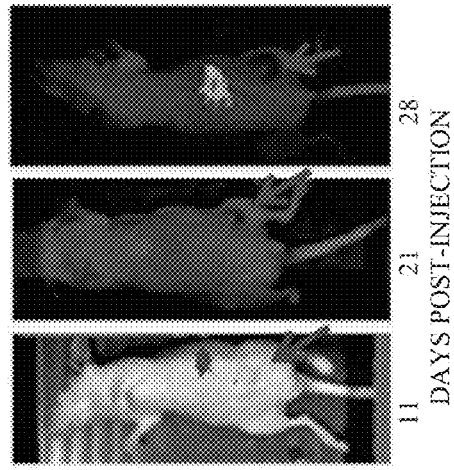
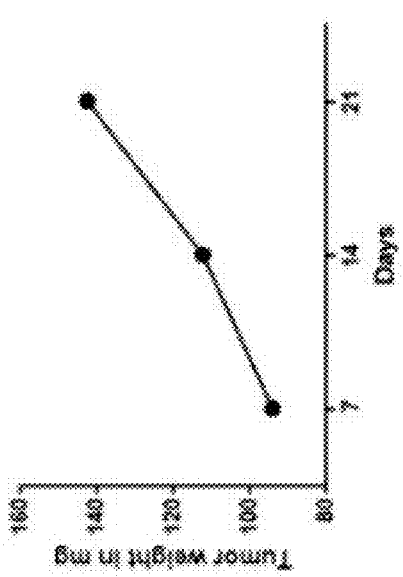
FIG. 18A
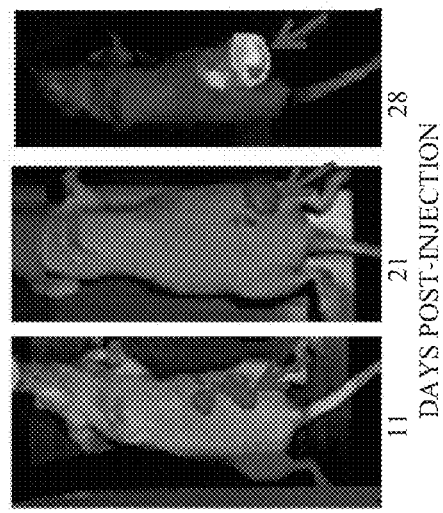
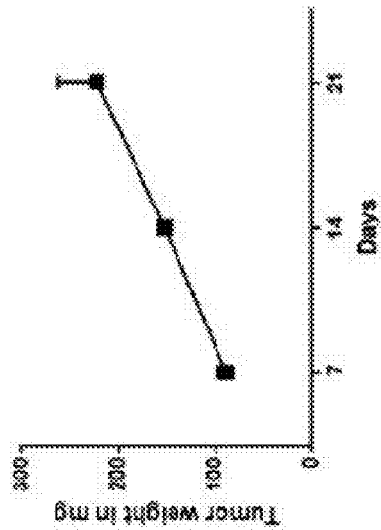
FIG. 18B

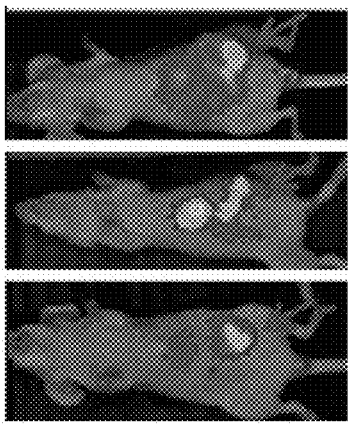
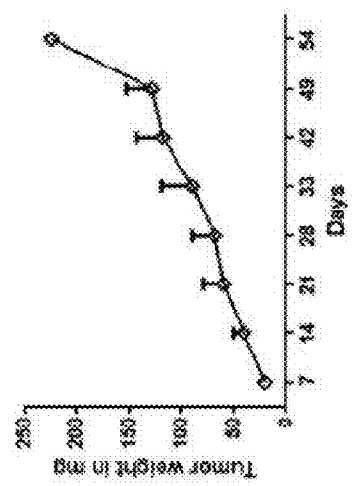
*FIG. 18C*
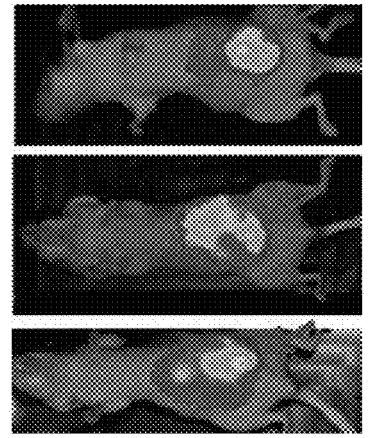
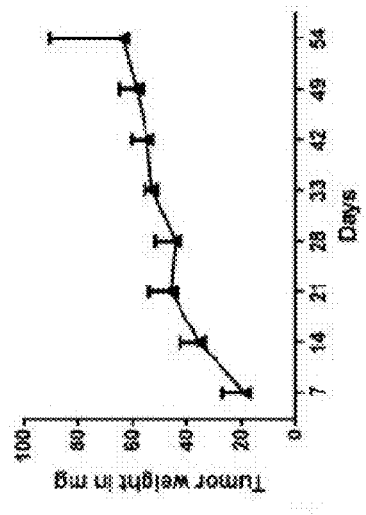
*FIG. 18D*

SEQUENCE LISTING

<160> NUMBER OF SEQ ID NOS: 34

<210> SEQ ID NO 1
<211> LENGTH: 1255
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

```
Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
            290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
            325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
            370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
            405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
            450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
            485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
            530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
            565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
            595                 600                 605

Gly Ser Thr Ala Pro Pro Ala His Gly Val Thr Ser Ala Pro Asp Thr
            610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
            645                 650                 655

Gly Val Thr Ser Ala Pro Asp Thr Arg Pro Ala Pro Gly Ser Thr Ala
            660                 665                 670
```

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser

```
                1085                1090                1095
Val Val Val Gln Leu Thr Leu Ala Phe Arg Glu Gly Thr Ile Asn
        1100                1105                1110

Val His Asp Val Glu Thr Gln Phe Asn Gln Tyr Lys Thr Glu Ala
        1115                1120                1125

Ala Ser Arg Tyr Asn Leu Thr Ile Ser Asp Val Ser Val Ser Asp
        1130                1135                1140

Val Pro Phe Pro Phe Ser Ala Gln Ser Gly Ala Gly Val Pro Gly
        1145                1150                1155

Trp Gly Ile Ala Leu Leu Val Leu Val Cys Val Leu Val Ala Leu
        1160                1165                1170

Ala Ile Val Tyr Leu Ile Ala Leu Ala Val Cys Gln Cys Arg Arg
        1175                1180                1185

Lys Asn Tyr Gly Gln Leu Asp Ile Phe Pro Ala Arg Asp Thr Tyr
        1190                1195                1200

His Pro Met Ser Glu Tyr Pro Thr Tyr His Thr His Gly Arg Tyr
        1205                1210                1215

Val Pro Pro Ser Ser Thr Asp Arg Ser Pro Tyr Glu Lys Val Ser
        1220                1225                1230

Ala Gly Asn Gly Gly Ser Ser Leu Ser Tyr Thr Asn Pro Ala Val
        1235                1240                1245

Ala Ala Ala Ser Ala Asn Leu
        1250                1255

<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 3
<211> LENGTH: 25
<212> TYPE: PRT
<213> ORGANISM: Homo sapiens

<400> SEQUENCE: 3

Ser Thr Ala Pro Pro Val His Asn Val Thr Ser Ala Pro Asp Thr Arg
1               5                   10                  15

Pro Ala Pro Gly Ser Thr Ala Pro Pro
            20                  25

<210> SEQ ID NO 4
<211> LENGTH: 354
<212> TYPE: DNA
<213> ORGANISM: Mus musculus

<400> SEQUENCE: 4

```
gaggtccagc tgcagcagtc tgggggtgaa cgggcaacac ctggggcctc agtgaagatg     60
tcctgcaaga cttctggcta caccttract aactactgga tgcactgggt aaaacagagg    120
cctggacagg gtctggaatg gattggatac attaatccta gcagtggtta tactcagtac    180
aatcagaagt tcaaggacaa ggccacattg actgcagaca atcctccag cacagcctac     240 atacaactaa gcagcctgac atctgaagac tctgcagtct attactgttc aacctactat    300
ggtgactact tgtttcctta ctggggccaa gggactctgg tcactgtctc tgca           354
```

<210> SEQ ID NO 5
<211> LENGTH: 118
<212> TYPE: PRT
<213> ORGANISM: Mus musculus

<400> SEQUENCE: 5

Glu Val Gln Leu Gln Gln Ser Gly Gly Glu Arg Ala Thr Pro Gly Ala
1               5                   10                  15

Ser Val Lys Met Ser Cys Lys Thr Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Gln Tyr Asn Gln Lys Phe
    50                  55                  60

Lys Asp Lys Ala Thr Leu Thr Ala Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ser Thr Tyr Tyr Gly Asp Tyr Leu Phe Pro Tyr Trp Gly Gln Gly Thr
            100                 105                 110

Leu Val Thr Val Ser Ala
        115

<210> SEQ ID NO 6
<211> LENGTH: 339
<212> TYPE: DNA
<213> ORGANISM: Mus musculus

<400> SEQUENCE: 6

```
gatgttttga tgacccaaac tccactctcc ctgcctgtca gtcttggaga tcaagcctcc     60
atctcttgca gatctagtca ggacattgta tatggtaatg aaacaccta tttagaatgg    120 tacctgcaga aaccaggcca gtctccaaag ctcctgatct acaaagtttc caaccggttt    180
```

```
tctggggtcc cagacaggtt cagtggcagt ggatcaggga cagatttcac actcaagatc    240
agcagagtgg aggctgagga tctgggagtt tattactgct ttcaaggttc acatgttccg    300
tacacgttcg gaggggggac caagctggaa ataaaacgg                           339
```

<210> SEQ ID NO 7
<211> LENGTH: 113
<212> TYPE: PRT
<213> ORGANISM: Mus musculus

<400> SEQUENCE: 7

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asp Ile Val Tyr Gly
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg
```

<210> SEQ ID NO 8
<211> LENGTH: 8
<212> TYPE: PRT
<213> ORGANISM: Mus musculus

<400> SEQUENCE: 8

```
Gly Tyr Thr Phe Thr Asn Tyr Trp
1               5
```

<210> SEQ ID NO 9
<211> LENGTH: 8
<212> TYPE: PRT
<213> ORGANISM: Mus musculus

<400> SEQUENCE: 9

```
Ile Asn Pro Ser Ser Gly Tyr Thr
1               5
```

<210> SEQ ID NO 10
<211> LENGTH: 11
<212> TYPE: PRT
<213> ORGANISM: Mus musculus

<400> SEQUENCE: 10

```
Ser Thr Tyr Tyr Gly Asp Tyr Leu Phe Pro Tyr
1               5                   10
```

<210> SEQ ID NO 11
<211> LENGTH: 11
<212> TYPE: PRT
<213> ORGANISM: Mus musculus

<400> SEQUENCE: 11

```
Gln Asp Ile Val Tyr Gly Asn Gly Asn Thr Tyr
1               5                   10

<210> SEQ ID NO 12
<211> LENGTH: 3
<212> TYPE: PRT
<213> ORGANISM: Mus musculus

<400> SEQUENCE: 12

Lys Val Ser
1

<210> SEQ ID NO 13
<211> LENGTH: 9
<212> TYPE: PRT
<213> ORGANISM: Mus musculus

<400> SEQUENCE: 13

Phe Gln Gly Ser His Val Pro Tyr Thr
1               5

<210> SEQ ID NO 14
<211> LENGTH: 1482
<212> TYPE: DNA
<213> ORGANISM: Artificial Sequence
<220> FEATURE:
<223> OTHER INFORMATION: Artificially synthesized human CAR open reading
      frame
<220> FEATURE:
<221> NAME/KEY: CDS
<222> LOCATION: (1)..(1482)

<400> SEQUENCE: 14 atg gcc ctg ccc gtg acc gcc ctg ctc ttg ccc ctg gcc ctt ctg ctc        48
Met Ala Leu Pro Val Thr Ala Leu Leu Leu Pro Leu Ala Leu Leu Leu
1               5                   10                  15 cac gcc gcc aga ccc gag gtg cag ctg cag cag agc gga ggc gag aga        96
His Ala Ala Arg Pro Glu Val Gln Leu Gln Gln Ser Gly Gly Glu Arg
                20                  25                  30 gcc acc cct ggc gcc agc gtg aag atg agc tgc aag acc agc ggc tac       144
Ala Thr Pro Gly Ala Ser Val Lys Met Ser Cys Lys Thr Ser Gly Tyr
            35                  40                  45 acc ttc acc aac tac tgg atg cac tgg gtg aag cag aga ccc ggc cag       192
Thr Phe Thr Asn Tyr Trp Met His Trp Val Lys Gln Arg Pro Gly Gln
        50                  55                  60 ggc ctg gag tgg atc ggc tac atc aac cct agc tcc ggc tac acc cag       240
Gly Leu Glu Trp Ile Gly Tyr Ile Asn Pro Ser Ser Gly Tyr Thr Gln
65                  70                  75                  80 tac aac cag aag ttc aag gac aag gcc acc ctg acc gcc gac aag agc       288
Tyr Asn Gln Lys Phe Lys Asp Lys Ala Thr Leu Thr Ala Asp Lys Ser
                85                  90                  95 tcc agc acc gcc tac atc cag ctg agc tcc ctg acc agc gag gac tcc       336
Ser Ser Thr Ala Tyr Ile Gln Leu Ser Ser Leu Thr Ser Glu Asp Ser
            100                 105                 110 gcc gtg tac tat tgc agc acc tac tac ggc gac tac ctg ttc ccc tac       384
Ala Val Tyr Tyr Cys Ser Thr Tyr Tyr Gly Asp Tyr Leu Phe Pro Tyr
        115                 120                 125 tgg ggc cag ggc acc ctg gtg acc gtg agc gcc ggc gga ggc gga agc       432
Trp Gly Gln Gly Thr Leu Val Thr Val Ser Ala Gly Gly Gly Gly Ser
    130                 135                 140 gga ggc ggc gga tcc gga gga ggc ggc agc gac gtg ctg atg acc cag       480
Gly Gly Gly Gly Ser Gly Gly Gly Gly Ser Asp Val Leu Met Thr Gln
145                 150                 155                 160
```

```
acc cct ctg agc ctg ccc gtg agc ctg ggc gac cag gcc agc atc agc      528
Thr Pro Leu Ser Leu Pro Val Ser Leu Gly Asp Gln Ala Ser Ile Ser
                165             170             175 tgc aga agc tcc cag gac atc gtg tac ggc aac gga aac acc tac ctg      576
Cys Arg Ser Ser Gln Asp Ile Val Tyr Gly Asn Gly Asn Thr Tyr Leu
            180             185             190 gag tgg tac ctc cag aag ccc ggc cag agc ccc aag ctg ctg atc tac      624
Glu Trp Tyr Leu Gln Lys Pro Gly Gln Ser Pro Lys Leu Leu Ile Tyr
        195             200             205 aag gtg agc aac aga ttc agc ggc gtg ccc gac aga ttc agc ggc tcc      672
Lys Val Ser Asn Arg Phe Ser Gly Val Pro Asp Arg Phe Ser Gly Ser
    210             215             220 gga agc gga acc gac ttc acc ctg aag atc agc aga gtg gag gcc gag      720
Gly Ser Gly Thr Asp Phe Thr Leu Lys Ile Ser Arg Val Glu Ala Glu
225             230             235             240 gac ctg ggc gtg tac tat tgc ttc cag ggc agc cac gtg ccc tac acc      768
Asp Leu Gly Val Tyr Tyr Cys Phe Gln Gly Ser His Val Pro Tyr Thr
                245             250             255 ttc ggc gga ggc acc aag ctg gag atc aag aga gcg gcc gct atc gag      816
Phe Gly Gly Gly Thr Lys Leu Glu Ile Lys Arg Ala Ala Ala Ile Glu
            260             265             270 gtg gag cag aag ctg atc agc gag gag gac ctg cta gac aat gag aag      864
Val Glu Gln Lys Leu Ile Ser Glu Glu Asp Leu Leu Asp Asn Glu Lys
        275             280             285 agc aat gga acc att atc cat gtg aaa ggg aaa cac ctt tgt cca agt      912
Ser Asn Gly Thr Ile Ile His Val Lys Gly Lys His Leu Cys Pro Ser
    290             295             300 ccc cta ttt ccc gga cct tct aag ccc ttt tgg gtg ctg gtg gtg gtt      960
Pro Leu Phe Pro Gly Pro Ser Lys Pro Phe Trp Val Leu Val Val Val
305             310             315             320 ggt gga gtc ctg gct tgc tat agc ttg cta gta aca gtg gcc ttt att     1008
Gly Gly Val Leu Ala Cys Tyr Ser Leu Leu Val Thr Val Ala Phe Ile
                325             330             335 att ttc tgg gtg agg agt aag agg agc agg ctc ctg cac agt gac tac     1056
Ile Phe Trp Val Arg Ser Lys Arg Ser Arg Leu Leu His Ser Asp Tyr
            340             345             350 atg aac atg act ccc cgc cgc ccc ggg ccc acc cgc aag cat tac cag     1104
Met Asn Met Thr Pro Arg Arg Pro Gly Pro Thr Arg Lys His Tyr Gln
        355             360             365 ccc tat gcc cca cca cgc gac ttc gca gcc tat cgc tcc aga gtg aag     1152
Pro Tyr Ala Pro Pro Arg Asp Phe Ala Ala Tyr Arg Ser Arg Val Lys
    370             375             380 ttc agc agg agc gca gac gcc ccc gcg tac cag cag ggc cag aac cag     1200
Phe Ser Arg Ser Ala Asp Ala Pro Ala Tyr Gln Gln Gly Gln Asn Gln
385             390             395             400 ctc tat aac gag ctc aat cta gga cga aga gag gag tac gat gtt ttg     1248
Leu Tyr Asn Glu Leu Asn Leu Gly Arg Arg Glu Glu Tyr Asp Val Leu
                405             410             415 gac aag aga cgt ggc cgg gac cct gag atg ggg gga aag ccg aga agg     1296
Asp Lys Arg Arg Gly Arg Asp Pro Glu Met Gly Gly Lys Pro Arg Arg
            420             425             430 aag aac cct cag gaa ggc ctg tac aat gaa ctg cag aaa gat aag atg     1344
Lys Asn Pro Gln Glu Gly Leu Tyr Asn Glu Leu Gln Lys Asp Lys Met
        435             440             445 gcg gag gcc tac agt gag att ggg atg aaa ggc gag cgc cgg agg ggc     1392
Ala Glu Ala Tyr Ser Glu Ile Gly Met Lys Gly Glu Arg Arg Arg Gly
    450             455             460 aag ggg cac gat ggc ctt tac cag ggt ctc agt aca gcc acc aag gac     1440
Lys Gly His Asp Gly Leu Tyr Gln Gly Leu Ser Thr Ala Thr Lys Asp
465             470             475             480
```

```
acc tac gac gcc ctt cac atg cag gcc ctg ccc cct cgc taa          1482
Thr Tyr Asp Ala Leu His Met Gln Ala Leu Pro Pro Arg
                485                 490
```

<210> SEQ ID NO 15
<211> LENGTH: 493
<212> TYPE: PRT
<213> ORGANISM: Artificial Sequence
<220> FEATURE:
<223> OTHER INFORMATION: Synthetic Construct

<400> SEQUENCE: 15

```
Met Ala Leu Pro Val Thr Ala Leu Leu Pro Leu Ala Leu Leu Leu
1               5                  10                  15

His Ala Ala Arg Pro Glu Val Gln Leu Gln Gln Ser Gly Gly Glu Arg
                20                  25                  30

Ala Thr Pro Gly Ala Ser Val Lys Met Ser Cys Lys Thr Ser Gly Tyr
                35                  40                  45

Thr Phe Thr Asn Tyr Trp Met His Trp Val Lys Gln Arg Pro Gly Gln
    50                  55                  60

Gly Leu Glu Trp Ile Gly Tyr Ile Asn Pro Ser Ser Gly Tyr Thr Gln
65                  70                  75                  80

Tyr Asn Gln Lys Phe Lys Asp Lys Ala Thr Leu Thr Ala Asp Lys Ser
                85                  90                  95

Ser Ser Thr Ala Tyr Ile Gln Leu Ser Ser Leu Thr Ser Glu Asp Ser
                100                 105                 110

Ala Val Tyr Tyr Cys Ser Thr Tyr Tyr Gly Asp Tyr Leu Phe Pro Tyr
                115                 120                 125

Trp Gly Gln Gly Thr Leu Val Thr Val Ser Ala Gly Gly Gly Gly Ser
            130                 135                 140

Gly Gly Gly Gly Ser Gly Gly Gly Ser Asp Val Leu Met Thr Gln
145                 150                 155                 160

Thr Pro Leu Ser Leu Pro Val Ser Leu Gly Asp Gln Ala Ser Ile Ser
                165                 170                 175

Cys Arg Ser Ser Gln Asp Ile Val Tyr Gly Asn Gly Asn Thr Tyr Leu
            180                 185                 190

Glu Trp Tyr Leu Gln Lys Pro Gly Gln Ser Pro Lys Leu Leu Ile Tyr
        195                 200                 205

Lys Val Ser Asn Arg Phe Ser Gly Val Pro Asp Arg Phe Ser Gly Ser
            210                 215                 220

Gly Ser Gly Thr Asp Phe Thr Leu Lys Ile Ser Arg Val Glu Ala Glu
225                 230                 235                 240

Asp Leu Gly Val Tyr Tyr Cys Phe Gln Gly Ser His Val Pro Tyr Thr
                245                 250                 255

Phe Gly Gly Gly Thr Lys Leu Glu Ile Lys Arg Ala Ala Ala Ile Glu
            260                 265                 270

Val Glu Gln Lys Leu Ile Ser Glu Glu Asp Leu Leu Asp Asn Glu Lys
        275                 280                 285

Ser Asn Gly Thr Ile Ile His Val Lys Gly Lys His Leu Cys Pro Ser
    290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
```

```
                    340                 345                 350
Met Asn Met Thr Pro Arg Arg Pro Gly Pro Thr Arg Lys His Tyr Gln
                355                 360                 365

Pro Tyr Ala Pro Pro Arg Asp Phe Ala Ala Tyr Arg Ser Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 16
<211> LENGTH: 1464
<212> TYPE: DNA
<213> ORGANISM: Artificial Sequence
<220> FEATURE:
<223> OTHER INFORMATION: Artificially synthesized mouse CAR open reading
      frame
<220> FEATURE:
<221> NAME/KEY: CDS
<222> LOCATION: (1)..(1464)

<400> SEQUENCE: 16 atg gcc ctg ccc gtg acc gcc ctg ctc ttg ccc ctg gcc ctt ctg ctc      48
Met Ala Leu Pro Val Thr Ala Leu Leu Leu Pro Leu Ala Leu Leu Leu
1               5                   10                  15 cac gcc gcc aga ccc gag gtg cag ctg cag cag agc gga ggc gag aga      96
His Ala Ala Arg Pro Glu Val Gln Leu Gln Gln Ser Gly Gly Glu Arg
                20                  25                  30 gcc acc cct ggc gcc agc gtg aag atg agc tgc aag acc agc ggc tac     144
Ala Thr Pro Gly Ala Ser Val Lys Met Ser Cys Lys Thr Ser Gly Tyr
            35                  40                  45 acc ttc acc aac tac tgg atg cac tgg gtg aag cag aga ccc ggc cag     192
Thr Phe Thr Asn Tyr Trp Met His Trp Val Lys Gln Arg Pro Gly Gln
        50                  55                  60 ggc ctg gag tgg atc ggc tac atc aac cct agc tcc ggc tac acc cag     240
Gly Leu Glu Trp Ile Gly Tyr Ile Asn Pro Ser Ser Gly Tyr Thr Gln
65                  70                  75                  80 tac aac cag aag ttc aag gac aag gcc acc ctg acc gcc gac aag agc     288
Tyr Asn Gln Lys Phe Lys Asp Lys Ala Thr Leu Thr Ala Asp Lys Ser
                85                  90                  95 tcc agc acc gcc tac atc cag ctg agc tcc ctg acc agc gag gac tcc     336
Ser Ser Thr Ala Tyr Ile Gln Leu Ser Ser Leu Thr Ser Glu Asp Ser
            100                 105                 110 gcc gtg tac tat tgc agc acc tac tac ggc gac tac ctg ttc ccc tac     384
Ala Val Tyr Tyr Cys Ser Thr Tyr Tyr Gly Asp Tyr Leu Phe Pro Tyr
        115                 120                 125 tgg ggc cag ggc acc ctg gtg acc gtg agc gcc ggc gga ggc gga agc     432
Trp Gly Gln Gly Thr Leu Val Thr Val Ser Ala Gly Gly Gly Gly Ser
    130                 135                 140
```

| | | |
|---|---|---|
| gga ggc ggc gga tcc gga gga ggc ggc agc gac gtg ctg atg acc cag<br>Gly Gly Gly Gly Ser Gly Gly Gly Gly Ser Asp Val Leu Met Thr Gln<br>145                      150                    155                  160 | 480 |
| acc cct ctg agc ctg ccc gtg agc ctg ggc gac cag gcc agc atc agc<br>Thr Pro Leu Ser Leu Pro Val Ser Leu Gly Asp Gln Ala Ser Ile Ser<br>                  165                    170                    175 | 528 |
| tgc aga agc tcc cag gac atc gtg tac ggc aac ggc aac acc tac ctg<br>Cys Arg Ser Ser Gln Asp Ile Val Tyr Gly Asn Gly Asn Thr Tyr Leu<br>                  180                    185                    190 | 576 |
| gag tgg tac ctc cag aag ccc ggc cag agc ccc aag ctg ctg atc tac<br>Glu Trp Tyr Leu Gln Lys Pro Gly Gln Ser Pro Lys Leu Leu Ile Tyr<br>      195                    200                    205 | 624 |
| aag gtg agc aac aga ttc agc ggc gtg ccc gac aga ttc agc ggc tcc<br>Lys Val Ser Asn Arg Phe Ser Gly Val Pro Asp Arg Phe Ser Gly Ser<br>210                      215                    220 | 672 |
| gga agc gga acc gac ttc acc ctg aag atc agc aga gtg gag gcc gag<br>Gly Ser Gly Thr Asp Phe Thr Leu Lys Ile Ser Arg Val Glu Ala Glu<br>225                      230                    235                  240 | 720 |
| gac ctg ggc gtg tac tat tgc ttc cag ggc agc cac gtg ccc tac acc<br>Asp Leu Gly Val Tyr Tyr Cys Phe Gln Gly Ser His Val Pro Tyr Thr<br>                    245                    250                    255 | 768 |
| ttc ggc gga ggc acc aag ctg gag atc aag aga gcg gcc gcc atc gag<br>Phe Gly Gly Gly Thr Lys Leu Glu Ile Lys Arg Ala Ala Ala Ile Glu<br>                  260                    265                    270 | 816 |
| ttc atg tac ccc ccc ccc tac ctg gac aac gag agg agc aac ggc acc<br>Phe Met Tyr Pro Pro Pro Tyr Leu Asp Asn Glu Arg Ser Asn Gly Thr<br>      275                    280                    285 | 864 |
| atc atc cac atc aag gag aag cac ctg tgc cac acc cag agc agc ccc<br>Ile Ile His Ile Lys Glu Lys His Leu Cys His Thr Gln Ser Ser Pro<br>290                      295                    300 | 912 |
| aag ctg ttc tgg gcc ctg gtg gtg gtg gcc ggc gtg ctg ttc tgc tac<br>Lys Leu Phe Trp Ala Leu Val Val Val Ala Gly Val Leu Phe Cys Tyr<br>305                      310                    315                  320 | 960 |
| ggc ctg ctg gtg acc gtg gcc ctg tgc gtg atc tgg acc aac agc agg<br>Gly Leu Leu Val Thr Val Ala Leu Cys Val Ile Trp Thr Asn Ser Arg<br>                  325                    330                    335 | 1008 |
| agg aac agg ctg ctg cag agc gac tac atg aac atg acc ccc agg agg<br>Arg Asn Arg Leu Leu Gln Ser Asp Tyr Met Asn Met Thr Pro Arg Arg<br>                  340                    345                    350 | 1056 |
| ccc ggc ctg acc agg aag ccc tac cag ccc tac gcc ccc gcc agg gac<br>Pro Gly Leu Thr Arg Lys Pro Tyr Gln Pro Tyr Ala Pro Ala Arg Asp<br>      355                    360                    365 | 1104 |
| ttc gcc gcc tac agg ccc agg gcc aag ttc agc agg agc gcc gag acc<br>Phe Ala Ala Tyr Arg Pro Arg Ala Lys Phe Ser Arg Ser Ala Glu Thr<br>370                      375                    380 | 1152 |
| gcc gcc aac ctg cag gac ccc aac cag ctg tac aac gag ctg aac ctg<br>Ala Ala Asn Leu Gln Asp Pro Asn Gln Leu Tyr Asn Glu Leu Asn Leu<br>385                      390                    395                  400 | 1200 |
| ggc agg agg gag gag tac gac gtg ctg gag aag aag agg gcc agg gac<br>Gly Arg Arg Glu Glu Tyr Asp Val Leu Glu Lys Lys Arg Ala Arg Asp<br>                  405                    410                    415 | 1248 |
| ccc gag atg ggc ggc aag cag cag agg agg agg aac ccc cag gag ggc<br>Pro Glu Met Gly Gly Lys Gln Gln Arg Arg Arg Asn Pro Gln Glu Gly<br>                  420                    425                    430 | 1296 |
| gtg tac aac gcc ctg cag aag gac aag atg gcc gag gcc tac agc gag<br>Val Tyr Asn Ala Leu Gln Lys Asp Lys Met Ala Glu Ala Tyr Ser Glu<br>                    435                    440                    445 | 1344 |
| atc ggc acc aag ggc gag agg agg agg ggc aag ggc cac gac ggc ctg<br>Ile Gly Thr Lys Gly Glu Arg Arg Arg Gly Lys Gly His Asp Gly Leu<br>450                      455                    460 | 1392 |

```
tac cag ggc ctg agc acc gcc acc aag gac acc tac gac gcc ctg cac      1440
Tyr Gln Gly Leu Ser Thr Ala Thr Lys Asp Thr Tyr Asp Ala Leu His
465                 470                 475                 480 atg cag acc ctg gcc ccc agg tga                                       1464
Met Gln Thr Leu Ala Pro Arg
                485
```

<210> SEQ ID NO 17
<211> LENGTH: 487
<212> TYPE: PRT
<213> ORGANISM: Artificial Sequence
<220> FEATURE:
<223> OTHER INFORMATION: Synthetic Construct

<400> SEQUENCE: 17

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Gly Glu Arg
            20                  25                  30

Ala Thr Pro Gly Ala Ser Val Lys Met Ser Cys Lys Thr Ser Gly Tyr
        35                  40                  45

Thr Phe Thr Asn Tyr Trp Met His Trp Val Lys Gln Arg Pro Gly Gln
    50                  55                  60

Gly Leu Glu Trp Ile Gly Tyr Ile Asn Pro Ser Ser Gly Tyr Thr Gln
65                  70                  75                  80

Tyr Asn Gln Lys Phe Lys Asp Lys Ala Thr Leu Thr Ala Asp Lys Ser
                85                  90                  95

Ser Ser Thr Ala Tyr Ile Gln Leu Ser Ser Leu Thr Ser Glu Asp Ser
            100                 105                 110

Ala Val Tyr Tyr Cys Ser Thr Tyr Tyr Gly Asp Tyr Leu Phe Pro Tyr
        115                 120                 125

Trp Gly Gln Gly Thr Leu Val Thr Val Ser Ala Gly Gly Gly Gly Ser
    130                 135                 140

Gly Gly Gly Gly Ser Gly Gly Gly Ser Asp Val Leu Met Thr Gln
145                 150                 155                 160

Thr Pro Leu Ser Leu Pro Val Ser Leu Gly Asp Gln Ala Ser Ile Ser
                165                 170                 175

Cys Arg Ser Ser Gln Asp Ile Val Tyr Gly Asn Gly Asn Thr Tyr Leu
            180                 185                 190

Glu Trp Tyr Leu Gln Lys Pro Gly Gln Ser Pro Lys Leu Leu Ile Tyr
        195                 200                 205

Lys Val Ser Asn Arg Phe Ser Gly Val Pro Asp Arg Phe Ser Gly Ser
    210                 215                 220

Gly Ser Gly Thr Asp Phe Thr Leu Lys Ile Ser Arg Val Glu Ala Glu
225                 230                 235                 240

Asp Leu Gly Val Tyr Tyr Cys Phe Gln Gly Ser His Val Pro Tyr Thr
                245                 250                 255

Phe Gly Gly Gly Thr Lys Leu Glu Ile Lys Arg Ala Ala Ala Ile Glu
            260                 265                 270

Phe Met Tyr Pro Pro Pro Tyr Leu Asp Asn Glu Arg Ser Asn Gly Thr
        275                 280                 285

Ile Ile His Ile Lys Glu Lys His Leu Cys His Thr Gln Ser Ser Pro
    290                 295                 300

Lys Leu Phe Trp Ala Leu Val Val Val Ala Gly Val Leu Phe Cys Tyr
305                 310                 315                 320
```

Gly Leu Leu Val Thr Val Ala Leu Cys Val Ile Trp Thr Asn Ser Arg
            325                 330                 335

Arg Asn Arg Leu Leu Gln Ser Asp Tyr Met Asn Met Thr Pro Arg Arg
        340                 345                 350

Pro Gly Leu Thr Arg Lys Pro Tyr Gln Pro Tyr Ala Pro Ala Arg Asp
    355                 360                 365

Phe Ala Ala Tyr Arg Pro Arg Ala Lys Phe Ser Arg Ser Ala Glu Thr
370                 375                 380

Ala Ala Asn Leu Gln Asp Pro Asn Gln Leu Tyr Asn Glu Leu Asn Leu
385                 390                 395                 400

Gly Arg Arg Glu Glu Tyr Asp Val Leu Glu Lys Lys Arg Ala Arg Asp
                405                 410                 415

Pro Glu Met Gly Gly Lys Gln Gln Arg Arg Arg Asn Pro Gln Glu Gly
            420                 425                 430

Val Tyr Asn Ala Leu Gln Lys Asp Lys Met Ala Glu Ala Tyr Ser Glu
        435                 440                 445

Ile Gly Thr Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Thr Leu Ala Pro Arg
            485

<210> SEQ ID NO 18
<211> LENGTH: 21
<212> TYPE: PRT
<213> ORGANISM: Homo sapiens

<400> SEQUENCE: 18

Met Ala Leu Pro Val Thr Ala Leu Leu Leu Pro Leu Ala Leu Leu Leu
1               5                   10                  15

His Ala Ala Arg Pro
            20

<210> SEQ ID NO 19
<211> LENGTH: 15
<212> TYPE: PRT
<213> ORGANISM: Artificial Sequence
<220> FEATURE:
<223> OTHER INFORMATION: Artifically synthesized peptide linker

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 98
<212> TYPE: PRT
<213> ORGANISM: Homo sapiens

<400> SEQUENCE: 20

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro Phe Trp
            20                  25                  30

Val Leu Val Val Val Gly Gly Val Leu Ala Cys Tyr Ser Leu Leu Val
        35                  40                  45

Thr Val Ala Phe Ile Ile Phe Trp Val Arg Ser Lys Arg Ser Arg Leu
    50                  55                  60

```
Leu His Ser Asp Tyr Met Asn Met Thr Pro Arg Pro Gly Pro Thr
 65                  70                  75                  80

Arg Lys His Tyr Gln Pro Tyr Ala Pro Pro Arg Asp Phe Ala Ala Tyr
                 85                  90                  95

Arg Ser

<210> SEQ ID NO 21
<211> LENGTH: 27
<212> TYPE: PRT
<213> ORGANISM: Homo sapiens

<400> SEQUENCE: 21

Phe Trp Val Leu Val Val Gly Val Leu Ala Cys Tyr Ser Leu
 1               5                  10                  15

Leu Val Thr Val Ala Phe Ile Ile Phe Trp Val
                20                  25

<210> SEQ ID NO 22
<211> LENGTH: 95
<212> TYPE: PRT
<213> ORGANISM: Mus musculus

<400> SEQUENCE: 22

Leu Asp Asn Glu Arg Ser Asn Gly Thr Ile Ile His Ile Lys Glu Lys
 1               5                  10                  15

His Leu Cys His Thr Gln Ser Ser Pro Lys Leu Phe Trp Ala Leu Val
                20                  25                  30

Val Val Ala Gly Val Leu Phe Cys Tyr Gly Leu Leu Val Thr Val Ala
             35                  40                  45

Leu Cys Val Ile Trp Thr Asn Ser Arg Arg Asn Arg Leu Leu Gln Ser
     50                  55                  60

Asp Tyr Met Asn Met Thr Pro Arg Arg Pro Gly Leu Thr Arg Lys Pro
 65                  70                  75                  80

Tyr Gln Pro Tyr Ala Pro Ala Arg Asp Phe Ala Ala Tyr Arg Pro
                 85                  90                  95

<210> SEQ ID NO 23
<211> LENGTH: 27
<212> TYPE: PRT
<213> ORGANISM: Mus musculus

<400> SEQUENCE: 23

Phe Trp Ala Leu Val Val Val Ala Gly Val Leu Phe Cys Tyr Gly Leu
 1               5                  10                  15

Leu Val Thr Val Ala Leu Cys Val Ile Trp Thr
                20                  25

<210> SEQ ID NO 24
<211> LENGTH: 112
<212> TYPE: PRT
<213> ORGANISM: Homo sapiens

<400> SEQUENCE: 24

Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
             35                  40                  45
```

```
Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 113
<212> TYPE: PRT
<213> ORGANISM: Mus musculus

<400> SEQUENCE: 25

Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
            20                  25                  30

Asp Val Leu Glu Lys Lys Arg Ala Arg Asp Pro Glu Met Gly Gly Lys
        35                  40                  45

Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Thr Leu Ala Pro
            100                 105                 110

Arg

<210> SEQ ID NO 26
<211> LENGTH: 58
<212> TYPE: PRT
<213> ORGANISM: Homo sapiens

<400> SEQUENCE: 26

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
    50                  55

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 27
aggactccgc cgtgtactat                                              20

<210> SEQ ID NO 28
<211> LENGTH: 20
```

```
<212> TYPE: DNA
<213> ORGANISM: Artificial Sequence
<220> FEATURE:
<223> OTHER INFORMATION: Artificially synthesized oligonucleotide primer

<400> SEQUENCE: 28
tacacgatgt cctgggagct                                                    20

<210> SEQ ID NO 29
<211> LENGTH: 2217
<212> TYPE: DNA
<213> ORGANISM: Artificial Sequence
<220> FEATURE:
<223> OTHER INFORMATION: Artificially constructed CAR expression
      cassette
<220> FEATURE:
<221> NAME/KEY: CDS
<222> LOCATION: (1)..(2217)

<400> SEQUENCE: 29
```

| | | | | | | | | | | | | | | | | |
|---|---|---|---|---|---|---|---|---|---|---|---|---|---|---|---|---|
| atg | gcc | ctg | ccc | gtg | acc | gcc | ctg | ctc | ttg | ccc | ctg | gcc | ctt | ctg | ctc | 48 |
| Met | Ala | Leu | Pro | Val | Thr | Ala | Leu | Leu | Leu | Pro | Leu | Ala | Leu | Leu | Leu | |
| 1 | | | | 5 | | | | | 10 | | | | | 15 | | |
| cac | gcc | gcc | aga | ccc | gag | gtg | cag | ctg | cag | cag | agc | gga | ggc | gag | aga | 96 |
| His | Ala | Ala | Arg | Pro | Glu | Val | Gln | Leu | Gln | Gln | Ser | Gly | Gly | Glu | Arg | |
| | | 20 | | | | | 25 | | | | | 30 | | | | |
| gcc | acc | cct | ggc | gcc | agc | gtg | aag | atg | agc | tgc | aag | acc | agc | ggc | tac | 144 |
| Ala | Thr | Pro | Gly | Ala | Ser | Val | Lys | Met | Ser | Cys | Lys | Thr | Ser | Gly | Tyr | |
| | 35 | | | | | 40 | | | | | 45 | | | | | |
| acc | ttc | acc | aac | tac | tgg | atg | cac | tgg | gtg | aag | cag | aga | ccc | ggc | cag | 192 |
| Thr | Phe | Thr | Asn | Tyr | Trp | Met | His | Trp | Val | Lys | Gln | Arg | Pro | Gly | Gln | |
| 50 | | | | | 55 | | | | | 60 | | | | | | |
| ggc | ctg | gag | tgg | atc | ggc | tac | atc | aac | cct | agc | tcc | ggc | tac | acc | cag | 240 |
| Gly | Leu | Glu | Trp | Ile | Gly | Tyr | Ile | Asn | Pro | Ser | Ser | Gly | Tyr | Thr | Gln | |
| 65 | | | | 70 | | | | | 75 | | | | | 80 | | |
| tac | aac | cag | aag | ttc | aag | gac | aag | gcc | acc | ctg | acc | gcc | gac | aag | agc | 288 |
| Tyr | Asn | Gln | Lys | Phe | Lys | Asp | Lys | Ala | Thr | Leu | Thr | Ala | Asp | Lys | Ser | |
| | | | 85 | | | | | 90 | | | | | 95 | | | |
| tcc | agc | acc | gcc | tac | atc | cag | ctg | agc | tcc | ctg | acc | agc | gag | gac | tcc | 336 |
| Ser | Ser | Thr | Ala | Tyr | Ile | Gln | Leu | Ser | Ser | Leu | Thr | Ser | Glu | Asp | Ser | |
| | | | 100 | | | | | 105 | | | | | 110 | | | |
| gcc | gtg | tac | tat | tgc | agc | acc | tac | tac | ggc | gac | tac | ctg | ttc | ccc | tac | 384 |
| Ala | Val | Tyr | Tyr | Cys | Ser | Thr | Tyr | Tyr | Gly | Asp | Tyr | Leu | Phe | Pro | Tyr | |
| | | 115 | | | | | 120 | | | | | 125 | | | | |
| tgg | ggc | cag | ggc | acc | ctg | gtg | acc | gtg | agc | gcc | gga | gga | ggc | gga | agc | 432 |
| Trp | Gly | Gln | Gly | Thr | Leu | Val | Thr | Val | Ser | Ala | Gly | Gly | Gly | Gly | Ser | |
| | 130 | | | | | 135 | | | | | 140 | | | | | |
| gga | ggc | ggc | gga | tcc | gga | gga | ggc | ggc | agc | gac | gtg | ctg | atg | acc | cag | 480 |
| Gly | Gly | Gly | Gly | Ser | Gly | Gly | Gly | Gly | Ser | Asp | Val | Leu | Met | Thr | Gln | |
| 145 | | | | | 150 | | | | | 155 | | | | | 160 | |
| acc | cct | ctg | agc | ctg | ccc | gtg | agc | ctg | ggc | gac | cag | gcc | agc | atc | agc | 528 |
| Thr | Pro | Leu | Ser | Leu | Pro | Val | Ser | Leu | Gly | Asp | Gln | Ala | Ser | Ile | Ser | |
| | | | | 165 | | | | | 170 | | | | | 175 | | |
| tgc | aga | agc | tcc | cag | gac | atc | gtg | tac | ggc | aac | gga | aac | acc | tac | ctg | 576 |
| Cys | Arg | Ser | Ser | Gln | Asp | Ile | Val | Tyr | Gly | Asn | Gly | Asn | Thr | Tyr | Leu | |
| | | | 180 | | | | | 185 | | | | | 190 | | | |
| gag | tgg | tac | ctc | cag | aag | ccc | ggc | cag | agc | ccc | aag | ctg | ctg | atc | tac | 624 |
| Glu | Trp | Tyr | Leu | Gln | Lys | Pro | Gly | Gln | Ser | Pro | Lys | Leu | Leu | Ile | Tyr | |
| | | 195 | | | | | 200 | | | | | 205 | | | | |
| aag | gtg | agc | aac | aga | ttc | agc | ggc | gtg | ccc | gac | aga | ttc | agc | ggc | tcc | 672 |
| Lys | Val | Ser | Asn | Arg | Phe | Ser | Gly | Val | Pro | Asp | Arg | Phe | Ser | Gly | Ser | |
| | 210 | | | | | 215 | | | | | 220 | | | | | |

```
gga agc gga acc gac ttc acc ctg aag atc agc aga gtg gag gcc gag      720
Gly Ser Gly Thr Asp Phe Thr Leu Lys Ile Ser Arg Val Glu Ala Glu
225                 230                 235                 240 gac ctg ggc gtg tac tat tgc ttc cag ggc agc cac gtg ccc tac acc      768
Asp Leu Gly Val Tyr Tyr Cys Phe Gln Gly Ser His Val Pro Tyr Thr
                245                 250                 255 ttc ggc gga ggc acc aag ctg gag atc aag aga gcg gcc gct atc gag      816
Phe Gly Gly Gly Thr Lys Leu Glu Ile Lys Arg Ala Ala Ala Ile Glu
                260                 265                 270 gtg gag cag aag ctg atc agc gag gag gac ctg cta gac aat gag aag      864
Val Glu Gln Lys Leu Ile Ser Glu Glu Asp Leu Leu Asp Asn Glu Lys
                275                 280                 285 agc aat gga acc att atc cat gtg aaa ggg aaa cac ctt tgt cca agt      912
Ser Asn Gly Thr Ile Ile His Val Lys Gly Lys His Leu Cys Pro Ser
290                 295                 300 ccc cta ttt ccc gga cct tct aag ccc ttt tgg gtg ctg gtg gtg gtt      960
Pro Leu Phe Pro Gly Pro Ser Lys Pro Phe Trp Val Leu Val Val Val
305                 310                 315                 320 ggt gga gtc ctg gct tgc tat agc ttg cta gta aca gtg gcc ttt att     1008
Gly Gly Val Leu Ala Cys Tyr Ser Leu Leu Val Thr Val Ala Phe Ile
                325                 330                 335 att ttc tgg gtg agg agt aag agg agc agg ctc ctg cac agt gac tac     1056
Ile Phe Trp Val Arg Ser Lys Arg Ser Arg Leu Leu His Ser Asp Tyr
                340                 345                 350 atg aac atg act ccc cgc cgc ccc ggg ccc acc cgc aag cat tac cag     1104
Met Asn Met Thr Pro Arg Arg Pro Gly Pro Thr Arg Lys His Tyr Gln
                355                 360                 365 ccc tat gcc cca cca cgc gac ttc gca gcc tat cgc tcc aga gtg aag     1152
Pro Tyr Ala Pro Pro Arg Asp Phe Ala Ala Tyr Arg Ser Arg Val Lys
370                 375                 380 ttc agc agg agc gca gac gcc ccc gcg tac cag cag ggc cag aac cag     1200
Phe Ser Arg Ser Ala Asp Ala Pro Ala Tyr Gln Gln Gly Gln Asn Gln
385                 390                 395                 400 ctc tat aac gag ctc aat cta gga cga aga gag gag tac gat gtt ttg     1248
Leu Tyr Asn Glu Leu Asn Leu Gly Arg Arg Glu Glu Tyr Asp Val Leu
                405                 410                 415 gac aag aga cgt ggc cgg gac cct gag atg ggg gga aag ccg aga agg     1296
Asp Lys Arg Arg Gly Arg Asp Pro Glu Met Gly Gly Lys Pro Arg Arg
                420                 425                 430 aag aac cct cag gaa ggc ctg tac aat gaa ctg cag aaa gat aag atg     1344
Lys Asn Pro Gln Glu Gly Leu Tyr Asn Glu Leu Gln Lys Asp Lys Met
                435                 440                 445 gcg gag gcc tac agt gag att ggg atg aaa ggc gag cgc cgg agg ggc     1392
Ala Glu Ala Tyr Ser Glu Ile Gly Met Lys Gly Glu Arg Arg Arg Gly
450                 455                 460 aag ggg cac gat ggc ctt tac cag ggt ctc agt aca gcc acc aag gac     1440
Lys Gly His Asp Gly Leu Tyr Gln Gly Leu Ser Thr Ala Thr Lys Asp
465                 470                 475                 480 acc tac gac gcc ctt cac atg cag gcc ctg ccc cct cgc gcc cga ggc     1488
Thr Tyr Asp Ala Leu His Met Gln Ala Leu Pro Pro Arg Ala Arg Gly
                485                 490                 495 gca gca gcg gga gca gga gca ggt cga atg gtg agc gag ctg att     1536
Ala Ala Ala Gly Ala Gly Ala Gly Arg Met Val Ser Glu Leu Ile
                500                 505                 510 aag gag aac atg cac atg aag ctg tac atg gag ggc acc gtg aac aac     1584
Lys Glu Asn Met His Met Lys Leu Tyr Met Glu Gly Thr Val Asn Asn
                515                 520                 525 cac cac ttc aag tgc aca tcc gag ggc gaa ggc aag ccc tac gag ggc     1632
His His Phe Lys Cys Thr Ser Glu Gly Glu Gly Lys Pro Tyr Glu Gly
                530                 535                 540
```

```
acc cag acc atg aga atc aag gcg gtc gag ggc ggc cct ctc ccc ttc     1680
Thr Gln Thr Met Arg Ile Lys Ala Val Glu Gly Gly Pro Leu Pro Phe
545                 550                 555                 560 gcc ttc gac atc ctg gct acc agc ttc atg tac ggc agc aaa acc ttc     1728
Ala Phe Asp Ile Leu Ala Thr Ser Phe Met Tyr Gly Ser Lys Thr Phe
                565                 570                 575 atc aac cac acc cag ggc atc ccc gac ttc ttt aag cag tcc ttc ccc     1776
Ile Asn His Thr Gln Gly Ile Pro Asp Phe Phe Lys Gln Ser Phe Pro
            580                 585                 590 gag ggc ttc aca tgg gag aga gtc acc aca tac gaa gac ggg ggc gtg     1824
Glu Gly Phe Thr Trp Glu Arg Val Thr Thr Tyr Glu Asp Gly Gly Val
        595                 600                 605 ctg acc gct acc cag gac acc agc ctc cag gac ggc tgc ctc atc tac     1872
Leu Thr Ala Thr Gln Asp Thr Ser Leu Gln Asp Gly Cys Leu Ile Tyr
    610                 615                 620 aac gtc aag atc aga ggg gtg aac ttc cca tcc aac ggc cct gtg atg     1920
Asn Val Lys Ile Arg Gly Val Asn Phe Pro Ser Asn Gly Pro Val Met
625                 630                 635                 640 cag aag aaa aca ctc ggc tgg gag gcc tcc acc gag acc ctg tac ccc     1968
Gln Lys Lys Thr Leu Gly Trp Glu Ala Ser Thr Glu Thr Leu Tyr Pro
                645                 650                 655 gct gac ggc ggc ctg gaa ggc aga gcc gac atg gcc ctg aag ctc gtg     2016
Ala Asp Gly Gly Leu Glu Gly Arg Ala Asp Met Ala Leu Lys Leu Val
            660                 665                 670 ggc ggg ggc cac ctg atc tgc aac ttg aag acc aca tac aga tcc aag     2064
Gly Gly Gly His Leu Ile Cys Asn Leu Lys Thr Thr Tyr Arg Ser Lys
        675                 680                 685 aaa ccc gct aag aac ctc aag atg ccc ggc gtc tac tat gtg gac aga     2112
Lys Pro Ala Lys Asn Leu Lys Met Pro Gly Val Tyr Tyr Val Asp Arg
    690                 695                 700 aga ctg gaa aga atc aag gag gcc gac aaa gag acc tac gtc gag cag     2160
Arg Leu Glu Arg Ile Lys Glu Ala Asp Lys Glu Thr Tyr Val Glu Gln
705                 710                 715                 720 cac gag gtg gct gtg gcc aga tac tgc gac ctc cct agc aaa ctg ggg     2208
His Glu Val Ala Val Ala Arg Tyr Cys Asp Leu Pro Ser Lys Leu Gly
                725                 730                 735 cac aga tga                                                         2217
His Arg <210> SEQ ID NO 30
<211> LENGTH: 738
<212> TYPE: PRT
<213> ORGANISM: Artificial Sequence
<220> FEATURE:
<223> OTHER INFORMATION: Synthetic Construct

<400> SEQUENCE: 30

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Gly Glu Arg
                20                  25                  30

Ala Thr Pro Gly Ala Ser Val Lys Met Ser Cys Lys Thr Ser Gly Tyr
            35                  40                  45

Thr Phe Thr Asn Tyr Trp Met His Trp Val Lys Gln Arg Pro Gly Gln
        50                  55                  60

Gly Leu Glu Trp Ile Gly Tyr Ile Asn Pro Ser Ser Gly Tyr Thr Gln
65                  70                  75                  80

Tyr Asn Gln Lys Phe Lys Asp Lys Ala Thr Leu Thr Ala Asp Lys Ser
                85                  90                  95
```

```
Ser Ser Thr Ala Tyr Ile Gln Leu Ser Ser Leu Thr Ser Glu Asp Ser
            100                 105                 110

Ala Val Tyr Tyr Cys Ser Thr Tyr Gly Asp Tyr Leu Phe Pro Tyr
            115                 120                 125

Trp Gly Gln Gly Thr Leu Val Thr Val Ser Ala Gly Gly Gly Ser
        130                 135                 140

Gly Gly Gly Gly Ser Gly Gly Gly Ser Asp Val Leu Met Thr Gln
145                 150                 155                 160

Thr Pro Leu Ser Leu Pro Val Ser Leu Gly Asp Gln Ala Ser Ile Ser
                165                 170                 175

Cys Arg Ser Ser Gln Asp Ile Val Tyr Gly Asn Gly Asn Thr Tyr Leu
            180                 185                 190

Glu Trp Tyr Leu Gln Lys Pro Gly Gln Ser Pro Lys Leu Leu Ile Tyr
            195                 200                 205

Lys Val Ser Asn Arg Phe Ser Gly Val Pro Asp Arg Phe Ser Gly Ser
210                 215                 220

Gly Ser Gly Thr Asp Phe Thr Leu Lys Ile Ser Arg Val Glu Ala Glu
225                 230                 235                 240

Asp Leu Gly Val Tyr Tyr Cys Phe Gln Gly Ser His Val Pro Tyr Thr
                245                 250                 255

Phe Gly Gly Gly Thr Lys Leu Glu Ile Lys Arg Ala Ala Ala Ile Glu
            260                 265                 270

Val Glu Gln Lys Leu Ile Ser Glu Glu Asp Leu Leu Asp Asn Glu Lys
            275                 280                 285

Ser Asn Gly Thr Ile Ile His Val Lys Gly Lys His Leu Cys Pro Ser
            290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
            355                 360                 365

Pro Tyr Ala Pro Pro Arg Asp Phe Ala Ala Tyr Arg Ser Arg Val Lys
370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Ala Arg Gly
                485                 490                 495

Ala Ala Ala Gly Ala Gly Gly Ala Gly Arg Met Val Ser Glu Leu Ile
            500                 505                 510
```

```
Lys Glu Asn Met His Met Lys Leu Tyr Met Glu Gly Thr Val Asn Asn
            515                 520                 525

His His Phe Lys Cys Thr Ser Glu Gly Glu Gly Lys Pro Tyr Glu Gly
        530                 535                 540

Thr Gln Thr Met Arg Ile Lys Ala Val Glu Gly Gly Pro Leu Pro Phe
545                 550                 555                 560

Ala Phe Asp Ile Leu Ala Thr Ser Phe Met Tyr Gly Ser Lys Thr Phe
                565                 570                 575

Ile Asn His Thr Gln Gly Ile Pro Asp Phe Phe Lys Gln Ser Phe Pro
            580                 585                 590

Glu Gly Phe Thr Trp Glu Arg Val Thr Thr Tyr Glu Asp Gly Gly Val
        595                 600                 605

Leu Thr Ala Thr Gln Asp Thr Ser Leu Gln Asp Gly Cys Leu Ile Tyr
610                 615                 620

Asn Val Lys Ile Arg Gly Val Asn Phe Pro Ser Asn Gly Pro Val Met
625                 630                 635                 640

Gln Lys Lys Thr Leu Gly Trp Glu Ala Ser Thr Glu Thr Leu Tyr Pro
                645                 650                 655

Ala Asp Gly Gly Leu Glu Gly Arg Ala Asp Met Ala Leu Lys Leu Val
            660                 665                 670

Gly Gly Gly His Leu Ile Cys Asn Leu Lys Thr Thr Tyr Arg Ser Lys
        675                 680                 685

Lys Pro Ala Lys Asn Leu Lys Met Pro Gly Val Tyr Tyr Val Asp Arg
690                 695                 700

Arg Leu Glu Arg Ile Lys Glu Ala Asp Lys Glu Thr Tyr Val Glu Gln
705                 710                 715                 720

His Glu Val Ala Val Ala Arg Tyr Cys Asp Leu Pro Ser Lys Leu Gly
                725                 730                 735

His Arg

<210> SEQ ID NO 31
<211> LENGTH: 1668
<212> TYPE: DNA
<213> ORGANISM: Artificial Sequence
<220> FEATURE:
<223> OTHER INFORMATION: Artificially constructed CAR expression
      cassette
<220> FEATURE:
<221> NAME/KEY: CDS
<222> LOCATION: (1)..(1668)

<400> SEQUENCE: 31 atg gcc ctg ccc gtg acc gcc ctg ctc ttg ccc ctg gcc ctt ctg ctc     48
Met Ala Leu Pro Val Thr Ala Leu Leu Leu Pro Leu Ala Leu Leu Leu
1               5                   10                  15 cac gcc gcc aga ccc gag gtg cag ctg cag cag agc gga ggc gag aga     96
His Ala Ala Arg Pro Glu Val Gln Leu Gln Gln Ser Gly Gly Glu Arg
                20                  25                  30 gcc acc cct ggc gcc agc gtg aag atg agc tgc aag acc agc ggc tac    144
Ala Thr Pro Gly Ala Ser Val Lys Met Ser Cys Lys Thr Ser Gly Tyr
            35                  40                  45 acc ttc acc aac tac tgg atg cac tgg gtg aag cag aga ccc ggc cag    192
Thr Phe Thr Asn Tyr Trp Met His Trp Val Lys Gln Arg Pro Gly Gln
        50                  55                  60 ggc ctg gag tgg atc ggc tac atc aac cct agc tcc ggc tac acc cag    240
Gly Leu Glu Trp Ile Gly Tyr Ile Asn Pro Ser Ser Gly Tyr Thr Gln
65                  70                  75                  80 tac aac cag aag ttc aag gac aag gcc acc ctg acc gcc gac aag agc    288
```

|   |   |   |   |   |   |   |   |   |   |   |   |   |
|---|---|---|---|---|---|---|---|---|---|---|---|---|
| Tyr | Asn | Gln | Lys | Phe | Lys | Asp | Lys | Ala | Thr | Leu | Thr | Ala | Asp | Lys | Ser |
|   |   |   |   | 85 |   |   |   | 90 |   |   |   | 95 |

```
tcc agc acc gcc tac atc cag ctg agc tcc ctg acc agc gag gac tcc      336
Ser Ser Thr Ala Tyr Ile Gln Leu Ser Ser Leu Thr Ser Glu Asp Ser
            100                 105                 110 gcc gtg tac tat tgc agc acc tac tac ggc gac tac ctg ttc ccc tac      384
Ala Val Tyr Tyr Cys Ser Thr Tyr Tyr Gly Asp Tyr Leu Phe Pro Tyr
            115                 120                 125 tgg ggc cag ggc acc ctg gtg acc gtg agc gcc ggc gga ggc gga agc      432
Trp Gly Gln Gly Thr Leu Val Thr Val Ser Ala Gly Gly Gly Gly Ser
    130                 135                 140 gga ggc ggc gga tcc gga gga ggc ggc agc gac gtg ctg atg acc cag      480
Gly Gly Gly Gly Ser Gly Gly Gly Gly Ser Asp Val Leu Met Thr Gln
145                 150                 155                 160 acc cct ctg agc ctg ccc gtg agc ctg ggc gac cag gcc agc atc agc      528
Thr Pro Leu Ser Leu Pro Val Ser Leu Gly Asp Gln Ala Ser Ile Ser
                165                 170                 175 tgc aga agc tcc cag gac atc gtg tac ggc aac gga aac acc tac ctg      576
Cys Arg Ser Ser Gln Asp Ile Val Tyr Gly Asn Gly Asn Thr Tyr Leu
            180                 185                 190 gag tgg tac ctc cag aag ccc ggc cag agc ccc aag ctg ctg atc tac      624
Glu Trp Tyr Leu Gln Lys Pro Gly Gln Ser Pro Lys Leu Leu Ile Tyr
        195                 200                 205 aag gtg agc aac aga ttc agc ggc gtg ccc gac aga ttc agc ggc tcc      672
Lys Val Ser Asn Arg Phe Ser Gly Val Pro Asp Arg Phe Ser Gly Ser
210                 215                 220 gga agc gga acc gac ttc acc ctg aag atc agc aga gtg gag gcc gag      720
Gly Ser Gly Thr Asp Phe Thr Leu Lys Ile Ser Arg Val Glu Ala Glu
225                 230                 235                 240 gac ctg ggc gtg tac tat tgc ttc cag ggc agc cac gtg ccc tac acc      768
Asp Leu Gly Val Tyr Tyr Cys Phe Gln Gly Ser His Val Pro Tyr Thr
                245                 250                 255 ttc ggc gga ggc acc aag ctg gag atc aag aga gcg gcc gct atc gag      816
Phe Gly Gly Gly Thr Lys Leu Glu Ile Lys Arg Ala Ala Ala Ile Glu
            260                 265                 270 gtg gag cag aag ctg atc agc gag gag gac ctg cta gac aat gag aag      864
Val Glu Gln Lys Leu Ile Ser Glu Glu Asp Leu Leu Asp Asn Glu Lys
        275                 280                 285 agc aat gga acc att atc cat gtg aaa ggg aaa cac ctt tgt cca agt      912
Ser Asn Gly Thr Ile Ile His Val Lys Gly Lys His Leu Cys Pro Ser
290                 295                 300 ccc cta ttt ccc gga cct tct aag ccc ttt tgg gtg ctg gtg gtg gtt      960
Pro Leu Phe Pro Gly Pro Ser Lys Pro Phe Trp Val Leu Val Val Val
305                 310                 315                 320 ggt gga gtc ctg gct tgc tat agc ttg cta gta aca gtg gcc ttt att     1008
Gly Gly Val Leu Ala Cys Tyr Ser Leu Leu Val Thr Val Ala Phe Ile
                325                 330                 335 att ttc tgg gtg agg agt aag agg agc agg ctc ctg cac agt gac tac     1056
Ile Phe Trp Val Arg Ser Lys Arg Ser Arg Leu Leu His Ser Asp Tyr
            340                 345                 350 atg aac atg act ccc cgc cgc ccc ggg ccc acc cgc aag cat tac cag     1104
Met Asn Met Thr Pro Arg Arg Pro Gly Pro Thr Arg Lys His Tyr Gln
        355                 360                 365 ccc tat gcc cca cca cgc gac ttc gca gcc tat cgc tcc agg gac cag     1152
Pro Tyr Ala Pro Pro Arg Asp Phe Ala Ala Tyr Arg Ser Arg Asp Gln
370                 375                 380 agg ctg ccc ccc gat gcc cac aag ccc cct ggt gag tgc ctc atg gcc     1200
Arg Leu Pro Pro Asp Ala His Lys Pro Pro Gly Glu Cys Leu Met Ala
385                 390                 395                 400
```

```
ctg ccg cac tgc tcc tgg cgg gtg agg ccc acc cac caa tct ctc ctt   1248
Leu Pro His Cys Ser Trp Arg Val Arg Pro Thr His Gln Ser Leu Leu
            405                 410                 415 ttt tcc tcc cca ggg gga ggc agt ttc cgg acc ccc atc caa gag gag   1296
Phe Ser Ser Pro Gly Gly Gly Ser Phe Arg Thr Pro Ile Gln Glu Glu
            420                 425                 430 cag gcc gac gcc cac tcc acc ctg gcc aag atc aga gtg aag ttc agc   1344
Gln Ala Asp Ala His Ser Thr Leu Ala Lys Ile Arg Val Lys Phe Ser
            435                 440                 445 agg agc gca gac gcc ccc gcg tac cag cag ggc cag aac cag ctc tat   1392
Arg Ser Ala Asp Ala Pro Ala Tyr Gln Gln Gly Gln Asn Gln Leu Tyr
        450                 455                 460 aac gag ctc aat cta gga cga aga gag gag tac gat gtt ttg gac aag   1440
Asn Glu Leu Asn Leu Gly Arg Arg Glu Glu Tyr Asp Val Leu Asp Lys
465                 470                 475                 480 aga cgt ggc cgg gac cct gag atg ggg gga aag ccg aga agg aag aac   1488
Arg Arg Gly Arg Asp Pro Glu Met Gly Gly Lys Pro Arg Arg Lys Asn
                485                 490                 495 cct cag gaa ggc ctg tac aat gaa ctg cag aaa gat aag atg gcg gag   1536
Pro Gln Glu Gly Leu Tyr Asn Glu Leu Gln Lys Asp Lys Met Ala Glu
            500                 505                 510 gcc tac agt gag att ggg atg aaa ggc gag cgc cgg agg ggc aag ggg   1584
Ala Tyr Ser Glu Ile Gly Met Lys Gly Glu Arg Arg Arg Gly Lys Gly
            515                 520                 525 cac gat ggc ctt tac cag ggt ctc agt aca gcc acc aag gac acc tac   1632
His Asp Gly Leu Tyr Gln Gly Leu Ser Thr Ala Thr Lys Asp Thr Tyr
        530                 535                 540 gac gcc ctt cac atg cag gcc ctg ccc cct cgc taa                   1668
Asp Ala Leu His Met Gln Ala Leu Pro Pro Arg
545                 550                 555
```

<210> SEQ ID NO 32
<211> LENGTH: 555
<212> TYPE: PRT
<213> ORGANISM: Artificial Sequence
<220> FEATURE:
<223> OTHER INFORMATION: Synthetic Construct

<400> SEQUENCE: 32

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Gly Glu Arg
            20                  25                  30

Ala Thr Pro Gly Ala Ser Val Lys Met Ser Cys Lys Thr Ser Gly Tyr
        35                  40                  45

Thr Phe Thr Asn Tyr Trp Met His Trp Val Lys Gln Arg Pro Gly Gln
    50                  55                  60

Gly Leu Glu Trp Ile Gly Tyr Ile Asn Pro Ser Gly Tyr Thr Gln Tyr
65                  70                  75                  80

Tyr Asn Gln Lys Phe Lys Asp Lys Ala Thr Leu Thr Ala Asp Lys Ser
                85                  90                  95

Ser Ser Thr Ala Tyr Ile Gln Leu Ser Ser Leu Thr Ser Glu Asp Ser
            100                 105                 110

Ala Val Tyr Tyr Cys Ser Thr Tyr Tyr Gly Asp Tyr Leu Phe Pro Tyr
        115                 120                 125

Trp Gly Gln Gly Thr Leu Val Thr Val Ser Ala Gly Gly Gly Gly Ser
    130                 135                 140

Gly Gly Gly Gly Ser Gly Gly Gly Ser Asp Val Leu Met Thr Gln
145                 150                 155                 160
```

Thr Pro Leu Ser Leu Pro Val Ser Leu Gly Asp Gln Ala Ser Ile Ser
                165                 170                 175

Cys Arg Ser Ser Gln Asp Ile Val Tyr Gly Asn Gly Asn Thr Tyr Leu
            180                 185                 190

Glu Trp Tyr Leu Gln Lys Pro Gly Gln Ser Pro Lys Leu Leu Ile Tyr
        195                 200                 205

Lys Val Ser Asn Arg Phe Ser Gly Val Pro Asp Arg Phe Ser Gly Ser
    210                 215                 220

Gly Ser Gly Thr Asp Phe Thr Leu Lys Ile Ser Arg Val Glu Ala Glu
225                 230                 235                 240

Asp Leu Gly Val Tyr Tyr Cys Phe Gln Gly Ser His Val Pro Tyr Thr
                245                 250                 255

Phe Gly Gly Gly Thr Lys Leu Glu Ile Lys Arg Ala Ala Ala Ile Glu
            260                 265                 270

Val Glu Gln Lys Leu Ile Ser Glu Glu Asp Leu Leu Asp Asn Glu Lys
        275                 280                 285

Ser Asn Gly Thr Ile Ile His Val Lys Gly Lys His Leu Cys Pro Ser
    290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Asp Gln
    370                 375                 380

Arg Leu Pro Pro Asp Ala His Lys Pro Pro Gly Glu Cys Leu Met Ala
385                 390                 395                 400

Leu Pro His Cys Ser Trp Arg Val Arg Pro Thr His Gln Ser Leu Leu
                405                 410                 415

Phe Ser Ser Pro Gly Gly Gly Ser Phe Arg Thr Pro Ile Gln Glu Glu
            420                 425                 430

Gln Ala Asp Ala His Ser Thr Leu Ala Lys Ile Arg Val Lys Phe Ser
        435                 440                 445

Arg Ser Ala Asp Ala Pro Ala Tyr Gln Gln Gly Gln Asn Gln Leu Tyr
    450                 455                 460

Asn Glu Leu Asn Leu Gly Arg Arg Glu Glu Tyr Asp Val Leu Asp Lys
465                 470                 475                 480

Arg Arg Gly Arg Asp Pro Glu Met Gly Gly Lys Pro Arg Arg Lys Asn
                485                 490                 495

Pro Gln Glu Gly Leu Tyr Asn Glu Leu Gln Lys Asp Lys Met Ala Glu
            500                 505                 510

Ala Tyr Ser Glu Ile Gly Met Lys Gly Glu Arg Arg Arg Gly Lys Gly
        515                 520                 525

His Asp Gly Leu Tyr Gln Gly Leu Ser Thr Ala Thr Lys Asp Thr Tyr
    530                 535                 540

Asp Ala Leu His Met Gln Ala Leu Pro Pro Arg
545                 550                 555

<210> SEQ ID NO 33
<211> LENGTH: 1608

<212> TYPE: DNA
<213> ORGANISM: Artificial Sequence
<220> FEATURE:
<223> OTHER INFORMATION: Artificially constructed CAR expression cassette
<220> FEATURE:
<221> NAME/KEY: CDS
<222> LOCATION: (1)..(1608)

<400> SEQUENCE: 33

```
atg gcc ctg ccc gtg acc gcc ctg ctc ttg ccc ctg gcc ctt ctg ctc     48
Met Ala Leu Pro Val Thr Ala Leu Leu Leu Pro Leu Ala Leu Leu Leu
1               5                   10                  15 cac gcc gcc aga ccc gag gtg cag ctg cag cag agc gga ggc gag aga     96
His Ala Ala Arg Pro Glu Val Gln Leu Gln Gln Ser Gly Gly Glu Arg
            20                  25                  30 gcc acc cct ggc gcc agc gtg aag atg agc tgc aag acc agc ggc tac    144
Ala Thr Pro Gly Ala Ser Val Lys Met Ser Cys Lys Thr Ser Gly Tyr
        35                  40                  45 acc ttc acc aac tac tgg atg cac tgg gtg aag cag aga ccc ggc cag    192
Thr Phe Thr Asn Tyr Trp Met His Trp Val Lys Gln Arg Pro Gly Gln
    50                  55                  60 ggc ctg gag tgg atc ggc tac atc aac cct agc tcc ggc tac acc cag    240
Gly Leu Glu Trp Ile Gly Tyr Ile Asn Pro Ser Ser Gly Tyr Thr Gln
65                  70                  75                  80 tac aac cag aag ttc aag gac aag gcc acc ctg acc gcc gac aag agc    288
Tyr Asn Gln Lys Phe Lys Asp Lys Ala Thr Leu Thr Ala Asp Lys Ser
                85                  90                  95 tcc agc acc gcc tac atc cag ctg agc tcc ctg acc agc gag gac tcc    336
Ser Ser Thr Ala Tyr Ile Gln Leu Ser Ser Leu Thr Ser Glu Asp Ser
            100                 105                 110 gcc gtg tac tat tgc agc acc tac tac ggc gac tac ctg ttc ccc tac    384
Ala Val Tyr Tyr Cys Ser Thr Tyr Tyr Gly Asp Tyr Leu Phe Pro Tyr
        115                 120                 125 tgg ggc cag ggc acc ctg gtg acc gtg agc gcc ggc gga ggc gga agc    432
Trp Gly Gln Gly Thr Leu Val Thr Val Ser Ala Gly Gly Gly Gly Ser
    130                 135                 140 gga ggc ggc gga tcc gga gga ggc ggc agc gac gtg ctg atg acc cag    480
Gly Gly Gly Gly Ser Gly Gly Gly Gly Ser Asp Val Leu Met Thr Gln
145                 150                 155                 160 acc cct ctg agc ctg ccc gtg agc ctg ggc gac cag gcc agc atc agc    528
Thr Pro Leu Ser Leu Pro Val Ser Leu Gly Asp Gln Ala Ser Ile Ser
                165                 170                 175 tgc aga agc tcc cag gac atc gtg tac ggc aac gga aac acc tac ctg    576
Cys Arg Ser Ser Gln Asp Ile Val Tyr Gly Asn Gly Asn Thr Tyr Leu
            180                 185                 190 gag tgg tac ctc cag aag ccc ggc cag agc ccc aag ctg ctg atc tac    624
Glu Trp Tyr Leu Gln Lys Pro Gly Gln Ser Pro Lys Leu Leu Ile Tyr
        195                 200                 205 aag gtg agc aac aga ttc agc ggc gtg ccc gac aga ttc agc ggc tcc    672
Lys Val Ser Asn Arg Phe Ser Gly Val Pro Asp Arg Phe Ser Gly Ser
    210                 215                 220 gga agc gga acc gac ttc acc ctg aag atc agc aga gtg gag gcc gag    720
Gly Ser Gly Thr Asp Phe Thr Leu Lys Ile Ser Arg Val Glu Ala Glu
225                 230                 235                 240 gac ctg ggc gtg tac tat tgc ttc cag ggc agc cac gtg ccc tac acc    768
Asp Leu Gly Val Tyr Tyr Cys Phe Gln Gly Ser His Val Pro Tyr Thr
                245                 250                 255 ttc ggc gga ggc acc aag ctg gag atc aag aga gcg gcc gct atc gag    816
Phe Gly Gly Gly Thr Lys Leu Glu Ile Lys Arg Ala Ala Ala Ile Glu
            260                 265                 270
```

| | | | | | | | | | | | | | | | | |
|---|---|---|---|---|---|---|---|---|---|---|---|---|---|---|---|---|
| gtg | gag | cag | aag | ctg | atc | agc | gag | gag | gac | ctg | cta | gac | aat | gag | aag | 864 |
| Val | Glu | Gln | Lys | Leu | Ile | Ser | Glu | Glu | Asp | Leu | Leu | Asp | Asn | Glu | Lys | |
| | | | 275 | | | | 280 | | | | | 285 | | | | |
| agc | aat | gga | acc | att | atc | cat | gtg | aaa | ggg | aaa | cac | ctt | tgt | cca | agt | 912 |
| Ser | Asn | Gly | Thr | Ile | Ile | His | Val | Lys | Gly | Lys | His | Leu | Cys | Pro | Ser | |
| | 290 | | | | | 295 | | | | | 300 | | | | | |
| ccc | cta | ttt | ccc | gga | cct | tct | aag | ccc | ttt | tgg | gtg | ctg | gtg | gtg | gtt | 960 |
| Pro | Leu | Phe | Pro | Gly | Pro | Ser | Lys | Pro | Phe | Trp | Val | Leu | Val | Val | Val | |
| 305 | | | | | 310 | | | | | 315 | | | | | 320 | |
| ggt | gga | gtc | ctg | gct | tgc | tat | agc | ttg | cta | gta | aca | gtg | gcc | ttt | att | 1008 |
| Gly | Gly | Val | Leu | Ala | Cys | Tyr | Ser | Leu | Leu | Val | Thr | Val | Ala | Phe | Ile | |
| | | | | 325 | | | | | 330 | | | | | 335 | | |
| att | ttc | tgg | gtg | agg | agt | aag | agg | agc | agg | ctc | ctg | cac | agt | gac | tac | 1056 |
| Ile | Phe | Trp | Val | Arg | Ser | Lys | Arg | Ser | Arg | Leu | Leu | His | Ser | Asp | Tyr | |
| | | | 340 | | | | | 345 | | | | | 350 | | | |
| atg | aac | atg | act | ccc | cgc | cgc | ccc | ggg | ccc | acc | cgc | aag | cat | tac | cag | 1104 |
| Met | Asn | Met | Thr | Pro | Arg | Arg | Pro | Gly | Pro | Thr | Arg | Lys | His | Tyr | Gln | |
| | | 355 | | | | | 360 | | | | | 365 | | | | |
| ccc | tat | gcc | cca | cca | cgc | gac | ttc | gca | gcc | tat | cgc | tcc | aaa | cgg | ggc | 1152 |
| Pro | Tyr | Ala | Pro | Pro | Arg | Asp | Phe | Ala | Ala | Tyr | Arg | Ser | Lys | Arg | Gly | |
| | 370 | | | | | 375 | | | | | 380 | | | | | |
| aga | aag | aaa | ctc | ctg | tat | ata | ttc | aaa | caa | cca | ttt | atg | aga | cca | gta | 1200 |
| Arg | Lys | Lys | Leu | Leu | Tyr | Ile | Phe | Lys | Gln | Pro | Phe | Met | Arg | Pro | Val | |
| 385 | | | | | 390 | | | | | 395 | | | | | 400 | |
| caa | act | act | caa | gag | gaa | gat | ggc | tgt | agc | tgc | cga | ttt | cca | gaa | gaa | 1248 |
| Gln | Thr | Thr | Gln | Glu | Glu | Asp | Gly | Cys | Ser | Cys | Arg | Phe | Pro | Glu | Glu | |
| | | | | 405 | | | | | 410 | | | | | 415 | | |
| gaa | gaa | gga | gga | tgt | gaa | ctg | aga | gtg | aag | ttc | agc | agg | agc | gca | gac | 1296 |
| Glu | Glu | Gly | Gly | Cys | Glu | Leu | Arg | Val | Lys | Phe | Ser | Arg | Ser | Ala | Asp | |
| | | | 420 | | | | | 425 | | | | | 430 | | | |
| gcc | ccc | gcg | tac | cag | cag | ggc | cag | aac | cag | ctc | tat | aac | gag | ctc | aat | 1344 |
| Ala | Pro | Ala | Tyr | Gln | Gln | Gly | Gln | Asn | Gln | Leu | Tyr | Asn | Glu | Leu | Asn | |
| | | 435 | | | | | 440 | | | | | 445 | | | | |
| cta | gga | cga | aga | gag | gag | tac | gat | gtt | ttg | gac | aag | aga | cgt | ggc | cgg | 1392 |
| Leu | Gly | Arg | Arg | Glu | Glu | Tyr | Asp | Val | Leu | Asp | Lys | Arg | Arg | Gly | Arg | |
| | 450 | | | | | 455 | | | | | 460 | | | | | |
| gac | cct | gag | atg | ggg | gga | aag | ccg | aga | agg | aag | aac | cct | cag | gaa | ggc | 1440 |
| Asp | Pro | Glu | Met | Gly | Gly | Lys | Pro | Arg | Arg | Lys | Asn | Pro | Gln | Glu | Gly | |
| 465 | | | | | 470 | | | | | 475 | | | | | 480 | |
| ctg | tac | aat | gaa | ctg | cag | aaa | gat | aag | atg | gcg | gag | gcc | tac | agt | gag | 1488 |
| Leu | Tyr | Asn | Glu | Leu | Gln | Lys | Asp | Lys | Met | Ala | Glu | Ala | Tyr | Ser | Glu | |
| | | | | 485 | | | | | 490 | | | | | 495 | | |
| att | ggg | atg | aaa | ggc | gag | cgc | cgg | agg | ggc | aag | ggg | cac | gat | ggc | ctt | 1536 |
| Ile | Gly | Met | Lys | Gly | Glu | Arg | Arg | Arg | Gly | Lys | Gly | His | Asp | Gly | Leu | |
| | | | 500 | | | | | 505 | | | | | 510 | | | |
| tac | cag | ggt | ctc | agt | aca | gcc | acc | aag | gac | acc | tac | gac | gcc | ctt | cac | 1584 |
| Tyr | Gln | Gly | Leu | Ser | Thr | Ala | Thr | Lys | Asp | Thr | Tyr | Asp | Ala | Leu | His | |
| | | 515 | | | | | 520 | | | | | 525 | | | | |
| atg | cag | gcc | ctg | ccc | cct | cgc | taa | | | | | | | | | 1608 |
| Met | Gln | Ala | Leu | Pro | Pro | Arg | | | | | | | | | | |
| | 530 | | | | | 535 | | | | | | | | | | |

<210> SEQ ID NO 34
<211> LENGTH: 535
<212> TYPE: PRT
<213> ORGANISM: Artificial Sequence
<220> FEATURE:
<223> OTHER INFORMATION: Synthetic Construct

<400> SEQUENCE: 34

Met Ala Leu Pro Val Thr Ala Leu Leu Leu Pro Leu Ala Leu Leu Leu

-continued

```
1               5                   10                  15
His Ala Ala Arg Pro Glu Val Gln Leu Gln Gln Ser Gly Gly Glu Arg
                20                  25                  30

Ala Thr Pro Gly Ala Ser Val Lys Met Ser Cys Lys Thr Ser Gly Tyr
                35                  40                  45

Thr Phe Thr Asn Tyr Trp Met His Trp Val Lys Gln Arg Pro Gly Gln
        50                  55                  60

Gly Leu Glu Trp Ile Gly Tyr Ile Asn Pro Ser Ser Gly Tyr Thr Gln
65                  70                  75                  80

Tyr Asn Gln Lys Phe Lys Asp Lys Ala Thr Leu Thr Ala Asp Lys Ser
                85                  90                  95

Ser Ser Thr Ala Tyr Ile Gln Leu Ser Ser Leu Thr Ser Glu Asp Ser
                100                 105                 110

Ala Val Tyr Tyr Cys Ser Thr Tyr Tyr Gly Asp Tyr Leu Phe Pro Tyr
                115                 120                 125

Trp Gly Gln Gly Thr Leu Val Thr Val Ser Ala Gly Gly Gly Gly Ser
        130                 135                 140

Gly Gly Gly Gly Ser Gly Gly Gly Ser Asp Val Leu Met Thr Gln
145                 150                 155                 160

Thr Pro Leu Ser Leu Pro Val Ser Leu Gly Asp Gln Ala Ser Ile Ser
                165                 170                 175

Cys Arg Ser Ser Gln Asp Ile Val Tyr Gly Asn Gly Asn Thr Tyr Leu
                180                 185                 190

Glu Trp Tyr Leu Gln Lys Pro Gly Gln Ser Pro Lys Leu Leu Ile Tyr
                195                 200                 205

Lys Val Ser Asn Arg Phe Ser Gly Val Pro Asp Arg Phe Ser Gly Ser
                210                 215                 220

Gly Ser Gly Thr Asp Phe Thr Leu Lys Ile Ser Arg Val Glu Ala Glu
225                 230                 235                 240

Asp Leu Gly Val Tyr Tyr Cys Phe Gln Gly Ser His Val Pro Tyr Thr
                245                 250                 255

Phe Gly Gly Gly Thr Lys Leu Glu Ile Lys Arg Ala Ala Ala Ile Glu
                260                 265                 270

Val Glu Gln Lys Leu Ile Ser Glu Glu Asp Leu Leu Asp Asn Glu Lys
                275                 280                 285

Ser Asn Gly Thr Ile Ile His Val Lys Gly Lys His Leu Cys Pro Ser
                290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
                340                 345                 350

Met Asn Met Thr Pro Arg Arg Pro Gly Pro Thr Arg Lys His Tyr Gln
                355                 360                 365

Pro Tyr Ala Pro Pro Arg Asp Phe Ala Ala Tyr Arg Ser Lys Arg Gly
                370                 375                 380

Arg Lys Lys Leu Leu Tyr Ile Phe Lys Gln Pro Phe Met Arg Pro Val
385                 390                 395                 400

Gln Thr Thr Gln Glu Glu Asp Gly Cys Ser Cys Arg Phe Pro Glu Glu
                405                 410                 415

Glu Glu Gly Gly Cys Glu Leu Arg Val Lys Phe Ser Arg Ser Ala Asp
                420                 425                 430
```

-continued

```
Ala Pro Ala Tyr Gln Gln Gly Gln Asn Gln Leu Tyr Asn Glu Leu Asn
    435                 440                 445

Leu Gly Arg Arg Glu Glu Tyr Asp Val Leu Asp Lys Arg Arg Gly Arg
    450                 455                 460

Asp Pro Glu Met Gly Gly Lys Pro Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Gly Lys Gly His Asp Gly Leu
            500                 505                 510

Tyr Gln Gly Leu Ser Thr Ala Thr Lys Asp Thr Tyr Asp Ala Leu His
        515                 520                 525

Met Gln Ala Leu Pro Pro Arg
    530                 535
```

COMPOSITIONS COMPRISING CHIMERIC ANTIGEN RECEPTORS, T CELLS COMPRISING THE SAME, AND METHODS OF USING THE SAME

REFERENCE TO SEQUENCE LISTING

The Sequence Listing associated with the instant disclosure has been electronically submitted to the United States Patent and Trademark Office as an 88 kilobyte ASCII text file created on Dec. 10, 2015 and entitled "1276_5_5_PCT_US_ST25.txt". The Sequence Listing submitted via EFS-Web is hereby incorporated by reference in its entirety.

TECHNICAL FIELD

The presently disclosed subject matter relates to isolated antibodies, or fragments or derivatives thereof, including but not limited to chimeric antigen receptors (CARs) and cells comprising CARs, which bind to antigens present in tumors, and methods of use therefor.

BACKGROUND

Pancreatic cancer is the fourth and fifth leading cause of cancer-related death for men and women, respectively, following lung, colon, and prostate cancers in men and lung, breast, colon, and ovarian cancers in women. Patients usually present with advanced disease, making treatment difficult. Surgery is the only curative therapy, yet local disease recurrence with or without spread to distant organs occurs in over 80% of patients. Attempts at better therapeutic modalities are necessary in order to improve outcome in this disease.

Frequently, neoplastic transformation leads to alterations in the expression of various polypeptides in tumor cells. For example, certain mucins and mutated forms of K-ras oncogene polypeptides are overexpressed in 90% of pancreatic ductal adenocarcinomas (hereinafter referred to as "PDA"), and have been targets for therapeutic interventions. To date, however, vaccines that target these polypeptides have not been particularly successful clinically. Vaccines have failed to generate long-term immune memory, likely due at least in part to tumors adapting in ways that allows them to escape immune recognition and killing. Several agents that can modulate immune tolerance have been tested clinically, but with only modest responses, perhaps due to an insufficient amount of the agents reaching the tumor site and/or because the agents themselves have been associated with unwanted side effects such as can result from their binding to normal cells.

Additionally, it is a major challenge in oncology to not only treat a patient's primary disease, but also to prevent the occurrence of metastases. It is currently believed that metastatic disease could result from the migration of tumorigenic cells, frequently referred to as tumor stem cells or cancer stem cells, from the primary tumor site to other sites, where they can infiltrate the site and form new tumors (see e.g., Bonnet & Dick, 1997; Reya et al., 2001; Al-Hajj et al., 2003; Pardal et al., 2003; Dontu et al., 2004; Singh et al., 2004; Brabletz et al., 2005). As a result, it would be beneficial to be able to identify and eliminate these cells should they be present in a patient.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list all possible combinations of such features.

In various embodiments, the presently disclosed subject matter provides the following:

Isolated antibodies, as well as fragments and derivatives thereof, which specifically bind to mucin-1 (MUC1) and/or to mutated K-ras oncogene polypeptides present on epithelial tumors.

Antibodies, as well as fragments and derivatives thereof, which bind specifically to an epitope present within a MUC1 polypeptide and/or a K-ras$^{G12D}$ polypeptide, in some embodiments to an epitope present within a human MUC1 polypeptide. In some embodiments, the epitope is present within a tumor-associated form of a MUC1 polypeptide that comprises any of SEQ ID NOs: 1-3, in some embodiments a form of a MUC1 polypeptide that is characterized by a tumor-specific glycosylation pattern.

Antibodies, as well as fragments and derivatives thereof, that are specific for a K-ras$^{G12D}$ gene product.

Antibodies, as well as fragments and derivatives thereof, which bind specifically to MUC1 (in some embodiments, human MUC1) and K-ras$^{G12D}$ created using protein lysates from a triple transgenic mouse model which presents MUC1 and K-ras$^{G12D}$ as tumor-associated antigens.

Isolated antibodies, as well as fragments and derivatives thereof, which specifically bind to an epitope present within SEQ ID NO: 3 of the MUC1 tandem repeat (TR).

Chimeric molecules comprising antibodies, as well as fragments and derivatives thereof, attached to effectors and/or immune modulating agents, wherein the antibodies, or the fragments or derivatives thereof, bind specifically to epitopes present within a MUC1 polypeptide and/or a mutated K-ras polypeptide. In some embodiments, the effectors are selected from the group consisting of epitope tags, second antibodies (or fragments or derivatives thereof), labels, cytotoxins, liposomes, radionuclides, drugs, prodrugs, and chelates, and further wherein the immune modulating agents are selected from, for example, the agents listed in Table 3.

Antibodies, as well as fragments and derivatives thereof, coupled to an immune modulating agent; for example, the immune modulating agents listed in Table 3 herein below.

Antibodies, as well as fragments and derivatives thereof, coupled to diagnostic agents.

Antibodies, as well as fragments and derivatives thereof, prepared in compositions that comprise one or more pharmaceutically acceptable carriers and/or excipients.

Methods for inducing immune responses, which in some embodiments comprise introducing the antibodies, fragments, and/or derivatives thereof, and/or the compositions disclosed herein, into a subject such as, but not limited to, a human.

Methods for detecting cancerous cells, comprising introducing into a subject such as but not limited to a human an antibody, or a fragment or derivative thereof, coupled to a detectable label that bind specifically to a MUC1 polypeptide and/or a mutated K-ras polypeptide.

Hybridoma cells that produce the antibodies, fragments, and/or derivatives of the presently disclosed subject matter, such as but not limited to monoclonal antibodies that bind specifically to a MUC1 polypeptide, a mutated K-ras polypeptide, or both.

Vaccines against epithelial cancers comprising the antibodies, fragments, and/or derivatives of the presently disclosed subject matter and one or more pharmaceutically accepted carriers and/or excipients, optionally further comprising one or more immune modulating agents.

More particularly, in some embodiments the presently disclosed subject matter provides isolated antibodies, or fragments or derivatives thereof, which bind to MUC1 polypeptide (optionally a tumor-specific epitope thereof), a K-ras$^{G12D}$ polypeptide, or both. In some embodiments, the antibodies, or the fragments or the derivatives thereof, comprising the complementarity determining regions (CDRs) of monoclonal antibody TAB-004. In some embodiments, the isolated antibodies, or the fragments or derivatives thereof, are polyclonal. In some embodiments, the isolated antibodies, or the fragments or derivatives thereof, are monoclonal. In some embodiments, the isolated antibodies, or the fragments or derivatives thereof, are human or humanized. In some embodiments, the isolated antibodies, or the fragments or derivatives thereof, are selected from the group consisting of (a) a monoclonal antibody produced by hybridoma cell line TAB-004 deposited with the American Type Culture Collection (ATCC), 10801 University Boulevard, Manassas, Va., 20110-2209, United States of America, as Accession No. PTA-11550 on Dec. 16, 2010; (b) a chimeric derivative thereof, humanized derivative thereof, single chain derivative thereof, Fab fragment thereof, F(ab')$_2$ fragment thereof, Fv fragment thereof, and/or Fab' fragment thereof, wherein the chimeric derivative, the humanized derivative, the single chain derivative, the Fab fragment thereof, the F(ab')$_2$ fragment thereof, the Fv fragment thereof, or the Fab' fragment thereof binds to a MUC1 polypeptide (optionally a tumor-specific epitope thereof), a K-ras$^{G12D}$ polypeptide, or both; (c) humanized antibodies, or fragments or derivatives thereof; (d) human antibodies, or fragments or derivatives thereof; (e) single chain antibodies, or fragments or derivatives thereof; and (f) Fab fragments, wherein the chimeric antibodies, the humanized antibodies, the human antibodies, the single chain antibodies, or the Fab fragments comprise the CDRs of monoclonal antibody TAB-004. In some embodiments of the isolated antibodies, or the fragments or derivatives thereof, the CDRs comprise one or more of the following: (i) heavy chain CDR1 comprises SEQ ID NO: 8; (ii) heavy chain CDR2 comprises SEQ ID NO: 9; (iii) heavy chain CDR3 comprises SEQ ID NO: 10; (iv) light chain CDR1 comprises SEQ ID NO: 11; (v) light chain CDR2 comprises SEQ ID NO: 12; and (vi) light chain CDR3 comprises SEQ ID NO: 13. In some embodiments of the isolated antibodies, or the fragments or derivatives thereof, the heavy chain variable region comprises SEQ ID NO: 5 or is encoded by a nucleic acid molecule comprising SEQ ID NO: 4; and/or the light chain variable region comprises SEQ ID NO: 7 or is encoded by a nucleic acid molecule comprising SEQ ID NO: 6.

The presently disclosed subject matter also provides compositions comprising the presently disclosed antibodies, or the fragments or derivatives thereof, and one more pharmaceutically acceptable carriers and/or excipients. In some embodiments, the one or more pharmaceutically acceptable carriers and/or excipients are acceptable for use in a human.

The presently disclosed subject matter also provides compositions comprising the presently disclosed antibodies, or the fragments or derivatives thereof, conjugated to an active agent. In some embodiments, the active agent is selected from the group consisting of a radioactive molecule, a radionuclide, a sensitizer molecule, an imaging reagent, a radioisotope, a toxin, a cytotoxin, an anti-angiogenic agent, an anti-tumor agent, a chemotherapeutic agent, an immunomodulator, a cytokine, a reporter group, and combinations thereof. In some embodiments, the radioisotope is selected from the group consisting of $^{10}$B, $^{211}$At, $^{212}$Pb, $^{212}$Bi, $^{125}$I, $^{131}$I, $^{35}$S, and $^{3}$H. In some embodiments, immunomodulator is selected from the group consisting of an indoleamine 2,3-dioxygenase (IDO) inhibitor, optionally, 1-methyl-DL-tryptophan (1MT); an EP2/EP4 receptor antagonist; a cyclooxygenase inhibitor, optionally indomethacin; and a dendritic cell activator, optionally CpG oligodeoxynucleotides (CpG ODN).

The presently disclosed subject matter also provides kits comprising the presently disclosed antibodies, or the fragments or derivatives thereof. In some embodiments, the presently disclosed kits comprise instructions for use of the presently disclosed antibodies, or the fragments or derivatives thereof.

The presently disclosed subject matter also provides delivery vehicles for use in targeted delivery of active agents to tumor cells. In some embodiments, the delivery vehicles comprise one or more targeting agents that comprise the presently disclosed antibodies, or the fragments or derivatives thereof. In some embodiments, the active agent comprises a radioactive molecule, a radionuclide, a sensitizer molecule, an imaging reagent, a radioisotope, a toxin, a cytotoxin, an anti-angiogenic agent, an anti-tumor agent, a chemotherapeutic agent, an immunomodulator, a cytokine, a reporter group, or a combination thereof.

The presently disclosed subject matter also provides isolated cells that produce the presently disclosed antibodies, or the fragments or derivative thereof. In some embodiments, the isolated cell is a hybridoma that produces the presently disclosed antibodies. In some embodiments, the hybridoma is hybridoma cell line ATCC Accession No. PTA-11550 deposited with the American Type Culture Collection (ATCC), 10801 University Boulevard, Manassas, Va., 20110-2209, United States of America, on Dec. 16, 2010 under the terms of the Budapest Treaty.

The presently disclosed subject matter also provides methods for detecting the presence of an epitope to which monoclonal antibody TAB-004 binds in a biological sample. In some embodiments, the methods comprise: contacting the biological sample with one or more presently disclosed isolated antibodies, or fragments or derivatives thereof; and detecting the presence of an epitope to which monoclonal antibody TAB-004 binds in the biological sample. In some embodiments, the isolated antibodies, or the fragments or derivatives thereof, bind to an epitope that is present within a mucin (MUC1) polypeptide and/or an epitope that is present within a K-ras polypeptide, optionally a mutant K-ras polypeptide.

The presently disclosed subject matter also provides methods for making an antibody or a fragment or derivative thereof. In some embodiments, the methods comprise culturing an isolated cell of the presently disclosed subject matter or a hybridoma of the presently disclosed subject matter under conditions such that said antibody, the fragment, or the derivative thereof is expressed; and recovering the antibody or the fragment or derivative thereof from the cell or the hybridoma and/or from the environment in which the cell or the hybridoma is growing.

The presently disclosed subject matter also provides methods for detecting a tumor and/or a cancer cell in a subject. In some embodiments, the methods comprise contacting a biological sample in the subject or isolated from the subject with composition comprising a presently disclosed antibody, or a fragment or derivative thereof, under conditions sufficient for the presently disclosed antibody, or the fragment or derivative thereof, to bind to an epitope present on a tumor and/or a cancer cell, if present, in the biological sample; and detecting binding of the presently disclosed antibody, or the fragment or derivative thereof, to the epitope, wherein the detecting is indicative of a tumor and/or a cancer cell being present in the subject. In some embodiments, the tumor and/or the cancer cell is a tumor of the pancreas, breast, ovary, colon, or rectum, and/or a metastatic cell derived therefrom, which optionally expresses MUC1, a mutant K-ras, or both. In some embodiments, the presently disclosed antibody, or the fragment or derivative thereof, is conjugated to a detectable label comprising an imaging agent, which in some embodiments is selected from the group consisting of paramagnetic, radioactive, and fluorogenic ions. In some embodiments, the radioactive imaging agent is selected from the group consisting of gamma-emitters, positron-emitters, and x-ray-emitters. In some embodiments, the radioactive imaging agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb, and $^{206}$Bi. In some embodiments, the biological sample is a blood sample, or a fraction derived therefrom.

The presently disclosed subject matter also provides methods for treating a tumor in a subject. In some embodiments, the methods comprise administering to the subject a composition comprising a presently disclosed antibody, or a fragment or derivative thereof, conjugated to an active agent, whereby the active agent contacts the tumor to thereby treat the tumor. In some embodiments, the active agent comprises a therapeutic agent, optionally a chemotherapeutic agent, a toxin, a radiotherapeutic agent, or a combination thereof. In some embodiments, the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof. In some embodiments, the toxin is selected from the group consisting of Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin, and combinations thereof. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$Bi, $^{32}$P, $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg.

The presently disclosed subject matter also provides methods for suppressing tumor growth in a subject. In some embodiments, the methods comprise administering to a subject bearing a tumor an effective amount of an isolated antibody, or a fragment or derivative thereof, comprising the complementarity determining regions (CDRs) of monoclonal antibody TAB-004. In some embodiments, the tumor is a tumor of the pancreas, breast, ovary, colon, or rectum, and/or a metastatic cell derived therefrom, which optionally expresses MUC1, a mutant K-ras, or both. In some embodiments, the CDRs of TAB-004 comprise one or more of the following: heavy chain CDR1 comprises SEQ ID NO: 8; heavy chain CDR2 comprises SEQ ID NO: 9; heavy chain CDR3 comprises SEQ ID NO: 10; light chain CDR1 comprises SEQ ID NO: 11; light chain CDR2 comprises SEQ ID NO: 12; and/or light chain CDR3 comprises SEQ ID NO: 13. In some embodiments, the heavy chain variable region comprises SEQ ID NO: 5 or is encoded by a nucleic acid molecule comprising SEQ ID NO: 4, and/or the light chain variable region comprises SEQ ID NO: 7 or is encoded by a nucleic acid molecule comprising SEQ ID NO: 6.

With respect to the treatment methods disclosed herein, in some embodiments the methods further comprise administering to the subject one or more additional anti-tumor treatments. In some embodiments, the one or more additional anti-tumor treatments are selected from the group consisting of radiotherapy, chemotherapy, an additional immunotherapy, an anti-inflammatory therapy, and combinations thereof. In some embodiments, the anti-inflammatory therapy comprises administering to the subject a cyclooxygenase inhibitor, optionally a cyclooxygenase-2-specific inhibitor. In some embodiments, the one or more additional anti-tumor therapies comprise administering gemcitabine (4-amino-1-(2-deoxy-2,2-difluoro-β-D-erythro-pentofuranosyl)pyrimidin-2(1H)-on-2',2'-difluoro-2'-deoxycytidine) and celecoxib (4-[5-(4-methylphenyl)-3-(trifluoromethyl)pyrazol-1-yl]benzenesulfonamide), or pharmaceutically acceptable salts of either or both thereof, to the subject.

The presently disclosed subject matter also provides methods for purifying cancer stem cells. In some embodiments, the methods comprise providing a population of cells suspected of comprising cancer stem cells; identifying a subpopulation of the cells that bind to an antibody, or a fragment or derivative thereof, comprising the CDRs of monoclonal antibody TAB-004; and purifying the subpopulation. In some embodiments, the population of cells comprises circulating cells isolated from a subject that has a tumor and/or a cancer. In some embodiments, the presently disclosed methods further comprise removing lineage-positive (lin$^+$) cells from the population of cells before the identifying step and/or after the purifying step.

The presently disclosed subject matter also provides methods for targeting active agents to circulating cancer stem cells in subjects. In some embodiments, the methods comprise contacting the circulating cancer stem cells with a composition comprising a presently disclosed antibody, or a fragment or derivative thereof, comprising the CDRs of monoclonal antibody TAB-004 and one or more active agents, optionally wherein the one or more active agents comprise a therapeutic agent, optionally a chemotherapeutic agent, a toxin, a radiotherapeutic agent, or a combination thereof. In some embodiments, the therapeutic agent comprises an immunomodulator, optionally wherein the immunomodulator is selected from the group consisting of wherein the immunomodulator is selected from the group consisting of an indoleamine 2,3-dioxygenase (IDO) inhibitor, optionally, 1-methyl-DL-tryptophan (1MT); an EP2/EP4 receptor antagonist; and a dendritic cell activator, optionally CpG oligodeoxynucleotides (CpG ODN).

The presently disclosed subject matter also provides methods for prognosing recurrence of cancer in a subject previously treated for the cancer. In some embodiments, the methods comprise isolating a biological sample comprising circulating cells from a subject with a cancer; contacting the biological sample with the presently disclosed antibodies, or the fragments or derivatives thereof, under conditions sufficient for the antibodies, or the fragments or derivatives thereof, to bind to an epitope present on a tumor and/or a cancer cell, if present, in the biological sample; and identifying in the biological sample one or more circulating cells that bind to the antibody, or the fragment or derivative thereof, whereby recurrence of a cancer is prognosed in the subject. In some embodiments, the biological sample comprises a blood sample, a lymph sample, or a fraction thereof. In some embodiments, the cancer is a pancreatic cancer or a breast cancer. In some embodiments, the antibodies, or the fragments or derivatives thereof, are selected from the group consisting of monoclonal antibodies produced by hybridoma cell line TAB-004 deposited with the American Type Culture Collection (ATCC), 10801 University Boulevard, Manassas, Va., 20110-2209, United States of America, on Dec. 16, 2010 under the terms of the Budapest Treaty, as Accession No. PTA-11550; chimeric antibodies, or fragments or derivatives thereof; humanized antibodies, or fragments or derivatives thereof; human antibodies, or fragments or derivatives thereof; single chain antibodies, or fragments or derivatives thereof; and Fab fragments, and further wherein the chimeric antibodies, the humanized antibodies, the human antibodies, the single chain antibodies, or the Fab fragments comprise the complementarity determining regions (CDRs) of monoclonal antibody TAB-004. In some embodiments, the CDRs of monoclonal antibody TAB-004 comprise the following amino acid sequences: heavy chain CDR1 comprises SEQ ID NO: 8; heavy chain CDR2 comprises SEQ ID NO: 9; heavy chain CDR3 comprises SEQ ID NO: 10; light chain CDR1 comprises SEQ ID NO: 11; light chain CDR2 comprises SEQ ID NO: 12; and light chain CDR3 comprises SEQ ID NO: 13. In some embodiments, the heavy chain variable region comprises SEQ ID NO: 5 or is encoded by a nucleic acid molecule comprising SEQ ID NO: 4; and/or the light chain variable region comprises SEQ ID NO: 7 or is encoded by a nucleic acid molecule comprising SEQ ID NO: 6.

The presently disclosed subject matter also provides methods for prognosing progression of a cancer in a subject. In some embodiments, the methods comprise isolating a biological sample comprising circulating cells from a subject with a cancer; contacting the biological sample with an antibody, or a fragment or derivative thereof, of the presently disclosed subject matter under conditions sufficient for the antibody, or the fragment or derivative thereof, to bind to an epitope present on a tumor and/or a cancer cell, if present, in the biological sample; and identifying in the biological sample one or more circulating cells that bind to the antibody, or the fragment or derivative thereof, whereby progression of a cancer is prognosed in the subject. In some embodiments, the biological sample comprises a blood sample, a lymph sample, or a fraction thereof. In some embodiments, the cancer is a pancreatic cancer or a breast cancer. In some embodiments, the antibody, or the fragment or derivative thereof, is selected from the group consisting of a monoclonal antibody produced by hybridoma cell line TAB-004 deposited with the American Type Culture Collection (ATCC), 10801 University Boulevard, Manassas, Va., 20110-2209, United States of America, on Dec. 16, 2010 under the terms of the Budapest Treaty as Accession No. PTA-11550 on Dec. 16, 2010; a chimeric antibody, or a fragment or derivative thereof; a humanized antibody, or a fragment or derivative thereof; a human antibody, or a fragment or derivative thereof; a single chain antibody, or a fragment or derivative thereof; and a Fab fragment, and further wherein the chimeric antibody, the humanized antibody, the human antibody, the single chain antibody, or the Fab fragment comprises the complementarity determining regions (CDRs) of monoclonal antibody TAB-004. In some embodiments, the CDRs of monoclonal antibody TAB-004 comprise the following amino acid sequences: heavy chain CDR1 comprises SEQ ID NO: 8; heavy chain CDR2 comprises SEQ ID NO: 9; heavy chain CDR3 comprises SEQ ID NO: 10; light chain CDR1 comprises SEQ ID NO: 11; light chain CDR2 comprises SEQ ID NO: 12; and light chain CDR3 comprises SEQ ID NO: 13. In some embodiments, the heavy chain variable region comprises SEQ ID NO: 5 or is encoded by a nucleic acid molecule comprising SEQ ID NO: 4; and/or the light chain variable region comprises SEQ ID NO: 7 or is encoded by a nucleic acid molecule comprising SEQ ID NO: 6. In some embodiments, progression of the cancer comprises metastasis of the cancer in the subject.

The presently disclosed subject matter also provides isolated nucleic acid molecules comprising any of SEQ ID NOs: 4, 6, 14, and 16, and/or encoding any of SEQ ID NOs: 5, 7-13, 15, and 17. In some embodiments, the isolated nucleic acid molecule is present within a vector, which in some embodiments is an expression vector. In some embodiments, the isolated nucleic acid molecule is present within an expression vector operably linked to one or more additional nucleotide sequences encoding subsequences of antibody molecules such that upon introduction of the expression vector into an appropriate host, an intact recombinant antibody comprising one or more of SEQ ID NOs: 5, 7-13, 15, and 17, or a fragment or derivative thereof, is expressed by the host cell.

Isolated nucleic acids that encode the isolated antibodies of the presently disclosed subject matter and/or subsequences thereof.

Antibodies, such as monoclonal antibodies, and/or peptides, fragments, and/or derivatives thereof, that bind specifically to tumors such as epithelial tumors, including pancreatic tumors, ovarian tumors, breast tumors, colorectal tumors, and metastatic lesions derived therefrom.

In some embodiments, the presently disclosed subject matter provides isolated nucleic acid molecules, including but not limited to DNA molecules and RNA molecules such as mRNA molecules, which encode a chimeric antigen receptor (CAR). In some embodiments, the CAR comprises an antibody or antibody fragment that includes a binding domain, a transmembrane domain, and an intracellular signaling domain comprising a stimulatory domain, wherein the binding domain binds to a tumor-exclusive epitope of a human MUC1 polypeptide. In some embodiments, the anti-MUC1 binding domain comprises a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10); and a light chain complementary determining region 1 (LC CDR1) comprising QDIVYGNGNTY (SEQ ID NO: 11), a light chain complementary determining region 2 (LC CDR2) comprising KVS (SEQ ID NO: 12), and a light chain complementary determining region 3 (LC CDR3) comprising FQGSHVPYT (SEQ ID NO: 13). In some embodiments, the CAR comprises a light chain variable region comprising SEQ ID NO: 7 and/or a heavy chain variable region comprising SEQ ID NO: 5. In some embodiments, the anti-MUC1 binding domain is a single chain fragment variable (scFv) polypeptide. In some embodiments, the light chain variable region comprises an amino acid sequence having at least one, two, or three but not more than 30, 20, or 10 modifications of the amino acid sequence set forth in SEQ ID NO: 7, or comprises an amino acid sequence with at least 95% identity to SEQ ID NO: 7 and/or the heavy chain variable region comprises an amino acid sequence having at least one, two, or three but not more than 30, 20, or 10 modifications of the amino acid sequence set forth in SEQ ID NO: 5, or comprises an amino acid sequence with at least 95% identity to SEQ ID NO: 5.

In some embodiments, the CAR comprises a transmembrane domain that comprises a transmembrane domain of a protein selected from the group consisting of a T cell receptor (TCR) alpha chain, a TCR beta chain, a TCR zeta chain, CD28, CD3 epsilon, CD45, CD4, CD5, CD8, CD9, CD16, CD22, CD33, CD37, CD64, CD80, CD86, CD134, CD137, and CD154. In some embodiments, the transmembrane domain comprises SEQ ID NO: 21 or SEQ ID NO: 23. In some embodiments, the transmembrane domain comprises an amino acid sequence having at least one, two, or three but not more than 20, 10, or 5 modifications of the amino acid sequence as set forth in SEQ ID NO: 21 or SEQ ID NO: 23, or comprises an amino acid sequence with at least 95% identity to SEQ ID NO: SEQ ID NO: 21 or SEQ ID NO: 23. In some embodiments, the nucleic acid sequence encoding the transmembrane domain comprises a sequence at least 95% identical to nucleotides 940-1020 of SEQ ID NO: 14 or nucleotides 919-999 of SEQ ID NO: 16.

In some embodiments, the encoded anti-MUC1 binding domain is connected to the transmembrane domain by a hinge region.

In some embodiments, the presently disclosed isolated nucleic acid molecules further comprise a sequence encoding a costimulatory domain. In some embodiments, the costimulatory domain comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof. In some embodiments, the costimulatory domain comprises an amino acid sequence selected from the group consisting of SEQ ID NOs: 20 and 22. In some embodiments, the encoded costimulatory domain comprises an amino acid sequence having at least one, two, or three but not more than 20, 10, or 5 modifications of an amino acid sequence of any of SEQ ID NOs: 20 and 22, or comprises an amino acid sequence with at least 95% identity thereto.

In some embodiments, the presently disclosed isolated nucleic acid molecules further comprise a sequence encoding an intracellular signaling domain. In some embodiments, the encoded intracellular signaling domain comprises a functional signaling domain of 4-1BB and/or a functional signaling domain of CD3 zeta. In some embodiments, the encoded intracellular signaling domain comprises an amino acid sequence having at least one, two, or three but not more than 20, 10 or 5 modifications of an amino acid sequence as set forth in SEQ ID NO: 24 or SEQ ID NO: 25, or comprises a amino acid sequence with at least 95% identity to the amino acid sequence of any of SEQ ID NO: 24 or SEQ ID NO: 25. In some embodiments, the encoded intracellular signaling domain comprises the amino acid sequence of SEQ ID NO: 20 and the amino acid sequence of SEQ ID NO: 24 or the amino acid sequence of SEQ ID NO: 22 and the amino acid sequence of SEQ ID NO: 25, wherein the sequences comprising the intracellular signaling domain are expressed in the same frame and as a single polypeptide chain. In some embodiments, the nucleic acid sequence encoding the intracellular signaling domain comprises (i) nucleotides 850-1143 of SEQ ID NO: 14 or a sequence with at least 95% identity thereto and/or nucleotides 1144-1479 of SEQ ID NO: 14 or a sequence with at least 95% identity thereto; or (ii) nucleotides 840-1122 of SEQ ID NO: 16 or a sequence with at least 95% identity thereto and/or nucleotides 1123-1461 of SEQ ID NO: 16 or a sequence with at least 95% identity thereto.

In some embodiments, the presently disclosed isolated nucleic acid molecules further comprise a leader sequence, optionally wherein the leader sequence comprises SEQ ID NO: 18.

The presently disclosed subject matter also provides isolated nucleic acid sequences encoding chimeric antigen receptors (CARs), wherein the CARs comprise (i) a binding domain that binds to a tumor-exclusive epitope of a human MUC1 polypeptide and (ii) a CD3 zeta signaling domain. In some embodiments, the isolated nucleic acids further encode a co-stimulatory signaling domain. In some embodiments, the co-stimulatory signaling domain is selected from the group consisting of the CD28 signaling domain and the 4-1BB signaling domain. In some embodiments, the binding domain is a human antibody or a fragment thereof comprising at least one paratope. In some embodiments, the antibody or the fragment thereof comprises a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10); and a light chain complementary determining region 1 (LC CDR1) comprising QDIVYGNGNTY (SEQ ID NO: 11), a light chain complementary determining region 2 (LC CDR2) comprising KVS (SEQ ID NO: 12), and a light chain complementary determining region 3 (LC CDR3) comprising FQGSHVPYT (SEQ ID NO: 13). In some embodiments, the CAR comprises an amino acid sequence as set forth in SEQ ID NO: 15 or SEQ ID NO: 17.

In some embodiments, the presently disclosed subject matter provides isolated polypeptides encoded by the isolated nucleic acid molecules disclosed herein. In some embodiments, the isolated polypeptides comprise an amino acid sequence selected from the group consisting of SEQ ID NO: 15 and SEQ ID NO: 17.

In some embodiments, the presently disclosed subject matter also provides vectors comprising the presently disclosed isolated nucleic acid molecules or the presently disclosed nucleotide sequences encoding a CAR of the presently disclosed subject matter. In some embodiments, the vector is selected from the group consisting of a DNA vector, an RNA vector, a plasmid, a lentivirus vector, an adenovirus vector, an adeno-associated virus (AAV) vector, and a retrovirus vector. In some embodiments, the presently disclosed vectors further comprise a promoter operably linked to the isolated nucleic acid molecule or the nucleotide sequence. In some embodiments, the promoter is an EF-1 promoter. In some embodiments, the vector is an in vitro transcribed vector. In some embodiments of the presently disclosed vectors, the isolated nucleic acid molecule or the nucleotide sequence further comprises and/or encodes a polyadenylation signal and/or a poly(A) tail. In some embodiments, the nucleic acid molecule or the nucleotide sequence in the vector further comprises a 3' untranslated region (3'-UTR).

The presently disclosed subject matter also provides in some embodiments vectors comprising a nucleic acid sequence encoding a chimeric antigen receptor (CAR), wherein the CAR comprises an antigen binding domain that binds to a tumor-exclusive epitope of human MUC1, a transmembrane domain, a costimulatory signaling domain of CD28, and a CD3 zeta signaling domain. In some embodiments, the isolated nucleic acid sequence encoding the CAR comprises the nucleic acid sequence of SEQ ID NO: 14 or SEQ ID NO: 16. In some embodiments, the antigen binding domain is an antibody or fragment thereof that binds to the tumor-exclusive epitope of human MUC1.

The presently disclosed subject matter also provides in some embodiments cells comprising the vectors disclosed herein. In some embodiments, the cell is a human T cell, optionally a $CD8^+$ T cell. In some embodiments, the presently disclosed cells comprise a nucleic acid sequence encoding a chimeric antigen receptor (CAR), the CAR comprising an antigen binding domain that binds to a tumor-exclusive epitope of MUC1, a transmembrane domain, a costimulatory signaling region comprising a CD28 signaling domain, and a CD3 zeta signaling domain. In some embodiments, the antigen binding domain is an antibody or a fragment thereof that binds to a tumor-exclusive epitope of MUC1. In some embodiments, the costimulatory signaling region further comprises an intracellular domain of a costimulatory molecule selected from the group consisting of CD2, CD27, 4-1BB, OX40, CD30, CD40, PD-1, ICOS, lymphocyte function-associated antigen-1 (LFA-1), CD7, LIGHT, NKG2C, B7-H3, and a ligand that specifically binds with CD83, or any combination thereof. In some embodiments, the cell is selected from the group consisting of a T cell, a Natural Killer (NK) cell, a cytotoxic T lymphocyte (CTL), and a regulatory T cell. In some embodiments, the cell exhibits an anti-tumor immunity when the antigen binding domain binds to the tumor-exclusive epitope of MUC1.

The presently disclosed subject matter also provides in some embodiments chimeric antigen receptor (CAR) molecules comprising a binding domain, a transmembrane domain, and an intracellular signaling domain, wherein the binding domain binds to a tumor-exclusive epitope of a human MUC1 polypeptide. In some embodiments, the binding domain is a subsequence of an antibody that binds to the tumor-exclusive epitope of a human MUC1 polypeptide, or a fragment thereof comprising a paratope of the antibody, optionally wherein the binding domain is human or humanized. In some embodiments, the binding domain comprises a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10); and a light chain complementary determining region 1 (LC CDR1) comprising QDIVYGNGNTY (SEQ ID NO: 11), a light chain complementary determining region 2 (LC CDR2) comprising KVS (SEQ ID NO: 12), and a light chain complementary determining region 3 (LC CDR3) comprising FQGSHVPYT (SEQ ID NO: 13). In some embodiments, the CAR comprises a light chain variable region comprising SEQ ID NO: 7 and/or a heavy chain variable region comprising SEQ ID NO: 5. In some embodiments, the binding domain is a scFv. In some embodiments, the binding domain comprises a light chain variable region comprising an amino acid sequence having at least one, two, or three but not more than 30, 20, or 10 modifications of an amino acid sequence of a light chain variable comprising SEQ ID NO: 7, or an amino acid sequence with at least 95% identity to SEQ ID NO: 7 and/or the binding domain comprises a heavy chain variable region comprising an amino acid sequence having at least one, two, or three but not more than 30, 20, or 10 modifications of an amino acid sequence of a heavy chain variable comprising SEQ ID NO: 5 or an amino acid sequence with at least 95% identity to SEQ ID NO: 5. In some embodiments, the transmembrane domain comprises a transmembrane domain of a protein selected from the group consisting of the T-cell receptor (TCR) alpha chain, the TCR beta chain, the TCR zeta chain, CD28, CD3 epsilon, CD45, CD4, CD5, CD8, CD9, CD16, CD22, CD33, CD37, CD64, CD80, CD86, CD134, CD137, and CD154. In some embodiments, the transmembrane domain comprises: (i) SEQ ID NO: 21 or SEQ ID NO: 23; (ii) an amino acid sequence having at least one, two, or three but not more than 20, 10, or 5 modifications of the amino acid sequence set forth in SEQ ID NO: 21 or SEQ ID NO: 23; or (iii) a sequence with at least 95% identity to SEQ ID NO: 21 or SEQ ID NO: 23. As used herein, the phrase "at least 95% identity" refers to a percent identity of in some embodiments at least 95%, in some embodiments at least 96%, in some embodiments at least 97%, in some embodiments at least 98%, and in some embodiments at least 99%. In some embodiments, an amino acid sequence is 100% identical to given nucleotide or amino acid sequence.

In some embodiments, the binding domain is connected to the transmembrane domain by a hinge region.

In some embodiments, the presently disclosed CAR molecules further comprise a costimulatory domain. In some embodiments, the costimulatory domain comprises a functional signaling domain of a protein selected from the group consisting of OX40, CD2, CD3, CD27, CD28, CD S, ICAM-1, LFA-1 (CD11a/CD18), and 4-1BB (CD137). In some embodiments, the costimulatory domain comprises SEQ ID NO: 20 or SEQ ID NO: 22. In some embodiments, the costimulatory domain comprises an amino acid sequence having at least one, two, or three but not more than 20, 10, or 5 modifications of SEQ ID NO: 20 or SEQ ID NO: 22, or a sequence with at least 95% identity to the amino acid sequence set forth in SEQ ID NO: 20 or SEQ ID NO: 22.

In some embodiments of the presently disclosed CAR molecules, the intracellular signaling domain comprises a functional signaling domain of 4-1BB, a functional signaling domain of CD3 zeta, or both. In some embodiments, the intracellular signaling domain comprises (i) an amino acid sequence as set forth in SEQ ID NO: 20 and/or SEQ ID NO: 24; or (ii) the amino acid sequence as set forth in SEQ ID NO: 22 and/or SEQ ID NO: 25. In some embodiments, the intracellular signaling domain comprises an amino acid sequence having at least one, two, or three but not more than 20, 10, or 5 modifications of the amino acid sequence as set forth in (i) SEQ ID NO: 20 and/or SEQ ID NO: 24; or (ii) SEQ ID NO: 22 and/or SEQ ID NO: 25. In some embodiments, the intracellular signaling domain comprises (a) the amino acid sequence as set forth in SEQ ID NO: 20 and the amino acid sequence as set forth in SEQ ID NO: 24; or (b) the amino acid sequence as set forth in SEQ ID NO: 22 and the amino acid sequence as set forth in SEQ ID NO: 25; and further wherein the sequences comprising the intracellular signaling domain are expressed in the same frame as each other and as a single polypeptide chain.

In some embodiments, the presently disclosed CAR molecules further comprise a leader sequence. In some embodiments, the leader sequence comprises an amino acid sequence as set forth in SEQ ID NO: 18 or an amino acid sequence with at least 95% identity thereto.

In some embodiments, the presently disclosed subject matter provides chimeric antigen receptors (CARs) comprising a human MUC1 binding domain, a hinge region, a transmembrane domain, a signaling domain, and a co-stimulatory domain, wherein the MUC1 binding domain comprises a monoclonal antibody TAB-004-derived single-chain variable fragment (scFv). In some embodiments, (i) the TAB-004-derived scFv comprises a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10); and a light chain complementary determining region 1 (LC CDR1) comprising QDIVYGNGNTY (SEQ ID NO: 11), a light chain complementary determining region 2 (LC CDR2) comprising KVS (SEQ ID NO: 12), and a light chain complementary determining region 3 (LC CDR3) comprising FQGSHVPYT (SEQ ID NO: 13); and/or (ii) the TAB-004-derived scFv comprises a light chain variable region comprises SEQ ID NO: 6; and/or (iii) the TAB-004-derived scFv comprises a heavy chain variable region comprises SEQ ID NO: 5; and/or (iv) the signaling domain comprises a CD3 zeta signaling domain; and/or (v) the co-stimulatory domain comprises a CD28 co-stimulatory domain. In some embodiments, the presently disclosed CARs comprise an amino acid sequence selected from the group consisting of SEQ ID NO: 15 and SEQ ID NO: 17. In some embodiments, the binding domain is human or humanized.

The presently disclosed subject matter also provides in some embodiments methods for making cells expressing anti-MUC1 CARs. In some embodiments, the methods comprise transducing a T cell with a vector as disclosed herein.

The presently disclosed subject matter also provides in some embodiments methods for generating persisting populations of genetically engineered T cells in a subject, optionally a human, diagnosed with cancer, in some embodiments a MUC1-associated cancer. In some embodiments, the methods comprise administering to a subject a T cell genetically engineered to express a CAR as disclosed herein. In some embodiments, the CAR comprises an antigen binding domain that binds to a tumor-exclusive epitope of a human MUC1 polypeptide, a transmembrane domain, a costimulatory signaling region comprising the CD28 signaling domain, and a CD3 zeta signaling domain, wherein the persisting population of genetically engineered T cells persists in the human for at least one month after administration. In some embodiments, the persisting population of genetically engineered T cells comprises at least one T cell that was administered to the human and/or a progeny cell thereof. In some embodiments, the persisting population of genetically engineered T cells comprises a memory T cell. In some embodiments, the persisting population of genetically engineered T cells persists in the human for at least three months after administration, optionally for at least four months, five months, six months, seven months, eight months, nine months, ten months, eleven months, twelve months, two years, or three years after administration. In some embodiments, the cancer is a MUC1-associated cancer.

The presently disclosed subject matter also provides in some embodiments methods for expanding a population of genetically engineered T cells in a subject, optionally a human, diagnosed with cancer, in some embodiments a MUC1-associated cancer, the method comprising administering to the human a T cell genetically engineered to express a CAR, wherein the CAR comprises an antigen binding domain that binds to a tumor-exclusive epitope of a human MUC1 polypeptide, a transmembrane domain, a costimulatory signaling region comprising the CD28 signaling domain, and a CD3 zeta signaling domain, wherein the administered genetically engineered T cell produces a population of progeny T cells in the human. In some embodiments, the progeny T cells in the human comprise a memory T cell. In some embodiments, the T cell administered to the human is an autologous T cell. In some embodiments, the population of progeny T cells persists in the human for at least three months, four months, five months, six months, seven months, eight months, nine months, ten months, eleven months, twelve months, two years, or three years after administration.

The presently disclosed subject matter also provides in some embodiments methods for modulating the amount of cytokine secreted by a T cell. In some embodiments, the methods comprise genetically engineering the T cell to express a CAR, wherein the CAR comprises an antigen binding domain that binds to a tumor-exclusive epitope of MUC1, a transmembrane domain, a costimulatory signaling region comprising the CD28 signaling domain, and a CD3 zeta signaling domain. In some embodiments, modulating the amount of cytokine secreted by a T cell reduces the proliferation of T regulatory cells in vivo, in vitro, or ex vivo.

The presently disclosed subject matter also provides in some embodiments methods for reducing the amount of activation-induced calcium influx into a T cell. In some embodiments, the methods comprise genetically engineering the T cell to express a CAR, wherein the CAR comprises an antigen binding domain that binds to a tumor-exclusive epitope of MUC1, a transmembrane domain, a costimulatory signaling region comprising the CD28 signaling domain, and a CD3 zeta signaling domain. In some embodiments, reducing the amount of activation-induced calcium influx into a T cell prevents activation-induced cell death of the T cell in vivo, in vitro, or ex vivo.

The presently disclosed subject matter also provides in some embodiments methods for providing an anti-tumor immunity to a mammal, optionally a human. In some embodiments, the methods comprise administering to the mammal an effective amount of a cell expressing a CAR molecule of the presently disclosed subject matter. In some embodiments, the cell is an autologous T cell. In some embodiments, the cell is an allogeneic T cell.

The presently disclosed subject matter also provides in some embodiments methods for treating a mammal having a MUC1-associated disease or disorder, the method comprising administering to the mammal an effective amount of a cell comprising a CAR molecule of the presently disclosed subject matter. In some embodiments, the MUC1-associated disease or disorder is selected from a proliferative disease such as a cancer or malignancy or a precancerous condition such as a myelodysplasia, a myelodysplastic syndrome, or a preleukemia, or is a non-cancer related indication associated with expression of MUC1. In some embodiments, the MUC1-associated disease or disorder is a cancer that expresses MUC1 selected from the group consisting of breast cancer, optionally Triple Negative Breast Cancer (TNBC; both BaA and BaB), Luminal A, Luminal B, and/or HER-2-type breast cancer; pancreatic cancer; and ovarian cancer. In some embodiments, the cells expressing the CAR molecule are administered as part of a combination therapy that also comprises administration of a cyclooxygenase inhibitor. In some embodiments, the cells expressing a CAR molecule are administered as part of a combination therapy that also comprises administering an agent that ameliorates one or more side effects associated with administration of the cell expressing the CAR molecule.

The presently disclosed subject matter also provides in some embodiments methods for providing anti-tumor immunity to a mammal, optionally a human. In some embodiments, the methods comprise administering to the mammal an effective amount of a genetically modified cell comprising an isolated nucleic acid sequence encoding a chimeric antigen receptor (CAR), wherein the isolated nucleic acid sequence comprises a sequence encoding a binding domain that binds to a tumor-exclusive epitope of MUC1 and a CD3 zeta signaling domain. In some embodiments, the cell is an autologous T cell.

The presently disclosed subject matter also provides in some embodiments methods for treating a MUC1-associated cancer in a human patient. In some embodiments, the methods comprise administering to the human patient a pharmaceutical composition comprising an anti-tumor effective amount of a population of modified human T cells, optionally modified autologous T cells, wherein the T cells comprise a nucleic acid sequence that encodes a chimeric antigen receptor (CAR), wherein the CAR comprises an antigen binding domain that binds to a tumor-exclusive epitope of MUC1, a hinge domain, a transmembrane domain, a CD28 costimulatory signaling region, and a CD3 zeta signaling domain. In some embodiments, the anti-tumor effective amount of T cells is $10^4$ to $10^9$ cells per kg body weight of the human patient. In some embodiments, the anti-tumor effective amount of T cells is $10^5$ to $10^6$ cells per kg body weight of the human patient. In some embodiments, the antigen binding domain is an antibody or a fragment thereof that binds to the tumor-exclusive epitope of MUC1. In some embodiments, the antigen binding fragment comprises a Fab fragment or an scFv. In some embodiments, the scFv comprises an amino acid sequence as set forth in amino acid residues 22-267 of SEQ ID NO: 15 or SEQ ID NO: 17, or an amino acid sequence with at least 95% identity to SEQ ID NO: 15 or SEQ ID NO: 17. In some embodiments, the scFv is encoded by a nucleic acid sequence comprising nucleotides 64-803 of SEQ ID NO: 14 or nucleotides 64-803 of SEQ ID NO: 16. In some embodiments, the transmembrane domain comprises an amino acid sequence as set forth in SEQ ID NO: 16 or SEQ ID NO: 18. In some embodiments, the CD3 zeta signaling domain comprises an amino acid sequence as set forth in SEQ ID NO: 19 or SEQ ID NO: 20. In some embodiments, the MUC1-associated cancer is selected from the group consisting of breast cancer, optionally Triple Negative Breast Cancer (TNBC; both BaA and BaB), Luminal A, Luminal B, and/or HER-2-type breast cancer; pancreatic cancer; ovarian cancer. In some embodiments, the modified T cells replicate in vivo in the human patient. In some embodiments, the modified T cells form memory T cells in the human patient. In some embodiments, the modified T cells are administered intravenously to the human patient. In some embodiments, the modified T cells persist in the human patient. In some embodiments, the modified T cells persist in the human patient for a period of at least three, four, five, six, seven, eight, nine, ten, eleven, twelve, eighteen, twenty-four, thirty, or thirty-six months after administration.

The presently disclosed subject matter also provides in some embodiments methods for stimulating a T cell-mediated immune response to a target cell population or tissue in a mammal, optionally a human. In some embodiments, the methods comprise administering to a mammal an effective amount of a cell genetically modified to express a CAR, wherein the CAR comprises an antigen binding domain that binds to a tumor-exclusive epitope of MUC1, a transmembrane domain, a costimulatory signaling region comprising the CD28 signaling domain, and a CD3 zeta signaling domain.

The presently disclosed subject matter also provides in some embodiments methods for inducing an anti-tumor immunity in a mammal, optionally a human. In some embodiments, the methods comprise administering to the mammal an effective amount of a cell genetically modified to express a CAR, wherein the CAR comprises an antigen binding domain that binds to a tumor-exclusive epitope of MUC1, a transmembrane domain, a costimulatory signaling region comprising the CD28 signaling domain, and a CD3 zeta signaling, thereby inducing an anti-tumor immunity in the mammal.

The presently disclosed subject matter also provides in some embodiments methods for treating a mammal, optionally a human, having a disease, disorder, or condition associated with expression of a tumor-exclusive epitope of MUC1. In some embodiments, the methods comprise administering to the mammal an effective amount of a cell genetically modified to express a CAR, wherein the CAR comprises an antigen binding domain that binds to the tumor-exclusive epitope of MUC1, a transmembrane domain, a costimulatory signaling region comprising the CD28 signaling domain, and a CD3 zeta signaling domain, thereby treating the mammal. In some embodiments, the cell is an autologous T cell.

The presently disclosed subject matter also provides in some embodiments methods for treating a human with cancer. In some embodiments, the methods comprise administering to the human a T cell genetically engineered to express a CAR, wherein the CAR comprises an antigen binding domain that binds to a tumor-exclusive form of MUC1, a transmembrane domain, a costimulatory signaling region comprising the CD28 signaling domain, and a CD3 zeta signaling domain. In some embodiments, the methods further comprise administering a cyclooxygenase inhibitor, optionally a cyclooxygenase-2-selective inhibitor, to the subject as part of a combination therapy with the T cell genetically engineered to express the CAR.

The presently disclosed subject matter also provides in some embodiments methods for imaging a MUC1-associated tumor. In some embodiments, the methods comprise (a) providing a mammal with a MUC1-associated tumor; (b) administering to the mammal a CAR as disclosed herein, wherein the CAR further comprises a detectable moiety; and (c) detecting the detectable moiety in the mammal, whereby a tumor is imaged in the mammal. In some embodiments, the MUC1-associated tumor is selected from the group consisting of a breast tumor, optionally a Triple Negative Breast Cancer (TNBC; both BaA and BaB) tumor, a Luminal A tumor, a Luminal B tumor, and/or a HER-2-type breast tumor; a pancreatic tumor; and an ovarian tumor. In some embodiments, detectable moiety is detectable using a technique selected from the group consisting of X-ray imaging, positron emission tomography (PET) imaging, single photon emission computed tomography (SPECT) imaging, computed tomography (CT) imaging, and magnetic resonance imaging (MRI).

The presently disclosed subject matter also provides in various embodiments the presently disclosed isolated nucleic acid molecules, the presently disclosed isolated polypeptide molecules, the presently disclosed CARs, the presently disclosed vectors, and the presently disclosed cells for use in the treatment of a disease, condition, or disorder associated with overexpression of MUC1, optionally wherein the disease is a cancer.

Thus, it is an object of the presently disclosed subject matter to provide isolated antibodies, and fragments and derivatives thereof, including but not limited to CARs, which bind to antigens present in tumors.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a series of photomicrographs depicting the binding of the exemplary antibody to human tumors at Stages 0 (normal pancreatic tissue as a negative control) and 2-4. FIG. 1B is a series of photomicrographs depicting the binding of an exemplary antibody of the presently disclosed subject matter to spontaneous tumors present in the pancreas of 6, 16, 26, and 34 week old transgenic mice that carried a human MUC1 transgene and a K-ras$^{G12D}$ mutation.

FIG. 2A depicts binding of the exemplary antibody of the presently disclosed subject matter to breast tissue at various stages of disease progression including a lack of binding to normal breast tissue, binding to cells of preinvasive ductal carcinoma in situ (DCIS), binding to cancer cells in invasive breast cancer but not to adjacent normal cells surrounding the invasive breast cancer, and binding to cells of intralymphatic metastasis but not to adjacent normal cells. FIG. 2B provides 100× and 400× magnifications of photomicrographs showing a lack of binding of the exemplary antibody of the presently disclosed subject matter to cells associated with benign conditions (exemplified by benign breast tissue, fibroadenoma tissue, and tissue in which inflammation was observed), and specific binding of the exemplary antibody of the presently disclosed subject matter to cells of malignant conditions reparesented by invasive triple negative breast cancer (TNBC) and invasive breast cancer and not surrounding normal cells.

FIG. 4A is a line graph showing that the exemplary TAB-004 antibody (black diamonds) enhanced specific lysis of KCM tumor cells at various effector (NK cells) to target ratios (E:T ratio) relative to a negative control (minus TAB-004 antibody; open circles). FIG. 4B is a bar graph showing that conjugation of the exemplary TAB-004 antibody to CpG ODN (TAB+ CpG ODN) further enhanced specific lysis of tumor cells at various E:T ratios relative to the unconjugated antibody (TAB).

FIG. 5A is a line graph showing the measured tumor volumes (in mm measured by digital calipers) in mice treated with phosphate-buffered saline (PBS) alone (negative control; filled squares), CpG ODN alone (X's), the unconjugated TAB-004 antibody (open circles), or the TAB-004-CpG ODN conjugate (filled circles). FIG. 5B is a bar graph showing the changes in tumor volumes in mice at 19 and 27 days after the final treatment was administered. Of note is the observation that at 19 and 27 days post-treatment, the tumor volumes in the mice treated with TAB-004-CpG ODN had not increased as compared to the control mice (i.e., PBS alone, CpG ODN alone, or TAB-004 alone). *: p<0.5. PBS alone (negative control; white bars); CpG ODN alone (hatched bars); unconjugated TAB-004 antibody (black bars); TAB-004-CpG ODN conjugate (cross-hatched bars).

FIGS. 7A and 7B are histograms of fluorescence-activated cell sorting (FACS) separations of CD133$^+$ (FIG. 7A) versus CD24$^+$/CD44$^+$/EpCAM$^+$ (FIG. 7B) cells and the extent to which the TAB-004 antibody disclosed herein bound to these populations. The left trace in each panel corresponds to sorting with a negative control antibody, and the right trace in each panel corresponds to sorting with the TAB-004 antibody.

FIG. 8A is a scatter plot showing the distributions of cells in the absence of either antibody. FIG. 8B is a scatter plot showing the distributions of cells stained with an isotype control. FIG. 8C is a series of scatter plots showing the distributions of cells in normal tissue stained with the TAB-004 antibody versus a CXCR4 antibody. FIG. 8D is a series of scatter plots showing the distributions of cells in pancreatic adenocarcinoma tissue stained with the TAB-004 antibody versus a CXCR4 antibody.

In FIG. 9A, PANC1 pancreatic cancer cell line cells were detected by the TAB-004-PE antibody. In FIGS. 9B and 9C, circulating tumor cells present in the blood from two patients (patient number 1 and patient number 2, respectively) were detected by the TAB-004-PE antibody (see the blue line in FIG. 9B and the blue, yellow, and green lines in FIG. 9C) but not the EpCAM-PE antibody (see the red lines in FIGS. 9B and 9C) that is currently in use.

FIG. 16A is a depiction of a first basic structure of an exemplary anti-tMUC CAR expression vector. In this embodiment, an anti-tMUC CAR cassette (depicted in purple) is operably linked downstream of a 5'-LTR and CMV promoter. The expression vector further includes neomycin resistance gene ($neo^r$) and a 3'LTR. An ampicillin resistance gene ($Amp^r$) is present in the vector backbone for propagating the vector in bacteria. FIG. 16B is a depiction of exemplary structures for $2^{nd}$ and $3^{rd}$ generation CAR constructs. A $2^{nd}$ generation control CAR construct can comprise a CD8a leader sequence upstream of a Myc tag, a transmembrane domain (TM), a CD28 costimulatory signaling region, and a CD3 zeta signaling domain (see "$2^{nd}$ Generation Control CAR", first example). A second generation control CAR construct can optionally also include an mKate domain (see "$2^{nd}$ Generation Control CAR", second example). A $2^{nd}$ generation MUC1* CAR control construct can be derived from the $2^{nd}$ Generation Control CAR by cloning an anti-MUC1* scFv between the CD8a leader sequence upstream and the Myc tag. The anti-MUC1* scFv can comprise a TAB-004 light chain coding sequence/linker/TAB-004 heavy chain coding sequence cassette cloned between the CD8a leader sequence and the Myc tag (see "$2^{nd}$ Generation MUC1* CAR", first example). Here as well, the second generation MUC1* CAR construct can optionally include an mKate domain, in some embodiments downstream of the CD3 zeta signaling domain (see "$2^{nd}$ Generation MUC1* CAR", second example). $3^{rd}$ generation MUC1* CAR constructs further comprise an additional stimulatory domain, which in some embodiments can be a 4-1BB (CD137) stimulatory domain (e.g., comprising amino acids 382-423 of SEQ ID NO: 34, or a biologically active fragment or derivative thereof; see "$3^{rd}$ Generation MUC1* CAR", first example), or an OX40 (CD134) stimulatory domain (e.g., comprising amino acids 382-443 of SEQ ID NO: 32, or a biologically active fragment or derivative thereof; see "$3^{rd}$ Generation MUC1* CAR", second example), which in some embodiments is present between the CD28 costimulatory signaling region and the CD3 zeta signaling domain (see "$3^{rd}$ Generation MUC1* CAR", second example). FIG. 16C is a graph of the results of FACS analysis of T cells infected with viral supernatants recovered from GP2-293 cells 48 hours after being transfected with a VSV-G virus envelope plasmid DNA together with an exemplary TAB-004 CAR plasmid DNA (blue trace), or a VSV-G virus envelope plasmid DNA together with a control CAR plasmid DNA in which the TAB-004 scFv had been removed (red trace). T cells were harvested and stained with Protein L-FITC. Cells were evaluated for fluorescence intensity and percent FITC+ cells on Fortessa, and analyzed by FlowJo. FIG. 16D is a fluorescence micrograph of T cells infected with an exemplary CAR of the presently disclosed subject matter that included an mKate fluorescence moiety. Comparison of FIGS. 16C and 16D suggested that at least 80% of the cells were infected with the CAR constructs.

FIGS. 17A-17E are a series of fluorescent images and photographs of binding of an IndoCyanine Green (ICG)-tagged TAB-004 monoclonal antibody to tumors present in a transgenic mouse model of spontaneous metastatic breast cancer (PyV MT) expressing human MUC1 (MMT mice). In FIGS. 17A-17C, MMT mice with tumors and/or hyperplastic glands were injected intravenously with 12.5 µg of TAB-ICG and imaged using an IVIS imager 24 hours post injection. MMT mice are shown at 12 weeks (FIG. 17A), 16 weeks (FIG. 17B), and 18 weeks of age (FIG. 17C). FIG. 17D shows the presence of palpable tumors at 20 weeks of age. FIG. 17E shows TAB-ICG accumulation ex vivo in all of the mammary gland tumors.

FIGS. 18A-18D are a series of fluorescent images showing specific homimg of the ICG-tagged TAB-004 antibody to tumor sites in mice bearing PyV MT tumors (MUC1 null negative control; FIG. 18A), PyV MT.MUC1 tumors (MMT, MUC1+ positive control; FIG. 18B), HCC70 cell triple negative breast cancer (TNBC) tumors (MUC1+; FIG. 18C), and AU565 TNBC cell tumors (MUC1+; FIG. 18C) imaged 4 hours post-injection with antibody. Imaging was repeated as tumors progressed (indicated as days post tumor challenge). No localization of the ICD-tagged TAB-004 was detected in the MUC1-null tumors. Each of FIGS. 18A-18D is accompanied by a graph showing the growth of the tumor from 7-21 days (FIGS. 18A and 18B) or from 7 to 54 days (FIGS. 18C and 18D).

FIG. 19A shows expression of an exemplary $2^{nd}$ generation CAR referred to herein as TAB-28z-mKate (see FIG. 16B, "$2^{nd}$ Generation MUC1* CAR, second example). FIG. 19B shows expression of an exemplary $3^{rd}$ generation CAR referred to herein as TAB-28OXz-mKate (see FIG. 16B, "$3^{rd}$ Generation MUC1* CAR, second example) Expression of the CARs is noted in red due to the presence of the mKate label in the constructs. In each of FIGS. 19A and 19B, the right panel is the detection of mKate expression alone (red), and the left panel is an overlay of mKate expression (red) and DAPI staining (blue), the latter of which stains the nuclei of the cells.

FIG. 20A shows the results for an exemplary $2^{nd}$ generation CAR (TAB-28z-mKate), and FIG. 20B shows the results for an exemplary $3^{rd}$ generation CAR (TAB-28OXz-mKate). For each of FIGS. 20A and 20B, the left panel provides a schematic diagram of binding of the CAR-expressing T cell to a tumor cell, the center panel is a light microscopy image of complex formation between a CAR-expressing T cell and a tumor cell, and the right panel is a fluorescence microscopy image showing the CAR-expressing T cell binding to one but not all tumor cells. The surface expression of the CARs is shown in reference fluorescence due to the presence of the mKate moiety in the $2^{nd}$ and $3^{rd}$ generation CARs. FIG. 21C shows that T cells that express an exemplary CAR of the presently disclosed subject matter (see the red fluorescence in the right panel of FIG. 20C) does not bind to a tumor cell that lacks MUC1 expression (see the light microscopy image in the left panel and the blue DAPI-stained nucleus of the tumor cell in the right panel). It is notable that despite the apparent proximity of the T cell and the tumor cell as shown in the left panel, the T cell did not become activated and did not bind to the MUC1-minus tumor cell as evidenced by the lack of CAR accumulation at the interface between the T cell and the tumor cell (compare the increased accumulation of mKate signal in FIGS. 20A and 20B when the T cell interacts with a MUC1+ tumor cell).

FIG. 16B, "$2^{nd}$ Generation MUC1* CAR, first example) killed approximately 30% of tumor cells at a 25:1 E:T ratio.

BRIEF DESCRIPTION OF THE SEQUENCE LISTING

Figure 1A:
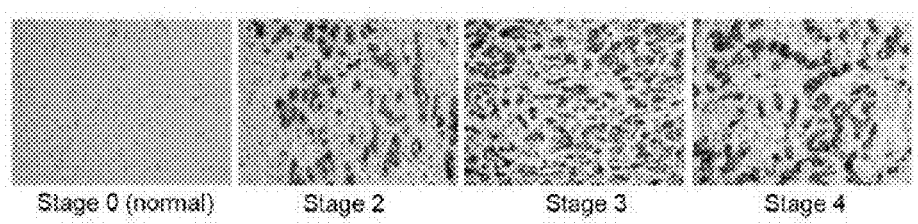
FIGS. 1A and 1B are a series of photomicrographs depicting specific binding of an exemplary antibody of the presently disclosed subject matter to human and mouse pancreatic tumors. The dark staining in the panels is indicative of positive binding of the exemplary antibody to cells present in the sample.

SEQ ID NO: 1 is an amino acid sequence of a human MUC1 gene product. It corresponds to GENBANK® Accession No. AAA60019.

SEQ ID NO: 2 is an amino acid sequence of a human K-ras oncogene product. It corresponds to GENBANK® Accession No. NP_004976.

SEQ ID NO: 3 is an amino acid sequence of peptide to which the TAB-004 antibody disclosed herein can bind in an ELISA assay. The peptide thus includes an epitope to which the TAB-004 antibody binds specifically.

SEQ ID NOs: 4 and 5 are the nucleotide and encoded amino acid sequences, respectively, of the heavy chain of the TAB-004 antibody disclosed herein.

SEQ ID NOs: 6 and 7 are the nucleotide and encoded amino acid sequences, respectively, of the light chain of the TAB-004 antibody disclosed herein.

SEQ ID NOs: 8-10 are the amino acid sequences of CDR1, CDR2, and CDR3, respectively, of the heavy chain of the TAB-004 antibody disclosed herein.

SEQ ID NOs: 11-13 are the amino acid sequences of CDR1, CDR2, and CDR3, respectively, of the light chain of the TAB-004 antibody disclosed herein.

SEQ ID NO: 14 is a nucleic acid sequence of an open reading frame encoding an exemplary human sequence-based anti-tMUC CAR.

SEQ ID NO: 15 is the amino acid sequence encoded by SEQ ID NO: 14.

SEQ ID NO: 16 is a nucleic acid sequence of an open reading frame encoding an exemplary mouse sequence-based anti-tMUC CAR.

SEQ ID NO: 17 is the amino acid sequence encoded by SEQ ID NO: 16.

SEQ ID NO: 18 is an amino acid sequence of an exemplary human T-cell surface glycoprotein CD8 leader sequence. It corresponds to amino acids 1-21 of SEQ ID NOs: 15 and 17 and also amino acids 1-21 of GENBANK® Accession No. NP_741969.1.

SEQ ID NO: 19 is the amino acid sequence of an exemplary peptide linker. It corresponds to amino acids 140-154 of SEQ ID NOs: 15 and 17.

SEQ ID NO: 20 is an amino acid sequence of a human CD28 domain. It corresponds to amino acids 284-381 of SEQ ID NO: 15 and also amino acids 123-220 of GENBANK® Accession No. NP_006130.1.

SEQ ID NO: 21 is an amino acid sequence of a transmembrane domain of the human CD28 domain of SEQ ID NO: 15. It corresponds to amino acids 314-340 of SEQ ID NO: 15 and also amino acids 153-179 of GENBANK® Accession No. NP_006130.1.

SEQ ID NO: 22 is an amino acid sequence of a mouse CD28 domain. It corresponds to amino acids 280-374 of SEQ ID NO: 17 and also amino acids 124-218 of GENBANK® Accession No. NP_031668.3.

SEQ ID NO: 23 is an amino acid sequence of a transmembrane domain of the mouse CD28 domain of SEQ ID NO: 17. It corresponds to amino acids 307-333 of SEQ ID NO: 17 and also amino acids 151-177 of GENBANK® Accession No. NP_031668.3.

SEQ ID NO: 24 is an amino acid sequence of a human CD3zeta domain. It corresponds to amino acids 382-493 of SEQ ID NO: 15 and also amino acids 52-163 of GENBANK® Accession No. NP_000725.1.

SEQ ID NO: 25 is an amino acid sequence of a mouse CD3zeta domain. It corresponds to amino acids 375-487 of SEQ ID NO: 17 and also amino acids 52-164 of GENBANK® Accession No. NP_001106862.1.

SEQ ID NO: 26 is an amino acid sequence of a human IgD hinge region. It corresponds to amino acids 101-158 of GENBANK® Accession No. AAA52771.1.

SEQ ID NOs: 27 and 28 are the nucleotide sequences of exemplary oligonucleotide primers that can be employed for amplifying subsequences of the light and heavy chains of an exemplary human CAR plasmid. The amplified product corresponds to nucleotides 329-554 of SEQ ID NO: 14.

SEQ ID NO: 29 is an exemplary nucleotide sequence of a representative $2^{nd}$ generation CAR of the presently disclosed subject matter. This CAR, referred to as human CAR "TAB-28z-mKATE", includes an open reading frame that encodes a CD8 leader (nucleotides 1-63 of SEQ ID NO: 29) fused to the TAB-004 heavy chain variable region sequence (nucleotides 64-417 of SEQ ID NO: 29), a first linker (nucleotides 418-462 of SEQ ID NO: 29), the TAB-004 light chain variable region sequence (nucleotides 463-801 of SEQ ID NO: 29), a myc epitope tag (nucleotides 802-849 of SEQ ID NO: 29), a CD28/CD3zeta domain (nucleotides 850-1479 of SEQ ID NO: 29), a second linker (nucleotides 1480-1518 of SEQ ID NO: 29), and an mKATE2 fluorescent moiety (nucleotides 1519-2214 of SEQ ID NO: 29).

SEQ ID NO: 30 is the amino acid sequence encoded by nucleotides 1-2214 of SEQ ID NO: 29. It includes amino acids that correspond to a CD8 leader (amino acids 1-21 of SEQ ID NO: 30) fused to the TAB-004 heavy chain variable region sequence (amino acids 22-139 of SEQ ID NO: 30), a first linker (amino acids 140-154 of SEQ ID NO: 30), the TAB-004 light chain variable region sequence (amino acids 155-267 of SEQ ID NO: 30), a myc epitope tag (amino acids 268-283 of SEQ ID NO: 30), a CD28/CD3zeta domain (amino acids 284-493 of SEQ ID NO: 30), a second linker (amino acids 494-506 of SEQ ID NO: 30), and an mKATE2 fluorescent moiety (amino acids 507-738 of SEQ ID NO: 30).

SEQ ID NO: 31 is an exemplary nucleotide sequence of a representative $3^{rd}$ generation CAR of the presently disclosed subject matter. This CAR, referred to as human CAR "TAB-28-OX40-z", includes an open reading frame that encodes a CD8 leader (nucleotides 1-63 of SEQ ID NO: 31) fused to the TAB-004 heavy chain variable region sequence (nucleotides 64-417 of SEQ ID NO: 31), a first linker (nucleotides 418-462 of SEQ ID NO: 31), the TAB-004 light chain variable region sequence (nucleotides 463-801 of SEQ ID NO: 31), a myc epitope tag (nucleotides 802-849 of SEQ ID NO: 31), a CD28 stimulatory domain (nucleotides 850-1143 of SEQ ID NO: 31), an OX40 stimulatory domain (nucleotides 1144-1329 of SEQ ID NO: 31), and a CD3zeta domain (nucleotides 1330-1665 of SEQ ID NO: 31).

SEQ ID NO: 32 is the amino acid sequence encoded by nucleotides 1-1668 of SEQ ID NO: 31. It includes amino acids that correspond to a CD8 leader (amino acids 1-21 of SEQ ID NO: 32) fused to the TAB-004 heavy chain variable region sequence (amino acids 22-139 of SEQ ID NO: 32), a first linker (amino acids 140-154 of SEQ ID NO: 32), the TAB-004 light chain variable region sequence (amino acids 155-267 of SEQ ID NO: 32), a myc epitope tag (amino acids 268-283 of SEQ ID NO: 32), a CD28 stimulatory domain (amino acids 284-381 of SEQ ID NO: 32), an OX40 stimulatory domain (amino acids 382-443 of SEQ ID NO: 32), and a CD3zeta domain (amino acids 444-555 of SEQ ID NO: 32).

SEQ ID NO: 33 is an exemplary nucleotide sequence of a representative $3^{rd}$ generation CAR of the presently disclosed subject matter. This CAR, referred to as human CAR "TAB-28BBz", includes an open reading frame that encodes a CD8 leader (nucleotides 1-63 of SEQ ID NO: 33) fused to the TAB-004 heavy chain variable region sequence (nucleotides 64-417 of SEQ ID NO: 33), a first linker (nucleotides 418-462 of SEQ ID NO: 33), the TAB-004 light chain variable region sequence (nucleotides 463-801 of SEQ ID NO: 33), a myc epitope tag (nucleotides 802-849 of SEQ ID NO: 31), a CD28 stimulatory domain (nucleotides 850-1143 of SEQ ID NO: 33), a 4-1BB stimulatory domain (nucleotides 1144-1269 of SEQ ID NO: 33), and a CD3zeta domain (nucleotides 1270-1605 of SEQ ID NO: 33).

SEQ ID NO: 34 is the amino acid sequence encoded by nucleotides 1-1668 of SEQ ID NO: 33. It includes amino acids that correspond to a CD8 leader (amino acids 1-21 of SEQ ID NO: 34) fused to the TAB-004 heavy chain variable region sequence (amino acids 22-139 of SEQ ID NO: 34), a first linker (amino acids 140-154 of SEQ ID NO: 34), the TAB-004 light chain variable region sequence (amino acids 155-267 of SEQ ID NO: 34), a myc epitope tag (amino acids 268-283 of SEQ ID NO: 34), a CD28 stimulatory domain (amino acids 284-381 of SEQ ID NO: 34), a 4-1BB stimulatory domain (amino acids 382-423 of SEQ ID NO: 34), and a CD3zeta domain (amino acids 424-535 of SEQ ID NO: 34).

DETAILED DESCRIPTION

About 15-20 percent of all breast cancers in the U.S. are Triple Negative Breast Cancer (TNBC). Although anyone can get this type of breast cancer, research shows that younger women, African American women, and women who have BRCA1 gene mutations are more likely to get TNBC. TNBC normally grows faster and is treated with surgery, chemotherapy, and radiation as first line treatment. However, tumors frequently recur quickly and generally cannot be effectively treated with hormone or Her2-targeted therapy. Once chemoresistance sets in, it is typically very difficult to treat and tumors more often than not metastasize to distant organs. Thus, treatment-refractory metastatic TNBC is a major challenge.

Further, most TNBC is basal-like, a molecular subtype that is generally associated with poor prognosis. Patients with early-stage basal-like TNBC are at a higher risk of relapse.

Approximately 94% of early stage TNBCs overexpresses an altered form of MUC1 on its surface (Siroy et al., 2013), and this can potentially serve as a protein for targeted therapy. A unique antibody that can recognize and bind a tumor-specific form of MUC1 (referred to herein as "tMUC") but not the normal form of MUC1 (referred to herein as "nMUC") is described in U.S. Pat. No. 8,518,405 to Mukherjee (incorporated herein by reference in its entirety).

Given the high expression of tMUC in TNBC, the presently disclosed subject matter related in some embodiments to generating designer T cells that comprise a chimeric antigen receptor (CAR) targeted against tMUC using scFv fragments isolated from the unique tMUC antibody described in U.S. Pat. No. 8,518,405 to Mukherjee. This will target the T cells that comprise the anti-tMUC CAR to tumors that express the tMUC epitope, leading to activation of the anti-tMUC CAR-T cells and killing of the tumor cells expressing tMUC. Because tumors produce an abundance of prostaglandins (PGE2) that can render T cells non-functional (Basu et al., 2004; Basu et al., 2005; Basu et al., 2006), MUC1-specific immune therapies have been demonstrated to fail when given in the absence of inhibitors of COX-2/PGE2 pathway (Basu et al., 2006; Muller & Scherle, 2006; Mukherjee et al., 2009). Furthermore, when adoptively transferred, MUC1-CTLs have been shown to become non-functional in the tumor microenvironment (Mukherjee et al., 2003a), possibly due to tumor-associated PGE2 production. Thus, in some embodiments a combination therapy of an anti-tMUC CAR-T cell with oral administration of cyclooxygenase inhibitors including, but not limited to celecoxib, that will reduce the production of PGE2 in the tumor microenvironment is also disclosed herein.

Immunotherapy of cancer has gained much attention in the past decade with the development of CAR technology that can activate and redirect patient T cells to kill tumors that overexpress specific antigens. CARs are fusion receptors that comprise an antibody-derived single-chain fragment variable (scFv) polypeptide coupled via hinge and transmembrane elements to a T cell signaling and co-stimulatory domain. This technology is in its early stages of development and has not been fully exploited for the treatment of metastatic TNBC.

In particular, anti-MUC1-based immunotherapies have not lived up to their promise, possibly due to several factors. First, the shedding of soluble MUC1 might inhibit antibody binding to tumor cells. Second, structural diversity occurs in the MUC1 gene products from alternative splicing and altered glycosylation. Additionally, tumor-derived MUC1 can impair T cell growth and shield transformed cells from killing by NK and T cells. Unlike T cell receptors (TCRs) generally, CARs are targeted to native tumor-associated cell surface molecules.

Recently, a new antibody that specifically recognizes the tumor-associated form of MUC1 (tMUC) but not the normal form of MUC1 in several subtypes of breast cancers including TNBC was described (designated TAB-004; see U.S. Pat. No. 8,518,405 to Mukherjee). tMUC is an aberrant form of MUC1 and is expressed in greater than 95% of human breast cancers. tMUC therefore is a promising target for therapeutic intervention including immunotherapy.

MUC1 is a transmembrane mucin glycoprotein that is normally expressed on all glandular epithelial cells that form the major organs including the breast. In normal cells, MUC1 is only expressed on the apical surface and is heavily glycosylated with the core protein sequestered by the carbohydrates. As cells transform to a malignant phenotype, expression of MUC1 increases several fold, and the expression is no longer restricted to the apical surface but it is found all around the cell surface and in the cytoplasm. In addition, the glycosylation of tumor-synthesized MUC1 is aberrant, with greater exposure of the peptide core than is found in normal tissues. Little is known regarding the specifics of the aberrant glycosylation.

Thus, MUC1 has been an interesting target molecule for immunotherapy (reviewed in Acres & Limacher, 2005; Kimura & Finn, 2013). In 2009, National Cancer Institute launched a pilot project to prioritize cancer antigens to target for immunotherapy and identified MUC1 as the 2nd most optimal target (Cheever et al., 2009). MUC1 is upregulated on several epithelial tumors and its pattern of expression, its role in tumor progression, and its therapeutic potential has been extensively studied (reviewed in Gendler, 2001; Singh & Hollingsworth, 2006; Kufe, 2009; Beatson et al., 2010; Nath & Mukherjee, 2014). However, specific targeting of tumor-specific MUC1 epitopes versus epitopes present on normal MUC1 polypeptides remains a challenge.

Several antibodies are being developed against MUC1 for therapeutic use. Pemtumomab (also known as HMFG1) is in Phase III clinical trials as a carrier to deliver the radioisotope Yttrium-90 into tumors in ovarian cancer (reviewed in Scott et al., 2012). CA15-3 (also the HMFG1 antibody), CA27-29, and CA19-9 are all antibodies to MUC1 that are used to assess levels of circulating MUC1 in patients with cancer. However, these antibodies have shown limited utility as therapeutic agents or as biomarkers because they cannot distinguish effectively between MUC1 expressed on normal versus transformed tumor epithelia. Stated another way, none of these antibodies appear to be targeted to a tumor-specific MUC1 epitope.

A new antibody that is highly specific for a tumor-specific form of MUC1 (tMUC) is designated TAB-004 and is described in U.S. Pat. No. 8,518,405 (see also Curry et al., 2013). While Pemtumomab (HMFG1) was developed using human milk fat globules as the antigen (Parham et al., 1988), TAB-004 was developed using tumors expressing an altered form of MUC1 (Tinder et al., 2008). TAB-004 recognizes the altered glycosylated epitope within the MUC1 tandem repeat sequence. This area is accessible for antigenic detection in tMUC but is blocked from antigenic detection in normal MUC1 by large branches of glycosylation (Gendler, 2001; Mukherjee et al., 2003b; Hollingsworth & Swanson, 2004; Kufe, 2009). Importantly, TAB-004 is different from the epitopes recognized by other MUC1 antibody and has unique complementary determinant regions (CDRs) of the heavy and light chains. The antibody binds the target antigen with high binding affinity at 3 ng/ml (20 pM) and does not bind unrelated antigens (Curry et al., 2013). Thus, TAB-004 distinguishes between normal and tumor form of MUC1 while HMFG1 (Pemtumomab) does not (see U.S. Pat. No. 8,518,405).

Immunotherapy of cancer has gained much attention in the past decade with the development of chimeric antigen receptor (CAR) technology that can activate and redirect patient T cells to kill tumors that over-express a specific antigen. Recent clinical trial data demonstrate that modification of T cells with CARs is a promising strategy. T cells containing CARs with costimulatory domains exhibit improved activity against tumors (Bollard et al., 2007; Rosenberg et al., 2008; Porter et al., 2011; Till et al., 2012).

Numerous preclinical studies have demonstrated that CARs endowed with costimulatory endodomains, such as CD28, OX40, or 4-1BB (commonly referred to as "second generation" CARs), augment T-cell activity both in vitro and in vivo compared with first-generation CARs, which lack the costimulatory endodomains. These enhanced CARs were designed to mimic normal physiology, where both a primary TCR signal and a second costimulatory signal are required for full activation of T cells (Wang et al., 2007). Most of the promising results have been seen in patients with CLL, B-cell lymphomas, other hematopoietic tumors, and melanoma. However, to date this technology has not been successfully employed for the treatment of metastatic TNBC.

The presently disclosed subject matter will be now be described more fully hereinafter with reference to the accompanying Figures and EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Following long-standing patent law convention, the terms "a", "an", and "the" refer to "one or more" when used in this application, including in the claims. For example, the phrase "an antibody" refers to one or more antibodies, including a plurality of the same antibody. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition, and are encompassed within the nature of the phrase "consisting essentially of".

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

As used herein, the terms "condition", "disease condition", "disease", "disease state", and "disorder" refer to physiological states in which diseased cells can be targeted with the CARs of the presently disclosed subject matter, expressing, for example, antibodies against specific antigens and/or epitopes on the diseased cells (e.g., tMUC). Any cell that expresses a tMUC epitope can be targeted with the CARs of the presently disclosed subject matter, and any disease, disorder, or condition associated with expression of a tMUC epitope can be treated, and/or a symptom thereof can be ameliorated, using the CARs of the presently disclosed subject matter.

As used herein, the phrase "disease targeted by genetically modified cells" encompasses the targeting of any cell involved in any manner in any disease by the genetically modified cells of the presently disclosed subject matter, irrespective of whether the genetically modified cells target diseased cells or healthy cells to effectuate a therapeutically beneficial result. In some embodiments, the genetically modified cells target diseased cells only in order to effectuate a therapeutically beneficial result. The genetically modified cells include but are not limited to genetically modified T-cells, NK cells, hematopoietic stem cells, pluripotent embryonic stem cells, and embryonic stem cells. The genetically modified cells express the CARs of the presently disclosed subject matter, which CARs can target any of the antigens and/or epitopes expressed on the surface of target cells, including the tMUC epitope expressed on the surface of various cancer and tumor cells.

As used herein in the context of molecules, the term "effector" refers to any molecule or combination of molecules whose activity it is desired to deliver/into and/or localize at a cell. Effectors include, but are not limited to labels, cytotoxins, enzymes, growth factors, transcription factors, drugs, etc. As used herein in the context of cells of the immune system, the term "effector" refers to an immune system cell that can be induced to perform a specific function associated with an immune response to a stimulus. Exemplary effector cells include, but are not limited to natural killer (NK) cells and cytotoxic T cells ($T_c$ cells).

As used herein, the phrase "effector function" refers to the specialized function of a differentiated cell. An effector function of a T-cell, for example, can be cytolytic activity or helper activity including the secretion of cytokines.

As used herein, the phrases "genetically modified cells", "redirected cells", "genetically engineered cells", and "modified cells" refer to cells that express a CAR of the presently disclosed subject matter.

As used herein, the phrase "immune cell" refers to the cells of a mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

As used herein, the phrase "immune response" refers to immunities including but not limited to innate immunity, humoral immunity, cellular immunity, immunity, inflammatory response, acquired (adaptive) immunity, autoimmunity, and/or overactive immunity.

As used herein, the term "mammal" refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

As used herein, the phrase "MUC1-associated cancer" is a tumor or cancer or a cell therefrom in which a MUC1 gene product is overexpressed to an extent that the MUC1 gene product can be used to distinguish cancerous from non-cancerous cells. Exemplary MUC1-associated cancers include but are not limited to Triple Negative Breast Cancer (TNBC; both BaA and BaB), Luminal A, Luminal B, and/or HER-2-type breast cancer; pancreatic cancer; and ovarian cancer.

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection. For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters. In some embodiments, a percent identity is calculated over the full length of one or both of the two sequences being compared.

Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (e.g., GAP, BESTFIT, FASTA, and TFASTA), or by visual inspection. See generally, Ausubel et al., 1992.

An exemplary algorithm for determining percent sequence identity and sequence similarity is the BLAST algorithm, which is described in Altschul et al., 1990. Software for performing BLAST analyses is publicly available through the website of the United States National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1989.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

The term "polynucleotide" as used herein includes but is not limited to DNA, RNA, complementary DNA (cDNA), messenger RNA (mRNA), ribosomal RNA (rRNA), small hairpin RNA (shRNA), small nuclear RNA (snRNA), short nucleolar RNA (snoRNA), microRNA (miRNA), genomic DNA, synthetic DNA, synthetic RNA, and/or tRNA.

As used herein, the phrases "single chain variable fragment", "single-chain antibody variable fragments", and "scFv" antibodies refer to forms of antibodies comprising the variable regions of only the heavy and light chains, connected by a linker peptide.

The term "subject" as used herein refers to a member of any invertebrate or vertebrate species. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Ayes (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

As used herein, the phrase "target cell" refers to any cell that is associated with a disease, disease state, or disorder that can be targeted by the genetically modified cells of the presently disclosed subject matter (including but not limited to genetically modified T-cells, NK cells, hematopoietic stem cells, pluripotent stem cells, and embryonic stem cells).

In some embodiments, a target cell is a tumor cell, a cancer cell, or a cancer stem cell that expresses a tMUC epitope.

As used herein, the terms "T-cell" and "T-lymphocyte" are interchangeable and used synonymously. Examples include, but are not limited to, naive T cells, central memory T cells, effector memory T cells, and combinations thereof.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease or disorder.

As used herein, the term "transduction" refers to the introduction of a foreign nucleic acid into a cell using a vector, in some embodiments a viral vector.

As used herein, the term "transfection" as used herein refers to the introduction of a foreign nucleic acid into a cell using recombinant DNA technology. The term "transformation" means the introduction of a "foreign" (i.e., extrinsic or exogenous) gene, DNA, or RNA sequence to a host cell, such that the host cell will express the introduced gene or sequence to produce a desired substance, such as a protein or enzyme, coded by the introduced gene or sequence. The introduced gene or sequence can also be called a "cloned", "foreign", or "heterologous" gene or sequence or a "transgene", and can include regulatory and/or control sequences, such as start, stop, promoter, signal, secretion, or other sequences used by a cell's genetic machinery. The gene or sequence can include nonfunctional sequences or sequences with no known function. A host cell that receives and expresses introduced DNA or RNA has been "transformed" and is a "transformant" or a "clone", and is "transgenic". The DNA or RNA introduced to a host cell can come from any source, including cells of the same genus or species as the host cell, or cells of a different genus or species The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

As used herein, the term "tumor" refers to any neoplastic cell growth and/or proliferation, whether malignant or benign, and all pre-cancerous and cancerous cells and tissues. The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas, and meningiomas). As used herein, the terms "cancer and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein, the phrase "tumor-associated" refers to a disease, disorder, condition, status, antigen, epitope, or glycosylation state that is primarily or secondarily the result of the presence of a tumor or cancer or a cell's status as being a tumor cell or a cancer cell. As such, in some embodiments a tumor-associated antigen or epitope is an antigen or epitope that is present on a tumor cell or a cancer cell or a cell that results from the presence of a tumor or cancer (e.g., an endothelial cell that results from tumor-associated angiogenesis). Similarly, "tumor-associated PGE2 production" refers to PGE2 production that results from the presence of a tumor or tumor cells and that would not occur at all or to the same extent if the tumor or tumor cells were not present. Also similarly, "tumor-associated glycosylation" and grammatical variants thereof refers to a glycosylation pattern or status of a polypeptide that occurs in the presence of, on, or in a tumor or a tumor cell that differs from the glycosylation pattern or status of the same polypeptide that occurs in the absence of, on, or in a non-tumor cell from which the tumor or tumor cell was derived. In some embodiments, the MUC1 gene product undergoes tumor-associated glycosylation in cancer cells including but not limited to breast cancer, pancreatic cancer, and ovarian cancer cells that differs from the glycosylation pattern than is found in breast cells, pancreas cells, and ovary cells in the absence of cancer.

As used herein, the phrases "tumor-specific" and "tumor-exclusive" refer to an antigen or an epitope thereof that is expressed by a tumor cell but that is substantially or completed absent from a normal cell from which the tumor cell was derived. In some embodiments, a tumor-specific or tumor-exclusive antigen or epitope is one that is overexpressed in tumor cells relative to normal cells. In some embodiments, a tumor-specific or tumor-exclusive antigen or epitope can be targeted by an antibody of the presently disclosed subject matter or a fragment or derivative thereof including but not limited to a CAR. In some embodiments, a tumor-specific or tumor-exclusive antigen or epitope comprises the tMUC epitope to which the TAB-004 monoclonal antibody described in U.S. Pat. No. 8,518,405, fragments thereof, and derivatives thereof including but not limited to the presently disclosed CARs bind. Tumor-specific and/or tumor-exclusive antigens and epitopes can in some embodiments be distinguished from "tumor-associated" antigens and epitopes in that a tumor-associated antigen or epitope is an antigen or epitope expressed on a tumor cell, in a tumor, or in another cell the presence of which is indicative of a tumor or a cancer. Thus, the phrase "tumor-associated" in the context of antigens and epitopes is broader than and encompasses the phrases "tumor-specific" and "tumor-exclusive".

As used herein, the terms "vector", "cloning vector", and "expression vector" refer to a vehicle by which a polynucleotide sequence (e.g., a foreign gene) can be introduced into a host cell, so as to transduce and/or transform the host cell in order to promote expression (e.g., transcription and translation) of the introduced sequence. Vectors include plasmids, phages, viruses, etc.

As used herein, the term "expression vector" refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. In some embodiments, the expression vector comprises an isolated nucleic acid molecule of the presently disclosed subject matter, which in some embodiments comprises any of SEQ ID NOs: 4 and 6, or encodes any of SEQ ID NOs: 5 and 7-13. In some embodiments, the isolated nucleic acid molecule present within an expression vector is operably linked to one or more additional nucleotide sequences encoding subsequences of antibody molecules such that upon introduction of the expression vector into an appropriate host, an intact recombinant antibody comprising one or more of SEQ ID NOs: 5 and 7-13, or a fragment or derivative thereof, is expressed by the host cell.

Similarly, all genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes presented in GENBANK® Accession Nos: AAA60019 and NP_004976, the human amino acid sequences disclosed are intended to encompass homologous genes and gene products from other animals including, but not limited to other mammals, fish, amphibians, reptiles, and birds. Also encompassed are any and all nucleotide sequences that encode the disclosed amino acid sequences, including but not limited to those disclosed in the corresponding GENBANK® entries (i.e., J05582.1 and NM_004985, respectively).

As used herein, the term "hybridoma" refers to a cell or cell line that is produced in the laboratory from the fusion of an antibody-producing lymphocyte and a non-antibody-producing cancer cell, usually a myeloma or lymphoma cell. As would be known to those of one of ordinary skill in the art, a hybridoma can proliferate and produce a continuous supply of a specific monoclonal antibody. Methods for generating hybridomas are known in the art (see e.g., Harlow & Lane, 1988).

As used herein, the terms "operatively linked" and "operably linked refer to transcriptional regulatory elements (such as, but not limited to promoter sequences, transcription terminator sequences, etc.) that are connected to a nucleotide sequence (for example, a coding sequence or open reading frame) in such a way that the transcription of the nucleotide sequence is controlled and regulated by that transcriptional regulatory element. Similarly, a nucleotide sequence is said to be under the "transcriptional control" of a promoter to which it is operably linked. Techniques for operatively linking a promoter region to a nucleotide sequence are known in the art.

As used herein, the term "prodrug" refers to an analog and/or a precursor of a drug (e.g., a cytotoxic agent) that substantially lacks the biological activity of the drug (e.g., a cytotoxic activity) until subjected to an activation step. Activation steps can include enzymatic cleavage, chemical activation steps such as exposure to a reductant, and/or physical activation steps such as photolysis. In some embodiments, activation occurs in vivo within the body of a subject,

II. Antibodies, Fragments, and Derivatives thereof, and Methods of Producing the Same The presently disclosed subject matter provides in some embodiments isolated antibodies, as well as fragments and derivatives thereof, which bind to antigens present within tumors such as, but not limited to antigens present within MUC1 polypeptides.

As used herein, the terms "antibody" and "antibodies" refer to proteins comprising one or more polypeptides substantially encoded by immunoglobulin genes or fragments of immunoglobulin genes. Immunoglobulin genes typically include the kappa (κ), lambda (λ), alpha (α), gamma (γ), delta (δ), epsilon (ε), and mu (μ) constant region genes, as well as myriad immunoglobulin variable region genes. Light chains are classified as either κ or λ. In mammals, heavy chains are classified as γ, μ, α, δ, or ε, which in turn define the immunoglobulin classes, IgG, IgM, IgA, IgD, and IgE, respectively. Other species have other light and heavy chain genes (e.g., certain avians produced what is referred to as IgY, which is an immunoglobulin type that hens deposit in the yolks of their eggs), which are similarly encompassed by the presently disclosed subject matter. In some embodiments, the term "antibody" refers to an antibody that binds specifically to an epitope that is present on a tumor antigen including, but not limited to a MUC1 polypeptide and/or a mutant K-ras polypeptide. In some embodiments, the term "antibody" refers to an antibody that binds specifically to an epitope present within any of SEQ ID NOs: 1-3.

A typical immunoglobulin (antibody) structural unit is known to comprise a tetramer. Each tetramer is composed of two identical pairs of polypeptide chains, each pair having one "light" chain (average molecular weight of about 25 kiloDalton (kDa)) and one "heavy" chain (average molecular weight of about 50-70 kDa). The two identical pairs of polypeptide chains are held together in dimeric form by disulfide bonds that are present within the heavy chain region. The N-terminus of each chain defines a variable region of about 100 to 110 or more amino acids primarily responsible for antigen recognition (sometimes referred to as the "paratope"). The terms variable light chain ($V_L$) and variable heavy chain ($V_H$) refer to these light and heavy chains, respectively.

Antibodies typically exist as intact immunoglobulins or as a number of well-characterized fragments that can be produced by digestion with various peptidases. For example, digestion of an antibody molecule with papain cleaves the antibody at a position N-terminal to the disulfide bonds. This produces three fragments: two identical "Fab" fragments, which have a light chain and the N-terminus of the heavy chain, and an "Fc" fragment that includes the C-terminus of the heavy chains held together by the disulfide bonds. Pepsin, on the other hand, digests an antibody C-terminal to the disulfide bond in the hinge region to produce a fragment known as the "F(ab)'$_2$" fragment, which is a dimer of the Fab fragments joined by the disulfide bond. The F(ab)'$_2$ fragment can be reduced under mild conditions to break the disulfide linkage in the hinge region, thereby converting the F(ab')$_2$ dimer into two "Fab'" monomers. The Fab' monomer is essentially a Fab fragment with part of the hinge region (see e.g., Paul, 1993, for a more detailed description of other antibody fragments). With respect to these various fragments, Fab, F(ab')$_2$, and Fab' fragments include at least one intact antigen binding domain (paratope), and thus are capable of binding to antigens.

While various antibody fragments are defined in terms of the digestion of an intact antibody, one of skill will appreciate that several of these fragments (including, but not limited to Fab' fragments) can be synthesized de novo either chemically or by utilizing recombinant DNA methodology. Thus, the term "antibody" as used herein also includes antibody fragments produced by the modification of whole antibodies and/or synthesized de novo using recombinant DNA methodologies. In some embodiments, the term "antibody" comprises a fragment that has at least one antigen binding domain (paratope).

Antibodies can be polyclonal or monoclonal. As used herein, the term "polyclonal" refers to antibodies that are present together in a given collection of antibodies and that are derived from different antibody-producing cells (e.g., B cells). Exemplary polyclonal antibodies include, but are not limited to those antibodies that bind to a particular antigen and that are found in the blood of an animal after that animal has produced an immune response against the antigen. However, it is understood that a polyclonal preparation of antibodies can also be prepared artificially by mixing at least non-identical two antibodies. Thus, polyclonal antibodies typically include different antibodies that are directed against (i.e., bind to) the same and/or different epitopes (sometimes referred to as an "antigenic determinant" or just "determinant") of any given antigen.

As used herein, the term "monoclonal" refers to a single antibody species and/or a substantially homogeneous population of a single antibody species. Stated another way, "monoclonal" refers to individual antibodies or populations of individual antibodies in which the antibodies are identical in specificity and affinity except for possible naturally occurring mutations that can be present in minor amounts. Typically, a monoclonal antibody (mAb or moAb) is generated by a single B cell or a progeny cell thereof (although the presently disclosed subject matter also encompasses "monoclonal" antibodies that are produced by molecular biological techniques as described herein). Monoclonal antibodies (mAbs or moAbs) are highly specific, typically being directed against a single antigenic site. Furthermore, in contrast to polyclonal antibody preparations, a given mAb is typically directed against a single epitope on the antigen.

In addition to their specificity, mAbs can be advantageous for some purposes in that they can be synthesized uncontaminated by other antibodies. The modifier "monoclonal" is not to be construed as requiring production of the antibody by any particular method, however. For example, in some embodiments, the mAbs of the presently disclosed subject matter are prepared using the hybridoma methodology first described by Kohler et al., 1975, and in some embodiments are made using recombinant DNA methods in prokaryotic or eukaryotic cells (see e.g., U.S. Pat. No. 4,816,567, the entire contents of which are incorporated herein by reference). mAbs can also be isolated from phage antibody libraries using the techniques described in, for example, Clackson et al., 1991 and Marks et al., 1991.

The antibodies, fragments, and derivatives of the presently disclosed subject matter can also include chimeric antibodies. As used herein in the context of antibodies, the term "chimeric", and grammatical variants thereof, refers to antibody derivatives that have constant regions derived substantially or exclusively from antibody constant regions from one species and variable regions derived substantially or exclusively from the sequence of the variable region from another species.

The variable region allows an antibody to selectively recognize and specifically bind epitopes on antigens. That is, the $V_L$ domain and $V_H$ domain, or subsets of the complementarity determining regions (CDRs) within these variable domains, of an antibody combine to form the variable region that defines a three dimensional antigen binding site. This quaternary antibody structure forms the antigen binding site present at the end of each arm of the antibody. More specifically, the antigen binding site is defined by three CDRs on each of the $V_H$ and $V_L$ chains. In some instances (e.g., certain immunoglobulin molecules derived from camelid species or engineered based on camelid immunoglobulins), a complete immunoglobulin molecule can consist of heavy chains only with no light chains (see e.g., Hamers-Casterman et al., 1993).

In naturally occurring antibodies, there are six CDRs present in each antigen binding domain that are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see e.g., Chothia & Lesk, 1987; Kabat et al., 1991; Martin, 1996; Johnson & Wu, 2000).

A particular kind of chimeric antibody is a "humanized" antibody, in which the antibodies are produced by substituting the CDRs of, for example, a mouse antibody, for the CDRs of a human antibody (see e.g., PCT International Patent Application Publication No. WO 1992/22653). Thus, in some embodiments, a humanized antibody has constant regions and variable regions other than the CDRs that are derived substantially or exclusively from the corresponding regions of a human antibody, and CDRs that are derived substantially or exclusively from a mammal other than a human.

The antibodies, fragments, and derivatives of the presently disclosed subject matter can also be single chain antibodies and single chain antibody fragments. Single-chain antibody fragments contain amino acid sequences having at least one of the variable regions and/or CDRs of the whole antibodies described herein, but are lacking some or all of the constant domains of those antibodies. These constant domains are not necessary for antigen binding, but constitute a major portion of the structure of whole antibodies.

Single-chain antibody fragments can overcome some of the problems associated with the use of antibodies containing a part or all of a constant domain. For example, single-chain antibody fragments tend to be free of undesired interactions between biological molecules and the heavy-chain constant region, and/or other unwanted biological activities. Additionally, single-chain antibody fragments are considerably smaller than whole antibodies and can therefore be characterized by greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient. The single-chain antibody fragments of the presently disclosed subject matter include, but are not limited to single chain fragment variable (scFv) antibodies and derivatives thereof such as, but not limited to tandem di-scFv, tandem tri-scFv, diabodies, triabodies, tetrabodies, miniantibodies, and minibodies.

Fv fragments correspond to the variable fragments at the N-termini of immunoglobulin heavy and light chains. Fv fragments appear to have lower interaction energy of their two chains than Fab fragments. To stabilize the association of the $V_H$ and $V_L$ domains, they can be linked with peptides (see e.g., Bird et al., 1988; Huston et al., 1988), disulfide bridges (see e.g., Glockshuber et al., 1990), and/or "knob in hole" mutations (see e.g., Zhu et al., 1997). ScFv fragments can be produced by methods well known to those skilled in the art (see e.g., Whitlow et al., 1991; Huston et al., 1993). In some embodiments, a CAR molecule of the presently disclosed subject matter comprises an scFv based on the TAB-004 antibody disclosed in U.S. Pat. No. 8,518,405, which in some embodiments comprises all six CDRs of the TAB-004 antibody (e.g., comprises CDRs comprising each of SEQ ID NOs: 8-13). In some embodiments, the scFv comprise the light chain of TAB-004 (SEQ ID NO: 7) fused to the heavy chain of TAB-004 (SEQ ID NO: 5) using an intervening linker (such as, but not limited to SEQ ID NO: 19).

scFv can be produced in bacterial cells such as E. coli or in eukaryotic cells. One potential disadvantage of scFv is the monovalency of the product, which can preclude an increased avidity due to polyvalent binding, and their short half-life. Attempts to overcome these problems include bivalent (scFv')$_2$ produced from scFv containing an additional C-terminal cysteine by chemical coupling (see e.g., Adams et al., 1993; McCartney et al., 1995) or by spontaneous site-specific dimerization of scFv containing an unpaired C-terminal cysteine residue (see e.g., Kipriyanov et al., 1995).

Alternatively, scFv can be forced to form multimers by shortening the peptide linker to 3 to 12 residues to form "diabodies" (see e.g., Holliger et al., 1993). Reducing the linker still further can result in scFv trimers ("triabodies"; see e.g., Kortt et al., 1997) and tetramers ("tetrabodies"; see e.g., Le Gall et al., 1999). Construction of bivalent scFv molecules can also be achieved by genetic fusion with protein dimerizing motifs to form "miniantibodies" (see e.g., Pack et al., 1992) and "minibodies" (see e.g., Hu et al., 1996). scFv-scFv tandems ((scFv)$_2$) can be produced by linking two scFv units by a third peptide linker (see e.g., Kurucz et al., 1995).

Bispecific diabodies can be produced through the non-covalent association of two single chain fusion products consisting of $V_H$ domain from one antibody connected by a short linker to the $V_L$ domain of another antibody (see e.g., Kipriyanov et al., 1998). The stability of such bispecific diabodies can be enhanced by the introduction of disulfide bridges or "knob in hole" mutations as described hereinabove or by the formation of single chain diabodies (scDb) wherein two hybrid scFv fragments are connected through a peptide linker (see e.g., Kontermann et al., 1999).

Tetravalent bispecific molecules can be produced, for example, by fusing an scFv fragment to the $CH_3$ domain of an IgG molecule or to a Fab fragment through the hinge region (see e.g., Coloma et al., 1997). Alternatively, tetravalent bispecific molecules have been created by the fusion of bispecific single chain diabodies (see e.g., Alt et al., 1999). Smaller tetravalent bispecific molecules can also be formed by the dimerization of either scFv-scFv tandems with a linker containing a helix-loop-helix motif (DiBi miniantibodies; see e.g., Muller et al., 1998) or a single chain molecule comprising four antibody variable domains ($V_H$ and $V_L$) in an orientation preventing intramolecular pairing (tandem diabody; see e.g., Kipriyanov et al., 1999).

Bispecific F(ab')$_2$ fragments can be created by chemical coupling of Fab' fragments or by heterodimerization through leucine zippers (see e.g., Shalaby et al., 1992; Kostelny et al., 1992). Also available are isolated $V_H$ and $V_L$ domains (see U.S. Pat. Nos. 6,172,197; 6,248,516; and 6,291,158).

The presently disclosed subject matter also includes functional equivalents of the antibodies of the presently disclosed subject matter. As used herein, the phrase "functional equivalent" as it refers to an antibody refers to a molecule that has binding characteristics that are comparable to those of a given antibody. In some embodiments, chimerized, humanized, and single chain antibodies, as well as fragments thereof, are considered functional equivalents of the corresponding antibodies upon which they are based. In some embodiments, the presently disclosed subject matter provides functional equivalents of the TAB-004 mAb disclosed herein.

Functional equivalents also include polypeptides with amino acid sequences substantially the same as the amino acid sequence of the variable or hypervariable regions of the antibodies of the presently disclosed subject matter. As used herein with respect to nucleic acid and/or amino acid sequences, the phrase "substantially the same" refers to a biosequence with in some embodiments at least 80%, in some embodiments at least 85%, in some embodiments at least about 90%, in some embodiments at least 91%, in some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments at least about 99% sequence identity to another nucleic acid and/or amino acid sequence, as determined by the FASTA search method in accordance with Pearson & Lipman, 1988. In some embodiments, the percent identity calculation is performed over the full length of the nucleic acid and/or amino acid sequence of an antibody of the presently disclosed subject matter.

In some embodiments, a functional equivalent of a nucleotide sequence is a sequence that encodes the same amino acid sequence (i.e., that include one or more functionally equivalent codons). A listing of functionally equivalent codons is presented in Table 1.

TABLE 1

Functionally Equivalent Codons

| Amino Acid | Codons | Amino Acid | Codons |
|---|---|---|---|
| Alanine (Ala or A) | GCA; GCC; GCG; GCU | Leucine (Leu or L) | UUA; UUG; CUA; CUC; CUG; CUU |
| Arginine (Arg or R) | AGA; AGG; CGA; CGC; CGG; CGU | Lysine (Lys or K) | AAA; AAG |
| Asparagine (Asn or N) | AAC; AAU | Methionine (Met or M) | AUG |
| Aspartic Acid (Asp or D) | GAC; GAU | Phenylalanine (Phe or F) | UUC; UUU |
| Cysteine (Cys or C) | UGC; UGU | Proline (Pro or P) | CCA; CCC; CCG; CCU |
| Glutamic acid (Glu or E) | GAA; GAG | Serine (Ser or S) | ACG; AGU; UCA; UCC; UCG; UCU |
| Glutamine (Gln or Q) | CAA; CAG | Threonine (Thr or T) | ACA; ACC; ACG; ACU |
| Glycine (Gly or G) | GGA; GGC; GGG; GGU | Tryptophan (Trp or W) | UGG |
| Histidine (His or H) | CAC; CAU | Tyrosine (Tyr or Y) | UAC; UAU |
| Isoleucine (Ile or I) | AUA; AUC; AUU | Valine (Val or V) | GUA; GUC; GUG; GUU |

In some embodiments, a functional equivalent of a given amino acid sequence is an amino acid with one or more conservative amino acid substitutions. Conservative amino acid substitution refers to the substitution of one amino acid for another amino acid of the same class (e.g., valine for glycine, or arginine for lysine). Polypeptides that are functionally equivalent to prouroguanylin and/or prouroguanylin fragments can be made using random mutagenesis on the encoding nucleic acids by techniques well known to those having ordinary skill in the art. It is more likely, however, that such polypeptides will be generated by site-directed mutagenesis (again using techniques well known to those having ordinary skill in the art). These polypeptides can have increased functionality or decreased functionality.

Functional equivalents can also include fragments of antibodies that have the same or comparable binding characteristics to those of a whole antibody of the presently disclosed subject matter. Such fragments can contain one or both Fab fragments, the F(ab')$_2$ fragment, the F(ab') fragment, an Fv fragment, or any other fragment that includes at least one antigen binding domain. In some embodiments, the antibody fragments contain all six CDRs of a whole antibody of the presently disclosed subject matter (e.g., comprise CDRs comprising each of SEQ ID NOs: 8-13), although fragments containing fewer than all of such regions, such as three, four, or five CDRs, can also be functional equivalents as defined herein. Further, functional equivalents can be or can combine members of any one of the following immunoglobulin classes: IgG, IgM, IgA, IgD, and IgE, and the subclasses thereof, as well as other subclasses as might be appropriate for non-mammalian subjects (e.g., IgY for chickens and other avian species).

Functional equivalents also include aptamers and other non-antibody molecules, provided that such molecules have the same or comparable binding characteristics to those of a whole antibody of the presently disclosed subject matter.

In some embodiments, the antibodies, fragments, and derivatives thereof are selected from the group consisting of monoclonal antibody TAB-004 produced by hybridoma cell line ATCC No. PTA-11550, as well as chimeric antibodies or fragments or derivatives thereof, humanized antibodies or fragments or derivatives thereof, single chain antibodies or fragments or derivatives thereof, Fab fragments thereof, F(ab')$_2$ fragments thereof, Fv fragments thereof, and Fab' fragments thereof. In some embodiments, the antibodies, fragments, and derivatives of the presently disclosed subject matter have the binding characteristics of monoclonal antibody TAB-004. In some embodiments, the antibodies, fragments, and derivatives of the presently disclosed subject matter have at least some and in some cases all of the binding characteristics of monoclonal antibody TAB-004. In some embodiments, the antibodies, fragments, and derivatives of the presently disclosed subject matter bind to an epitope present within any of SEQ ID NOs: 1-3, in some embodiments an epitope present within SEQ ID NO: 3.

As used herein, the term "TAB-004" refers to a mAb that is produced by a hybridoma cell line designated "TAB-004" and that was deposited with the American Type Culture Collection (ATCC), 10801 University Boulevard, Manassas, Va., 20110-2209, United States of America, on Dec. 16, 2010 under Accession No. PTA-11550 pursuant to the terms of the Budapest Treaty. TAB-004 is a mAb of the IgG isotype that has been found to bind to an epitope present on a human mucin-1 (MUC1) polypeptide. More particularly, in some embodiments TAB-004 can bind to an epitope present within SEQ ID NO: 3. TAB-004 itself comprises the CDR sequences disclosed in SEQ ID NOs: 8-13.

As used herein, the term "MUC1" refers to a molecule defined as follows. MUC1 is one of the epithelial mucin family of molecules. MUC1 is widely expressed on a large number of epithelial cancers and is aberrantly glycosylated making it structurally and antigenically distinct from that expressed by non-malignant cells (see e.g., Barratt-Boyes, 1996; Price et al., 1998; Peterson et al., 1991). The dominant form of MUC1 is a high molecular weight molecule comprised of a large highly immunogenic extracellular mucin-like domain with a large number of twenty amino acid tandem repeats, a transmembrane region, and a cytoplasmic tail (Quin et al., 2000; McGucken et al., 1995; Dong et al., 1997).

MUC1 is overexpressed and aberrantly glycosylated in most epithelial adenocarcinomas including breast and pancreas. Adenocarcinoma of the breast and pancreas not only overexpress MUC1 but also shed MUC1 into the circulation. High MUC1 serum levels are associated with progressive disease. MUC1 has been exploited as a prospective biomarker because of the complex and heterogeneous nature of the epitopes expressed within the antigen. MUC1 synthesized by cancerous tissues usually displays an aberrant oligosaccharide profile, which gave rise to the expression of neomarkers such as sialyl-Lea (assayed in the CA19-9 test), sialyl-Lex, and sialyl-Tn (TAG-72), as well as the cryptic epitopes such as Tn.

In addition, because of underglycosylation, the peptide core of the mucin becomes exposed such that epitopes within the core that is not accessible within normal tissue-derived MUC1 might serve as potential biomarkers. Thus, differences between normal versus malignant tissue can provide for distinct epitopes that can show higher specificity for malignant tissues. Currently, tests for several of these epitopes are available in commercial form for use in patient management including CA15-3 (Abbott Laboratories, Abbott Park, Ill., United States of America), California 27-29 (Bayer Diagnostics, Tarrytown, N.Y., United States of America), and CA19-9 (Panomics Inc., Redwood City, Calif., United States of America). Thus far, none have proven to be of particular diagnostic value, probably due at least in part to low specificity as shown in Table 2.

TABLE 2

Assays Employed to Assess Overexpression of MUC1 in Various Tissues*

| Assay | Cancers in which MUC1 is Overexpressed | Non-cancerous Conditions in which MUC1 is Overexpressed |
|---|---|---|
| CA 15-5 | Breast, lung, ovarian, endometrial, bladder, pancreas, gastrointestinal | liver disease (cirrhosis, hepatitis), lupus, sarcoid, tuberculosis, non-cancerous breast lesions |
| CA 19-9 | Pancreas, colorectal, liver, stomach and biliary tree cancers | pancreatitis, ulcerative colitis, inflammatory bowel disease, inflammation or blockage of the bile duct |
| CA 27-29 | Breast, colon, gastric, liver, lung, pancreatic, ovarian, prostate cancers | ovarian cysts, liver and kidney disorders, non-cancerous breast problems |

*adapted from Perkins et al., 2002.

Recently, another MUC1 antibody known as PAM4 has gained attention for use in pancreatic cancer diagnosis due to its high sensitivity and specificity for pancreatic cancer but not any other epithelial cancers such as breast and ovarian cancers (Gold et al., 2007).

In normal epithelial tissue, MUC1 is localized to the apical region of the cells. Malignant transformation results in upregulation of MUC1 by gene amplification and/or increased transcriptional activation and the distribution of MUC1 on the cell surface is no longer confined to the apical region (Bieche & Lidereau, 1997). While the function of MUC1 still awaits clarification, high cytoplasmic expression of MUC1 has been associated with poor prognosis in patients with breast and/or ovarian cancers.

MUC1 has also been demonstrated to play a role in cell adhesion, cell signaling, and immune responses (Quin et al., 2000; McGucken et al., 1995; Dong et al., 1997; Henderson et al., 1998). A non-limiting example of an amino acid sequence of a MUC1 gene product from humans is presented in SEQ ID NO: 1. Nucleotide and amino acid sequences of MUC1 gene products from other species include GENBANK® Accession NOs: AAA39755, Q02496, and NP_038633 (mouse), NP_036734 (rat), NP_001181906 (dog), AAO063589 (pig), and NP_776540 (cow).

Additionally, it has been determined that TAB-004 binds to K-ras polypeptides, and in particular, mutant K-ras polypeptides. As used herein, the term "K-ras" refers to a K-ras oncogene gene and gene products therefrom (see e.g., Kahn et al., 1987). An exemplary K-ras gene product is a human K-ras gene product including, but not limited to that disclosed as SEQ ID NO: 2, which corresponds to GEN-BANK® Accession No. NP_004976.

As used herein, the term "K-ras" also encompasses mutated forms of K-ras. As used herein, the terms "mutated K-ras", "mutant K-ras polypeptide", and "mutant K-ras protein" are used interchangeably to refer to a K-ras polypeptide comprising at least one K-ras mutation as compared to SEQ ID NO: 2. In some embodiments, a mutant K-ras polypeptide comprises a mutation at either amino acid number 12 or 13 of the mature polypeptide (i.e., amino acid position 13 or 14 of SEQ ID NO: 2 since the mature polypeptide would not include the methionine residue at position 1 of SEQ ID NO: 2). In some embodiments, a mutant K-ras polypeptide comprises a mutation selected from among a glycine-12 mutation to serine (referred to herein as "G12S"), G12V, G12D, G12A, G12C, G13A, and G13D. A representative example of a mutant K-ras$^{G12D}$ polypeptide to which antibodies of the presently disclosed subject matter bind in part is shown in SEQ ID NO: 2 and described in Kahn et al., 1987. In some embodiments, the antibodies, and the fragments and derivatives thereof, of the presently disclosed subject matter bind to a portion of a K-ras polypeptide that comprises a G12D mutation (referred to herein as "mutant K-ras G12D" or "K-ras$^{G12D}$"). Additional exemplary mutant K-ras polypeptides include, but are not limited to, allelic variants, splice variants, derivative variants, substitution variants, deletion variants, insertion variants, fusion polypeptides, orthologs, and interspecies homologs. In some embodiments, a mutant K-ras polypeptide can include one or more additional residues at the C- or N-terminus, such as, but not limited to, leader sequence residues, targeting residues, amino terminal methionine residues, lysine residues, tag residues, and/or fusion protein residues.

Compositions Comprising Antibodies, Fragments, and/or Derivatives of the Presently Disclosed Subject Matter The presently disclosed subject matter also provides compositions comprising the presently disclosed antibodies, fragments, and/or derivatives. A schematic depiction of exemplary compositions of the presently disclosed subject matter and exemplary uses therefor are provided in FIGS. 6 and 16A-16C.

In some embodiments, a composition of the presently disclosed subject matter comprises the presently disclosed antibodies, fragments, and/or derivatives thereof and one or more pharmaceutically acceptable carriers and/or excipients. In some embodiments, the carrier(s) and/or excipient(s) is pharmaceutically acceptable for use in humans. Suitable formulations include aqueous and non-aqueous sterile injection solutions which can contain anti-oxidants, buffers, bacteriostats, bactericidal antibiotics, and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS) in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used.

The compositions of the presently disclosed subject matter can also comprise an active agent, wherein the active agent comprises a therapeutic moiety, a diagnostic moiety, and/or a biologically active moiety. As used herein, the phrase "active agent" thus refers to a component of the presently disclosed compositions that provides a therapeutic benefit to a subject, permits visualization of cells or tissues in which the compositions of the presently disclosed subject matter accumulate, detection of epitopes to which the presently disclosed antibodies, fragments, and derivatives bind, and/or enhances any of these activities. In some embodiments, an active agent of the presently disclosed subject matter is selected from the group consisting of a radioactive molecule (including, but not limited to radionuclides and radioisotopes), a sensitizer molecule, an imaging agent or other detectable agent, a toxin, a cytotoxin, an anti-angiogenic agent, an anti-tumor agent, a chemotherapeutic agent, an immunomodulator, a cytokine, a reporter group, and combinations thereof. It is understood that these categories are not intended to be mutually exclusive, as some radioactive molecules, for example, are also chemotherapeutic agents, some immunomodulators are cytokines, etc.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase I inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethyl stilbesterol, Chlorotriani sene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropin-releasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, sulfadiethoxane, and gemcitabine (4-amino-1-(2-deoxy-2,2-difluoro-β-D-erythro-pentofuranosyl)pyrimidin-2(1H)-on-2',2'-difluoro-2'-deoxycytidine).

In some embodiments, an active agent comprises an anti-angiogenic agent. Various anti-angiogenic agents are known to one of ordinary skill in the art, and include, but are not limited to inhibitors and/or antagonists of vascular endothelial growth factor (VEGF) family and its receptors (e.g., Bevacizumab and other anti-vascular endothelial growth factor (VEGF) antibodies) and neuropilin-1 antagonists.

In some embodiments, the compositions of the presently disclosed subject matter can be used with additional adjuvants and/or immunomodulators. As used herein, the phrases "immune modulating agent" and "immunomodulating agent" refer to molecules cable of modulating immune responses. Exemplary immunomodulators include, but are not limited to cytokines (including, but not limited to, the cytokines IFN-α, IFN-γ, IL-2, IL-4, IL-6, TNF, and other cytokines affecting immune cells), CpG oligodeoxynucleotides (CpG ODN), which function as a dendritic cell activator (Rothenfusser et al., 2002), and the immunomodulators set forth in Table 3.

TABLE 3

Exemplary Immunomodulators*

| Target | Modulators |
|---|---|
| indoleamine 2,3-dioxygenase (IDO) | 1MT; MTH-Trp |
| Arginase (ARG) | ABH; BEC |
| inducible nitric oxide synthase (iNOS) | L-NMMA |
| ARG/iNOS | NCX-4016 |
| COX-2 | Celecoxib; Rofecoxib |
| EP2/EP4 | CP-533536 |
| TGFβRI | SB-505124; SD-505124; LY580276 |
| JAK/STAT | JSI-124; CPA-7 |
| VEGFR1/FLT1 | SU5416; AG-013736 |
| CCR4 | IC-487892 |
| CXCR4 | AMD3100 |
| CCR2 | INCB3344 |

*see Muller & Scherle, 2006 and references therein.
MTH-TRP: methyl-thiohydantoin-tryptophan;
ABH: 2(S)-amino-6-boronohexanoic acid;
BEC: S-(2-boronoethyl)-L-cysteine;
L-NMMA: L-N$^G$-monomethyl arginine;
NCX-4016: nitroaspirin; see Emanueli et al., 2004;
CP-533536: see Cameron et al., 2009;
SB-505124: see DeCosta Byfield et al., 2004;
SD-505124: see Muller & Scherle, 2006;
LY580276: see Sawyer et al., 2004;
JSI-124: see Blaskovich et al., 2003;
CPA-7: see Littlefield et al., 2008;
SU5416: see Fong et al., 1999;
AG-013736 (Axitinib); see Rugo et al., 2005;
IC-487892: ICOS Corp., Bothell, Washington, United States of America;
AMD3100: see Donzella et al., 1998.

For therapeutic applications, a therapeutically effective amount of a composition of the presently disclosed subject matter is administered to a subject. A "therapeutically effective amount" is an amount of a composition sufficient to produce a measurable biological tumor response (such as, but not limited to an immunostimulatory, an anti-angiogenic response, a cytotoxic response, tumor regression, and/or tumor growth inhibition). Actual dosage levels of active ingredients in a composition of the presently disclosed subject matter can be varied so as to administer an amount of the active agent(s) that is effective to achieve the desired therapeutic response for a particular subject. The selected dosage level will depend upon a variety of factors including the activity of the composition, formulation, the route of administration, combination with other drugs or treatments, tumor size and longevity, and the physical condition and prior medical history of the subject being treated. In some embodiments of the presently disclosed subject matter, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the presently disclosed subject matter is administered to a subject. A "detectable amount", as used herein to refer to a composition, refers to a dose of such a composition that the presence of the composition can be determined in vivo or in vitro. A detectable amount will vary according to a variety of factors, including but not limited to chemical features of the composition being labeled, the detectable label, the labeling methods, the method for imaging and parameters related thereto, metabolism of the labeled drug in the subject, the stability of the label (including, but not limited to the half-life of a radionuclide label), the time elapsed following administration of the composition prior to imaging, the route of administration, the physical condition and prior medical history of the subject, and the size and longevity of the tumor or suspected tumor. Thus, a detectable amount can vary and can be tailored to a particular application. After study of the present disclosure, it is within the skill of one in the art to determine such a detectable amount.

As used herein, the terms "detectable moiety", "detectable label", and "detectable agent" refer to any molecule that can be detected by any moiety that can be added to an antibody, or a fragment or derivative thereof such as but not limited to a CAR, that allows for the detection of the antibody, fragment, or derivative in vitro and/or in vivo. Representative detectable moieties include, but are not limited to, chromophores, fluorescent moieties, enzymes, antigens, groups with specific reactivity, chemiluminescent moieties, and electrochemically detectable moieties, etc. In some embodiments, the antibodies are biotinylated.

In some embodiments, a detectable moiety comprises a fluorophore. Any fluorophore can be employed with the compositions of the presently disclosed subject matter, provided that the conjugation of fluorophore results in a composition that is detectable either in vivo (e.g., after administration to a subject) and/or in vitro, and further does not negatively impact the ability of the antibody, or the fragment or derivative thereof, to bind to its epitope. Representative fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). It is understood that these representative fluorophores are exemplary only, and additional fluorophores can also be employed. For example, there the ALEXA FLUOR® dye series includes at least 19 different dyes that are characterized by different emission spectra. These dyes include ALEXA FLUOR® 350, 405, 430, 488, 500, 514, 532, 546, 555, 568, 594, 610, 633, 635, 647, 660, 680, 700, and 750 (available from Invitrogen Corp., Carlsbad, Calif., United States of America), and the choice of which dye to employ can be made by the skilled artisan after consideration of the instant specification based on criteria including, but not limited to the chemical compositions of the specific ALEXA FLUOR®, whether multiple detectable moieties are to be employed and the emission spectra of each, the detection technique to be employed, etc.

In some embodiments, a detectable moiety comprises a cyanine dye. Non-limiting examples of cyanine dyes that can be conjugated to the antibodies, fragments, and/or derivatives of the presently disclosed subject matter include the succinimide esters Cy5, Cy5.5, and Cy7, supplied by Amersham Biosciences (Piscataway, N.J., United States of America).

In some embodiments, a detectable moiety comprises a near infrared (NIR) dye. Non-limiting examples of near infrared dyes that can be conjugated to the antibodies, fragments, and/or derivatives of the presently disclosed subject matter include NIR641, NIR664, NIT7000, and NIT782.

In some embodiments, the biotinylated antibodies are detected using a secondary antibody that comprises an avidin or streptavidin group and is also conjugated to a fluorescent label including, but not limited to Cy3, Cy5, Cy7, and any of the ALEXA FLUOR®® series of fluorescent labels available from INVITROGEN™ (Carlsbad, Calif., United States of America). In some embodiments, the antibody, fragment, or derivative thereof is directly labeled with a fluorescent label and cells that bind to the antibody are separated by fluorescence-activated cell sorting. Additional detection strategies are known to the skilled artisan.

For diagnostic applications (including but not limited to detection applications and imaging applications), the antibodies of the presently disclosed subject matter can be labeled with a detectable moiety. The detectable moiety can be any one that is capable of producing, either directly or indirectly, a detectable signal. For example, a detectable moiety can be a radioisotope, such as but not limited to $^3$H, $^{14}$C, $^{32}$P, $^{35}$S, $^{125}$I, or $^{131}$I; a fluorescent or chemiluminescent compound such as but not limited to fluorescein isothiocyanate, rhodamine, or luciferin; or an enzyme, such as but not limited to alkaline phosphatase, β-galactosidase, or horseradish peroxidase.

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent label, an epitope tag, or a radioactive label, each described briefly herein below.

Fluorescence.

Any detectable fluorescent dye can be used, including but not limited to FITC (fluorescein isothiocyanate), FLUOR X™, ALEXA FLUOR®, OREGON GREEN®, TMR (tetramethylrhodamine), ROX (X-rhodamine), TEXAS RED®, BODIPY® 630/650, Cy5 (available from Amersham Pharmacia Biotech of Piscataway, N.J., United States of America, or from Molecular Probes Inc. of Eugene, Oreg., United States of America), and mKATE/mKATE2 (see e.g., U.S. Pat. No. 8,481,307; Wang et al., 2011.

A fluorescent label can be detected directly using emission and absorbance spectra that are appropriate for the particular label used. Common research equipment has been developed for in vitro detection of fluorescence, including instruments available from GSI Lumonics (Watertown, Mass., United States of America) and Genetic MicroSystems Inc. (Woburn, Mass., United States of America). Most of the commercial systems use some form of scanning technology with photomultiplier tube detection. Criteria for consideration when analyzing fluorescent samples are summarized by Alexay et al., 1996.

Detection of an Epitope Tag.

If an epitope label has been used, a protein or compound that binds the epitope can be used to detect the epitope. A representative epitope label is biotin, which can be detected by binding of an avidin-conjugated fluorophore, for example avidin-FITC. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

Autoradiographic Detection.

In the case of a radioactive label (e.g., $^{131}$I or $^{99m}$Tc) detection can be accomplished by conventional autoradiography or by using a phosphorimager as is known to one of skill in the art. An exemplary, non-limiting autoradiographic method employs photostimulable luminescence imaging plates (Fuji Medical Systems of Stamford, Conn., United States of America). Briefly, photostimulable luminescence is the quantity of light emitted from irradiated phosphorous plates following stimulation with a laser during scanning. The luminescent response of the plates is linearly proportional to the activity (Amemiya et al., 1988; Hallahan et al., 2001a).

Any method known in the art for conjugating an antibody to a detectable moiety can be employed (see e.g., Hunter et al., 1962; David et al., 1974; Pain et al., 1981); and Nygren, 1982.

Drug Carriers.

The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan et al., 2001b; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997; U.S. Pat. Nos. 4,551,482; 5,714,166; 5,510,103; 5,490,840; and 5,855, 900), and a polysome (U.S. Pat. No. 5,922,545).

Conjugation of Targeting Ligands.

Antibodies, fragments, or derivatives can also be coupled to drugs or drug carriers using methods known in the art, including but not limited to carbodiimide conjugation, esterification, sodium periodate oxidation followed by reductive alkylation, and glutaraldehyde crosslinking (see e.g., Goldman et al., 1997; Cheng, 1996; Neri et al., 1997; Nabel, 1997; Park et al., 1997; Pasqualini et al., 1997; Bauminger & Wilchek, 1980; U.S. Pat. No. 6,071,890; and European Patent No. 0 439 095.

Administration.

Suitable methods for administration of a composition of the presently disclosed subject matter include, but are not limited to intravascular, subcutaneous, intramuscular, and intratumoral administration. In some embodiments, intravascular administration is employed. As used herein, the phrases "intravascular administration" and "intravascular provision" refer to administration of a composition directly into the vascular network of a subject. Techniques that can be employed for intravascular administration of compositions are known to those of skill in the art, and include, but are not limited to intravenous administration and intraarterial administration. It is understood that any site and method for intravascular administration can be chosen, depending at least in part on the species of the subject to which the composition is to be administered. For delivery of compositions to pulmonary pathways, compositions can be administered as an aerosol or coarse spray.

III. Methods for Detecting Epitopes in Biological Samples

The antibodies, and/or the fragments and/or derivatives thereof, of the presently disclosed subject matter also are useful for in vivo imaging, wherein an antibody labeled with a detectable moiety such as a radio-opaque agent and/or a radioisotope is administered to a subject, in some embodiments via intravenous administration, and the presence and location of the labeled antibody in the host is assayed. This imaging technique can be useful in the staging and treatment of malignancies.

Thus, in some embodiments, a composition of the presently disclosed subject matter comprises a label that can be detected in vivo. The term "in vivo" as used herein to describe imaging or detection methods, refers to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

In some embodiments, the detectable moiety can be conjugated or otherwise associated with an antibody, fragment, or derivative of the presently disclosed subject matter, a therapeutic, a diagnostic agent, a drug carrier, or combinations thereof as set forth in more detail hereinabove. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

Scintigraphic Imaging.

Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

Imaging instruments suitable for practicing the detection and/or imaging methods of the presently disclosed subject matter, and instruction for using the same, are readily available from commercial sources. Both PET and SPECT systems are offered by ADAC of Milpitas, Calif., United States of America, and Siemens of Hoffman Estates, Ill., United States of America. Related devices for scintigraphic imaging can also be used, such as a radio-imaging device that includes a plurality of sensors with collimating structures having a common source focus.

When scintigraphic imaging is employed, the detectable label comprises in some embodiments a radionuclide label, in some embodiments a radionuclide label selected from the group consisting of $^{18}$F, $^{64}$Cu, $^{65}$Cu, $^{67}$Ga, $^{68}$Ga, $^{77}$Br, $^{80m}$Br, $^{95}$Ru, $^{97}$Ru, $^{103}$Ru, $^{105}$Ru, $^{99m}$Tc, $^{107}$Hg, $^{203}$Hg, $^{123}$I, $^{124}$I, $^{125}$I, $^{126}$I, $^{131}$I, $^{133}$I, $^{111}$In, $^{113m}$In, $^{99m}$Re, $^{105}$Re, $^{101}$Re, $^{186}$Re, $^{188}$Re, $^{121m}$Te, $^{122m}$Te, $^{125m}$Te, $^{165}$Tm, $^{167}$Tm, $^{168}$Tm, and nitride or oxide forms derived there from. In some embodiments, the radionuclide label comprises $^{131}$I or $^{99m}$Tc.

Methods for radionuclide labeling of a molecule so as to be used in accordance with the disclosed methods are known in the art. For example, a targeting molecule can be derivatized so that a radioisotope can be bound directly to it (Yoo et al., 1997). Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (HMPAO; Chattopadhyay et al., 2001; Sagiuchi et al., 2001; and U.S. Pat. No. 6,024,938). Additional methods can be found in U.S. Pat. No. 6,080,384; Hnatowich et al., 1996; and Tavitian et al., 1998.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI).

Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging (fMRI; see e.g., Rovaris et al., 2001; Pomper & Port, 2000; and references cited therein).

Contrast agents for magnetic source imaging include but are not limited to paramagnetic or superparamagnetic ions, iron oxide particles (Weissleder et al., 1992; Shen et al., 1993), and water-soluble contrast agents. Paramagnetic and superparamagnetic ions can be selected from the group of metals including iron, copper, manganese, chromium, erbium, europium, dysprosium, holmium, and gadolinium. In some embodiments, a metal is iron, manganese, or gadolinium. In some embodiments, a metal is gadolinium.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetri-aminepentaacetic acid (DTPA). Lanthanide ions are chelated by tetraazacyclododocane compounds. See U.S. Pat. Nos. 5,738,837 and 5,707,605. Alternatively, a contrast agent can be carried in a liposome (Schwendener, 1992).

Images derived used a magnetic source can be acquired using, for example, a superconducting quantum interference device magnetometer (SQUID, available with instruction from Quantum Design of San Diego, Calif., United States of America; see also U.S. Pat. No. 5,738,837).

Ultrasound.

Ultrasound imaging can be used to obtain quantitative and structural information of a target tissue, including a tumor. Administration of a contrast agent, such as gas microbubbles, can enhance visualization of the target tissue during an ultrasound examination. In some embodiments, the contrast agent can be selectively targeted to the target tissue of interest, for example by using a peptide for guided drug delivery (e.g., radiation guided drug delivery) as disclosed herein. Representative agents for providing microbubbles in vivo include but are not limited to gas-filled lipophilic or lipid-based bubbles (e.g., U.S. Pat. Nos. 6,245,318; 6,231,834; 6,221,018; and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the presently disclosed subject matter include air; nitrogen; oxygen; is carbon dioxide; hydrogen; nitrous oxide; an inert gas such as helium, argon, xenon or krypton; a sulfur fluoride such as sulfur hexafluoride, disulfur decafluoride or trifluoromethylsulfur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus can be advantageous for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

A description of ultrasound equipment and technical methods for acquiring an ultrasound dataset can be found in Coatney, 2001; Lees, 2001; and references cited therein.

Fluorescence Imaging.

Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging (see e.g., Heredia et al., 1991; Ragnarson et al., 1992; Fraser, 1996). Representative labels include but are not limited to carbocyanine and aminostyryl dyes, in some embodiments long chain dialkyl carbocyanines (e.g., DiI, DiO, and DiD available from Molecular Probes Inc. of Eugene, Oreg., United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg., United States of America).

A fluorescent label can also comprise sulfonated cyanine dyes, including Cy5.5 and Cy5 (available from Amersham of Arlington Heights, Ill., United States of America), IRD41 and IRD700 (available from Li-Cor, Inc. of Lincoln, Neb.), NIR-1 (available from Dejindo of Kumamoto, Japan), and LaJolla Blue (available from Diatron of Miami, Fla., United States of America; see also Licha et al., 2000; Weissleder et al., 1999; Vinogradov et al., 1996).

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

IV. Methods for Detecting and Treating Tumors

In some embodiments, the antibodies, fragments, and/or derivatives of the presently disclosed subject matter are employed for in vivo imaging of tumors, wherein a composition of the presently disclosed subject matter that has been labeled with an imaging moiety such as a radio-opaque agent, a radioisotope, or other imaging agent is administered to a subject, and the presence and location of the detectibly-labeled composition in the subject is assayed. This imaging technique can be useful in the staging and treatment of malignancies. In some embodiments, an antibody is labeled with any moiety that is detectable in situ in a subject, for example by nuclear magnetic resonance, radiology, or other detection methods known in the art.

As such, the presently disclosed subject matter also provides methods for detecting tumors in subjects. In some embodiments, the presently disclosed methods comprise (a) administering to the subject a composition comprising the antibody, or the fragment or derivative thereof, of the presently disclosed subject matter conjugated to a detectable label; and (b) detecting the detectable label to thereby detect the tumor. In some embodiments, the tumor is a tumor of the pancreas, breast, ovary, colon, or rectum, and/or a metastatic cell derived therefrom, which optionally expresses MUC1, a mutant K-ras, or both.

In some embodiments of the presently disclosed subject matter, the detectable label comprises an imaging agent selected from the group consisting of paramagnetic, radioactive, and fluorogenic ions including, but not limited to those set forth in more detail hereinabove. In view of the disclosure above, the radioactive imaging agent can be, for example, gamma-emitters, positron-emitters, x-ray-emitters, or any other agents for which a detection method is available. Exemplary such radioactive imaging agents include $^{43}$K, $^{52}$Fe, $^{57}$Co, $^{67}$Cu, $^{67}$Ga, $^{68}$Ga, $^{77}$Br, $^{81}$Rb/$^{81m}$Kr, $^{87m}$Sr, $^{99m}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb, and $^{206}$Bi, but the presently disclosed subject matter is not limited to just these radioisotopes.

The presently disclosed subject matter also provides methods for treating tumors. In some embodiments, the methods comprise administering to the subject a composition comprising an antibody, or a fragment or derivative thereof of the presently disclosed subject matter conjugated to an active agent, whereby the active agent contacts the tumor to thereby treat the tumor. Exemplary active agents are disclosed herein, and include but are not limited to therapeutic agents, optionally chemotherapeutic agents, toxins, radiotherapeutic agents, and combinations of any of the foregoing.

For example, a composition of the presently disclosed subject matter can comprise an antibody, or a fragment or derivative thereof as disclosed herein conjugated to a chemotherapeutic agent. In some embodiments, the chemotherapeutic agent is selected from among an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cisplatinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof.

Additionally, a composition of the presently disclosed subject matter can comprise an antibody, or a fragment or derivative thereof as disclosed herein conjugated to a toxin. Exemplary toxins include, but are not limited to Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin, and combinations thereof.

The compositions of the presently disclosed subject matter can also comprise an antibody, or a fragment or derivative thereof as disclosed herein conjugated to a radiotherapeutic agent. Exemplary radiotherapeutic agents include, but are not limited to $^{47}Sc$, $^{67}Cu$, $^{90}Y$, $^{109}Pd$, $^{123}I$, $^{125}I$, $^{131}I$, $^{186}Re$, $^{188}Re$, $^{199}Au$, $^{211}At$, $^{212}Pb$, $^{212}Bi$, $^{32}P$, $^{33}P$, $^{71}Ge$, $^{77}As$, $^{103}Pb$, $^{105}Rh$, $^{111}Ag$, $^{119}Sb$, $^{121}Sn$, $^{131}Cs$, $^{143}Pr$, $^{161}Tb$, $^{177}Lu$, $^{191}Os$, $^{193M}Pt$, and $^{197}Hg$.

The presently disclosed subject matter also provides methods for suppressing tumor growth in a subject. In some embodiments, the methods comprise administering to a subject bearing a tumor an effective amount of an isolated antibody, fragment, or derivative of the presently disclosed subject matter. In some embodiments, the antibody, fragment, or derivative of the presently disclosed subject matter binds to an epitope present within any of SEQ ID NOs: 1-3. In some embodiments, the tumor is a tumor of the pancreas, breast, ovary, colon, or rectum, and/or a metastatic cell derived therefrom, which in some embodiments expresses MUC1, a mutant K-ras, or both.

The presently disclosed subject matter also encompasses employing the compositions and methods disclosed herein as part of a combination therapy. As such, the presently disclosed subject matter provides in some embodiments administering to the subject one or more additional anti-tumor treatments. Exemplary anti-tumor treatments include but are not limited to radiotherapy, chemotherapy, an additional immunotherapy, an anti-inflammatory therapy, and combinations thereof.

For example, an anti-inflammatory therapy can comprise administering to the subject an effective amount of an anti-inflammatory agent such as, but not limited to a non-steroidal anti-inflammatory drug (NSAID). Exemplary NSAIDs include, but are not limited to cyclooxygenase inhibitors (e.g., indomethacin), particularly cyclooxygenase-2-specific inhibitors such as, but not limited to celecoxib and rofecoxib. As used herein, the phrase "effective amount" refers to an amount of an active agent such as, but not limited to an anti-inflammatory agent, which induces in a subject a therapeutically relevant effect. An exemplary effective amount in the context of an NSAID, particularly a cyclooxygenase inhibitor, would be that amount of the cyclooxygenase inhibitor that reduces PGE3 production in a tumor sufficiently to enhance an anti-tumor effect produced by a CAR molecule of the presently disclosed subject matter or a cell comprising a CAR molecule of the presently disclosed subject matter.

Combination therapies can also include administration of one or more additional anti-tumor therapies such as, but not limited to administering gemcitabine, which is 4-amino-1-(2-deoxy-2,2-difluoro-β-D-erythro-pentofuranosyl)pyrimidin-2(1H)-on-2',2'-difluoro-2'-deoxycytidine; celecoxib, which is 4-[5-(4-methylphenyl)-3-(trifluoromethyl)pyrazol-1-yl]benzenesulfonamide, pharmaceutically acceptable salts thereof, and/or combinations thereof to the subject.

Combination therapies can also include administration of ionizing radiation to the subject, before, during, and/or after the administration course of any of the compositions of the presently disclosed subject matter.

For therapeutic applications, the antibodies, fragments, derivatives, and/or conjugates thereof can be administered to a subject, for example in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The antibodies and/or conjugates can also be administered by intratumoral, peritumoral, intralesional, or perilesional routes, to exert local as well as systemic therapeutic effects, as desired.

Suitable pharmaceutically acceptable carriers, diluents, and/or excipients are well known and can be employed by those of skill in the art as the clinical situation warrants. Examples of suitable carriers, diluents, and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

When present in an aqueous dosage form, rather than being lyophilized, the antibody typically will be formulated at a concentration of about 0.1 mg/ml to 100 mg/ml, although wide variation outside of these ranges is permitted.

For additional guidance regarding formulation and dose, see U.S. Pat. Nos. 5,326,902; 5,234,933; PCT International Publication No. WO 1993/25521; Gennaro, 1990; Goodman et al., 1996; Berkow et al., 1997; Speight et al., 1997; Duch et al., 1998; Ebadi, 1998; Katzung, 2001; Gennaro, 2003.

The compositions and methods of the presently disclosed subject matter can be employed in vitro, in vivo, or ex vivo.

The compositions and methods of the presently disclosed subject matter can be used for screening and/or treatment of a cancer in which MUC1 or mutated K-ras expression is elevated. Examples of such cancers include, but are not limited to, cancers of the ovary, breast, lung, pancreas, and prostate.

For the treatment of disease, an appropriate dosage of an antibody, fragment, or derivative thereof, and/or a conjugate thereof of the presently disclosed subject matter can depend on the type of disease to be treated, the severity and course of the disease, whether the antibodies and/or conjugates are administered for preventive or therapeutic purposes, the course of previous therapy, the patient's clinical history and response to the antibodies and/or conjugates, and the discretion of the attending physician. The antibodies and/or conjugates of the presently disclosed subject matter can be administered to a subject at one time or over a course of several or many treatments.

V. Methods for Detecting, Purifying, and Targeting Tumor Cells and Cancer Stem Cells The presently disclosed subject matter also provides methods for detecting, purifying, and targeting tumor cells, cancer stem cells, or both present in a subject or isolated from a subject using the antibodies, or the fragments or derivatives thereof, disclosed herein. In some embodiments, the presently disclosed subject matter provides methods for detecting tumor cells, cancer stem cells, or both by detecting the binding of an antibody, or a fragment or derivative thereof to tumor cells, cancer stem cells, or both present in biological samples isolated from subjects who had and/or presently have a cancer. The compositions disclosed herein that employ detectable labels can be employed for this purpose.

Additionally, the presently disclosed subject matter provides methods for purifying cancer stem cells. In some embodiments, the methods comprise (a) providing a population of cells suspected of comprising cancer stem cells; (b) identifying a subpopulation of the cells that bind to an antibody, or a fragment or derivative thereof, the binds to an epitope present within any of SEQ ID NOs: 1-3; and (b) purifying the subpopulation. With respect to purification methods, in some embodiments the population of cells comprises circulating cells isolated from a subject that has a cancer.

In some embodiments, the methods further comprise removing lineage positive ($lin^+$) cells from the population of cells before the identifying step or removing $lin^+$ cells from the purified subpopulation. Methods for removing $lin^+$ cells from cell populations are known in the art. An exemplary method is as follows:

Single cell suspensions are either isolated from a subject (e.g., from blood, lymph fluids, bone marrow aspirates, etc.) or are prepared from tissues. In the case of tissues, sections from a tissue suspected of having cancer stem cells (e.g., pancreatic adenocarcinoma tissue) can be mechanically homogenized and digested with collagenase IV and DNase for 30 minutes at 37° C. Whole blood and single cell suspension from the tumor can be subjected to lineage cell depletion using, for example, one of the several species-specific Lineage Cell Depletion Kits sold by Miltenyi Biotec (Bergisch Gladbach, Germany), which remove cells expressing the following lineage antigens: CD2, CD3, CD11b, CD14, CD15, CD16, CD19, CD56, CD123, and CD235a from the cell suspensions. The lineage negative subpopulation can then be then screened using flow cytometry for cells expressing MUC1 using, for example, the monoclonal TAB-004 antibody of the presently disclosed subject matter. It is understood that the steps of the various selections can be performed in any order. If desired, antibodies directed against the stem cell markers CD133 (AC133) and/or $CD24^+/CD44^+$ can also be employed.

The presently disclosed subject matter also provides methods for targeting an active agent to a circulating cancer stem cell in a subject. In some embodiments, the methods comprise contacting a cancer stem cell (optionally a circulating cancer stem cell) with a composition comprising an antibody, or a fragment or derivative thereof, of the presently disclosed subject matter and an active agent. The composition thus delivers the active agent to the cancer stem cell. Any of the active agents disclosed herein can be targeted to cancer stem cells by employing the presently disclosed compositions and methods. In some embodiments, the active agent comprises a therapeutic agent, a chemotherapeutic agent, a toxin, a radiotherapeutic agent, or a combination thereof.

For example, in some embodiments the therapeutic agent comprises an immunomodulator, which in some embodiments could one or more of an indoleamine 2,3-dioxygenase (IDO) inhibitor (e.g., 1-methyl-DL-tryptophan (1MT)); an EP2/EP4 receptor antagonist; a CXCR4 antagonist, a vascular endothelial growth factor receptor 1 antagonist, Celebrex, a TGFβR1 antagonist, and a dendritic cell activator. Non-limiting examples of these immunomodulators are provided in Table 3 above.

VI. Methods for Predicting the Recurrence and/or Progression of Cancer in a Subject As of the year 2010, breast cancer and pancreatic cancer are the third and fourth leading cause of cancer related deaths, respectively. Breast cancer is the most commonly diagnosed cancer among women, but while pancreatic cancer is less common, it has worst prognosis of all cancers. The poor prognosis associated with pancreatic cancer results at least in part from a lack of early detection methods resulting in diagnosis of the disease at an advanced stage. Although mammography has significantly improved early detection in breast cancer, it is not without its shortcomings. Up to 20% of breast cancers are missed, and false-positive results can lead to anxiety and expensive additional testing. The lack of specificity in mammography screening can lead to the "over-diagnosis" of benign tumors and unnecessary treatment.

Another concern is the presence of metastases from primary tumors to distant sites in patients, the presence of which generally correlates with poor prognosis and as such, drastically impacts the course of therapy administered to patients. Current methods that can be used to detect metastases include computed tomography (CT), positron emission tomography (PET) scans, and magnetic resonance imaging (MRI). These modalities are expensive, potentially hazardous to the individual, can lack specificity and sensitivity, and generally are incapable of detecting micrometastases.

Monitoring of recurrence in patients can also be necessary to appropriately tailor particular drug treatments. Blood-based tests for tumor antigens including, but not limited to the CA 19-9, CA 15-3, and CA 27-29 tumor antigens, can be employed for these purposes. However, these tests also frequently lack specificity as conditions other than cancer can lead to the elevation of these and other putative "tumor-associated antigens". Also frequently, the expression levels of these markers are insufficiently high during the early stages of the cancer enough in the progression of a cancer to detect the cancer before symptoms appear. The development of methodologies to specifically detect cancer at an early stage, as well as to detect micrometastases and recurrence would be beneficial to improving outcomes in pancreatic and breast cancer patients.

Methods for Predicting Recurrence of Cancer

In some embodiments, the presently disclosed subject matter also provides methods for predicting the recurrence of cancer in a subject. In some embodiments, the methods comprise (a) isolating a biological sample comprising circulating cells from a subject with a cancer; (b) contacting the biological sample with one or more of the antibodies, fragments, or derivatives of the presently disclosed subject matter; and (c) identifying in the biological sample one or more circulating cells that bind to the one or more of the antibodies, fragments, or derivatives of the presently disclosed subject matter, whereby the recurrence of a cancer is predicted in the subject. With respect to these methods, the identification of circulating cells that bind to the antibodies, fragments, and/or derivatives of the presently disclosed subject matter can be indicative of a recurrence of a subject's cancer when the subject had previously been negative for such circulating cells. In some embodiments, the presence of circulating cells that bind to the one or more of the antibodies, fragments, or derivatives of the presently disclosed subject matter indicates that the subject is at enhanced risk of metastatic disease relative to a subject that is negative for such circulating cells.

Methods for Prognosing Progression of Cancer

The presently disclosed subject matter also provides methods for prognosing progression of a cancer in subjects. In some embodiments, the methods comprise isolating a biological sample comprising circulating cells from a subject with a cancer; contacting the biological sample with the antibody, or the fragment or derivative thereof, of the presently disclosed subject matter under conditions sufficient for the antibody, or the fragment or derivative thereof, to bind to an epitope present on a tumor and/or a cancer cell, if present, in the biological sample; and identifying in the biological sample one or more circulating cells that bind to the antibody, or the fragment or derivative thereof, whereby progression of a cancer is prognosed in the subject. In some embodiments, the biological sample comprises a blood sample, a lymph sample, or a fraction thereof. In some embodiments, the cancer is a pancreatic cancer or a breast cancer.

In some embodiments, the antibody is a monoclonal antibody produced by hybridoma cell line TAB-004 deposited with the American Type Culture Collection (ATCC), 10801 University Boulevard, Manassas, Va., 20110-2209, United States of America, on Dec. 16, 2010 under the terms of the Budapest Treaty as Accession No. PTA-11550. In some embodiments, the fragment or derivative thereof is selected from the group consisting of a chimeric antibody, or a fragment or derivative thereof; a humanized antibody, or a fragment or derivative thereof; a human antibody, or a fragment or derivative thereof a single chain antibody, or a fragment or derivative thereof and a Fab fragment, wherein the chimeric antibody, the humanized antibody, the human antibody, the single chain antibody, or the Fab fragment comprises the CDRs of monoclonal antibody TAB-004, and further wherein the chimeric antibody, the humanized antibody, the human antibody, the single chain antibody, or the Fab fragment comprises the CDRs of monoclonal antibody TAB-004. In some embodiments, the CDRs of monoclonal antibody TAB-004 comprise heavy chain CDR1 comprising SEQ ID NO: 8; heavy chain CDR2 comprising SEQ ID NO: 9; heavy chain CDR3 comprising SEQ ID NO: 10; light chain CDR1 comprising SEQ ID NO: 11; light chain CDR2 comprising SEQ ID NO: 12; and light chain CDR3 comprising SEQ ID NO: 13.

As used herein, the phrase "prognosing progression of a cancer" refers to evaluating indicia of a cancer disease at a given time point and comparing the same to the indicia of the cancer disease taken at an earlier time point, wherein the comparison is indicative of a progression of the cancer in the subject. In some embodiments, progression of the cancer comprises metastasis of the cancer in the subject.

As such, the antibody, or the fragment or derivative thereof, of the presently disclosed subject matter can be employed to detect the presence of circulating tumor cells (CTCs) in the blood or other biological samples of cancer patients, as the presence of CTCs can be an important indicator of the potential for metastatic disease and poor prognosis. Currently, the CELLSEARCH® system (Vendex, LLC, Raritan, N.J., United States of America) is the only method approved by the United States Food and Drug Administration (FDA) to measure CTCs in metastatic breast, colorectal, and prostate cancer patients. This system is based on the detection of the epithelial cell surface marker EpCAM in CTCs. In metastatic breast cancer, detection of CTCs before initiation of first-line therapy has been shown to be highly predictive of progression free survival and overall survival. Patients with >5 CTCs per 7.5 ml of blood at baseline and at first follow-up (4 weeks) had a worse prognosis than patients with less than five CTCs (Cristofanilli et al., 2005). Similarly, in pancreas cancer, >1 CTCs/7.5 mL of blood correlated with poor prognosis (Kurihara et al., 2008).

However, the ability of CTCs to form actual metastatic lesions remains in question. Since tumor cells with invasive phenotypes lose several epithelial antigens in a transformation process called epithelial-mesenchymal transition (EMT), EpCAM-expressing CTCs are currently minimally predictive of metastasis. In fact, low EpCAM expression by micrometastases has been reported, and attempts to isolate CTCs using antibodies against EpCAM have not been successful to date. Since MUC1-expressing cells have high metastatic potential and MUC1 has been found to be expressed on CTCs, the presently disclosed antibodies, and the fragments and derivatives thereof, including but not limited to the TAB-004 antibody, can serve as a highly reliable and improved predictor of metastasis compared to strategies based on attempting to detect EpCAM-expressing CTCs.

VII. Other Uses

The antibodies of the presently disclosed subject matter can also be employed in various assay methods, such as but not limited to competitive binding assays, direct and indirect sandwich assays, and immunoprecipitation assays (see e.g., Zola, 1987; Harlow & Lane, 1988).

The antibodies of the presently disclosed subject matter also are useful as affinity purification agents. In this process, one or more antibodies are immobilized on a suitable support (such as, but not limited to a Sephadex resin or filter paper) using methods well known in the art. See e.g., Harlow & Lane, 1988.

VIII. CARs and Methods of Producing the Same

Chimeric antigen receptors (CARs) are artificially constructed hybrid proteins or polypeptides containing the antigen binding domains of an antibody (such as, but not limited to an scFv) linked to one or more T-cell signaling domains. Characteristics of CARs include their ability to redirect T-cell specificity and reactivity toward a selected target in a non-MHC-restricted manner, thereby exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As used herein, the phrases "have antigen specificity" and "elicit antigen-specific response" mean that a CAR can specifically bind to and immunologically recognize an antigen, in some embodiments a tMUC antigen or an epitope thereof, such that binding of the CAR to the antigen elicits an immune response.

As used herein, the phrase "antigen-specific targeting region" (ASTR) refers to the region of a CAR that targets (i.e., binds to) specific antigens and/or epitopes. The CARs of the presently disclosed subject matter comprise in some embodiments one ASTR (i.e., are monospecific) and in some embodiments comprise two targeting regions which target two different antigens and/or epitopes (i.e., are bispecific). In some embodiments, CARs comprise three or more targeting regions which target at least three or more different antigens (i.e., are trispecific or multispecific). The targeting regions on the CAR are extracellular. In some embodiments, the antigen-specific targeting regions comprise an antibody or a functional equivalent thereof or a fragment thereof or a derivative thereof, and in some embodiments each of the targeting regions targets a different antigen or epitope. The targeting regions can comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of the presently disclosed subject matter. In fact, almost any molecule that binds a given antigen with high affinity can be used as an ASTR, as will be appreciated by those of skill in the art.

Thus, as used herein, the terms "Chimeric Antigen Receptor", "CAR", or "CARs" refer to engineered receptors, which graft an antigen specificity onto cells (for example T cells such as naive T cells, central memory T cells, effector memory T cells or combination thereof). CARs are also known as artificial T-cell receptors, chimeric T-cell receptors, or chimeric immunoreceptors. The CARs of the presently disclosed subject matter comprise one or more ASTRs, an extracellular domain, a transmembrane domain, one or more co-stimulatory domains, and an intracellular signaling domain. In those embodiments where two or more ASTRs are present, the two or more ASTRs can target at least two different antigens and can be arranged in tandem and separated by linker sequences. In some embodiments, the extracellular spacer domain is optional. In some embodiments, the CAR is a monospecific CAR that targets a tMUC antigen or epitope.

As used herein, the phrase "co-stimulatory domain" (CSD) refers to the portion of the CAR that enhances the proliferation, survival, and/or development of memory cells. The CARs of the presently disclosed subject matter can comprise one or more co-stimulatory domains. In some embodiments, each co-stimulatory domain comprises the costimulatory domain of one or more of members of the TNFR superfamily, CD28, CD137 (4-1BB), CD134 (OX40), Dap10, CD27, CD2, CD5, ICAM-1, LFA-1 (CD11a/CD18), Lck, TNFR-I, TNFR-II, Fas, CD30, CD40, or any combinations thereof. Other co-stimulatory domains (e.g., from other proteins) will be apparent to those of skill in the art and can be used in connection with alternate embodiments of the presently disclosed subject matter.

As used herein, the phrase "extracellular spacer domain" (ESD) refers to the hydrophilic region that is between the ASTR and the transmembrane domain. In some embodiments, the CARs of the presently disclosed subject matter comprise an extracellular spacer domain. In some embodiments, the CARs of the presently disclosed subject matter do not comprise an extracellular spacer domain. The extracellular spacer domains can include, but are not limited to, Fc fragments of antibodies or fragments or derivatives thereof, hinge regions of antibodies or fragments or derivatives thereof, $CH_2$ regions of antibodies, $CH_3$ regions of antibodies, artificial spacer sequences, or combinations thereof. Examples of extracellular spacer domains include, but are not limited to, CD8α hinge, and artificial spacers made of polypeptides which can be as small as, for example, Gly3 or $CH_1$ and $CH_3$ domains of IgGs (such as but not limited to human $IgG_4$). In some embodiments, the extracellular spacer domain is any one or more of (i) a hinge, $CH_2$, and $CH_3$ regions of $IgG_4$; (ii) a hinge region of $IgG_4$; (iii) a hinge and $CH_2$ of $IgG_4$; (iv) a hinge region of CD8α; (v) a hinge, $CH_2$, and $CH_3$ regions of $IgG_1$; (vi) a hinge region of $IgG_1$; (vi) a hinge and $CH_2$ region of $IgG_1$; and/or (vii) a hinge region of IgD. Other extracellular spacer domains will be apparent to those of skill in the art and may be used in connection with any embodiments of the presently disclosed subject matter.

In some embodiments, the binding domain of a CAR of the presently disclosed subject matter is followed by a hinge region, which refers to the region that moves the antigen binding domain away from the effector cell surface to enable proper cell/cell contact, antigen binding, and activation (see e.g., Patel et al., 1999). In some embodiments, a hinge region is an immunoglobulin hinge region and can be a wild type immunoglobulin hinge region or a modified immunoglobulin hinge region. Other exemplary hinge regions used in the CARs described herein include the hinge region derived from the extracellular regions of type 1 membrane proteins such as CD8a, CD4, CD28, and CD7, which can be wild type hinge regions from these molecules or can be modified. In some embodiments, a hinge region is an IgD hinge region, which in some embodiments comprises the amino acid sequence as set forth in SEQ ID NO: 26 or a subsequence thereof.

As used herein, the phrase "modified hinge region" refers to (a) a wild type hinge region with in some embodiments up to 30% amino acid changes (e.g., up to 25% amino acid changes, up to 20% amino acid changes, up to 15% amino acid changes, up to 10% amino acid changes, or up to 5% amino acid changes, including but not limited to amino acid substitutions, additions, and/or deletions); (b) a portion of a wild type hinge region that is in some embodiments at least 10 amino acids in length (e.g., at least 11, 12, 13, 14, 15, 16, 17, 18, 19, 20, 25, 30, 35, 40, 45, 50, or more amino acids) in length with in some embodiments up to 30% amino acid changes (e.g., up to 25% amino acid changes, up to 20% amino acid changes, up to 15% amino acid changes, up to 10% amino acid changes, or up to 5% amino acid changes, including but not limited to amino acid substitutions, additions, and/or deletions); or (c) a portion of a wild type hinge region that comprises the core hinge region (which in some embodiments can be 4, 5, 6, 7, 8, 9, 10, 11, 12, 13, 14, or 15, or at least 4, 5, 6, 7, 8, 9, 10, 11, 12, 13, 14, or 15 amino acids in length). When a modified hinge region is interposed between and connecting a binding domain and another region (e.g., a transmembrane domain) in the CARs described herein, it allows the chimeric fusion protein to maintain specific binding to its target (e.g., tMUC).

As used herein, the phrase "intracellular signaling domain" (ISD) or "cytoplasmic domain" refer to the portion of the CAR which transduces the effector function signal and directs the cell to perform its specialized function. Examples of domains that transduce the effector function signal include but are not limited to the zeta chain of the T-cell receptor complex or any of its homologs (e.g., the eta chain, FcεR1 γ and β chains, MB1 (Igα) chain, B29 (Igβ) chain, etc.), human CD3 zeta chain, CD3 polypeptides (delta and epsilon), syk family tyrosine kinases (Syk, ZAP 70, etc.), src family tyrosine kinases (Lck, Fyn, Lyn, etc.), and other molecules involved in T-cell transduction, such as CD2, CD5, and CD28. Other intracellular signaling domains will be apparent to those of skill in the art and can be used in connection with any embodiments of the presently disclosed subject matter.

As used herein, the phrases "linker", "linker domain", and "linker region" refer to an oligo- or polypeptide region from about 1 to 100 amino acids in length, which links together any of the domains and/or regions of a CAR of the presently disclosed subject matter. In some embodiments, linkers comprise, consist essentially of, or consist of flexible residues like glycine and serine so that the adjacent protein domains are free to move relative to one another. Longer linkers can be used when it is desirable to ensure that two adjacent domains do not sterically interfere with one another, such as can be the case with bispecific, trispecific, and multispecific CARs. Linkers can be cleavable or non-cleavable. Examples of cleavable linkers include 2A linkers (for example T2A; see U.S. Pat. No. 8,802,374 to Jenson, incorporated herein by reference in its entirety), 2A-like linkers, or functional equivalents thereof, and combinations thereof. In some embodiments, the linkers include the picornaviral 2A-like linker, cis-acting hydrolase element (CHY-SEL) sequences of porcine teschovirus (P2A), *Thosea asigna* virus (T2A), or combinations, variants, and functional equivalents thereof. In some embodiments, the linker sequences can comprise Asp-Val/Ile-Glu-X-Asn-Pro-Gly$^{2A}$-Pro$^{2B}$ motif, which results in cleavage between the 2A glycine and the 2B proline. Other linkers will be apparent to those of skill in the art and may be used in connection with any embodiments of the presently disclosed subject matter.

As used herein, the phrase "transmembrane domain" (TMD or TD) refers to the region of the CAR that crosses the plasma membrane. The transmembrane domains of the CARs of the presently disclosed subject matter are the transmembrane regions of a transmembrane protein (for example Type I transmembrane proteins), an artificial hydrophobic sequence, or a combination thereof. Other transmembrane domains will be apparent to those of skill in the art and can be used in connection with any embodiments of the presently disclosed subject matter.

CARs and the T cells that have been modified to express CARs can be described as being "first generation", "second generation", "third generation", or "fourth generation" based on the various components that are present in the CARs. "First generation" CARs include an antigen binding domain, transmembrane domain, and an intracellular domain, typically a CD3zeta intracellular domain. "Second generation" CARs further comprise a costimulatory domain. "Third generation" CARs further comprise other signaling domains, such as but not limited to 4-IBB signaling domains and/or OX40 signaling domains. "Fourth generation" CAR T cells typically are characterized by the presence of a second or third generation CAR, and have been further modified to express proliferative cytokines (e.g., IL-12; Pegram et al., 2012) or additional costimulatory ligands (e.g., 4-1BBL; Stephan et al., 2007).

The presently disclosed subject matter thus provides in some embodiments CARs that bind to antigens present within tumors such as, but not limited to antigens and/or epitopes present within MUC1 polypeptides. In some embodiments, the antigens and/or epitopes to which the presently disclosed CARs bind are tumor-specific antigens and/or epitopes, meaning that the antigens and/or epitopes to which the presently disclosed CARs bind are expressed by tumor cells but are not expressed by non-tumor cells. In some embodiments, the tumor-specific antigens and/or epitopes to which the presently disclosed CARs bind result from glycosylation and/or folding of a MUC1 polypeptide in or on a particular tumor cell that does not occur on a corresponding non-tumor cell.

Nucleic Acids Encoding Anti-MUC1 CARs and Polypeptides Encoded Thereby

In some embodiments, the presently disclosed subject matter provides isolated nucleic acid molecules encoding chimeric antigen receptors (CARs) that are directed against tMUC epitopes. The nucleic acids can in some embodiments be DNA and/or RNA, optionally mRNA encoding the CARs. In some embodiments, the isolated nucleic acid molecules encode a CAR comprising an antibody or antibody fragment that includes a binding domain, a transmembrane domain, and an intracellular signaling domain comprising a stimulatory domain, wherein the binding domain binds to a tumor-exclusive epitope of a human MUC1 polypeptide referred to herein as tMUC. In some embodiments, the binding domain corresponds to the binding domain of the TAB-004 monoclonal antibody disclosed in U.S. Pat. No. 8,518,405. Thus, in some embodiments the anti-tMUC binding domain comprises a light chain complementary determining region 1 (LC CDR1) comprising QDIVYGNGNTY (SEQ ID NO: 1), a light chain complementary determining region 2 (LC CDR2) comprising KVS (SEQ ID NO: 12), and a light chain complementary determining region 3 (LC CDR3) comprising FQGSHVPYT (SEQ ID NO: 13), and a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10). In some embodiments, the CAR comprises a light chain variable region comprising SEQ ID NO: 7 and/or a heavy chain variable region comprising SEQ ID NO: 5. In some embodiments, the anti-tMUC binding domain is a single chain fragment variable (scFv) polypeptide.

As would be recognized by one of ordinary skill in the art, it is possible to modify sequences outside of the CDRs of an antibody without significantly altering the specificity of the antibody. As such, the presently disclosed subject matter also provides nucleic acid molecules with modifications of the overall light and/or heavy chain variable regions set forth in SEQ ID NOs: 7 and 5, respectively. Such modifications are designed in some embodiments to have little or no impact on the binding characteristics of the CARs that comprise SEQ ID NOs: 7 and 5, although modifications can also be introduced using routine techniques to fine tune the binding of the CAR to the tMUC epitope.

As such, in some embodiments the isolated nucleic acid molecules of the presently disclosed subject matter encode CARs wherein the light chain variable region comprises an amino acid sequence having at least one, two, or three but not more than 30, 20, or 10 modifications of the amino acid sequence set forth in SEQ ID NO: 7, or comprises an amino acid sequence with at least 95% identity to SEQ ID NO: 7, and/or the heavy chain variable region comprises an amino acid sequence having at least one, two, or three but not more than 30, 20, or 10 modifications of the amino acid sequence set forth in SEQ ID NO: 5, or comprises an amino acid sequence with at least 95% identity to SEQ ID NO: 5.

CARs also comprise a transmembrane domain (TD), and in some embodiments the TD of a presently disclosed CAR is a TD of a protein selected from the group consisting of a T cell receptor (TCR) alpha chain, a TCR beta chain, a TCR zeta chain, CD28, CD3 epsilon, CD45, CD4, CD5, CD8, CD9, CD16, CD22, CD33, CD37, CD64, CD80, CD86, CD134, CD137, and CD154. In some embodiments, the TD comprises SEQ ID NO: 21 or SEQ ID NO: 23. As a TD generally serves only to anchor the CAR in the membrane of a cell expressing the CAR, modifications in the sequences of known TDs are also permitted, provided that the modifications do not destroy the ability of the TD to function as a TD. Thus, in some embodiments, the TD comprises an amino acid sequence having at least one, two, or three but not more than 20, 10, or 5 modifications of the amino acid sequence as set forth in SEQ ID NO: 21 or SEQ ID NO: 23, or comprises an amino acid sequence with at least 95% identity to SEQ ID NO: SEQ ID NO: 21 or SEQ ID NO: 23. The isolated nucleic acid molecules encoding the TD can in some embodiments comprise a sequence at least 95% identical to nucleotides 940-1020 of SEQ ID NO: 14 or nucleotides 919-999 of SEQ ID NO: 16.

The isolated nucleic acid molecules of the presently disclosed subject matter can in some embodiments encode an anti-MUC1 binding domain that is connected to the TD by an extracellular hinge region and/or the TD connected to the intracellular domains via an intracellular hinge regions. Extracellular hinge regions provide the CARs with flexibility between the binding domain and the TD, and in some embodiments can influence cytokine secretion and cell-mediated killing of target cells by the CARs (Sadelain et al., 2009). Non-limiting examples of extracellular and intracellular hinge regions that can be employed in a CAR include Fc regions of immunoglobulins and immunoglobulin-like domains from CD8α or CD28 (e.g., the human CD8 and CD28 extracellular and intracellular hinges disclosed in U.S. Pat. No. 8,465,743). In some embodiments, the presently disclosed CARs comprise a hinge region, which in some embodiments comprises SEQ ID NO: 26 or a subsequence thereto.

CARs also comprise intracellular domains that generally include one or more costimulatory domains and one or more signaling domains. As such, the isolate nucleic acid molecules of the presently disclosed subject matter further comprise a sequence encoding a costimulatory domain. In some embodiments, the costimulatory domain comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof. A particular non-limiting example of a costimulatory domain of the presently disclosed subject matter comprises an amino acid sequence selected from the group consisting of SEQ ID NOs: 20 and 22. Modifications of the costimulatory domains that do not significantly impact the ability of the domain to function as a costimulatory domain are also permitted. Thus, in some embodiments the encoded costimulatory domain comprises an amino acid sequence having at least one, two, or three but not more than 20, 10, or 5 modifications of an amino acid sequence of any of SEQ ID NOs: 20 and 22, or comprises an amino acid sequence with at least 95% identity thereto.

The isolated nucleic acid molecules of the presently disclosed subject matter also encode CARs that comprise at least one intracellular signaling domain. Exemplary, non-limiting intracellular signaling domains include those derived from 4-1BB and/or from CD3zeta. More particularly, an intracellular signaling domain can comprise a human CD3zeta intracellular signaling domain comprising SEQ ID NO: 24 or a mouse CD3zeta intracellular signaling domain comprising SEQ ID NO: 25. Here as well, modifications in the sequences of intracellular signaling domains are also permitted, provided that the modifications do not destroy the ability of the intracellular signaling domains to function as an intracellular signaling domain. As such, in some embodiments the encoded intracellular signaling domain comprises an amino acid sequence having at least one, two, or three but not more than 20, 10 or 5 modifications of an amino acid sequence as set forth in SEQ ID NO: 24 or SEQ ID NO: 25, or comprises a amino acid sequence with at least 95% identity to the amino acid sequence of any of SEQ ID NO: 24 or SEQ ID NO: 25.

In some embodiments, a costimulatory domain is fused to an intracellular signaling domain to create an intracellular domain with dual functions. By way of example and not limitation, one of the costimulatory domains disclosed herein can be fused in frame with one of the intracellular signaling domains disclosed herein. In some embodiments, the intracellular domain comprises the amino acid sequence of SEQ ID NO: 20 fused to the amino acid sequence of SEQ ID NO: 24, or comprises the amino acid sequence of SEQ ID NO: 22 fused to the amino acid sequence of SEQ ID NO: 25, wherein the sequences comprising the intracellular domain are expressed in the same frame and as a single polypeptide chain. In some embodiments, the nucleic acid sequence encoding the intracellular signaling domain comprises (i) nucleotides 850-1143 of SEQ ID NO: 14 or a sequence with at least 95% identity thereto and/or nucleotides 1144-1479 of SEQ ID NO: 14 or a sequence with at least 95% identity thereto; or (ii) nucleotides 840-1122 of SEQ ID NO: 16 or a sequence with at least 95% identity thereto and/or nucleotides 1123-1461 of SEQ ID NO: 16 or a sequence with at least 95% identity thereto.

CARs can also comprise a leader sequence, such as but not limited to a CD8 leader sequence. Non-limiting examples of CD8 leader sequences that can be included in a CAR are the human CD8 leader sequence of SEQ ID NO: 18 (amino acids 1-21 of Accession No. NP_741969.1 of the GENBANK® biosequence database).

In some embodiments, an isolated nucleic acid sequence encoding a chimeric antigen receptor (CAR) of the presently disclosed subject matter comprises a (i) binding domain that binds to a tumor-exclusive epitope of a human MUC1 polypeptide and (ii) a CD3 zeta signaling domain. In some embodiments, the isolated nucleic acid further encodes a costimulatory signaling domain, which in some embodiments is selected from the group consisting of a CD28 signaling domain and a 4-1BB signaling domain. In some embodiments, the binding domain is a human antibody or a fragment thereof comprising at least one paratope. In some embodiments, the antibody or the fragment thereof comprises and a heavy chain complementary determining region 1 (HC CDR1) comprising SEQ ID NO: 8, a heavy chain complementary determining region 2 (HC CDR2) comprising SEQ ID NO: 9, and a heavy chain complementary determining region 3 (HC CDR3) comprising SEQ ID NO: 10 and a light chain complementary determining region 1 (LC CDR1) comprising SEQ ID NO: 11, a light chain complementary determining region 2 (LC CDR2) comprising SEQ ID NO: 12, and a light chain complementary determining region 3 (LC CDR3) comprising SEQ ID NO: 13. In some embodiments, the CAR comprises an amino acid sequence as set forth in SEQ ID NO: 15 or SEQ ID NO: 17.

Also provided herein are isolated polypeptides encoded by the presently disclosed nucleic acids. In some embodiments, the isolated polypeptide comprises an amino acid sequence encoded by SEQ ID NO: 14 or SEQ ID NO: 16, and/or that is selected from the group consisting of SEQ ID NO: 15 and SEQ ID NO: 17.

As such, the presently disclosed subject matter provides chimeric antigen receptor (CAR) molecules that in some embodiments comprise a binding domain, a transmembrane domain (TD), and an intracellular domain, wherein the binding domain binds to a tumor-exclusive epitope of a human MUC1 polypeptide such as, but not limited to tMUC. In some embodiments, the binding domain is a subsequence of an antibody that binds to a tumor-exclusive epitope of a human MUC1 polypeptide such as, but not limited to tMUC, or a fragment thereof comprising a paratope of the antibody, optionally wherein the binding domain is human or humanized. In some embodiments, the binding domain is a scFv. In some embodiments, the binding domain comprises a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10) and a light chain complementary determining region 1 (LC CDR1) comprising QDIVYGNGNTY (SEQ ID NO: 11), a light chain complementary determining region 2 (LC CDR2) comprising KVS (SEQ ID NO: 12), and a light chain complementary determining region 3 (LC CDR3) comprising FQGSHVPYT (SEQ ID NO: 13). In some embodiments, the CAR comprises a light chain variable region comprising SEQ ID NO: 7 or an amino acid sequence at least 95% identical thereto, a heavy chain variable region comprising SEQ ID NO: 5 or an amino acid sequence at least 95% identical thereto, or both a light chain comprising SEQ ID NO: 7 and a heavy chain comprising SEQ ID NO: 5 or an amino acid sequence at least 95% identical to SEQ ID NO: 7 fused to SEQ ID NO: 5, optionally wherein SEQ ID NO: 7 and SEQ ID NO: 5 or the amino acid sequences at least 95% identical thereto are separated by a linker.

In some embodiments of the presently disclosed CAR molecules, the TD comprises a TD of a protein selected from the group consisting of the T-cell receptor (TCR) alpha chain, the TCR beta chain, the TCR zeta chain, CD28, CD3 epsilon, CD45, CD4, CD5, CD8, CD9, CD16, CD22, CD33, CD37, CD64, CD80, CD86, CD134, CD137, and CD154. In some embodiments, the TD comprises: (i) SEQ ID NO: 21 or SEQ ID NO: 23; (ii) an amino acid sequence having at least one, two, or three but not more than 20, 10, or 5 modifications of the amino acid sequence set forth in SEQ ID NO: 21 or SEQ ID NO: 23; or (iii) a sequence with at least 95% identity to SEQ ID NO: 21 or SEQ ID NO: 23.

In some embodiments of the presently disclosed CAR molecules, the binding domain is connected to the transmembrane domain by a hinge region. In some embodiments, the hinge region comprises SEQ ID NO: 26 or a subsequence thereof.

In some embodiments, the presently disclosed CAR molecules further comprise a costimulatory domain, optionally a costimulatory domain comprising a functional signaling domain of a protein selected from the group consisting of OX40, CD2, CD3, CD27, CD28, CDS, ICAM-1, LFA-1 (CD11a/CD18), and 4-1BB (CD137). In some embodiments, the costimulatory domain comprises SEQ ID NO: 20 or SEQ ID NO: 22, or optionally an amino acid sequence with at least 95% identity to the amino acid sequence set forth in SEQ ID NO: 20 or SEQ ID NO: 22.

In some embodiments, the presently disclosed CAR molecules further comprise an intracellular signaling domain, wherein in some embodiments the intracellular signaling domain comprises a functional signaling domain of 4-1BB, a functional signaling domain of CD3 zeta, or both. In some embodiments, the intracellular signaling domain comprises (i) an amino acid sequence as set forth in SEQ ID NO: 20 and/or SEQ ID NO: 24; or (ii) an amino acid sequence as set forth in SEQ ID NO: 22 and/or SEQ ID NO: 25; or (iii) an amino acid sequence that has at least one, two, or three but not more than 20, 10, or 5 modifications of the amino acid sequence as set forth in SEQ ID NO: 20 and/or SEQ ID NO: 24; or SEQ ID NO: 22 and/or SEQ ID NO: 25.

In some embodiments, the presently disclosed CAR molecules further comprise a leader sequence, optionally a leader sequence comprising an amino acid sequence as set forth in SEQ ID NO: 18, or an amino acid sequence with at least 95% identity thereto.

In some embodiments, a chimeric antigen receptor (CAR) of the presently disclosed subject matter comprises a human tMUC binding domain, a hinge region, a transmembrane domain, a signaling domain, and a co-stimulatory domain, wherein the tMUC binding domain comprises a monoclonal antibody TAB-004-derived single-chain variable fragment (scFv), wherein: (i) the TAB-004-derived scFv comprises a heavy chain complementary determining region 1 (HC CDR1) comprising GYTFTNYW (SEQ ID NO: 8), a heavy chain complementary determining region 2 (HC CDR2) comprising INPSSGYT (SEQ ID NO: 9), and a heavy chain complementary determining region 3 (HC CDR3) comprising STYYGDYLFPY (SEQ ID NO: 10); and a light chain complementary determining region 1 (LC CDR1) comprising QDIVYGNGNTY (SEQ ID NO: 11), a light chain complementary determining region 2 (LC CDR2) comprising KVS (SEQ ID NO: 12), and a light chain complementary determining region 3 (LC CDR3) comprising FQGSHVPYT (SEQ ID NO: 13), and/or (ii) the TAB-004-derived scFv comprises a light chain variable region comprises SEQ ID NO: 6; and/or (iii) the TAB-004-derived scFv comprises a heavy chain variable region comprises SEQ ID NO: 5; and/or (iv) the signaling domain comprises a CD3 zeta signaling domain; and/or (v) the co-stimulatory domain comprises a CD28 co-stimulatory domain. In some embodiments, a CAR of the presently disclosed subject matter comprises an amino acid sequence selected from the group consisting of SEQ ID NO: 15 and SEQ ID NO: 17. In some embodiments, the binding domain of a CAR of the presently disclosed subject matter is human or humanized.

In some embodiments, the presently disclosed nucleic acid molecules are present in a vector, optionally an expression vector. Thus, the presently disclosed subject matter provides in some embodiments vectors comprising the isolated nucleic acid molecules of the presently disclosed subject matter and/or a nucleotide sequence encoding a presently disclosed CAR of the presently disclosed subject matter. In some embodiments, the vector is selected from the group consisting of a DNA vector, an RNA vector, a plasmid, a lentivirus vector, an adenovirus vector, an adeno-associated virus (AAV) vector, and a retrovirus vector, any of which can in some embodiments be an expression vector. In some embodiments, a vector of the presently disclosed subject matter further comprises a promoter, optionally an EF-1 promoter, operably linked to the isolated nucleic acid molecule or the nucleotide sequence. In some embodiments, the vector is an in vitro transcribed vector. In some embodiments, the isolated nucleic acid molecule or the nucleotide sequence further comprises and/or encodes a polyadenylation signal and/or a poly(A) tail. In some embodiments, the nucleic acid molecule or the nucleotide sequence in the vector further comprises a 3'-UTR.

Thus, in some embodiments the presently disclosed subject matter provides vectors comprising a nucleic acid sequence encoding a chimeric antigen receptor (CAR) of the presently disclosed subject matter, wherein the CAR comprises an antigen binding domain that binds to a tumor-exclusive epitope of human MUC1, a transmembrane domain, a costimulatory signaling domain of CD28, and a CD3 zeta signaling domain. In some embodiments, the isolated nucleic acid sequence encoding the CAR comprises the nucleic acid sequence of SEQ ID NO: 14 or SEQ ID NO: 16. In some embodiments, the antigen binding domain is an antibody or fragment thereof that binds to the tumor-exclusive epitope of human MUC1 (i.e., to tMUC).

In some embodiments of the presently disclosed subject matter, the vectors are present within host cells. In some embodiments, the host cell is a human T cell, optionally a CD8+ T cell.

The presently disclosed subject matter also provides in some embodiments methods for making a cell expressing an anti-MUC1 CAR in some embodiments, an anti-tMUC CAR) as disclosed herein. In some embodiments, the methods comprise transducing a T cell with a vector encoding an anti-MUC1 CAR as disclosed herein.

In some embodiments, the presently disclosed subject matter also provides methods for generating populations of RNA-engineered cells, which in some embodiments comprise introducing an in vitro transcribed RNA or synthetic RNA into a cell, where the RNA comprises a nucleic acid encoding an anti-MUC1 CAR molecule of the presently disclosed subject matter.

IX. Methods for Expressing CAR Nucleic Acids In Vivo

The presently disclosed subject matter also provides in some embodiments methods for expressing nucleic acids encoding CARs in vivo.

In some embodiments, the presently disclosed subject matter provides methods for generating a persisting population of genetically engineered T cells in a human or other mammal diagnosed with cancer. In some embodiments, the presently disclosed methods comprise administering to the human or other mammal a T cell genetically engineered to express a CAR that comprises an antigen binding domain that binds to a tumor-exclusive epitope of a human MUC1 polypeptide, a transmembrane domain, a costimulatory signaling region comprising the CD28 signaling domain, and a CD3 zeta signaling domain, wherein the persisting population of genetically engineered T cells persists in the human for at least one month after administration. In some embodiments, the persisting population of genetically engineered T cells comprises at least one T cell that was administered to the human and/or a progeny cell thereof. In some embodiments, the persisting population of genetically engineered T cells comprises a memory T cell. In some embodiments, the persisting population of genetically engineered T cells persists in the human for at least three months, four months, five months, six months, seven months, eight months, nine months, ten months, eleven months, twelve months, two years, or at least three years after administration. In some embodiments, the cancer is a MUC1-associated cancer.

The presently disclosed subject matter also provides in some embodiments methods for expanding a population of genetically engineered T cells in a human or other mammal diagnosed with cancer. In some embodiments, the methods comprise administering to the human or other mammal a T cell genetically engineered to express a CAR comprising an antigen binding domain that binds to a tumor-exclusive epitope of a human MUC1 polypeptide, a transmembrane domain, a costimulatory signaling region comprising the CD28 signaling domain, and a CD3 zeta signaling domain, wherein the administered genetically engineered T cell produces a population of progeny T cells in the human. In some embodiments, the progeny T cells in the human comprise a memory T cell. In some embodiments, the T cell administered to the human is an autologous T cell. In some embodiments, the population of progeny T cells persists in the human for at least three months, four months, five months, six months, seven months, eight months, nine months, ten months, eleven months, twelve months, two years, or at least three years after administration.

The presently disclosed subject matter also provides in some embodiments methods for modulating the amount of cytokine secreted by a T cell. In some embodiments, the methods comprise genetically engineering the T cell to express a CAR of the presently disclosed subject matter. In some embodiments, the amount of cytokine secreted by a T cell reduces the proliferation of T regulatory cells in vivo, in vitro, or ex vivo.

In some embodiments, the presently disclosed subject matter provides methods for reducing the amount of activation-induced calcium influx into a T cell. In some embodiments, the methods comprise genetically engineering the T cell to express a CAR of the presently disclosed subject matter. In some embodiments, reducing the amount of activation-induced calcium influx into a T cell prevents activation-induced cell death of the T cell in vivo, in vitro, or ex vivo.

X. Methods of Treatment and/or Prevention Employing CARs

The presently disclosed subject matter also provides methods for treating and/or preventing a disease, condition, or disorder associated with undesirable MUC1 expression.

In some embodiments, the presently disclosed methods relate to providing an anti-tumor immunity to a mammal, optionally a human. In some embodiments, the presently disclosed methods comprise administering to the mammal or the human an effective amount of a cell expressing a CAR molecule of the presently disclosed subject matter. The cell expressing the CAR molecule can be in some embodiments an autologous T cell and in some embodiments the cell is an allogeneic T cell.

The presently disclosed subject matter methods also relate to treating mammals, optionally humans, having a MUC1-associated disease, condition, or disorder, wherein the methods comprise administering to the mammal an effective amount of a cell comprising a CAR molecule of the presently disclosed subject matter. In some embodiments, the MUC1-associated disease or disorder is selected from a proliferative disease such as a cancer or malignancy or a precancerous condition such as a myelodysplasia, a myelodysplastic syndrome, or a preleukemia, or is a non-cancer related indication associated with aberrant expression of MUC1 wherein a tMUC epitope is expressed on a cell present within the mammal. In some embodiments, the MUC1-associated disease or disorder is a cancer that expresses tMUC, such as but not limited to breast cancer, optionally Triple Negative Breast Cancer (TNBC; both BaA and BaB), Luminal A, Luminal B, and/or HER-2-type breast cancer; pancreatic cancer; and/or ovarian cancer.

In some embodiments, the cells expressing the CAR molecule are administered as part of a combination therapy that also comprises administration of a cyclooxygenase inhibitor. Exemplary cyclooxygenase inhibitors include non-steroidal anti-inflammatory drugs (NSAIDs). In some embodiments, an NSAID can be selected from the group consisting of fenamic acids, indoles, phenylalkanoic acids, phenylacetic acids, coxibs, pharmaceutically acceptable salts thereof, and combinations thereof. In some embodiments, the NSAID is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11,14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, celecoxib, pharmaceutically acceptable salts thereof, and combinations thereof. In some embodiments, the NSAID is celecoxib.

In some embodiments, the cells expressing a CAR molecule are administered as part of a combination therapy that also comprises administering an agent that ameliorates one or more side effects associated with administration of the cell expressing the CAR molecule.

In some embodiments, the presently disclosed methods relate to providing anti-tumor immunity to a mammal, optionally a human. In some embodiments, the methods comprise administering to the mammal an effective amount of a genetically modified cell comprising an isolated nucleic acid sequence encoding a CAR as disclosed herein. In some embodiments, the isolated nucleic acid sequence comprises a sequence encoding a binding domain that binds to a tumor-exclusive epitope of MUC1 and a CD3 zeta signaling domain. In some embodiments, the cell is an autologous T cell.

The presently disclosed subject matter, also provides methods for treating a MUC1-associated cancer in a human patient. In some embodiments, the methods comprise administering to the human patient a pharmaceutical composition comprising an anti-tumor effective amount of a population of modified human T cells, optionally modified autologous T cells, wherein the T cells comprise a nucleic acid sequence that encodes a CAR of the presently disclosed subject matter. In some embodiments, the CAR comprises an antigen binding domain that binds to a tumor-exclusive epitope of MUC1 (tMUC), optionally a hinge domain, a transmembrane domain, a CD28 costimulatory signaling region, and a CD3 zeta signaling domain. In some embodiments, the anti-tumor effective amount of T cells is $10^4$ to $10^9$ cells per kg body weight of the human patient. In some embodiments, the anti-tumor effective amount of T cells is $10^5$ to $10^6$ cells per kg body weight of the human patient. In some embodiments, the antigen binding domain is an antibody or a fragment thereof that binds to the tMUC epitope. In some embodiments, the antigen binding fragment comprises a Fab fragment or an scFv. In some embodiments, the scFv comprises an amino acid sequence as set forth in amino acid residues 22-267 of SEQ ID NO: 15 or SEQ ID NO: 17, or an amino acid sequence with at least 95% identity to amino acid residues 22-267 of SEQ ID NO: 15 or SEQ ID NO: 17. In some embodiments, the scFv is encoded by a nucleic acid sequence comprising nucleotides 64-803 of SEQ ID NO: 14 or nucleotides 64-803 of SEQ ID NO: 16. In some embodiments, the modified T cells replicate in vivo in the human patient and/or form memory T cells in the human patient. In some embodiments, the modified T cells are administered intravenously to the human patient. In some embodiments, the modified T cells persist in the human patient, optionally for at least three, four, five, six, seven, eight, nine, ten, eleven, twelve, eighteen, twenty-four, thirty, or thirty-six months after administration.

The presently disclosed subject matter also relates in some embodiments to methods for stimulating T cell-mediated immune responses to a target cell population or tissue in a mammal, optionally a human. In some embodiments, the methods comprise administering to the mammal an effective amount of a cell genetically modified to express a CAR, wherein the CAR comprises an antigen binding domain that binds to tMUC, a transmembrane domain, a costimulatory signaling region comprising the CD28 signaling domain, and a CD3 zeta signaling domain.

In some embodiments, a method for inducing anti-tumor immunity in a mammal comprises administering to the mammal an effective amount of a cell genetically modified to express a CAR, wherein the CAR comprises an antigen binding domain that binds to a tumor-exclusive epitope of MUC1, a transmembrane domain, a costimulatory signaling region comprising the CD28 signaling domain, and a CD3 zeta signaling, thereby inducing an anti-tumor immunity in the mammal.

The presently disclosed subject matter also relates in some embodiments to methods for treating a mammal having a disease, disorder, or condition associated with expression of a tumor-exclusive epitope of MUC1. In some embodiments, the methods comprise administering to the mammal an effective amount of a cell genetically modified to express a CAR that comprises an antigen binding domain that binds to the tumor-exclusive epitope of MUC1, a transmembrane domain, a costimulatory signaling region comprising the CD28 signaling domain, and a CD3 zeta signaling domain, thereby treating the mammal. In some embodiments, the cell is an autologous T cell.

The presently disclosed subject matter also relates in some embodiments to methods for treating a human with cancer. In some embodiments, the methods comprise administering to the human a T cell genetically engineered to express a CAR that comprises an antigen binding domain that binds to a tumor-exclusive form of MUC1, a transmembrane domain, a costimulatory signaling region comprising the CD28 signaling domain, and a CD3 zeta signaling domain. In some embodiments, the presently disclosed methods further comprise administering a cyclooxygenase inhibitor, optionally a cyclooxygenase-2-selective inhibitor, to the subject as part of a combination therapy with the T cell genetically engineered to express the CAR.

XI. Methods for Imaging Cells Expressing Tumor-specific MUC1 Epitopes

The presently disclosed subject matter also provides methods for imaging cells expressing tumor-specific MUC1 epitopes such as, but not limited to, tMUC.

In some embodiments, the presently disclosed methods comprise (a) providing a mammal with a MUC1-associated tumor; (b) administering to the mammal a CAR of the presently disclosed subject matter, wherein the CAR further comprises a detectable moiety; and (c) detecting the detectable moiety in the mammal, whereby a tumor is imaged in the mammal. In some embodiments, the MUC1-associated tumor is selected from the group consisting of a breast tumor, optionally a Triple Negative Breast Cancer (TNBC; both BaA and BaB) tumor, a Luminal A tumor, a Luminal B tumor, and/or a HER-2-type breast tumor; a pancreatic tumor; and an ovarian tumor. In some embodiments, the detectable moiety is detectable using a technique selected from the group consisting of X-ray imaging, positron emission tomography (PET) imaging, single photon emission computed tomography (SPECT) imaging, computed tomography (CT) imaging, and magnetic resonance imaging (MRI).

Also provided are the presently disclosed isolated nucleic acid molecules, isolated polypeptide molecules, CARs, vectors, and/or cells for use in the treatment of a disease, condition, or disorder associated with overexpression of MUC1, optionally wherein the disease is a cancer.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Example 1

Generation of Pancreatic Adenocarcinoma Mice Expressing Human MUC1

Figure 3:
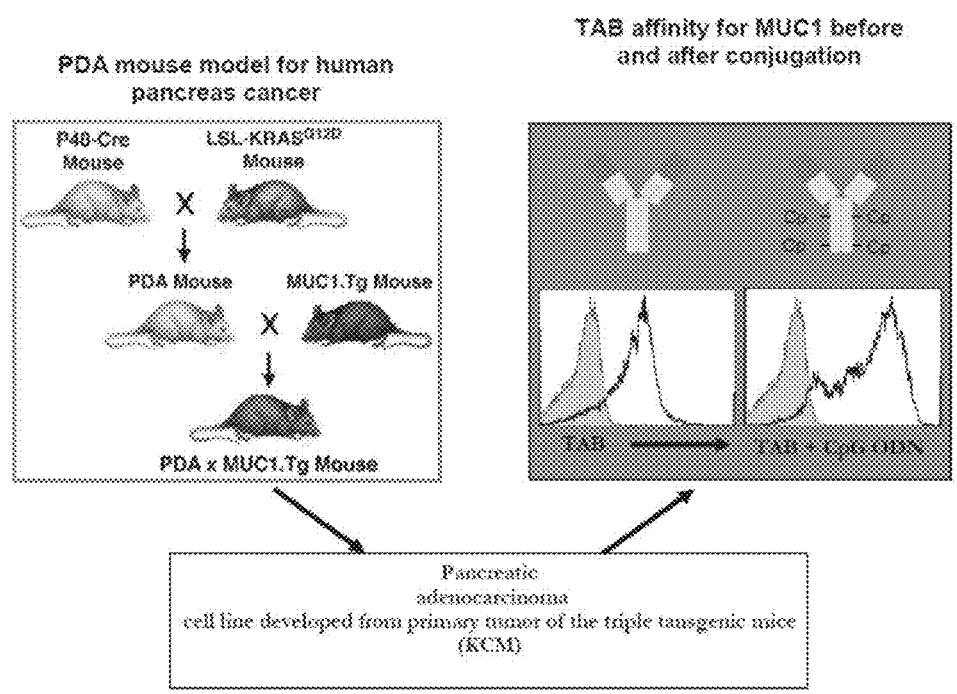
FIG. 3 is a schematic (upper left panel) showing an approach for creating a triple transgenic mouse line that expresses the Cre recombinase throughout the pancreas, a mutated K-ras oncogene polypeptide, and a human MUC1 polypeptide. This mouse develops pancreatic adenocarcinoma, cells of which were used to generate the primary tumor cell line KCM (lower panel). The KCM cell line was used to test the binding of an exemplary antibody of the presently disclosed subject matter (denoted in the Figure as "TAB" and in the instant disclosure as "TAB-004") either alone or conjugated to CpG oligodeoxynucleotides (CpG ODN). It was determined that both the unconjugated and conjugated antibodies bound to the KCM pancreatic cell line with equal affinity (upper right panel).

A strategy for generating a triple transgenic mouse line that expressed human MUC1 and develops pancreatic adenocarcinoma is depicted in FIG. 3. Briefly, P48$^{Cre/+}$ mice, which expressed the Cre recombinase throughout the developing and adult pancreas (Kawaguchi et al., 2002) were bred to LSL-Kras$^{G12D/+}$ mice, which contained a transcriptionally inactive K-ras$^{G12D}$ allele that was activated in cells expressing Cre (Jackson et al., 2001; Kawaguchi et al., 2002). The progeny that were positive for both P48$^{Cre/+}$ and LSL-Kras$^{G12D/+}$ (designated "PDA mice") were mated to a transgenic mouse line (MUC1.Tg) that carried a human MUC1 transgene and were maintained as heterozygotes (see FIG. 3). MUC1.Tg mice expressed human MUC1, exhibited B- and T-cell compartment tolerance, and were refractory to immunization with the protein encoded by the transgene (Rowse et al., 1998). Since the human MUC1 transgene was driven by its own promoter in these mice, its expression levels were tissue-specific and appropriate. Low-level luminal surfaces of simple epithelial tissue and increased expression in tumors were observed.

Figure 1B:
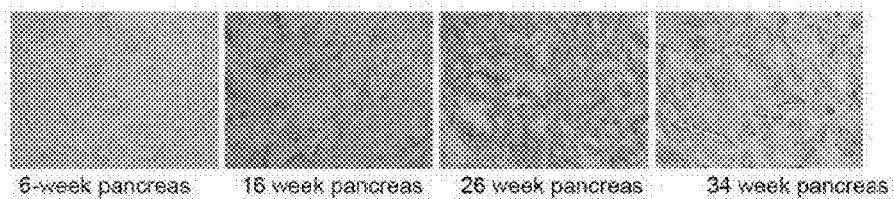

Mice that were positive for P48$^{Cre/+}$, LSL-Kras$^{G12D/+}$, and human MUC1 (referred to herein as "PDA.MUC1.Tg" mice) carried three transgenes. All PDAxMUC1.Tg mice developed pancreatic intraepithelial neoplasia (PanINs) of different stages including PanIN-IA, PanIN-IB, PanIN-2, PanIN-3, and adenocarcinoma (Tinder et al., 2008; Mukherjee et al., 2009). Representative sections from various ages of the PDAxMUC1.Tg pancreas are shown in FIG. 1B. Approximately 80% of these mice developed adenocarcinoma by 26 weeks of age, and almost 100% of the mice developed adenocarcinoma by 34 weeks of age.

From the PDA.MUC1.Tg mice (FIG. 3) that expressed human MUC1 and K-ras$^{G12D}$ tumor antigens, protein lysates were prepared in order to produce antisera to tumor-associated antigens expressed by the triple transgenic mice. Briefly, 5 mgs of the protein lysate was mixed with Incomplete Freund's Adjuvant (IFA) and used to immunize Balb/c mouse. Hybridomas were generated by fusion of spleen cells from immunized mice with myeloma cells, and the TAB-004 antibody was identified by screening hybridomas. This monoclonal antibody was determined to be of the IgG isotype. The purified antibody bound to tumor-associated glycosylated MUC1.

Figure 2A:
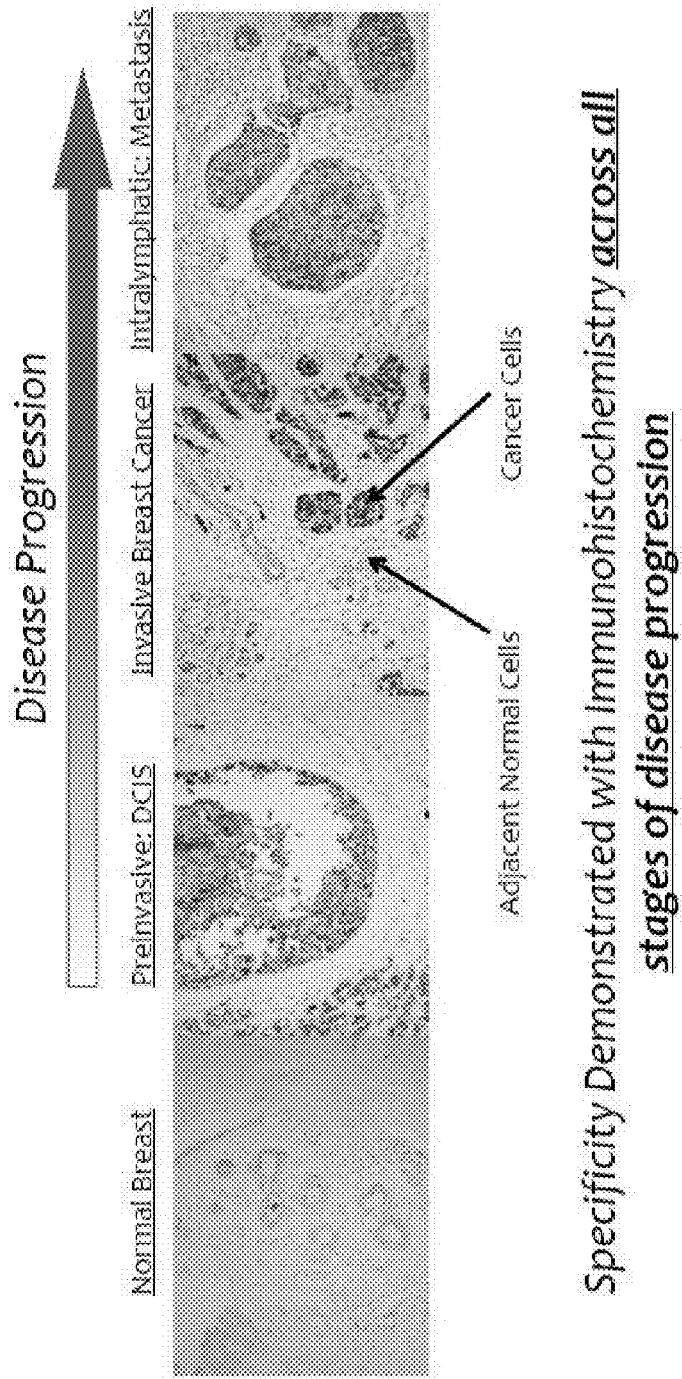
FIGS. 2A and 2B are a series of photomicrographs depicting specific binding of an exemplary antibody of the presently disclosed subject matter (i.e., a horse radish peroxidase (HRP)-labeled TAB-004 anti-MUC1 monoclonal antibody) to human breast tumor tissue.
Figure 2B:
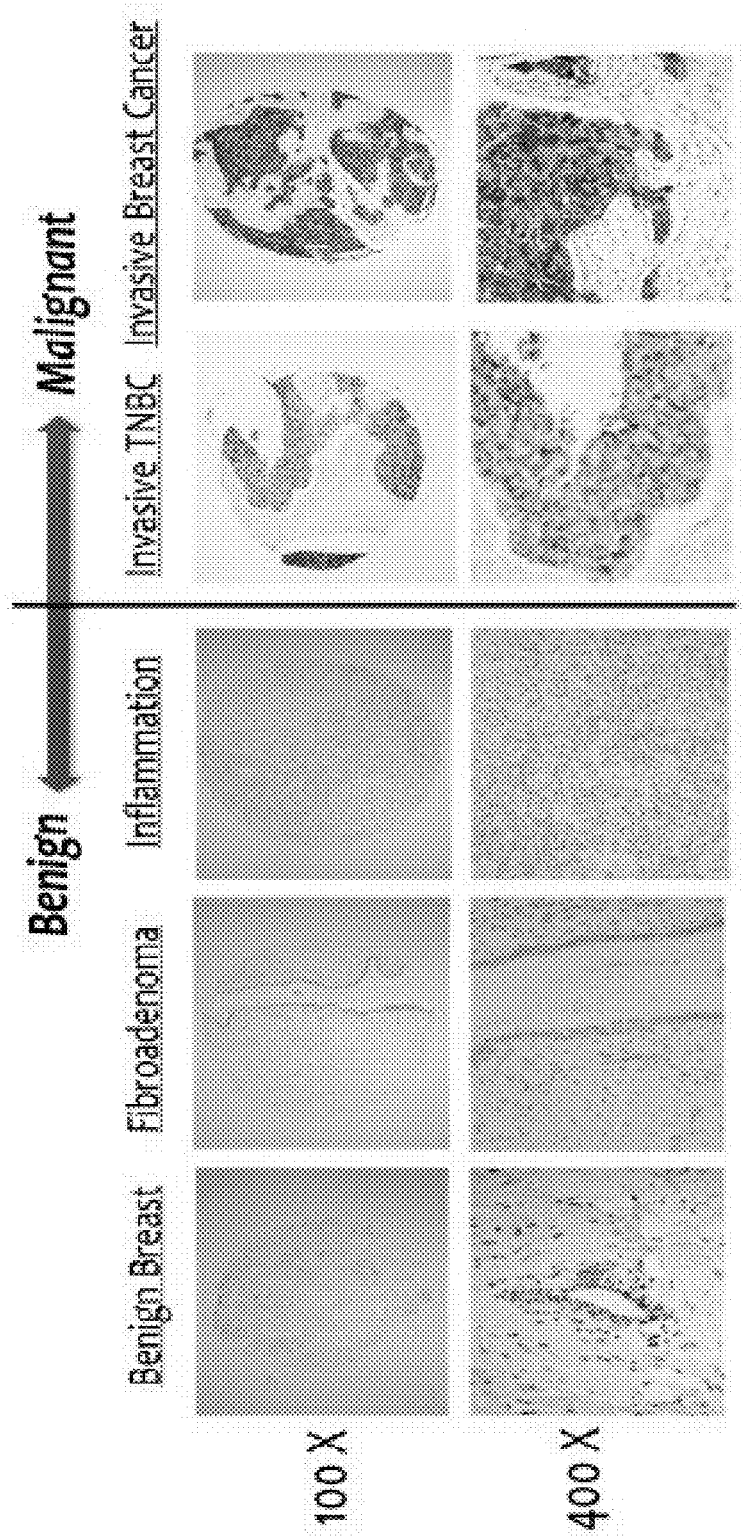

Epitope screening determined that the TAB-004 monoclonal antibody (mAb) described herein bound to an epitope present within SEQ ID NO: 3. The antibody reacted strongly with tumor tissue isolated from human pancreas (FIG. 1B), human breast (FIGS. 2A and 2B), but did not bind appreciably to normal pancreas or breast tissue (see FIGS. 1A, 2A, and 2B).

Interestingly, the TAB-004 antibody cross reacted with mutated K-ras such that tumor tissues expressing the K-ras mutation but not human MUC1 also showed positive staining with the antibody. All metastatic lesions showed positive reactivity, and it appeared that TAB-004 could bind to an epitope present within a mutated K-ras polypeptide.

Example 2

FACS Sorting of Tumor Cells

The TAB-004 antibody was tested with various samples to determine its ability to bind to and sort tumor cells that were present in different environments and under different conditions using Fluorescence Activating Cell Sorting (FACS).

In a first experiment, the TAB-004 antibody was employed for staining cells from purified populations of CD133$^+$ and CD24$^+$/CD44$^+$/EpCAM$^+$ cells. Sections from pancreatic adenocarcinomas are mechanically homogenized and digested in collagenase IV and DNase for 30 minutes at 37° C. Whole blood and single cell suspension from the tumor were subjected to lineage cell depletion using the Lineage Cell Depletion Kit (Miltenyi Biotec, Bergisch Gladbach, Germany, Catalogue No. 130-092-211), thus removing cells expressing the following lineage antigens: CD2, CD3, CD11b, CD14, CD15, CD16, CD19, CD56, CD123, and CD235a from the cell suspensions. Lineage negative (lin) cells from blood samples or tumor samples from patients with pancreatic cancer were then screened using flow cytometry for cells expressing MUC1, using the TAB-004 antibody, and the following pancreatic stem markers CD133 (AC133) or CD24$^+$/CD44$^+$.

FIGS. 7A and 7B are histograms of fluorescence-activated cell sorting (FACS) separations of CD133$^+$ (FIG. 7A) and CD24$^+$/CD44$^+$/EpCAM$^+$ (FIG. 7B) cells and the extent to which the TAB-004 antibody disclosed herein bound to these populations.

Next, FACS analysis was employed to compare MUC1 expression using the TAB-004 antibody in normal and pancreatic tumor cells isolated from pancreatic tumor tissues, and also the expression of CXCR4, a polypeptide that has been associated with mobility of cells including cancer cells. The results are shown in FIG. 8.

In FIG. 8, the distributions of cells in histologically normal pancreatic tissue (FIG. 8C) versus adjacent pancreatic adenocarcinoma tissue (FIG. 8D) stained with the TAB-004 antibody versus a CXCR4 antibody was compared. As can be seen, cells that were positive for MUC1 or for CXCR4 were more abundant in pancreatic adenocarcinoma tissue than in histologically normal adjacent pancreatic tissue. FIGS. 8A and 8B show the results of negative controls (FIG. 8A—no antibody; FIG. 8B—isotype control antibody).

Figure 9A:
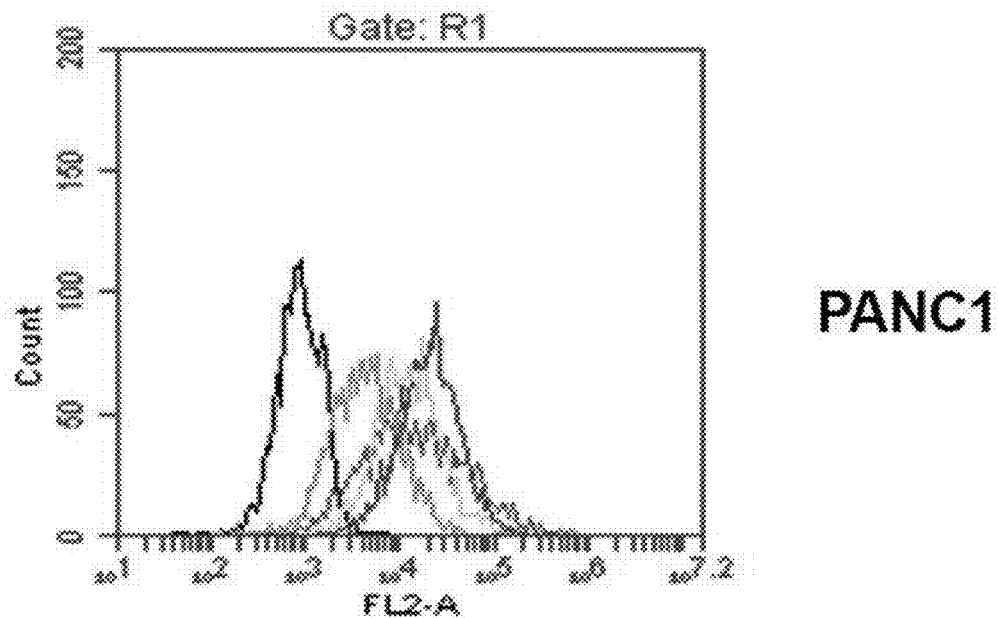
FIGS. 9A-9C are a series of FACS plots that show that the TAB-004 antibody of the presently disclosed subject matter is superior to a standard EpCAM antibody in detecting circulating tumor cells in pancreatic cancer patients. Unstained cells (black lines); EpCAM-PE (0.1 mg/ml) stained cells (red lines); TAB-004-PE (0.1 mg/ml) stained cells (blue lines); TAB-004-PE (0.02 mg/ml) stained cells (yellow lines); TAB-004-PE (0.004 mg/ml) stained cells (greenlines). "-PE" indicates that the antibodies were labeled with phycoerythrin for the purposes of sorting.

And finally, the TAB-004 antibody was compared to an EpCAM antibody that is currently in use for detecting epithelial cancers. FIG. 9 provides a series of FACS plots that show that the TAB-004 antibody was superior to a standard EpCAM antibody in detecting circulating tumor cells in pancreatic cancer patients.

First, whole blood from a normal control individual was spiked with 250 cells of the PANC1 pancreatic cancer cell line per 700 ml of blood, and the PANC1 cells were stained using the TAB-004 antibody. Comparison of the right-most black, light gray, and medium gray lines, which correspond to three different concentrations of TAB-004 antibody ranging from 0.1 mg/ml to 0.004 mg/ml, to the dark gray line, which corresponds to the EpCAM antibody, shows that all four of these preparations were able to detect the PANC1 cells in these preparations reasonably well.

Figure 9B:
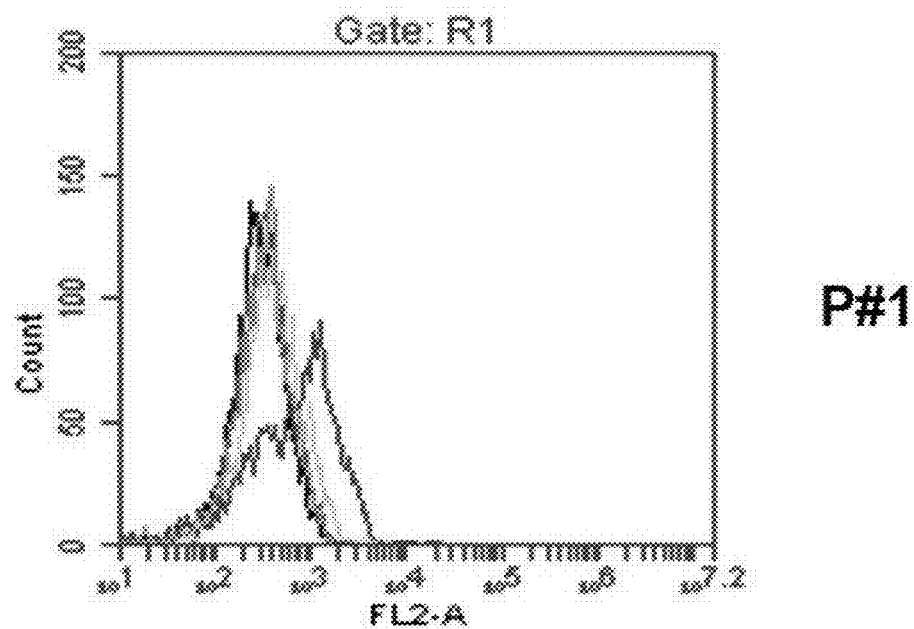
Figure 9C:
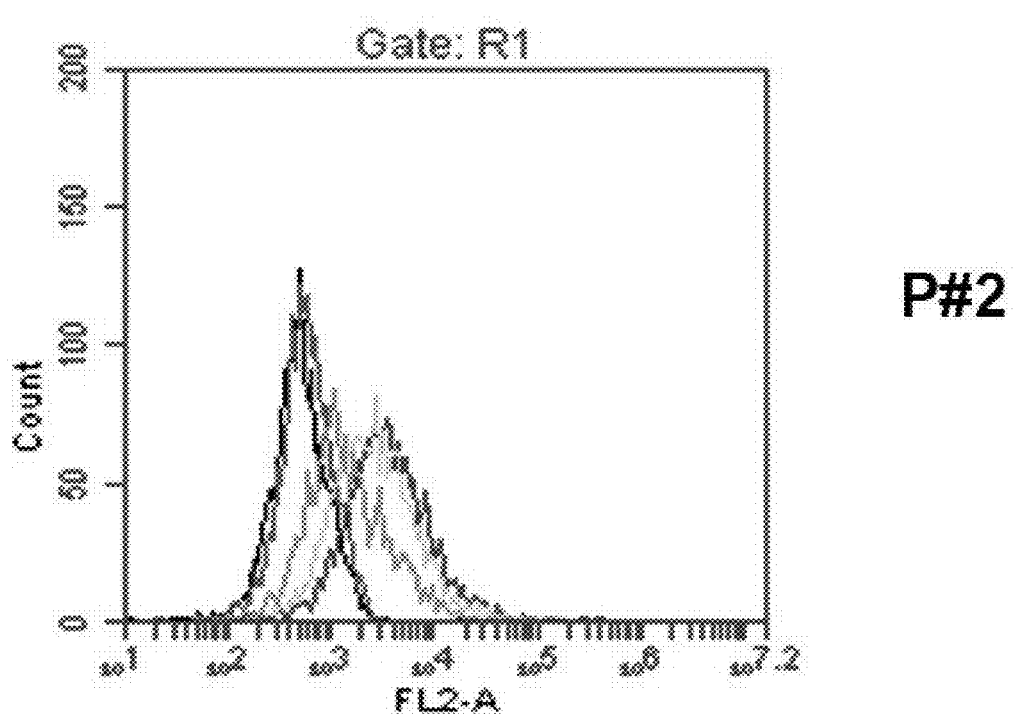

The TAB-004-PE antibody had been shown to detect MUC1 on PANC1 pancreatic cancer cells (see FIG. 9A), so the abilities of the TAB-004 and EpCAM antibodies to detect circulating tumor cells present in the blood from two patients was tested. As shown in FIGS. 9B and 9C (patients numbers 1 and 2, respectively), there was a clearly observable difference between the TAB-004 antibody and the EpCAM antibody to detect circulating tumor cells in patient blood. Particularly, the TAB-004-PE antibody (see the blue line in FIG. 9B and the blue, yellow, and green lines in FIG. 9C) but not the EpCAM-PE antibody (see the red lines in FIGS. 9B and 9C) was able to detect these circulating cells in the blood of patients, suggesting that the TAB-004 was far superior to the currently used EpCAM antibody for this purpose.

Example 3

Production of TAB-004 Conjugates

The TAB-004 antibody of the presently disclosed subject matter was conjugated to 1-methyl-DL-tryptophan (1MT), an indoleamine 2,3-dioxygenase (IDO) inhibitor; an EP2/EP4 receptor antagonist; and CpG oligodeoxynucleotides (CpG ODN), which function as dendritic cell activators (Rothenfusser et al., 2002). Data on the functional role of the TAB-004 antibody conjugated to CpG ODN is provided herewith as a non-limiting example of the functionality of the antibodies and conjugates of the presently disclosed subject matter.

Figure 4A:
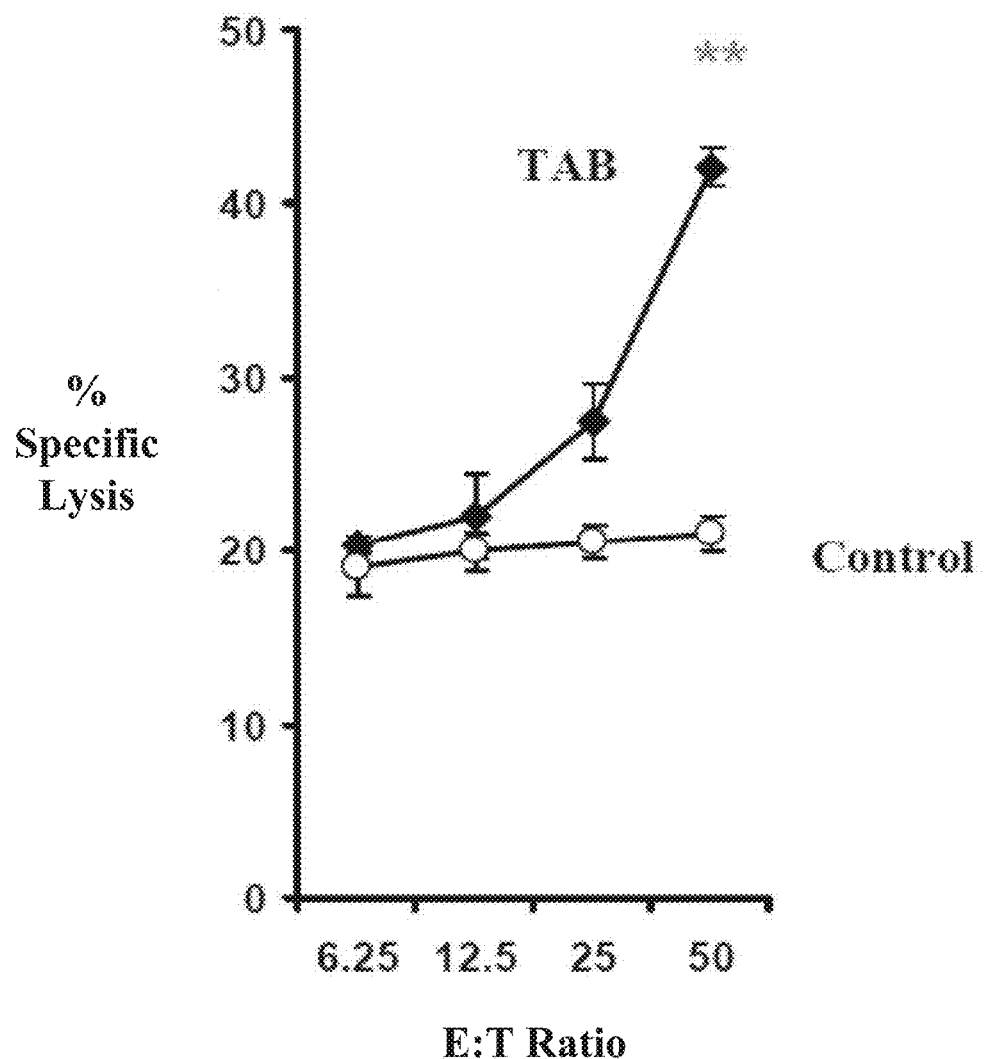
FIGS. 4A and 4B are graphs showing that an exemplary antibody of the presently disclosed subject matter (TAB-004) enhanced the cytotoxicity of Natural Killer (NK) cells to kill target tumor cells. Conjugation of the antibody to CpG ODN further enhanced this effect, thereby demonstrating that the exemplary antibody was capable of enhancing an anti-tumor immune response in vivo.
Figure 4B:
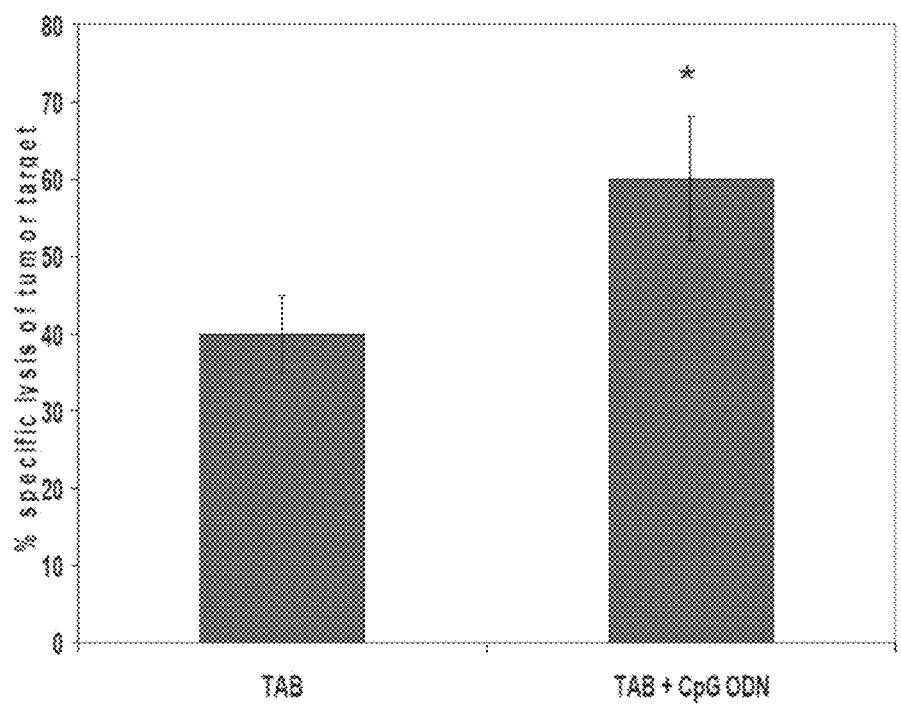

The TAB-004 antibody alone or conjugated to CpG ODN bound to a tumor cell line (referred to herein as the "KCM" cell line; see FIG. 3) generated from the triple transgenic PDA.MUC1.Tg mice. While applicants do not wish to be bound by any particular theory of operation, it appeared that the antibody activated natural killer cells (NK cells) and conjugation with CpG ODN further enhanced the NK cell lytic activity against its targets such as YAC cells as well as the KCM cells lines (see FIGS. 4A and 4B).

Example 4

In Vivo Anti-Tumor Activity of the TAB-004-CpG ODN Conjugate

Figure 5A:
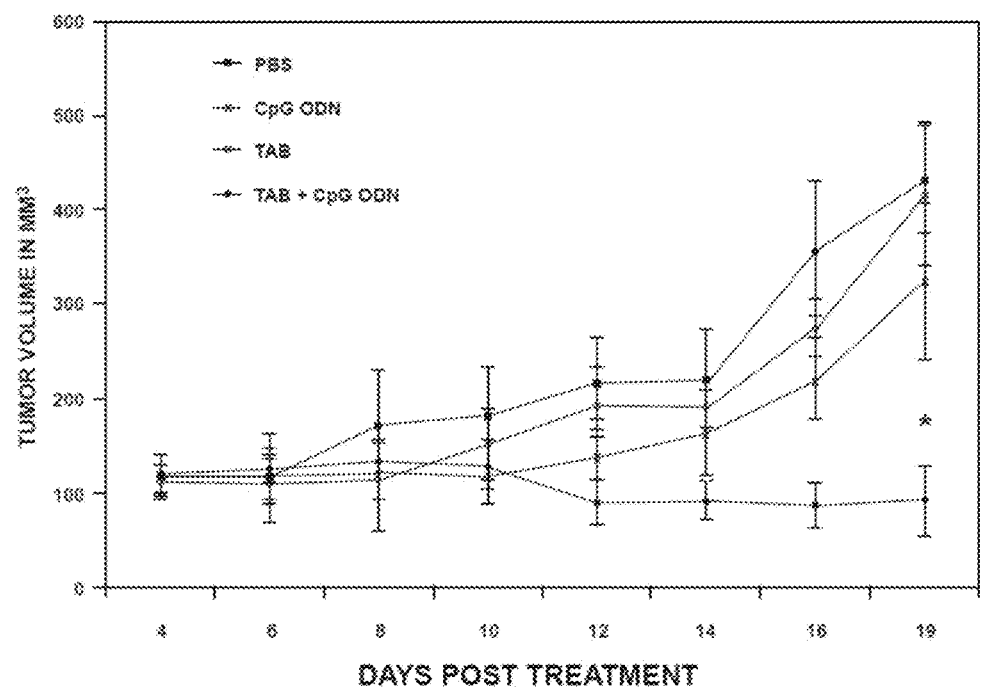
FIGS. 5A and 5B illustrate the results of experiments designed to test the ability of an exemplary antibody of the presently disclosed subject matter (TAB-004), and conjugates thereof, to reduce tumor volume of an established KCM tumor in MUC1 transgenic (MUC1 Tg) mice.
Figure 5B:
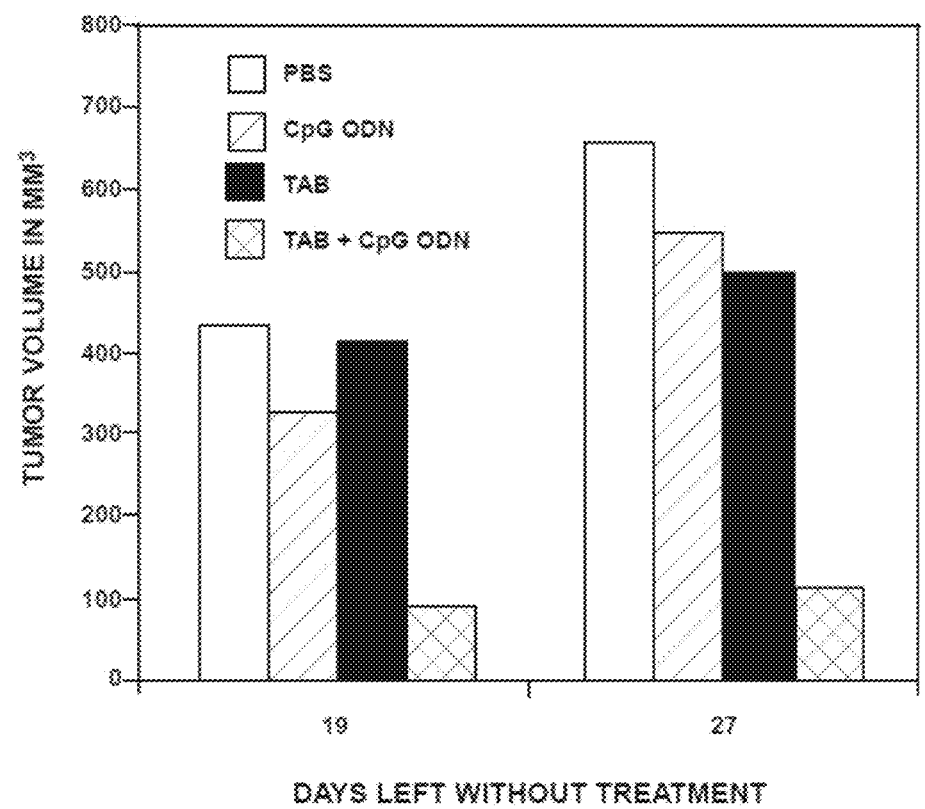
Figure 6:
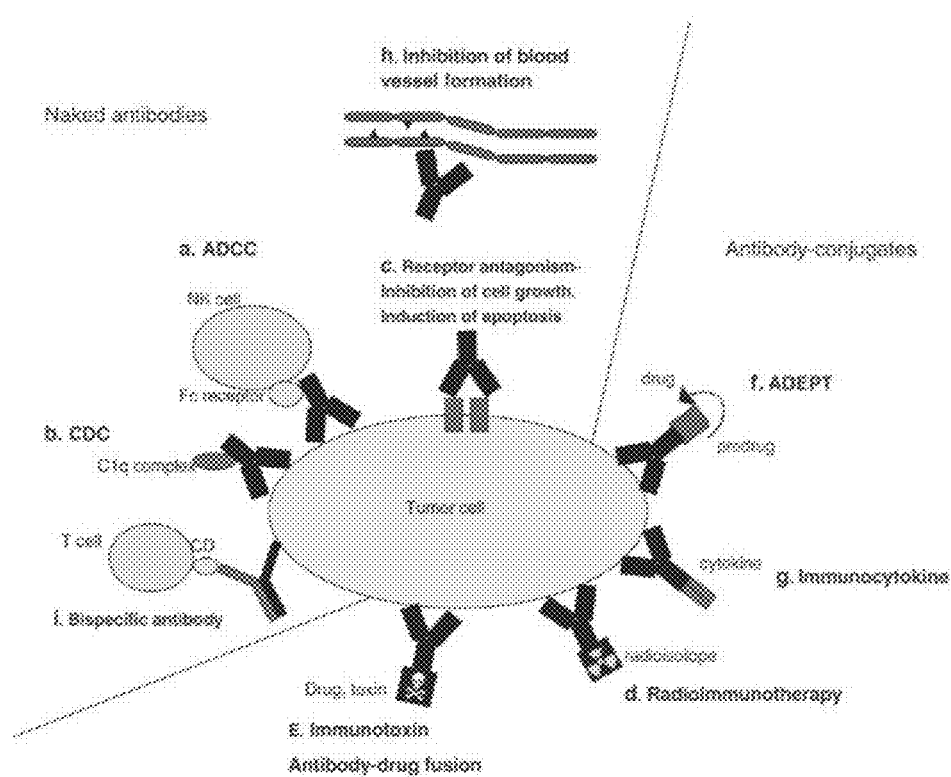
FIG. 6 is a schematic depiction of exemplary compositions of the presently disclosed subject matter and exemplary uses therefor. ADCC—antibody dependent cell-mediated cytotoxicity; CDC—complement dependent cytotoxicity; ADEPT—antibody directed enzyme prodrug therapy.
Figure 8A:
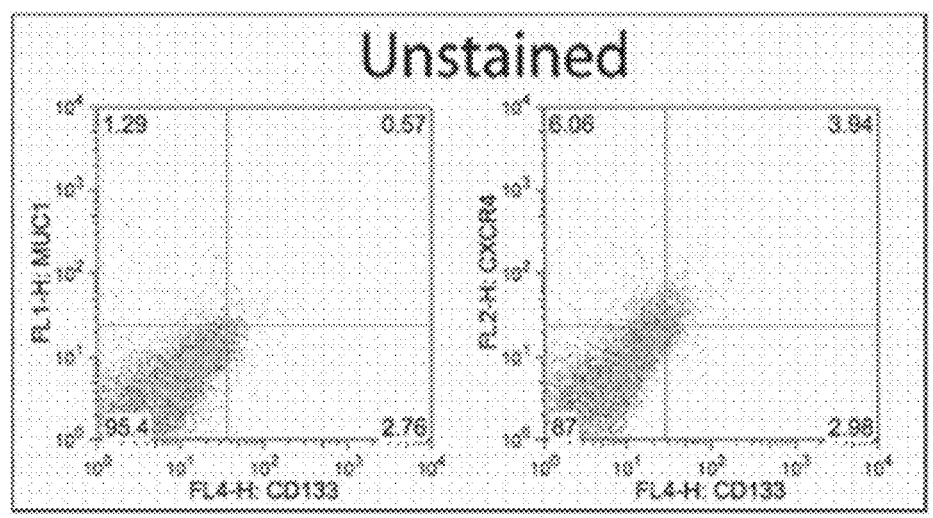
FIGS. 8A-8D are FACS scatter plots showing binding of the TAB-004 antibody to a pancreatic tumor ("Tumor1") and adjacent normal tissue ("Normal") using the TAB-004 antibody and an antibody directed against the CXC chemokine receptor 4 (CXCR4). MUC1: TAB-004 antibody; CXCR4: anti-CXCR4 antibody; FL1-H: Fluorescent stain 1 height (Fluorescein-FITC); FL2-H: Flourescent stain 2 height (Phycoerythrin-PE); SSC-H: side-scatter height; FSC-H: forward-scatter height; FL4-H: Flourescent stain 4—height (Allophycocyanin-APC).
Figure 8B:
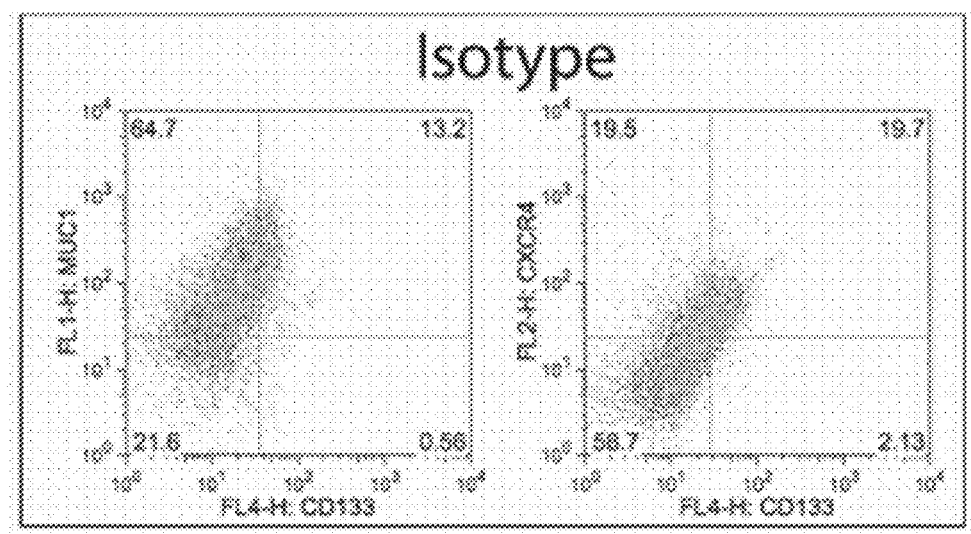
Figure 8C:
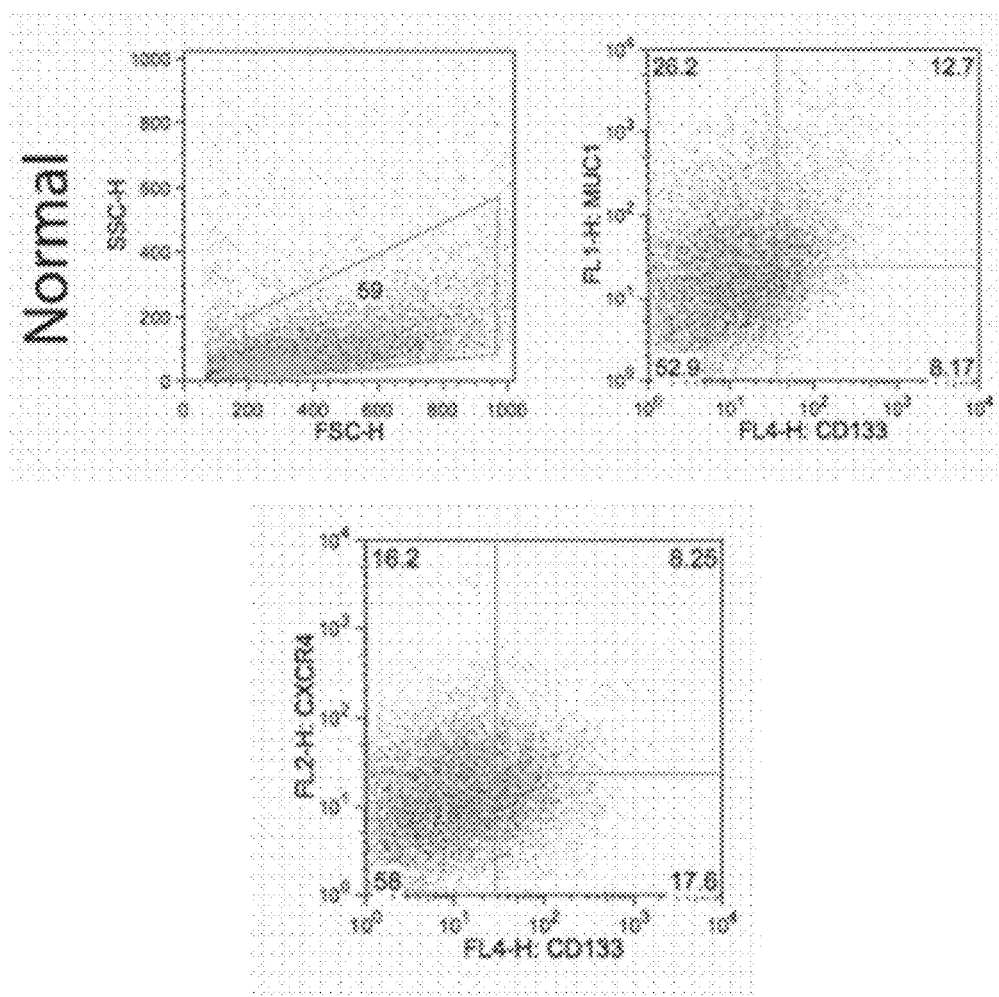
Figure 8D:
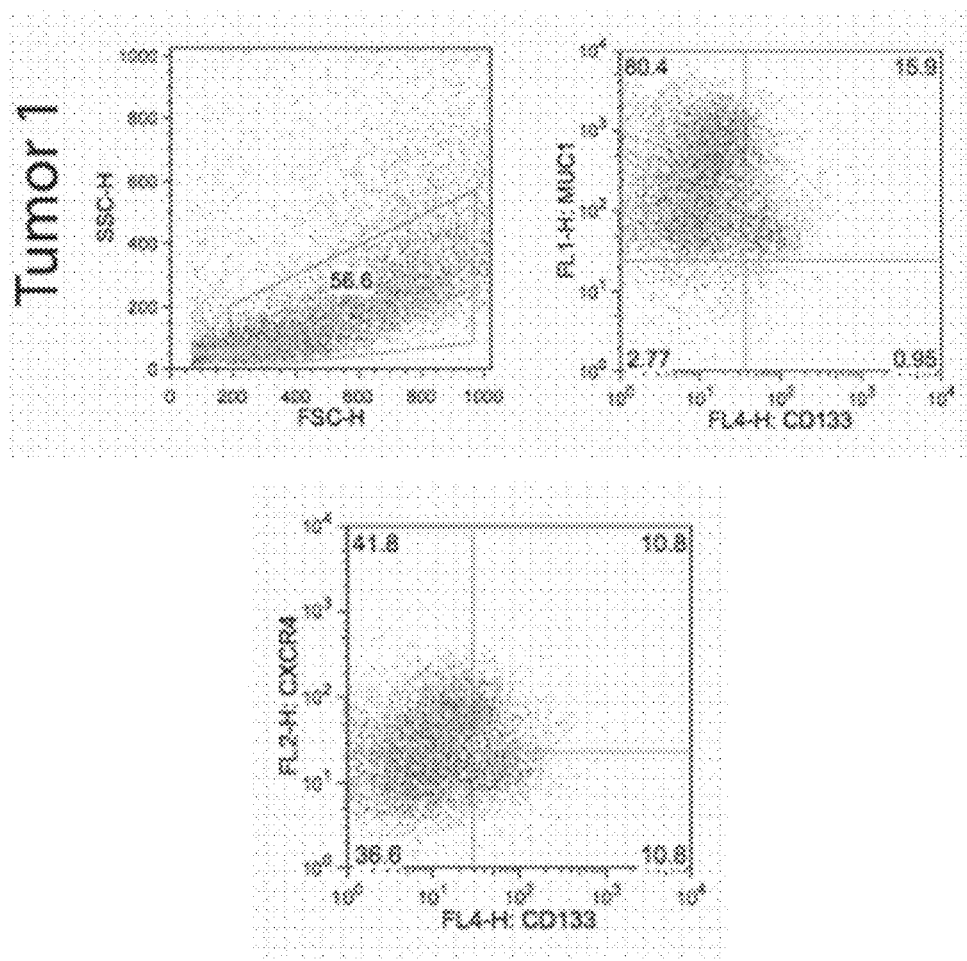

Ten (10) mice were injected with the KCM established pancreatic cancer cell line generated from the triple transgenic PDA.MUC1.Tg mice. The treatment groups and the schedule and dose were as illustrated in FIGS. 5A and 5B. Briefly, $3\times10^6$ KCM tumor cells were administered subcutaneously into the flank region of mice (n=10 mice) at day 0. At days 4, 10, and 16, 50 μg of a TAB-004-CpG ODN conjugate were administered intratumorally (without adjuvant) to each mouse. The same amounts of antibody were administered to an antibody alone group (unconjugated TAB-004) for comparison. Mice were sacrificed at day 20 and tumors recovered.

As shown in FIG. 5, treatment with the conjugated antibody completely stopped the growth of an established tumor leading to complete eradication. The data also showed that even after cessation of treatment, the mice treated with the TAB-004-CpG ODN conjugate did not grow back the tumors (see FIG. 5), supporting the use of the TAB-004-CpG ODN conjugate as a vaccine for cancer such as, but not limited to epithelial cancers, particularly pancreatic cancers.

Example 5

Antibody Cloning, Recombinant Antibody Production, Antigen Binding Confirmation, and Sequencing of (CDRs)

In order to confirm the ability of the TAB-004 antibody to bind to MUC1 and to determine the amino acid sequences of the CDRs, total RNA was extracted from hybridoma cell line ATCC No. PTA-11550 and reverse transcription PCR (RT-PCR) was performed using immunoglobulin heavy- and light chain-specific primer sets and a QIAGEN® OneStep RT-PCR Kit. For each set, multiple heavy chain and light chain RT-PCR reactions were performed using degenerate forward primer mixtures covering the leader sequences of variable regions. Forward primers were used at different concentrations, while reverse primers (located in the constant regions of the heavy or light chain genes) were 50 ng per reaction. The following RT-PCR conditions were employed: (1) Reverse transcription: 30 minutes at 50° C.; (2) Initial PCR activation step: 15 minutes at 95° C.; (3) Cycling: 20 cycles of 94° C. for 25 seconds; 54° C. for 30 seconds; and (4) 72° C. for 30 seconds; Final extension: 10 minutes at 72° C.

Next, second-round semi-nested PCR was employed. The forward primers were identical to the ones used in the first-round RT-PCR, although the amount of each primer was doubled relative to the RT-PCR conditions described above. Semi-nested reverse primers specific for heavy chain sequences were used at 100 ng per reaction. The PCR conditions employed were as follows: (1) Initial denaturing of 5 minutes at 95° C.; (2) Cycling: 25 cycles of 95° C. for 25 seconds; (3) 57° C. for 30 seconds; 68° C. for 30 seconds; (4) Final extension: 10 minutes at 68° C. After the PCR was completed, samples of the PCR products were separated on agarose gels and products were visualized. Several heavy chain and light chain PCR products were subcloned and the variable regions of the heavy and light chains were sequenced. The resulting nucleotide sequences, and the amino acid sequences encoded thereby, are shown in SEQ ID NOs: 4-7, and the amino acid sequences of the CDRs deduced therefrom are summarized in Table 4.

TABLE 4

Amino Acid Sequences of the CDRs of the Heavy and Light Chains of the TAB-004 Monoclonal Antibody

| IgG Chain | CDR1 Sequence | CDR2 Sequence | CDR3 Sequence |
|---|---|---|---|
| Heavy | GYTFTNYW (SEQ ID NO: 8) | INPSSGYT (SEQ ID NO: 9) | STYYGDYLFPY (SEQ ID NO: 10) |
| Light | QDIVYGNGNTY (SEQ ID NO: 11) | KVS (SEQ ID NO: 12) | FQGSHVPYT (SEQ ID NO: 13) |

Next, recombinant antibodies were produced by another round of RT-PCR amplification of the total RNA isolated from the hybridoma cell line ATCC No. PTA-11550 followed by second-round semi-nested PCR as set forth herein above. Amplified heavy chain sequences and light chain sequences were individually subcloned into plasmid antibody expression vectors.

Next, the plasmids from were transfected into CHO cells, and recombinant IgG having a human IgG1 backbone were produced. Supernatants from transfected CHO cells were tested for antigen binding in 96-well ELISA format. Several supernatant samples showed very strong binding, although the concentrations of the recombinant IgG in the supernatants were low (i.e., about 10 ng/ml). Given the relatively low concentration of antibody in the supernatant, the ELISA results indicated that the recombinant antibodies were very potent.

The sequences of the inserts of the recombinant antibody plasmids were determined by DNA sequencing. All corresponded to a single heavy chain sequence and a single light chain sequence. The nucleotide and amino acid sequences of the variable regions of the heavy and light chains were determined, and the CDR sequences deduced therefrom were as set forth in SEQ ID NOs: 8-13.

Example 6

Comparison of the Performance of the TAB-004 Antibody to Other Tumor Antigen-Based Detection Strategies in Breast and Pancreatic Cancers Clinical blood-based tests for tumor antigens currently available include CA 15-3 and CA 27-29 for breast cancer and CA 19-9 for pancreatic cancer. Non-cancerous conditions or benign disease can lead to elevated levels of these tumor antigens, thus negatively impacting the ability of these antibodies to be used for accurately detecting cancers. As a result of this low specificity, these tests have yet to be proven to be of significant diagnostic value.

To that end, the ability of TAB-004 to detect levels of shed MUC1 in the plasma of patients was compared to the performances of these antibodies in plasma samples. An enzyme immunoassay (EIA) has been optimized using the TAB-004 antibody to capture and detect levels of shed MUC1 present in circulation. Briefly, a 96-well ELISA plate was coated with 100 µl of TAB-004 antibody at 50 µg/mL in PBS and incubated overnight at 4° C. Following incubation, excess TAB-004 capture antibody was removed from the plate. The plate was blocked with 200 µl of 1% dry milk in PBS to avoid non-specific binding and incubated for 1 hour at 4° C. The plates were washed extensively (3 times) with 250 µl PBS containing 0.05% (v/v) TWEEN®-20 using an ELISA plate washer. A MUC1 standard using a 25-mer polypeptide preparation from MUC1 TR was prepared ranging from 0-2000 U/ml. The test plasma was diluted 1:2, and 1:10 in 0.1% milk in PBS, and 100 µl was added to the appropriate wells in triplicate, and the plates were incubated for 2 hours at 37° C.

Plates were then washed and 100 µl of a polyclonal rabbit anti-MUC1 antibody (Genway) were added at 1:300,000 dilution in 0.1% milk in PBS to each well, and the plate was incubated for 1 hour at 37° C. The polyclonal antibody was washed from the wells and horse radish peroxidase-labeled goat anti-rabbit IgG was added at a 1:1,000 dilution in 0.1% milk in PBS and incubated at 37° C. for 1 hour. After washing the plates, 100 µL of a solution consisting of peroxidase substrate (TMB) was added to the wells, and the plates incubated at room temperature for 30 minutes in the dark. The reaction was stopped by the addition of 25 µl of 4.0 N sulfuric acid, and the optical density read at a wavelength of 450 nm using a SPECTRA-MAX 250 spectrophotometer. Standard curves were generated with regression analyses to determine concentrations of the unknown samples.

Arbitrary units (U)/ml were chosen based on an initial reference standard of MUC1. A linear range was determined to be 50-800 units/ml of MUC1 antigen. Intra- and inter-assay variations were controlled by including normal and abnormal samples to ensure the equipment, the technologist, and the reagents used in the test were performing as expected.

The TAB-004 EIA assay was compared against CA15-3 (Abbott Laboratories, Abbott Park, Ill., United States of America) breast cancer samples. Comparison to CA27-29 (Bayer Diagnostics, Tarrytown, N.Y.) for breast cancer and to CA19-9 (Panomics Inc., Redwood City, Calif., United States of America) for pancreatic cancer samples using EIA assays are also performed. Statistical analyses were conducted to assess the sensitivity and specificity of TAB-004 EIA versus the commercially available EIAs.

The TAB-004 EIA was employed using plasma from 36 breast cancer patients, 24 prostate cancer patients, 4 pancreatic cancer patients, 13 esophageal cancer patients, 12 normal controls, 3 patients with pancreatitis, and 1 diabetic patient (pancreatitis and diabetes are two conditions known to detect as falsely positive using the assays that test for the presence of the CA 15-3, CA 27-29, and CA 19-9 antigens). Most cancer samples that were tested were from late stage cancers.

The cutoff value of <40 U/ml was reached from preliminary data for normal patients (n=12). Mean and standard deviation values of 17.42 and 7.07 units/ml of plasma respectively were found (see FIG. 10). Going into this study, we plan on using a value of less than 40 units/ml of plasma as normal. This would cover more than 99.8% of the population assuming a normal distribution. We plan on refining the cut-off value as part of this study given that we had only 12 samples in our preliminary data which has likely artificially inflated the standard deviation.

Figure 10:
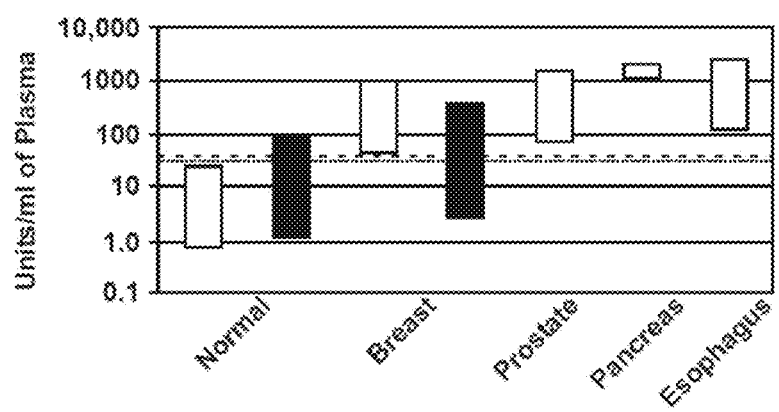
FIG. 10 is a bar graph of a comparison of performance of an antibody specific for the CA 15-3 antigen with TAB-004 in an enzyme immunoassay (EIA) for detecting cancer cells in plasma. White boxes: TAB-004 antibody. Black boxes: CA15-3. Dashed line: TAB-004 normal cutoff; dotted line: CA 15-3 normal cutoff.

At this cutoff value of <40 U/ml, none of the healthy or pancreatitis plasma were positive, while all plasma from cancer samples were >40 U/ml (see FIG. 10). The data demonstrated that compared to an assay that is designed to detect the CA 15-3 antigen, the TAB-004 EIA assay was superior in detecting more specifically and with higher sensitivity the tumor antigen in the plasma from breast cancer patients versus plasma from normal volunteers. While there were no false positives with TAB-004, 5 out of 12 normal patients produced false positive results with the CA15-3-based assay (p=0.031, using one-tailed test; <31 U/ml, is the published cutoff value for the CA15-3-based assay). All cancer patient plasma was positive for TAB-004 but 3 out of 36 plasma samples showed false negative with CA-15-3 (<31 U/ml). Overall, the difference between plasma from cancer versus normal was much larger with TAB-004 when compared with CA15-3 test in the breast cancer patients. There was also considerable overlap between normal and cancer plasma when CA 15-3 test was used whereas there was no overlap when TAB-004 test was used (see FIG. 10).

Figure 11:
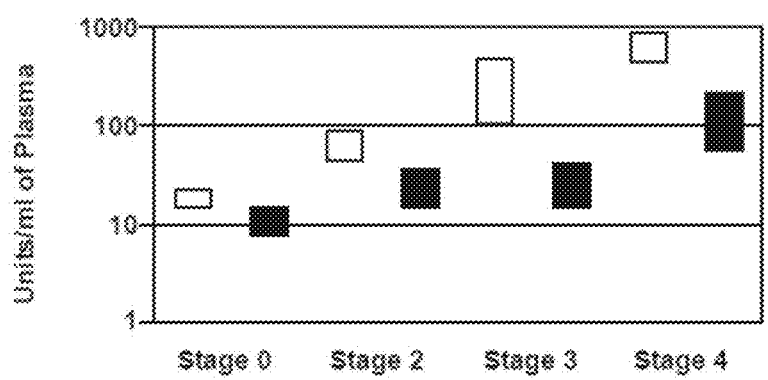
FIG. 11 is a bar graph of a comparison of performance of TAB-004 in an enzyme immunoassay (EIA) for detecting levels of shed MUC1 in plasma of pancreatic patients as a function of stage compared to a CA15-3-based EIA. White boxes: TAB-004 antibody. Black boxes: CA15-3.

To further evaluate the performance of the TAB-004 antibody to assess disease stage, the TAB-004 EIA was performed on plasma samples from n=5 stage 0, 2, 3, and 4 pancreatic cancer patients. FIG. 11 shows that the mean differences between the TAB-004 and CA 15-3 assays were statistically significant for all 4 cancer stages (stage 0 p=0.049; stage 2 p=0.008; stage 3 p=0.017; and stage 4 p=0.008). The TAB-004 assay provided values that were higher than CA 15-3 for all 20 samples. Further, the TAB-004 assay levels were dependent on tumor stage, as they increased with disease progression (p<0.0001) unlike the CA 15-3 assay, which was unable to predict differences between stages 0, 2, and 3. By comparing the stage data collected to the normal range found in FIG. 10 (<40 U/ml), it appears that TAB-004 was superior to CA 15-3 for diagnosing stage 2 and 3, as all stage 2 and stage 3 patients displayed TAB-004 assay values above the normal range while only 2 out of 10 were above normal for the CA 15-3 assay.

Example 7

Correlating Levels of Circulating MUC1 with Disease Progression and Recurrence

TAB-004 is employed to assess its potential in accurately predicting disease recurrence and progression. Plasma from n=100 patients at stages II and III/IV breast cancer are assessed pre-treatment and 6, 12, and 18-months post end of standard of care therapy. Recurrence in this group is assessed after 24 months. Plasma from n=50 pancreatic patients at stages 2, 3, and 4 is assessed pre-treatment, and 3, 6, 9, and 12 months post standard of care therapy.

Sample Collection.

Plasma is collected at routine follow-up visits. Disease stage is confirmed by pathological assessment and recurrence is confirmed by standard imaging techniques. Databases are maintained detailing any chemotherapies or adjunct therapies administered to the pancreatic cancer patients.

For breast cancer, the recurrence rate is generally much lower compared to pancreatic cancer, and therefore lower numbers of pancreas cancer patients (statistically justified below) are employed. The times for collecting plasma also differ between breast and pancreas cancer due to standard follow-up visit timing.

For pancreatic cancer patients, few stage 3 and 4 patients generally survive more than 6 months to a year, and thus it is not possible to wait for end of treatment to collect samples again due to the high mortality rate after diagnosis. The samples are collected while the patients are undergoing therapy. For patients that undergo surgery, samples are collected before surgery and 3, 6, 9, and 12 months post-surgery regardless of their treatment regimen. For patients that have un-resectable cancer, samples are collected at diagnosis prior to start of therapy and then at 3, 6, 9, 12 months post diagnosis regardless of the treatment regimen. Since most patients would be expected to recur within a year, the trial is stopped at 12 months. For breast cancer patients, only stages III/IV are generally expected to recur within 2 years. However for comparison, stage II patients are included. Plasma is collected pre-treatment and then at 6, 12, and 18 months post end of treatment.

Analysis and Statistics:

Analyses are performed to determine the ability of TAB-004 assays to predict recurrence and/or death of patients with breast cancer. Patients are divided into those that have a recurrence during the study period and those who do not. Receiver Operating Curves (ROCs) are constructed to determine if there is a natural cut-point for TAB-004 for predicting recurrence. For patients with a recurrence, the prior TAB-004 levels are used in the analysis, while the final TAB-004 values are used for those without a recurrence. For instance, if the recurrence occurs at 15 months, then the TAB-004 level at 12 months is used. Cox proportional hazard models are performed with time to recurrence as the dependent (outcome) variable. The Cox model is a multivariate procedure that correctly accounts for lost to follow-up and censored data. Age, cancer stage, and cancer grade, and TAB-004 values are entered as independent predictors. If the ROC determines a natural cut-point for predicting recurrence, then another Cox model is run with this dichotomous (above or below the cutoff) variable replacing the actual value of TAB-004 in the model. A statistically significant p-value for the TAB-004 variable indicates that TAB-004 is an independent predictor of recurrence when adjusting for the patient's age, cancer stage, and grade of the tumor. The previous set of analyses is repeated with time to recurrence or death as the dependent variable. For patients with stage 0, I, and II cancer, this same approach is used to predict time to stage III/IV (metastatic) cancer.

This set of analyses is also performed using the data from the patients with pancreatic cancer. With the extremely high death rate for pancreatic cancer, getting stable estimates of the coefficients in the Cox model when predicting time to recurrence or time to stage 4 disease can be difficult. As such, few recurrences of cancer or few cases of patients progressing from stages 2 or 3 to stage 4 metastatic cancers might occur during the study period.

Example 8

Correlating Levels of TAB-004-Positive CTCs with Disease Prognosis and TAB-004 Plasma Levels, and Comparing Numbers and Metastatic Potential of CTCs Isolated with TAB-004 Versus an EpCAM Antibody Circulating Tumor Cells (CTCs) are defined as tumor cells in the bloodstream. Currently, the Veridex CELL- SEARCH® system is the only FDA approved method to measure CTCs in metastatic breast, colorectal and prostate cancer patients. Using this system, CTCs in pancreatic cancer patients have shown a correlation between CTCs<1 and survival. Interestingly, in this same study, the presence of CTCs was shown to correlate with increased sera levels of the tumor antigen CA 19-9, indicating that sera levels of tumor antigens can also be predictive of tumor cells in circulation. In metastatic breast cancer patients, it was found that ≤5 CTCs was an independent predictor of progression-free survival and overall survival. Further, CTC levels in metastatic breast cancer patients are an earlier, more reproducible indication of disease status than current imaging methods.

The approved method for CTC assessment entails isolating EpCAM-expressing cells from the blood and then validating these cells as CTCs with the presence of epithelial-specific cytokeratin staining, proper nucleus staining, and the absence of leukocyte-specific CD45. A caveat to this method is the restriction to EpCAM expressing cells. Studies have suggested that cells acquiring a migratory phenotype lose their epithelial characteristics and acquire mesenchymal features, which phenotypically have been shown to be the cells responsible for aggressive tumor progression. As such, it is apparent that EpCAM isolation of CTCs could "miss" the most potent CTCs—those possessing a mesenchymal phenotype.

Both breast and pancreatic primary and metastatatic tumors express high levels of tumor-associated MUC1 recognized by the TAB-004 antibody of the presently disclosed subject matter. Therefore, CTCs in these patients should be recognized by the TAB-004 antibody. In preliminary experiments, levels of MUC1 were assessed using the TAB-004 antibody. First, the ability to use the Veridex CELLSEARCH® system to measure MUC1-expressing CTCs using 7.5 ml blood samples (analogous to human samples) spiked with PANC1 cells, which are a human pancreatic cancer cell line was tested. Approximately 90% of the CTCs (EpCAM+ cells) expressed MUC1. Further, patient samples were collected, and it was found that TAB-004 recognized CTCs at from about 33% to 100% efficiency. Therefore, using the TAB-004 antibody appears to accurately detect micrometastases in pancreatic and breast cancer patients.

Example 9

TNBC Cells Express tMUC Detected by the TAB-004 Antibody

Figure 12:
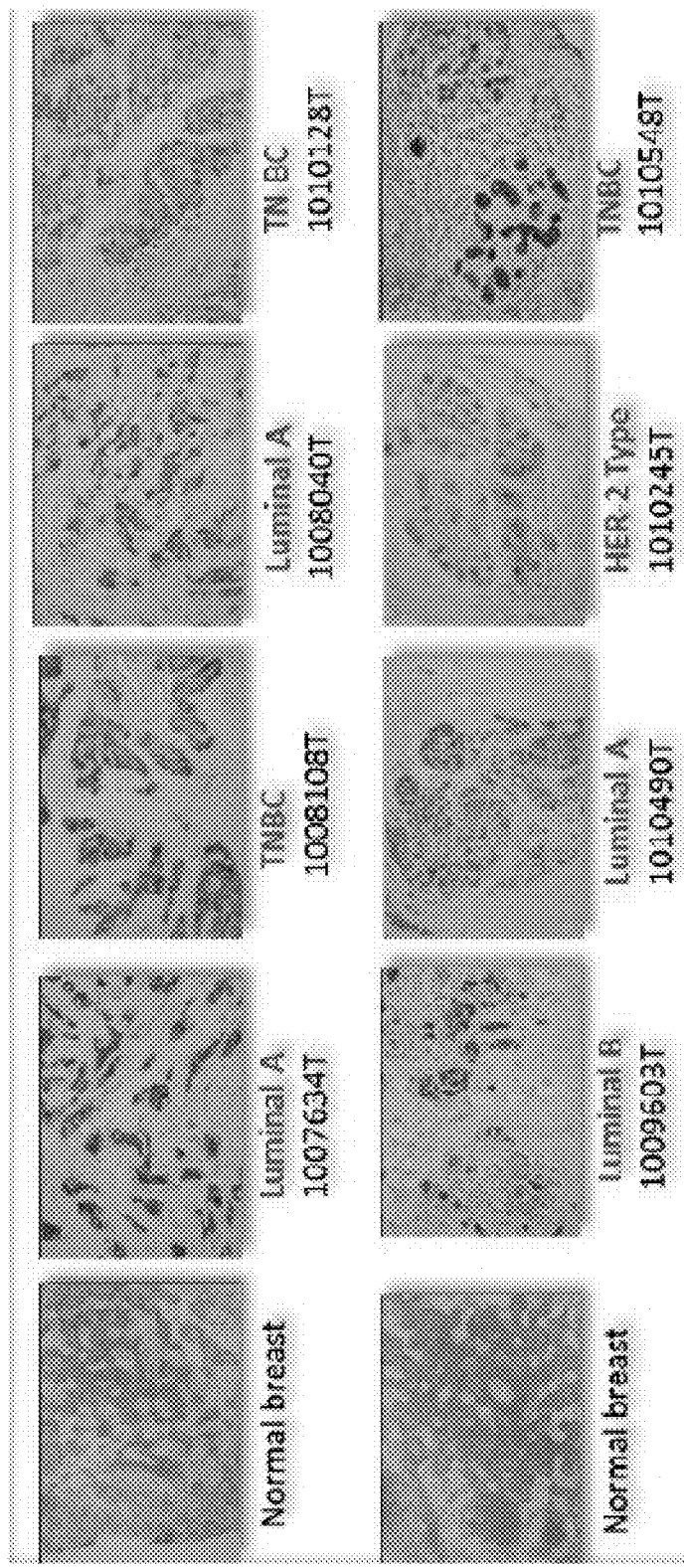
FIG. 12 is a series of immunohistochemistry (IHC) images of normal and primary human breast cancer tissue spanning different subtypes including TNBC stained with a horse radish peroxidase (HRP)-labeled TAB-004 anti-MUC1 monoclonal antibody. It is noted that Luminal A, Luminal B, TNBC, and Her-2 Type breast cancer cells stained positive for the tumor-specific MUC1 epitope (hereinafter "tMUC") to which TAB-004 binds.

FIG. 12 illustrates IHC staining using an HRP-conjugated TAB-004 antibody on a panel of primary tumor specimens from patients with various subtypes of breast cancer. Two normal breast tissue samples were included as a negative control. Luminal A, Luminal B, Her-2 type, and TNBC are shown in FIG. 12. The antibody strongly stained tumor tissue but did not bind to normal tissue. In contrast, tumor tissue was strongly stained by an HMFG1 antibody, but the HMFG1 antibody also stained normal lung and breast tissue. Therefore, the HMFG1 anti-MUC1 antibodies appear to be inferior to TAB-004-based antibodies for therapeutic applications.

Figure 13:
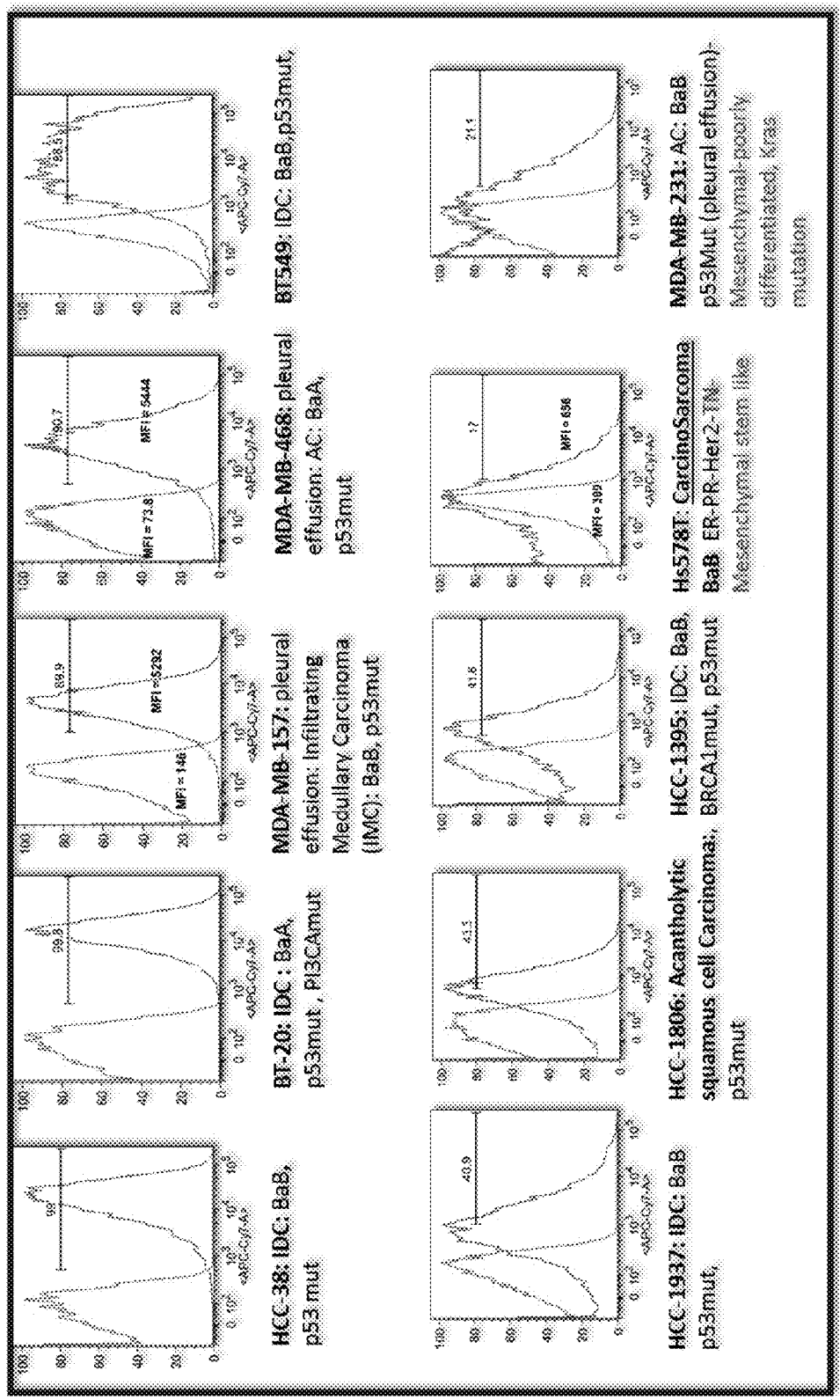
FIG. 13 is a series of plots of flow cytometric analyses of TNBC cell lines stained with a Cy7-conjugated TAB-004 monoclonal antibody (1 µg/sample). Compared to isotype control (red; left trace in each panel), all cell lines expressed high to moderate levels of tMUC. MDA-MB-231 is mesenchymal in phenotype and loses MUC1 in vitro while Hs578T is a mesenchymal stem-like carcinosarcoma that has low expression of tMUC.

A 45-panel human breast cancer cell lines were tested for tMUC expression with TAB-004 conjugated to Cy7 and flow cytometry. All subtypes including Luminal A, luminal B, TNBC (BaA and BaB), and HER-2-type stained strongly with TAB-004. FIG. 13 depicts flow cytometry analyses of ten TNBC cell lines, which demonstrated that these lines expressed high to moderate levels of tMUC. In particular, apart from those with a mesenchymal phenotype, all cell lines expressed high levels of tMUC. The MDA-MB-231 cell line, for example, is known to be negative for MUC1 in cell culture using commercially available MUC1 antibodies, and it similarly stained weakly with TAB-004.

Example 10

TAB-004 Administered Intravenously Specifically Accumulates in TNBC Tumors In Vivo To test if TAB-004 specifically reaches TNBC tumors in vivo in mice, orthotopic tumors (HCC-38 and MDA-MB-231) were generated in the mammary fat pad. At 4 days post-inoculation, 15 µg of TAB-004 directly conjugated to indocyanine green (ICG) were administered intravenously to the mice, which were then imaged using the IVIS system at 10 minutes, 4 hours, and 24 hours post-antibody injection. A negative breast cancer cell line that was null for human MUC1 was used as control to test specificity. The results are presented in FIG. 14.

Figure 14:
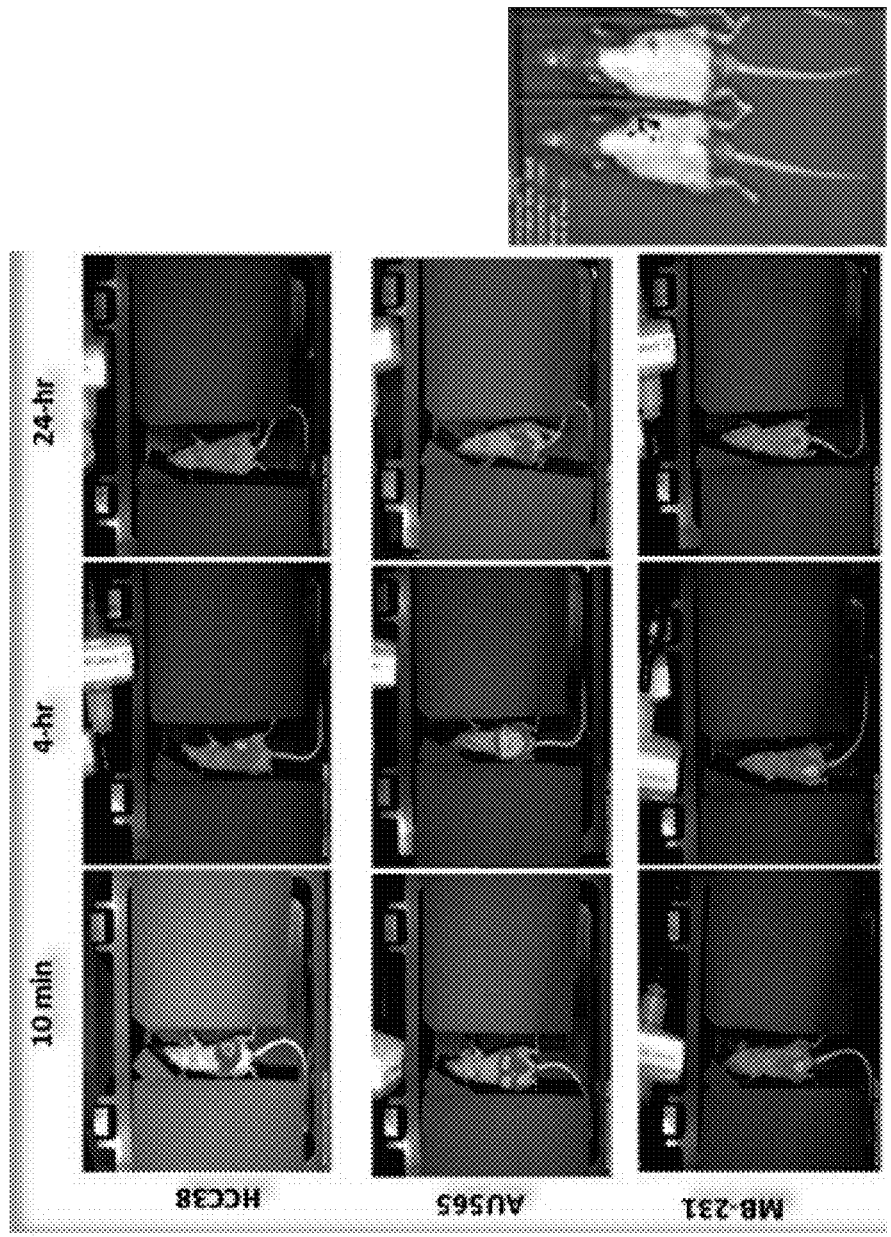
FIG. 14 is a series of fluorescent images showing specific homing of TAB-004 conjugated to indocyanine green (ICG; TAB-ICG) to the tumor site in TNBC (HCC38 and MBA-MD-231) and Her-2 (AU565) tumor. NU-J nude mice (8 week old) were injected with $1\times10^6$ cells in the lower right inguinal area of mammary fat pad. Day 4 post tumor challenge, mice were injected with 12.5 µg of TAB-004-ICG (ip) and imaged at 10 minutes, 4 hours, and 24 hours post antibody injection. At 24 hours, most of the antibody was cleared from the host. The insert to the right of the fluorescent images shows MUC1-null tumors. No localization of TAB-ICG was detected in MUC1-null tumors (Excitation Wavelength: 745 nm, Emission Wavelength: 840 nm IVIS System (Perkin Elmer)).

FIG. 14 shows specific localization of TAB-004 to the tumor site as early as 10 minutes post-injection, where it remained in the tumor for at least 24 hours. Between 24 and 48 hours, the antibody was cleared from the system in all mice tested. Note that ICG-conjugated TAB-004 accumulated in the MDA-MB-231 tumors also, strongly suggesting that the tMUC epitope is accessible to TAB-004 in vivo.

Example 11

Transgenic Mouse Model of Spontaneous Metastatic Breast cancer (PyV MT) Expressing Human MUC1 (MMT Mice)

Human MUC1.Tg mice spontaneously develop mammary gland tumors. These mice were generated by crossing the human MUC1.Tg mice (Rowse et al., 1998) to the PyV MT mammary tumor mice (Muller et al., 1988; Lin et al., 2003). These PyVMT.MUC1Tg mice are described in (Chen et al., 2003; Mukherjee et al., 2003b; Xia et al., 2003). They develop spontaneous tumors that arise naturally in the appropriate tissue background and in the context of a viable immune system (Gendler & Mukherjee, 2001; Mukherjee et al., 2003b). These mice are tolerant to the MUC1 protein and the tumors undergo evasion tactics similar to humans, such as down regulation of MHC class I molecules and expression of IL-10 and TGFβ immunosuppressive proteins. They develop palpable tumors at about 9 weeks of age. Tumors express tMUC and Tn epitopes (Mukherjee et al., 2003b) and large amounts of COX-2 (Basu et al., 2004; Basu et al., 2006).

Figure 15:
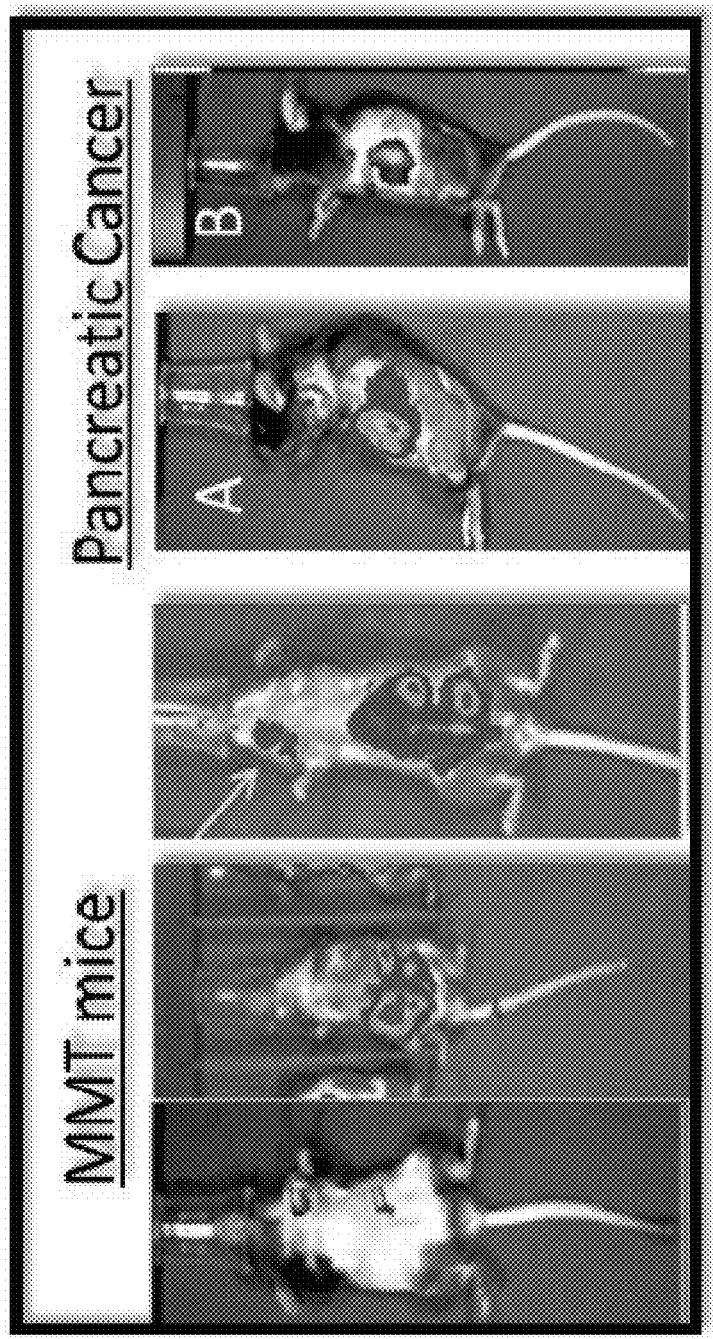
FIG. 15 is a series of fluorescent images showing specific localization of TAB-004 in breast and pancreas tumors in immune competent MUC1.Tg mice. 25 µg of TAB-ICG was injected (iv) in MMT mice (n=3) and imaged at 4 hours post-injection. TAB-ICG localized at multiple breast tumor site. The right two panels are fluorescent images of orthotopic LUC-KCM pancreatic tumor cells in MUC1.Tg mice. In the panel labeled "A", mice were injected with Luciferin and bioluminescence detected to confirm the presence of the tumor in the pancreas. In the panel labeled "B", the same mouse was injected (iv) with 25 µg of TAB-004-ICG, and a bioluminescence and ICG overlap showed that TAB-004 localized to the pancreatic tumor site only.

To determine if TAB-004 is specific in immune competent MUC1.Tg mice, it was tested in vivo in MUC1Tg mice with orthotopic MUC1+ tumors (LUC-KCM cells; Besmer et al., 2011) in the pancreas and in the MMT mice that develop spontaneous tumors. MMT mice with tumors and hyperplastic glands were injected intravenously with 25 µg of ICG-conjugated TAB-004 and imaged using the IVIS imager 4 hours post injection. Three (3) MMT mice were examined at 15 weeks, 16 weeks, and 19 weeks of age. As seen in FIG. 15, TAB-004 accumulated only in the tumor, sparing all normal tissue. Similarly, TAB-004 accumulated in the orthotopic pancreatic tumor. It is important to note that these were MUC1.Tg mice and that all glandular epithelial cells expressed the normal form of MUC1 in a tissue-specific manner in these mice. As such, MUC1.Tg mice were not a model of MUC1 overexpression as MUC1 expression was driven in these mice by its own promoter (Rowse et al., 1998).

Example 12

Design of tMUC-directed CARs

MUC1-based immune therapy has not lived up to its promise. This is due to several factors. First, the shedding of soluble MUC1 can inhibit Ab binding of tumor cells (Hayes et al., 1985). Second, structural diversity occurs from alternative splicing and altered glycosylation. Finally, tumor-derived MUC1 can impair T cell growth (Agrawal et al., 1998) and shield transformed cells from killing by NK and T cells. CARs are targeted to native tumor-associated cell surface molecules.

Figure 16A:
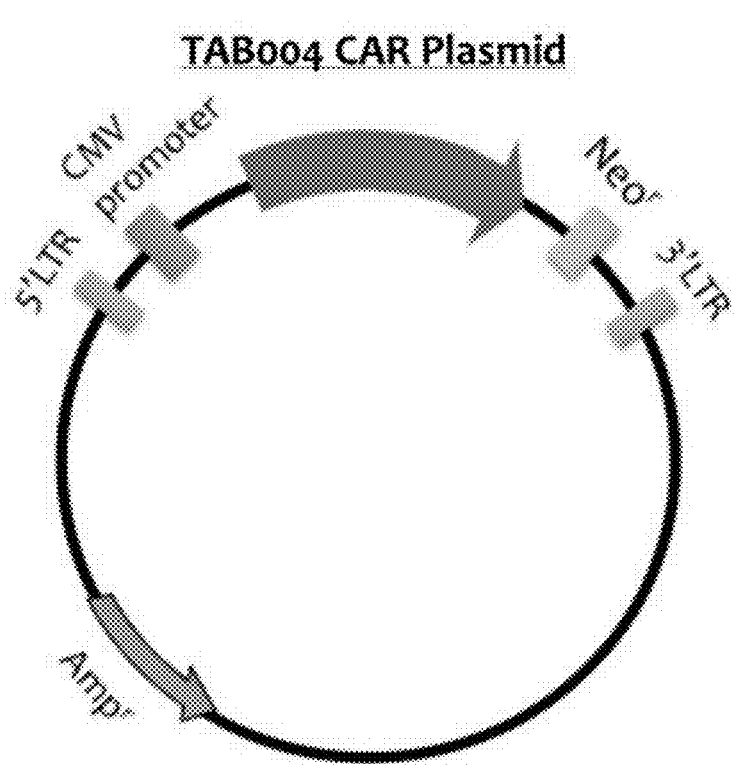
FIGS. 16A-16D relate to the construction and analysis of various expression vectors and/or cassettes that encode exemplary anti-tMUC CARs of the presently disclosed subject matter.
Figure 16B:
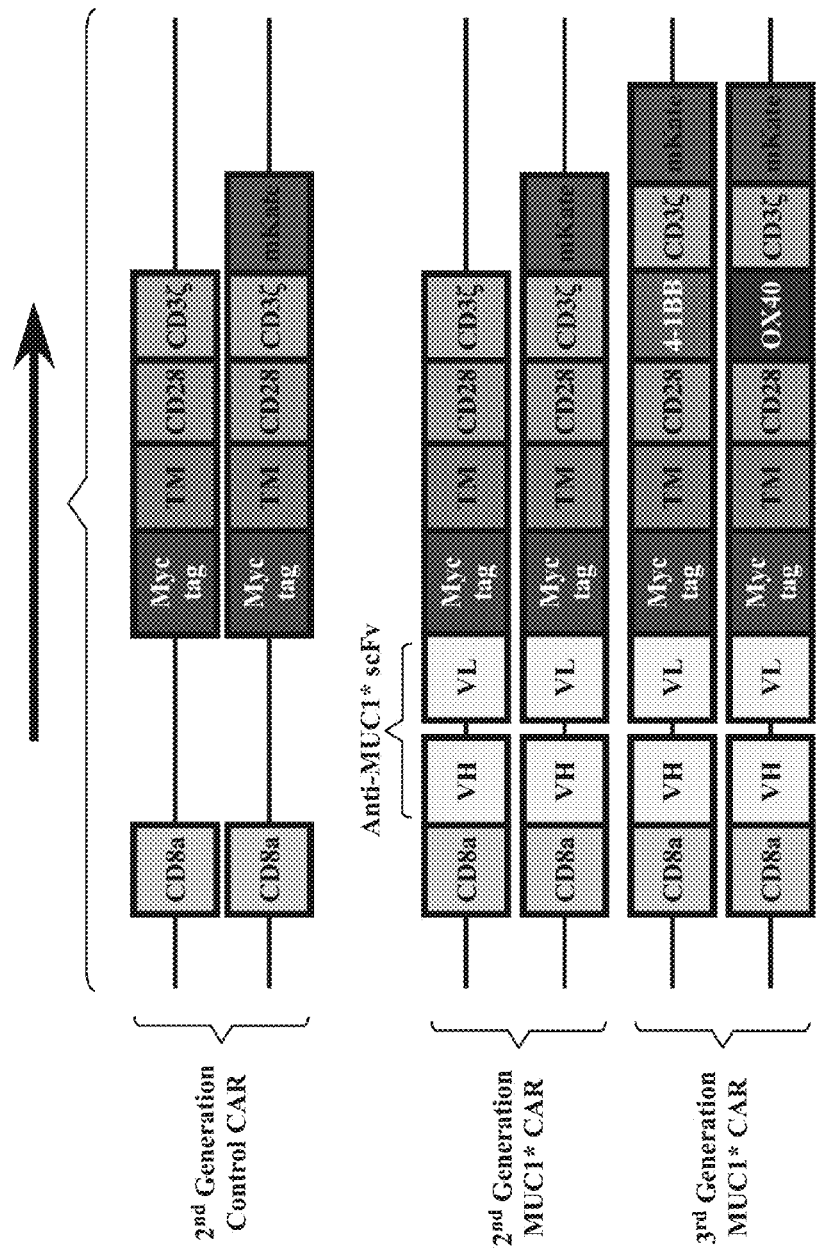

In 2008, a CAR was generated using HMFG2 and SM3 antibodies by Dr. Maher's group (Wilkie et al., 2008). Although promising data were generated, normal epithelial MUC1 can be impacted, and therefore clinical application could be limited. Given the data presented herein with respect to the specificity of TAB-004 for tMUC and its high expression in TNBC tumors and cell lines, TAB-004-based CAR T cells were developed and employed to combat TNBC. As set forth in more detail herein above, anti-tMUC CARs comprising a TAB-004 Ab-derived single-chain fragment variable (scFv) polypeptide coupled via a transmembrane domain to a co-stimulatory domain of CD28 and a signaling domain from CD3zeta were prepared using the basic approach outlined in Wilkie et al., 2008. Both mouse and human CARs have been generated. A schematic of the vector and the various CAR constructs are shown in FIGS. 16A and 16B.

More particularly, a human CAR sequence was PCR amplified using primers that had complementary sequences to the PLNCX.1 vector (Mayo-clinic K1060-C) and mKate2 gene. The mKate2 sequence was PCR amplified using primers that had complementary sequences to the CAR sequences and the PLNCX vector. High-fidelity DNA-polymerase was utilized (Q5® High-Fidelity DNA Polymerase, NEW ENGLAND BIOLABS®, Ipswich, Mass., United States of America). Human CAR and mKate2 gene fragments were gel purified. PLNCX vector was linearized at the multiple cloning site (MCS) using the single MluI reconition sequence and was gel purified. Both fragments were cloned into the MCS of PLNCX using NEBUILDER® HiFi DNA Assembly Cloning Kit (NEW ENGLAND BIOLABS®). Positive clones were identified by colony-PCR and the final construct was confirmed by enzyme digest and sequencing.

Example 13

FACS Analsyis of tMUC-Directed CAR Expression in T Cells

GP2-293 cells were transfected with a VSV-G virus envelop plasmid DNA together with an exemplary TAB-004 CAR plasmid DNA (control, 2nd generation wth and without mKate, and $3^{rd}$ generation with OX40-mkate). As a negative control, GP2-293 cells were transfected with a VSV-G virus envelop plasmid DNA together with a control CAR plasmid DNA in which the TAB-004 scFv was removed. After 48 hours, the virus-containing cell culture supernatants were filtered and frozen. For FACS analysis, T cells were infected with the virus supernatants in the presence of polybrene for 48 hours. Cells were harvested and stained with Protein L-FITC. Cells were evaluated for fluorescence intensity and % FITC positive cells on Fortessa, and analyzed by FlowJo. The results are presented in FIG. 16C.

Figure 19A:
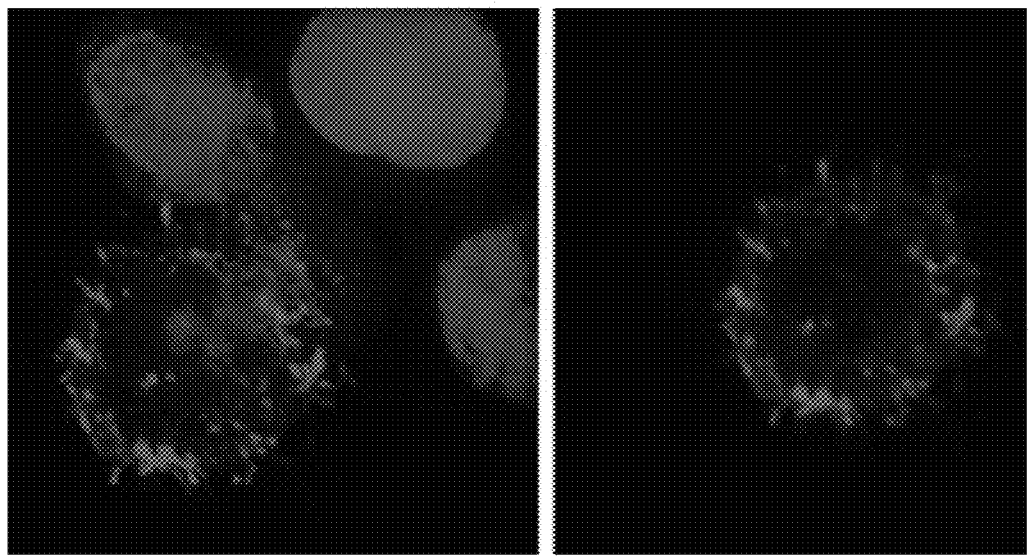
FIGS. 19A and 19B are confocal microscopy images of T cells expressing exemplary CARs of the presently disclosed subject matter.
Figure 19B:
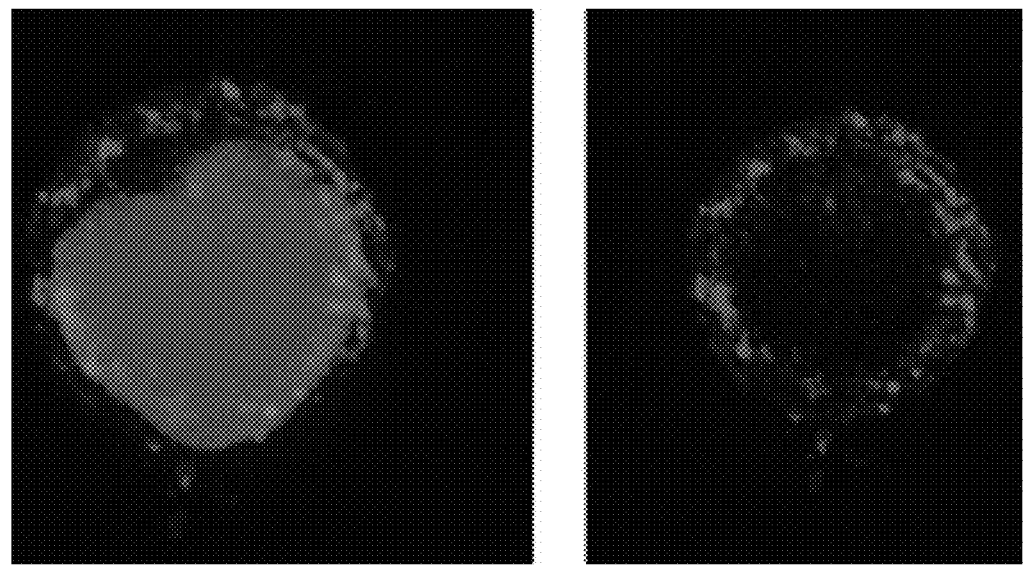

T cells expressing $2^{nd}$ Generation (e.g., TAB-28z-mKate) and $3^{rd}$ Generation (e.g., TAB-28OXz-mKate) CAR constructs on their surfaces as determined by confocal microscopy have been generated. Since the constructs included an mKate fluorescent moiety, it was possible to visualize surface expression of the $2^{nd}$ and $3^{rd}$ Generation CARs on the surfaces of T cells (see FIGS. 19A and 19B, respectively). Overall, between 30 and 40% of the cells expressed the TAB-based CARs on their surfaces.

Example 14

Fluorescent Labeling and Detection of tMUC-Directed CAR Expression in T Cells

Figure 16D:
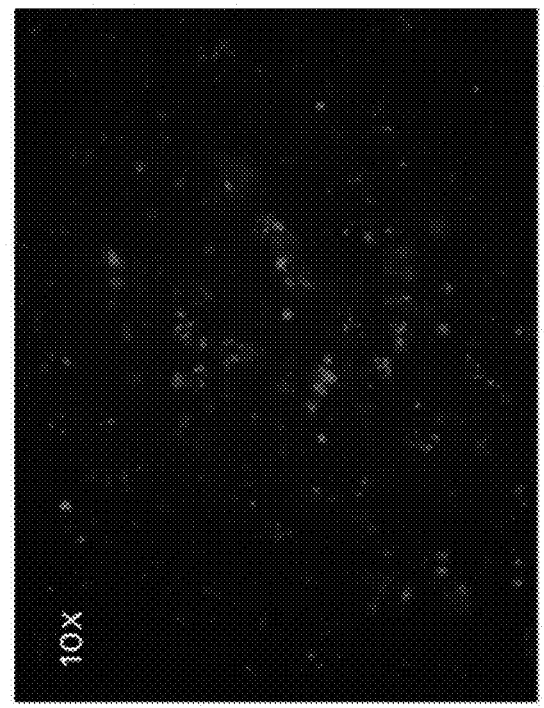
Figure 16C:
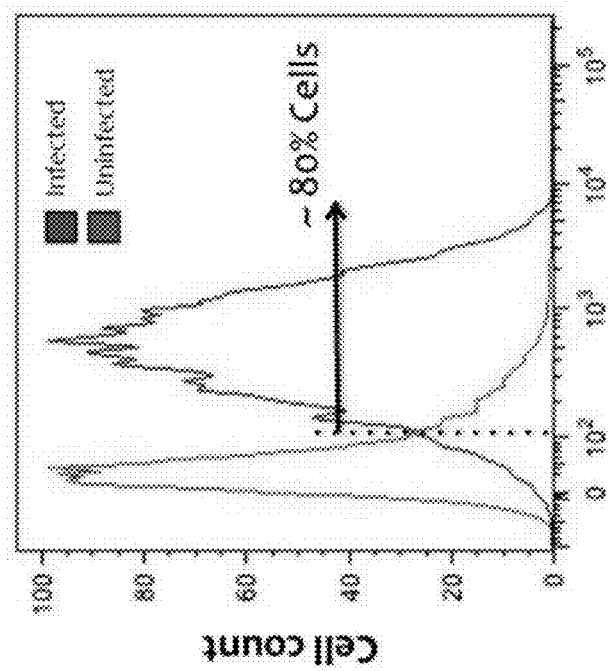

T cells infected with an exemplary CAR of the presently disclosed subject matter that has labeled with an mKate fluorescence moiety were examined under fluorescence microscopy. A representative fluorescence microscopy field is depicted in FIG. 16D. Based on the data from FIGS. 16C and 16D, approximately 80% of the T cells were infected using the disclosed methods.

Example 15 tMUC-CAR-T-Mediated TNBC Killing In Vitro

MUC1-expressing breast cancer cell lines (TNBC: HCC38, BT20, MDA-MB-157, MDA-MB-468, BT549, HCC1937, HCC1806, MDA-MB-1395, Hs578T, MDA-MB-231, and luminal: HCC1428, ZR75-1, and AU565 are used for in vitro experiments. The cell lines are described in Neve et al., 2006 and Chavez et al., 2010, and are selected based on high, moderate, and low levels of MUC1 expression. MUC1-null normal hTERT-HMEI and 184A1 cells generated from reduction mammoplasty and MCF10A generated from benign fibroadenoma are used as controls (Chavez et al., 2010). Briefly, T cells are isolated from PBMCs using T cell negative isolation kit. These T cells are infected with the retrovirus supernatant that expresses the CAR sequence to generate the tMUC-CAR-T. Tumor cells are cultured at $5 \times 10^5$ cells/well and tMUC-CAR-T cells are co-incubated at E:T ratios of 50:1, 10:1 and 5:1. After 3, 5, or 7 days of co-incubation, cells are harvested and stained with anti-CD3-FITC/7-AAD/annexin-V-APC for flow cytometry analysis.

Percentages of apoptosis induced in the cancer cell population (CD3 negative) are analyzed. Apoptotic death of cancer cells is evaluated by flow cytometry to confirm the T cell mediated tumor cell killing.

Several cell lines from primary tumor and lung metastatic lesion derived from the MMT mice have been generated. These cell lines (Mtag.MUC1, MMT, MMT-Lung) were basal subtype with ER-, PR-, Her2-ve. Cells null for human MUC1 (Mtag) serve as control. In addition C57 mg.MUC1 or C57 mg.Neo breast cancer cell lines (luminal subtype) that express full length human MUC1 or vector alone (no MUC1) are also available. Both cell lines are syngeneic to C57BL/6 mice.

Similar approaches to test in vitro killing by mouse tMUC-CAR-T cells are also employed.

Example 16 tMUC-CAR-T-Mediated Killing In Vivo in Xenograft Model of Human Metastatic TNBC with and without COX-2 Inhibition COX-2 inhibition enhances immunotherapy by downregulating the immune suppressive effects of prostaglandin $E_2$ (PGE2) and by downregulating the function of indoleamine 2,3 dioxygenase (IDO). See Basu et al., 2006; Mukherjee et al., 2009. Furthermore, active MUC1-CTLs become non-functional once within the tumor microenvironment (Mukherjee et al., 2003a). TNBC cells express high levels of COX-2/PGE2. Further, COX-2/PGE2 impacts T cell and dendritic cell function in BC patients (Pockaj et al., 2004).

To test the treatment efficacy of the combination treatment of tMUC-CAR-T and celecoxib, a specific COX-2 inhibitor in orthotopic implantation model in SCID mice, two TNBC cell lines that express Luciferase and have very high (>90%) levels of MUC1 are selected. One normal LUC-hTERT-HMEI is also selected for the in vivo experiments to demonstrate specificity. $5 \times 10^6$ cells from individual cell lines are injected with MATRIGEL® brand matrix (Corning Inc., Corning, N.Y., United States of America) in the mammary fat pad of female SCID-beige mice. Once tumors reach a certain size (5×5 mm; about day 6 post-tumor inoculation), $5 \times 10^6$ human tMUC-CAR T cells (T cells isolated from healthy normal donors) are adoptively transferred (iv injection). Mice are monitored daily for general health and tumor palpated every other day. Half of the mice receive daily gavage (5 days on 2 days off) of 100 mg/kg of celecoxib. Experimental groups are shown in Table 5.

TABLE 5

Experimental Groups for Combination Treatments

| Group | Mouse # | tMUC-CAR-T[b] | Celecoxib 100 mg/kg |
|---|---|---|---|
| A | 5 | − | − |
| B | 5 | + | − |
| C | 5 | + | + |
| D | 5 | − | + |

| Group | Mouse | tMUC CAR-T[c] | |
|---|---|---|---|
| A | 5 | − | − |
| B | 5 | + | − |
| C | 5 | + | + |
| D | 5 | − | + |

[a]3 cell lines and two CAR T cell sources, 120 mice total
[b]T cells from normal donor; $5 \times 10^6$
[c]T cells from TNBC patients; $5 \times 10^6$ Another set of mice receive $5 \times 10^6$ human tMUC-CAR T cells (T cells isolated from TNBC patients as shown in Table 5), allowing for recognizing if T cells from autologous patients are as effective. Tumor growth is monitored until tumors reach a humane endpoint (no larger than 20×20 $mm^3$). Tumors are dissected along with other organs. Tumors are prepared for protein lysate production and IHC. Serum is collected and stored. TUNEL assay and immuno-histochemical analysis for MUC1, COX-2, DO, Ki67 is performed. Tumor lysate and serum are tested for PGE2. Metastasis is assessed in the lung and other organs.

A CAR produced in a NIR767 vector system is employed so that the T cells can be tracked by an IVIS® brand In Vivo Imaging System (PerkinElmer Inc., Waltham, Mass., United States of America). The tumors are Luciferase$^+$ so the growth and metastatic spread can be monitored during the study.

Example 17 tMUC-CAR-t-Mediated Killing In Vivo in an Orthotopic Model of Mouse Metastatic TNBC in Human MUC1.Tg Syngeneic Mice with and without COX-2 Inhibition To determine if tMUC-CAR-t is effective in immunocompetent mice, three (3) cell lines are employed with a mouse-specific anti-tMUC-1 CAR (TAB-CAR-t). The cell lines are MMT, MMT-Lung, and Mtag.MUC1 cells. Mtag will be used as MUC1-null control. All cell lines express luciferase. All mice are in the C57BL/6 background.

Employing the same basic strategy outlined in EXAMPLE 16, the treatment efficacy of a combination treatment of tMUC-CAR-t and celecoxib in an orthotopic implantation model in MUC1.Tg mice is performed. Table 6 outlines the experimental groups. Normal syngeneic mouse T cells are employed. Since these are immune competent mice, testing for cytokine storm (arrays) and immune infiltrates in the tumors are also performed.

TABLE 6

Experimental Groups for Combination Treatments

| Group | Mouse # | tMUC-CAR-t[e] | Celecoxib 100 mg/kg |
|---|---|---|---|
| A | 5 | − | − |
| B | 5 | + | − |
| C | 5 | + | + |
| D | 5 | − | + |

[d]4 cells lines, and 80 mice;
[e]$5 \times 10^6$ cells

It is expected that the tMUC-CAR-t cells will be effective in specifically targeting TNBC tumor sparing normal organs and sparing MUC1-ve tumors. In the immune compromised mice, the CAR-T cells will be effective as seen in other studies.

In the immune competent MUC1.Tg mice, it is expected that celecoxib plays a role, and it is expected that the CAR-T cells are less than 100% effective unless given with daily gavage of celecoxib. Apoptosis is expected in the tumors and lower metastasis. The dose and possibly the dosing schedule are optimized. A cytokine storm in other immune infiltrates in the tumor might be observed. It is also possible that a one-time low-dose chemotherapeutic drug such as cyclophosphamide is administered prior to administration of CAR-T/t cells, particularly in immunocompetent model as $T_{regs}$ play a role in these models of cancer.

Summarily, several TNBC cell lines are tested for CAR T cell-mediated killing in vivo in immunocompromised and immunocompetent mice. T cells from healthy and TNBC patients are assessed. Optimal dosing schedules are determined. Enhanced antitumor effects of CAR-T/t cells when combined with COX-2 inhibition in an orthotopic implantation model are identified.

Example 18

Transgenic Mouse Model of Spontaneous Metastatic Breast Cancer (PyV MT) Expressing Human MUC1 (MMT Mice)

Human MUC1.Tg mice were employed to take advantage of the spontaneous mammary gland tumors that arise therein rather than relying only on injected tumor cells in immune compromised mice. These mice are generated by crossing the human MUC1.Tg mice (Mukherjee et al., 2003b) to the PyV MT mammary tumor mice (Muller et al., 1988; Lin et al., 2003). Descriptions of the PyVMT.MUC1Tg mice have been published (Chen et al., 2003; Mukherjee et al., 2003b; Xia et al., 2003). These mice develop spontaneous tumors that arise naturally in the appropriate tissue background and in the context of a viable immune system (Gendler & Mukherjee, 2001; Mukherjee et al., 2003b). These mice are tolerant to the MUC1 protein and the tumors undergo evasion tactics similar to humans, such as down regulation of MHC class I molecules and expression of IL-10 and TGFβ immunosuppressive proteins, so it is a particularly relevant model in which to study the presently disclosed compositions and methods. Mice typically develop palpable tumors at about 9 weeks of age. Tumors express tMUC1 and Tn epitopes (Mukherjee et al., 2003b and unpublished data) making them especially suitable for these studies.

To determine if the TAB-004 antibody was as specific in immune competent mice, the homing of this antibody was tested in vivo in the MMT mice that develop spontaneous mammary gland tumors. MMT mice with tumors and/or hyperplastic glands were injected intravenously with 12.5 µg of an IndoCyanine Green-Fluorescence tag (ICG) labeled TAB-004 monoclonal antibody and imaged using the IVIS imager 24 hours post injection. The results are presented in FIGS. 17A-17C.

In FIGS. 17A-17C, mice are shown at various ages (12 weeks, 16 weeks, and 18 weeks of age, respectively). As seen in FIGS. 17A-17C, the TAB-004 monoclonal antibody accumulated only in the tumors, sparing all normal tissue as early as 12 weeks of age when the tumors are not palpable but the mice had hyperplastic glands. As tumors developed, there was more accumulation of the ICG-labeled TAB004 in the palpable tumors.

FIG. 17D shows a representative example of a mouse with palpable tumors at 20 weeks of age. FIG. 17E shows TAB-ICG accumulation ex vivo in all of the mammary gland tumors. Note that these were present in human MUC1.Tg mice and all glandular epithelial cells expressed the normal murine form of MUC1 in a tissue-specific manner. However, ICG-labeled TAB-004 did not accumulate in any other organs. These mice were thus not a model of overexpression as the endogenous MUC1 expression was driven by its own promoter (Rowse et al., 1998; Mukherjee et al., 2003b).

PyV MT X MUC1.Tg (MMT) mice were also injected retroorbitally at 20 weeks of age with 12.5 µg of TAB 004-conjugated to ICG in 100 µl of PBS. 24 hours later, mice were euthanized, mammary glands were dissected, and were imaged using the IVIS system. FIG. 17D shows a representative MMT mouse bearing spontaneous multifocal mammary gland tumors. FIG. 17E shows mammary glands that were dissected from the same mouse after being injected with TAB-ICG 24 hours prior. The accumulation of the ICG-labeled TAB-004 to the tumors was clearly observed.

Example 19 tMUC-CAR-t-Mediated Killing in Human MUC1-PyV MT Bitransgenic (MMT) Mice with and without COX-2 Inhibition A test of the efficacy of CAR-t cells in a model that closely mimics human multi-step disease is performed. The mammary gland tumors arise spontaneously in an immunocompetent mouse model. These mice develop lung and bone metastasis spontaneously. The multistep progression of the tumors from hyperplasia to adenocarcinoma and metastasis mimics human multi-step progression. As tumors progress, they lose ER, PR, and integrin β, and overexpresses human tMUC (Lin et al., 2003; Mukherjee et al., 2003b). These mice are tolerant to MUC1 immunization. Importantly, these tumors express several immunosuppressive factors including COX-2/PGE2 and TGFβ. Thus, testing the efficacy of tMUC-CAR-t in this model provides information with respect to: 1) if an intact immune system affects the efficacy of CAR-T/t administration; and 2) at what stage in the multistep process of tumor development is CAR-T/t administration most efficacious.

MMT mice are characterized by multi-step progression from hyperplasia to late carcinoma, and MUC1 expression increases from low expression at the hyperplastic stage, to moderate expression at the adenoma/MIN stage, to high expression at the early carcinoma stage that persists in the late carcinoma stage. 60% of MMT mice also develop lung metastases (Mukherjee et al., 2003b).

Optimal doses of tMUC-CAR-t cells are injected into MMT mice as follows: (1) starting at 8 weeks of age (at the mammary intraepithelial neoplasia (MIN), MIN stage), a second cycle at 12 weeks of age, and a third cycle at 15 weeks of age; and (2) starting at 12 weeks of age (early carcinoma) and a second cycle at 15 weeks of age. This permits a determination of whether treatment early during tumor progression is more efficacious. CAR-t cells are injected with and without celecoxib. The experimental groups are shown in Table 7.

TABLE 7

Experimental Groups for Treatments of MMT Mice[f]

| Group | Mouse # | Day of tMUC-CAR-T cell injection | Celecoxib[g] |
|---|---|---|---|
| A | 12 | — | – |
| B | 12 | 8, 12, 15 wks of age | – |
| C | 12 | 8, 12, 15 wks of age | + |
| D | 12 | — | + |
| E | 12 | 12, 15 wks of age | – |
| F | 12 | 12, 15 wks of age | + |
| G | 12 | — | + |

[f]84 total mice treated
[g]dose is 100 mg/kg, 5 days on followed by 2 days off.

During treatment and thereafter, mice are palpated for tumor progression, and at euthanasia, various organs are assessed for gross metastasis and histologically evaluated. Serum and tumor lysates are also studied accordingly for immune infiltrates, cytokine storm, circulating and tumor MUC1, and COX-2 levels.

It is anticipated that treating early versus late is more efficacious and that celecoxib affects treatment efficacy. Whether the treatment regimen reduces lung metastasis in these mice is also tested.

Example 20 tMUC-CAR-T-Mediated Killing in Human Tumor Explant Models of Metastatic, Treatment-Refractory TNBC with and without Celecoxib The use of cultured cell lines can present certain disadvantages. For example, the phenotype of these cells can be considerably altered as compared to the original tumor cells of the patients. To assess the treatment efficacy for metastatic/treatment refractory TNBC, utilization of cancer explants derived from patients' surgical specimens is a reliable method. TNBC tissues are isolated from patients, and explants are generated in SCID mice.

In vitro generated cells isolated from human primary clinical samples are obtained. Briefly, tissues from the appropriate patients are collected by the Duke Biospecimen Repository and Processing Core Facility (Duke BRPC). Annotated tissue samples are used. Tumor tissues are minced and implanted into female SCID-beige mice with estrogen pellet. Once tumor size reaches 10 mm in diameter, tumors are isolated minced and transplanted to other SCID mice via in vivo passage. Breast cancer explants grown in SCID mice are minced and digested with triple enzyme buffer (collagenase, hyaluronidase, DNase). Cells are cultured in vitro and Luciferase positive cells are generated.

Example 21

Expression Analyses of tMUC-1 and COX-2 in Explant Cells

Breast cancer explant cells derived from patients are analyzed for MUC1 and COX-2 expression by flow cytometry and western blotting.

Example 22 tMUC-CAR-T-Mediated Killing of TNBC Explant Cells In Vitro

Cells that express high levels of MUC1 and COX-2 are employed. Cells from n=6 patients are tested first in vitro for their ability to be targeted by tMUC-CAR-T cells (T cells from normal donors) as described herein above.

Example 23 tMUC-CAR-T-Mediated Killing of TNBC Explant Cells In Vivo

Two cells are selected from the six (6) tested in EXAMPLE 21 that show optimal killing by CAR T cells for in vivo tests. SCID mice are injected into the mammary fat pad and tumors are treated as described herein above. Luc+/MUC1+/COX-2+ TNBC explant cells (1×10$^6$ cells in 100 μL saline) are administered on day 0, followed by the administration of tMUC-CAR-T cells and celecoxib as shown in Table 8. Mice are euthanized at humane endpoint (or at 20×20 tumor size). Tumor growth and any metastatic spread are followed by IVIS imaging as these cells express LUC. At time of euthanasia, the same endpoint analyses as described herein above are performed.

TABLE 8

Experimental Groups for tMUC-CAR-T-mediated Killing of TNBC Explant Cells In Vivo[h]
Expt 4: 2 cell lines: total mice: 144

| Group | Mouse # | Day of tMUC-CAR-T cell injection[i] | Celecoxib[j] |
|---|---|---|---|
| A | 12 | 3 | − |
| B | 12 | 3, 10 | − |

TABLE 8-continued

Experimental Groups for tMUC-CAR-T-mediated Killing of TNBC Explant Cells In Vivo[h]
Expt 4: 2 cell lines: total mice: 144

| Group | Mouse # | Day of tMUC-CAR-T cell injection[i] | Celecoxib[j] |
|---|---|---|---|
| C | 12 | 3 | + |
| D | 12 | 3, 10 | + |
| E | 12 | — | + |
| F | 12 | — | − |

[h]144 mice tested
[i]5 × 10$^6$ cells per injection
[j]100 mg/kg, 5 days on and 2 days off It is anticipated that TNBC explant cells implanted to SCID-beige mice are targeted by tMUC-CAR-T cells, and that celecoxib treatment enhances the effect. Optionally, NSG (NOD.Cg-Prkdcscid Il2rgtm1Wjl/SzJ) mice are also tested.

At least 15 breast cancer samples are collected and tested. At least 10 breast cancer explants are established in in SCID mice. Six (6) TNBC explants are tested in vitro and two (2) are tested in vivo in the orthotopic model for treatment. The primary endpoints are mostly tumor size. Based on previous data, sample sizes are determined to detect a moderate difference (a standardized effect size measure of interaction f=0.25). Power is approximated under a fixed effects model. Table 9 below summarizes sample sizes and power estimates to detect f=0.25 ($\alpha$=0.05). Thus, 12 mice are randomized to each treatment group.

TABLE 9

Summary of Sample Sizes and Power Estimates

| n | power $\alpha = 0.05$ | power $\alpha = 0.1$ |
|---|---|---|
| 10 | 0.73 | 0.82 |
| 12 | 0.80 | 0.88 |
| 15 | 0.90 | 0.94 |

A block design in which the total number of mice is injected in subgroups across treatments over three (3) or more days is employed as necessary. A regression model is used to describe tumor growth by treatment over time. Linear and quadratic terms are considered in the models. Time by treatment interactions are tested to determine the significance of the impact of treatment on tumor growth over time.

Example 24

Targeting of TNBC Tumors In Vivo

To test if TAB-004 can specifically reach TNBC tumors in vivo in mice, orthotopic tumors (PyVMT, PyVMT.MUC1, HCC-70, and AU565) were produced in the mammary fat pad of mice. Nu-J nude mice (8-week old) were injected with 10×10$^6$ cells in the lower right inquinal area of the mammary fat pad. When tumors were palpable, mice were injected retroorbitally with 12.5 μgs of TAB-004-directly conjugated to Indocyanine green (ICG) and imaged 4 hours post antibody injection. Each tumor cell line had a different kinetics of growth. A negative breast cancer cell line that is null for human MUC1 was used as control to test specificity (PyVMT; see FIG. 18A).

In FIGS. 18A-18D, the red arrows indicate the location of the tumors. FIGS. 18B-18D show specific localization of TAB-004 to the tumor sites as early as 11 days in the PyVMT.MUC1 tumors (FIG. 18B) and 21 days for the human cell lines (FIGS. 18C and 18D). Between 48 and 72 hours, the antibody was cleared from the system in all mice tested.

Example 25

Binding of Anti-tMUC CARs to Tumor Cells Expressing a Tumor-Associated MUC1 Epitope To test the ability of T cells expressing anti-tMUC1 CARs to bind specifically to tumor cells expressing a tumor-specific MUC1 epitope, tMUC1-expressing (HPAFII) and MUC1-negative (MiaPaCa2) human tumor cell lines were incubated with T cells expressing anti-tMUC1 CARs to determine specific binding and killing. 150,000 tumor cells were plated per plate, and the next day the cells reached ~50% confluency. Tumor cells were stained with the live cell stain Hoechst for 30 minutes and washed once. 1 million infected or uninfected T cells expressing $2^{nd}$ Generation TAB-28z-mKate or $3^{rd}$ Generation TAB-28OXz-mKate were added to the wells containing the Hoechst-labeled tumor cells and incubated for 3 hours. Media was removed and cells were washed once. Cells were examined by fluorescent microscopy.

Figure 20A:
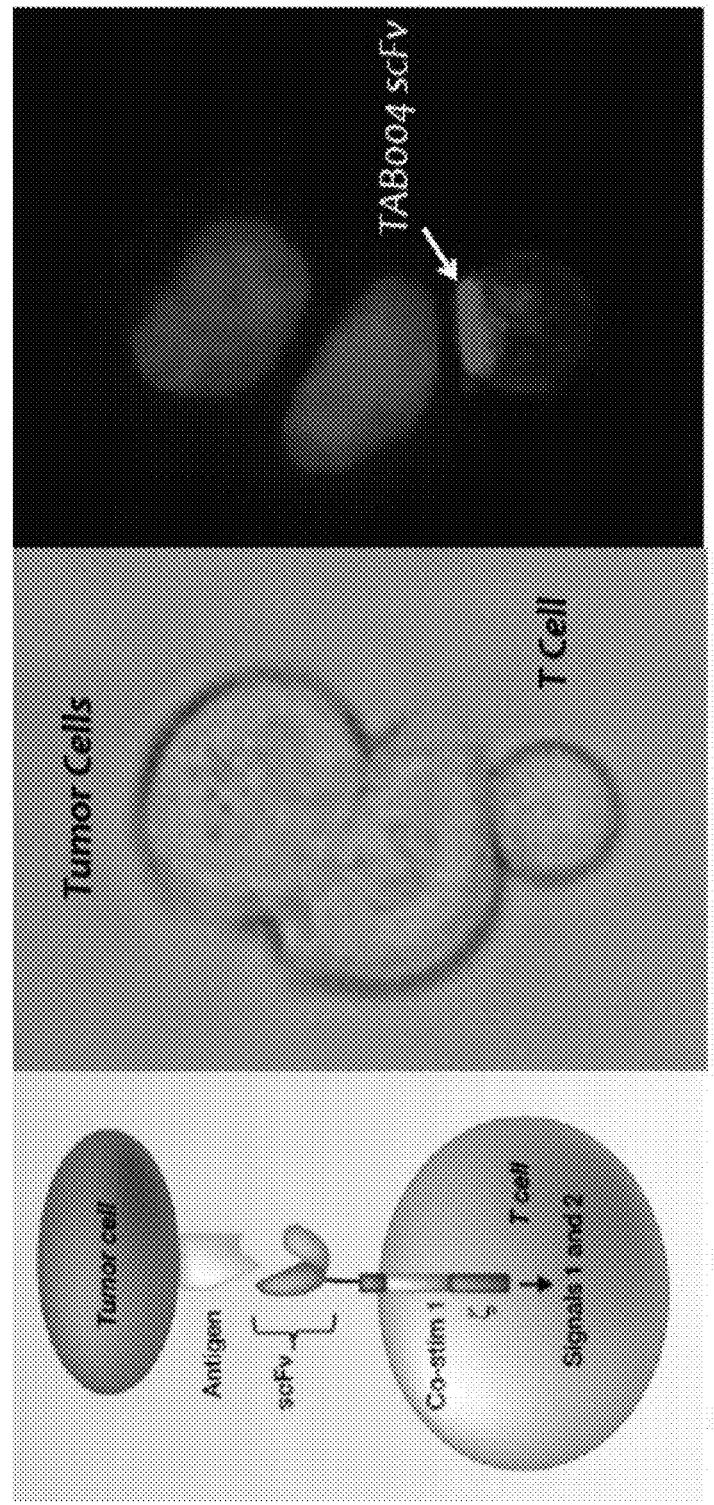
FIGS. 20A-20C are depict binding of T cells expressing the exemplary CARs of the presently disclosed subject matter to HPAFII (MUC1+) tumor cells but not to MiaPaCa2 (MUC1−) tumor cells.
Figure 20B:
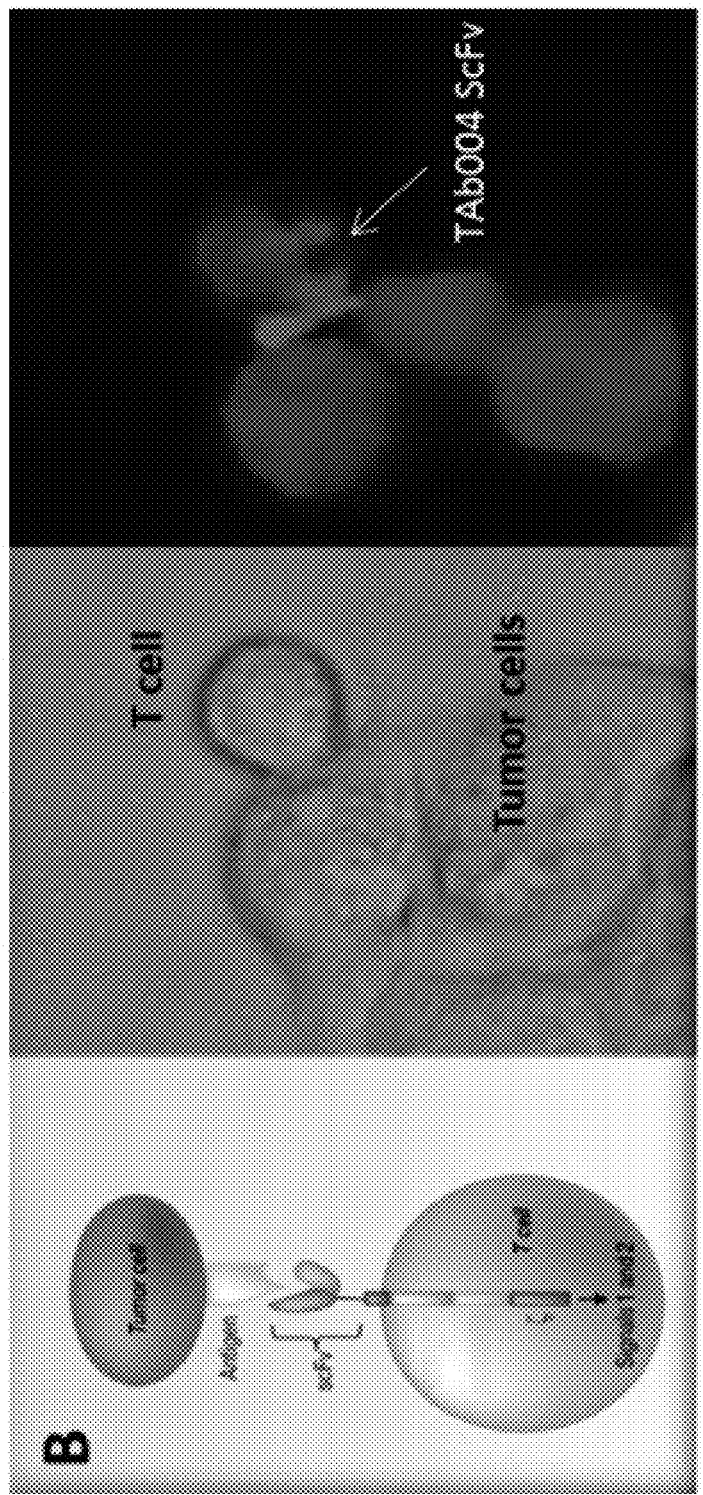
Figure 20C:
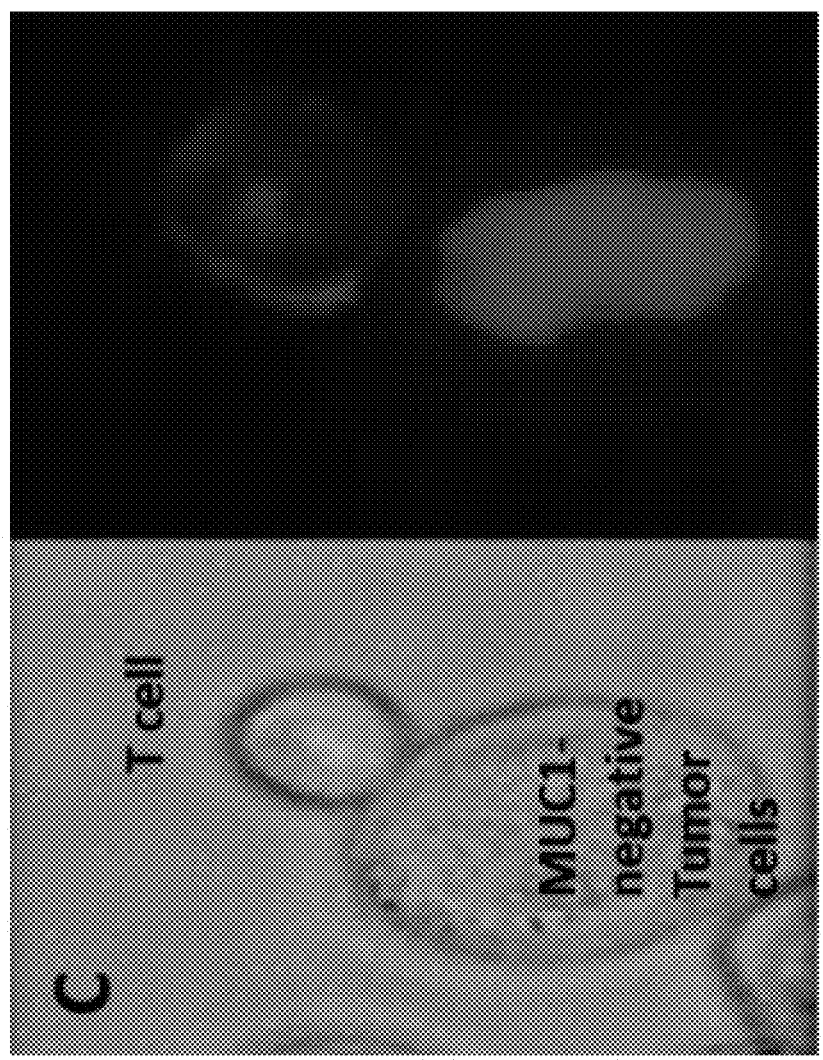

FIG. 20A presents the results with an exemplary $2^{nd}$ Generation CAR (TAB-28z-mKate) and FIG. 20B presents the results with an exemplary $3^{rd}$ Generation CAR (TAB-28OXz-mKate) binding to HPAFII cells (tMUC1$^+$). FIG. 20C presents the results for the tMUC-minus MiaPaCa2 cells. both the $2^{nd}$ and $3^{rd}$ Generation TAB-CAR-engineered T cells specifically became activated and formed synapses with the tMUC1-positive tumor cells (see FIGS. 20A and 20B) but not with tMUC1-negative tumor cells (see FIG. 20C).

Example 26

Tumor Cell Killing by an Examplary $2^{nd}$ Generation Anti-tMUC1 CAR In Vitro

Figure 21:
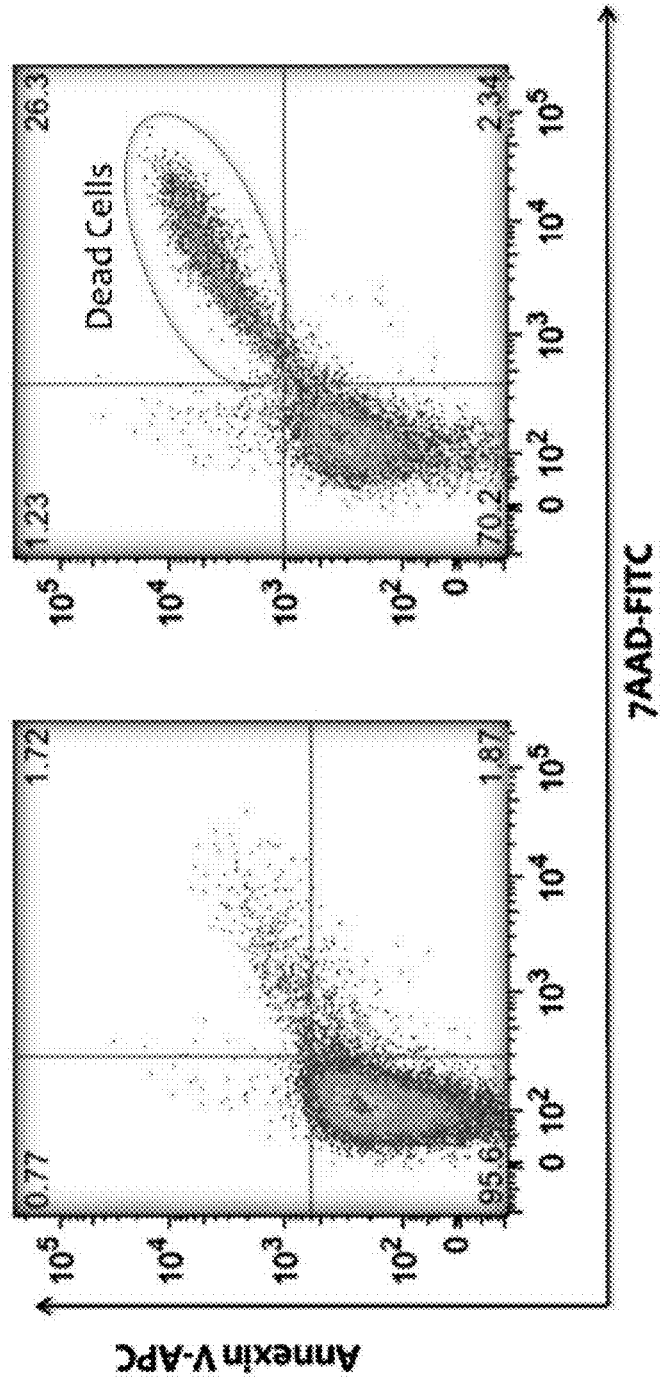
FIG. 21 is a pair of FACS scatter plots showing killing of MUC1-expressing (TNBC-HCC70) tumor cells in vitro. For each panel, the E:T ratio was 25:1 and T cells were co-cultured with tumor cells for 4 hours before staining with anti-CD3-FITC/7-AAD/annexin-V-APC. CD3-negative cells were gated to determine the percentage of tumor cells that were killed by apoptosis induced by the anti-TAB CAR. The left scatter plot is data derived from using a control T cell that expressed a CAR that did not bind to MUC1 and did not kill the TNBC-HCC70 tumor cells. In the right penal, T cells expressing an exemplary $2^{nd}$ generation CAR (TAB-28z.

T cells expressing an exemplary $2^{nd}$ Generation CAR (TAB28zCAR) were tested for their ability to kill tMUC1-expressing (TNBC-HCC70) tumor cells in vitro. The E:T ratio was 25:1 and T cells were co-cultured with tumor cells for 4 hours before staining with anti-CD3-FITC/7-AAD/annexin-V-APC. CD3-negative cells were gated to determine the percentage of tumor cells that were killed by apoptosis. Control CAR T cells did not kill the tumor cells, but the TAB28z CAR-engineered T cells killed about 30% of the tumor cells at a 25:1 ratio. The results are presented in FIG. 21.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Acres & Limacher (2005) *Expert Rev Vaccines* 4:493-502.
Adams et al. (1993) *Cancer Res* 53:4026-4034.
Alexay et al. (1996) *The PCT International Society of Optical Engineering* 2705/63.
Al-Hajj et al. (2003) *Proc Natl Acad Sci USA* 100:3983-3988.
Alt et al. (1999) *FEBS Lett* 454:90-94.
Altschul et al. (1990) *J Mol Biol* 215:403-410.
Amemiya et al. (1988) *Topics Curr Chem* 147:121-144.
Ausubel et al. (1992) *Current Protocols in Molecular Biology*, John Wylie & Sons, Inc., New York, N.Y., United States of America.
Barratt-Boyes (1996) *Cancer Immunol Immunother* 43:142-151.
Basu et al. (2004) *Mol Cancer Res* 2:632-642.
Basu et al. (2005) *Breast Cancer Res* 7:422-435.
Basu et al. (2006) *J Immunol* 177:2391-2402.
Bauminger & Wilchek (1980) *Meth Enzymol* 70:151-159.
Beatson et al. (2010) *Immunotherapy* 2:305-327.
Berkow et al. (1997) *The Merck Manual of Medical Information*, Home ed. Merck Research Laboratories, Whitehouse Station, N.J., United States of America.
Bieche & Lidereau (1997) *Cancer Genetics and Cytogenetics* 98:75-80.
Bird et al. (1988) *Science* 242:423-426.
Blaskovich et al. (2003) *Cancer Res* 63:1270-1279.
Bollard et al. (2007) *Blood* 110:2838-2845.
Bonnet & Dick (1997) *Nat Med* 3:730-737.
Brabletz et al. (2005) *Nat Rev Cancer* 5:744-749.
Cameron et al. (2009) *Bioorg Med Chem Lett* 19:2075-2078.
Chattopadhyay et al. (2001) *Nucl Med Biol* 28:741-744.
Chavez et al. (2010) *Breast Dis* 32: 35-48.
Cheever et al. (2009) *Clin Cancer Res* 15:5323-5337.
Chen et al. (2003) *Immunol* 109:300-307.
Cheng (1996) *Hum Gene Ther* 7:275-282.
Chothia & Lesk (1987) *J Mol Biol* 196:901-917.
Clackson et al. (1991) *Nature* 352:624-628.
Coatney (2001) *Ilar J* 42:233-247.
Coloma et al. (1997) *Nature Biotechnol* 15:159-163.
Cristofanilli et al. (2005) *J Clin Oncol* 23:1420-1430.
Curry et al. (2013) *J Surg Oncol* 107:713-722.
David et al. (1974) *Biochemistry* 13:1014.
DeCosta Byfield et al. (2004) *Mol Pharmacol* 65:744-752.
Dong et al. (1997) *J Patholo* 183:311-317.
Dontu et al. (2004) *Breast Cancer Res* 6:R605-615.
Donzella et al. (1998) *Nat Med* 4:72-77.
Duch et al. (1998) *Toxicol Lett* 100-101:255-263.
Ebadi (1998) *CRC Desk Reference of Clinical Pharmacology*. CRC Press, Boca Raton, Fla., United States of America.
Emanueli et al. (2004) *Arterioscler Thromb Vasc Biol* 24:2082-2087.
European Patent No 0 439 095.
Fong et al. (1999) *Cancer Res* 59:99-106.
Fraser (1996) *Meth Cell Biol* 51:147-160.
GENBANK® Accession Nos. AAA39755; AAA60019; AAO63589; J055821; NM_004985.3; NP_001181906; NP_004976; NP_036734; NP_038633; NP_776540; Q02496.
Gendler (2001) *J Mammary Gland Biol Neoplasia* 6:339-353.
Gendler & Mukherjee (2001) *Trends Mol Med* 7:471-475.
Gennaro (1990) *Remington's Pharmaceutical Sciences, 18th ed.*, Mack Pub. Co., Easton, Pa., United States of America.

Gennaro (ed.) (2003) *Remington: The Science and Practice of Pharmacy*, 20th edition Lippincott, Williams & Wilkins, Philadelphia, Pa., United States of America.
Glockshuber et al. (1990) *Biochemistry* 29:1362-1367.
Gold et al. (2007) *Clin Cancer Res* 13:7380-7387.
Goldman et al. (1997) *Cancer Res* 57:1447-1451.
Goodman et al. (1996) *Goodman & Gilman's the Pharmacological Basis of Therapeutics*, 9th ed. McGraw-Hill Health Professions Division, New York, N.Y., United States of America.
Hallahan et al. (2001a) *Am J Clin Oncol* 24:473-480.
Hallahan et al. (2001b) *J Control Release* 74:183-191.
Hamers-Casterman et al. (1993) *Nature* 363:446-448.
Harlow & Lane (1988) *Antibodies: A Laboratory Manual*, Cold Spring Harbor Laboratory Press, Cold Spring Harbor, N.Y., United States of America).
Heijnen et al. (1997) *J Immunol* 159:5629-5639.
Henderson et al. (1998) *J Immunother* 21:247-256.
Henikoff & Henikoff (1989) *Proc Natl Acad Sci USA* 89:10915-10919.
Heredia et al. (1991) *J Neurosci Meth* 36:17-25.
Hingorani et al. (2003) *Cancer Cell* 4:437-450.
Hnatowich et al. (1996) *J Pharmacol Exp Ther* 276:326-334.
Holliger et al. (1993) *Proc Natl Acad Sci USA* 90:6444-6448.
Holliger et al. (1999) *Cancer Res* 59:2909-2916.
Hollingsworth & Swanson (2004) *Nat Rev Cancer* 4:45-60.
Hu et al. (1996) *Cancer Res* 56:3055-3061.
Hunter et al. (1962) *Nature* 144:945.
Huston et al. (1988) *Proc Natl Acad Sci USA* 85:5879-5883.
Huston et al. (1993) *Int Rev Immunol* 10:195-217.
Jackson et al. (2001) *Genes Dev* 15:3243-3248.
Johnson & Wu (2000) *Nucleic Acids Res* 28:214-218.
Kabat et al. (1991) (1991) *Sequences of Proteins of Immunological Interest, Fifth Edition.* NIH Publication No. 91-3242.
Kahn et al. (1987) *Anticancer Res* 7:639-652.
Karlin & Altschul (1993) *Proc Natl Acad Sci USA* 90:5873-5887.
Katzung (2001) *Basic & Clinical Pharmacology*, 8th ed., Lange Medical Books/McGraw-Hill Medical Pub. Division, New York, N.Y., United States of America.
Kawaguchi et al. (2002) *Nat Genet* 32:128-134.
Kimura & Finn (2013) *Expert Opin Biol Ther* 13:35-49.
Kipriyanov et al. (1995) *Cell Biophys* 26:187-204.
Kipriyanov et al. (1998) *Int J Cancer* 77:763-772.
Kipriyanov et al. (1999) *J Mol Biol* 293:41-56.
Kohler et al. (1975) *Nature* 256:495.
Kontermann et al. (1999) *J Immunol Meth* 226:179-188.
Kortt et al. (1997) *Protein Eng* 10:423-433.
Kostelny et al. (1992), *J Immunol* 148:1547-1553.
Kufe (2009) *Nat Rev Cancer* 9:874-885.
Kurihara et al. (2008) *J Hepatobiliary Pancreat Surg* 15:189-195.
Kurucz et al. (1995) *J Immunol* 154:4576-4582.
Le Gall et al. (1999) *FEBS Lett* 453:164-168.
Lees (2001) *Semin Ultrasound CT MR* 22:85-105.
Licha et al. (2000) *Photochem Photobiol* 72:392-398.
Lin et al. (2003) *Am J Pathol* 163:2113-2126.
Littlefield et al. (2008) *Inorg Chem* 47:2798-2804.
Manome et al. (1994) *Cancer Res* 54:5408-5413.
Marks et al. (1991) *J Mol Biol* 222:581-597.
Martin (1996) *Proteins* 25:130-133.
McCartney et al. (1995) *Protein Eng* 8:301-314.
McGucken et al. (1995) *Human Pathology* 26: 432-439.
Mukherjee et al. (2000) *J Immunol* 165:3451-3460.
Mukherjee et al. (2003a) *Glycoconjugate J* 18:931-942.
Mukherjee et al. (2003b) *J Immunother* 26:47-62.
Mukherjee et al. (2007) *Vaccine* 25:1607-1618.
Mukherjee et al. (2009) *J Immunol* 182:216-224.
Muller & Scherle (2006) *Nature Rev Can* 6:613-625.
Muller et al. (1988) *Cell* 54:105-115.
Muller et al. (1998) *FEBS Lett* 432:45-49.
Nabel (1997) Vectors for Gene Therapy In *Current Protocols in Human Genetics*, John Wiley & Sons, New York, N.Y., United States of America.
Nath & Mukherjee (2014) *Trends Mol Med* 20:332-342.
Needleman & Wunsch (1970) *J Mol Biol* 48:443-453.
Neri et al. (1997) *Nat Biotechnol* 15:1271-1275.
Neve et al. (2006) *Cancer Cell* 10:515-527.
Nygren (1982) *J Histochem Cytochem* 30:407.
Pack et al. (1992) *Biochemistry* 31:1579-1584.
Pain et al. (1981) *J Immunol Meth* 40:219).
Pardal et al. (2003) *Nat Rev Cancer* 3:895-902.
Parham et al. (1988) *J Clin Pathol* 41:875-879.
Park et al. (1997) *Adv Pharmacol* 40:399-435.
Pasqualini et al. (1997) *Nat Biotechnol* 15:542-546.
Patel et al. (1999) *Gene Therapy* 6:412-419.
Paul (1993) *Fundamental Immunology*, Raven Press, New York, N.Y., United States of America.
PCT International Patent Application Publication Nos. WO 1992/22653; WO 1993/25521.
Pearson & Lipman (1988) *Proc Natl Acad Sci USA* 85:2444-2448.
Pegram et al. (2012) *Blood* 119:4133-4141.
Perkins et al. (2003) *Am Fam Physician* 68:1075-1082.
Peterson et al. (1991) in *Breast Epithelial Antigens*, (Ceriani, ed.), Plenum Press, New York, N.Y., United States of America, pages 55-68.
Pockaj et al. (2004) *Ann Surg Oncol* 11:328-339.
Pomper & Port (2000) *Magn Reson Imaging Clin N Am* 8:691-713.
Porter et al. (2011) *N Engl J Med* 365:725-733.
Price et al. (1998) *Tumor Biology* 19:1 20.
Quin et al. (2000) *Int J Cancer* 87:499-506.
Ragnarson et al. (1992) *Histochemistry* 97:329-333.
Reya et al. (2001) *Nature* 414:105-111.
Rosenberg et al. (2008) *Nat Rev Cancer* 8:299-308.
Rothenfusser et al. (2002) *Human Immunology* 63:1111-1119.
Rovaris et al. (2001) *J Neurol Sci* 186 Suppl 1:S3-9.
Rowse et al. (1998) *Cancer Res* 58:315-321.
Rugo et al. (2005) *J Clin Oncol* 23:5474-5483.
Sadelain et al. (2009) *Curr Opin Immunol* 21:215-223.
Sagiuchi et al. (2001) *Ann Nucl Med* 15:267-270.
Saltzman & Fung (1997) *Adv Drug Deliv Rev* 26:209-230.
Sambrook & Russell (2001) *Molecular Cloning: a Laboratory Manual*, 3rd ed Cold Spring Harbor Laboratory Press, Cold Spring Harbor, N.Y., United States of America.
Sawyer et al. (2004) *Bioorg Med Chem Lett* 14:3581-3584.
Schwendener (1992) *Chimia* 46:69-77.
Scott et al. (2012) *Nat Rev Cancer* 12:278-287.
Shalaby et al. (1992) *J Exp Med* 175:217-225.
Sharkey et al. (2003) *Cancer Res* 63:354-363.
Sharkey et al. (2003) *Clin Cancer Res* 9:3897S-3913S.
Shen et al. (1993) *Magn Reson Med* 29:599-604.
Singh & Hollingsworth (2006) *Trends Cell Biol* 16:467-476.
Singh et al. (2004) *Nature* 432:396-401.
Siroy et al. (2013) *Hum Pathol* 44:2159-2166.
Smith & Waterman (1981) *Adv Appl Math* 2:482-489.
Speight et al. (1997) *Avery's Drug Treatment: A Guide to the Properties, Choice, Therapeutic Use and Economic Value* of Drugs in Disease Management, 4th ed., Adis International, Auckland, New Zealand.
Stephan et al. (2007) Nat Med 13:1440-1449.
Tavitian et al. (1998) Nat Med 4:467-471.
Till et al. (2012) Blood 119:3940-3950.
Tinder et al. (2008) J Immunol 181:3116-3125.
U.S. Pat. Nos. 4,551,482; 4,816,567; 5,088,499; 5,147,631; 5,234,933; 5,326,902; 5,490,840; 5,510,103; 5,574,172; 5,651,991; 5,688,931; 5,707,605; 5,714,166; 5,738,837; 5,786,387; 5,855,900; 5,858,410; 5,865,754; 5,922,356; 5,922,545; 5,928,627; 5,994,392; 6,024,938; 6,071,890; 6,080,384; 6,083,486; 6,106,866; 6,127,339; 6,172,197; 6,221,018; 6,231,834; 6,245,318; 6,246,901; 6,248,516; 6,254,852; 6,291,158; 6,548,643; 7,183,388; 8,465,743; 8,481,307; 8,518,405.
Vinogradov et al. (1996) Biophys J 70:1609-1617.
Wang et al. (2007) Hum Gene Ther 18:712-725.
Wang et al. (2011) PLoS One 6:e23513.
Weissleder et al. (1992) Magn Reson Q 8:55-63.
Weissleder et al. (1999) Nat Biotechnol 17:375-378.
Whitlow et al. (1991) Methods companion Methods Enzymol 2:97-105.
Xia et al. (2003) J Immunol 170:1980-1986.
Yoo et al. (1997) J Nucl Med 38:294-300.
Zhu et al. (1997) Protein Sci 6:781-788.
Zola (1987) Monoclonal Antibodies: A Manual of Techniques, CRC Press, Inc., Boca Raton, Fla., United States of America, pp 147-158.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A chimeric antigen receptor (CAR) molecule comprising a binding domain (BD), a transmembrane domain (TD), an intracellular signaling domain (ISD), and at least one costimulatory domain (CD), wherein:
   (i) the BD comprises a heavy chain complementary determining region 1 (HC CDR1) comprising SEQ ID NO: 8, a heavy chain complementary determining region 2 (HC CDR2) comprising SEQ ID NO: 9, and a heavy chain complementary determining region 3 (HC CDR3) comprising SEQ ID NO: 10; a light chain complementary determining region 1 (LC CDR1) comprising SEQ ID NO: 11, a light chain complementary determining region 2 (LC CDR2) comprising SEQ ID NO: 12, and a light chain complementary determining region 3 (LC CDR3) comprising SEQ ID NO: 13; and/or a heavy chain variable region comprising an amino acid sequence at least 95% identical to SEQ ID NO: 5 and a light chain variable region comprising an amino acid sequence at least 95% identical to SEQ ID NO: 7, provided that the heavy chain variable region comprises an HC CDR1 comprising SEQ ID NO: 8, an HC CDR2 comprising SEQ ID NO: 9, and an HC CDR3 comprising SEQ ID NO: 10, and the light chain variable region comprises an LC CDR1 comprising SEQ ID NO: 11, an LC CDR2 comprising SEQ ID NO: 12, and an LC CDR3 comprising SEQ ID NO: 13; and further wherein BD binds to a tumor-exclusive epitope of a human MUC1 polypeptide (tMUC);
   (ii) the TD comprises a transmembrane domain of a protein selected from the group consisting of the T-cell receptor (TCR) alpha chain, the TCR beta chain, the TCR zeta chain, CD28, CD3 epsilon, CD45, CD4, CD5, CD8, CD9, CD16, CD22, CD33, CD37, CD64, CD80, CD86, CD134, CD137, and CD154;
   (iii) the ISD comprises a functional signaling domain of a 4-1BB polypeptide, a functional signaling domain of a CD3 zeta polypeptide, or both; and
   (iv) the CD comprises a functional signaling domain of a protein selected from the group consisting of OX40, CD2, CD3, CD27, CD28, CD5, ICAM-1, LFA-1 (CD11a/CD18), and 4-1BB (CD137), or any combination thereof.

2. The CAR molecule of claim 1, wherein the binding domain is an scFv.

3. The CAR molecule of claim 1, wherein the TD comprises SEQ ID NO: 21 or SEQ ID NO: 23.

4. The CAR molecule of claim 1, wherein the CD comprises SEQ ID NO: 20 or SEQ ID NO: 22.

5. The CAR molecule of claim 1, wherein the ISD comprises: (i) the amino acid sequence as set forth in SEQ ID NO: 20 and/or SEQ ID NO: 24; or (ii) the amino acid sequence as set forth in SEQ ID NO: 22 and/or SEQ ID NO: 25.

6. The CAR molecule of claim 5, wherein the ISD comprises: (i) the amino acid sequence as set forth in SEQ ID NO: 20 and the amino acid sequence as set forth in SEQ ID NO: 24; or (ii) the amino acid sequence as set forth in SEQ ID NO: 22 and the amino acid sequence as set forth in SEQ ID NO: 25; and further wherein the sequences of (i) or (ii) are expressed in the same frame as each other and as a single polypeptide chain.

7. The CAR molecule of claim 1, further comprising a leader sequence.

8. The CAR molecule of claim 7, wherein the leader sequence comprises the amino acid sequence as set forth in SEQ ID NO: 18.

9. The CAR molecule of claim 1, wherein the CAR molecule comprises the amino acid sequence of SEQ ID NO: 15 or SEQ ID NO: 17, or that is encoded by SEQ ID NO: 14 or SEQ ID NO: 16.

10. The CAR molecule of claim 1, wherein the BD is human or humanized.

11. An isolated nucleic acid molecule encoding the CAR molecule of claim 1, optionally wherein the isolated nucleic acid molecule comprises SEQ ID NO: 14 or SEQ ID NO: 16.

12. A vector the isolated nucleic acid molecule of claim 11, optionally wherein the vector is selected from the group consisting of a DNA vector, an RNA vector, a plasmid, a lentivirus vector, an adenovirus vector, an adeno-associated virus (AAV) vector, and a retrovirus vector.

13. The vector of claim 12, wherein the vector is an expression vector that further comprises a promoter operably linked to the isolated nucleic acid molecule or the nucleotide sequence.

14. The vector of claim 12, wherein the vector comprises a nucleic acid sequence encoding a chimeric antigen receptor (CAR) comprising an antigen binding domain that binds to a tumor-exclusive epitope of human MUC1, a transmembrane domain, a CD28 costimulatory signaling domain, and a CD3 zeta signaling domain.

15. A method for making a cell expressing an anti-MUC1 CAR, the method comprising transducing a T cell with a vector of claim 12.

16. A cell comprising the vector of claim 12.

* * * * *